US012655141B2

(12) United States Patent
Lehal et al.

(10) Patent No.: US 12,655,141 B2
(45) Date of Patent: Jun. 16, 2026

(54) INHIBITORS OF NOTCH SIGNALING PATHWAY AND USE THEREOF IN TREATMENT OF CANCERS

(71) Applicant: Cellestia Biotech AG, Basel (CH)

(72) Inventors: Rajwinder Lehal, Zürich (CH); Guido Bold, Gipf-Oberfrick (CH); Charlotte Urech, Basel (CH); Vincent Zoete, Morges (CH)

(73) Assignee: Cellestia Biotech AG, Basel (CH)

( * ) Notice: Subject to any disclaimer, the term of this patent is extended or adjusted under 35 U.S.C. 154(b) by 1018 days.

(21) Appl. No.: 17/602,959

(22) PCT Filed: Apr. 9, 2020

(86) PCT No.: PCT/EP2020/060153

§ 371 (c)(1),
(2) Date: Oct. 11, 2021

(87) PCT Pub. No.: WO2020/208139

PCT Pub. Date: Oct. 15, 2020

(65) Prior Publication Data

US 2022/0169642 A1 Jun. 2, 2022

(30) Foreign Application Priority Data

Apr. 10, 2019 (EP) .................................... 19168508

(51) Int. Cl.

| | |
|---|---|
| ***C07D 417/12*** | (2006.01) |
| ***A61P 35/00*** | (2006.01) |
| ***C07C 211/45*** | (2006.01) |
| ***C07C 217/90*** | (2006.01) |
| ***C07C 225/22*** | (2006.01) |
| ***C07D 213/30*** | (2006.01) |
| ***C07D 213/73*** | (2006.01) |
| ***C07D 213/74*** | (2006.01) |
| ***C07D 401/12*** | (2006.01) |

(52) U.S. Cl.

CPC ............ *C07D 417/12* (2013.01); *A61P 35/00* (2018.01); *C07C 211/45* (2013.01); *C07C 217/90* (2013.01); *C07C 225/22* (2013.01); *C07D 213/30* (2013.01); *C07D 213/73* (2013.01); *C07D 213/74* (2013.01); *C07D 401/12* (2013.01)

(58) Field of Classification Search

CPC .................................................... C07D 417/12

See application file for complete search history.

(56) References Cited

U.S. PATENT DOCUMENTS

| | | | |
|---|---|---|---|
| 4,219,474 | A | 8/1980 | Zalipsky et al. |
| 4,816,373 | A | 3/1989 | Ohashi et al. |
| 4,935,465 | A | 6/1990 | Garman |
| 5,780,482 | A | 7/1998 | Armitage et al. |
| 5,965,740 | A | 10/1999 | Kai et al. |
| 6,342,244 | B1 | 1/2002 | Zalipsky |
| 6,692,919 | B1 | 2/2004 | Artavanis Tsakonas et al. |
| 9,296,682 | B2 | 3/2016 | Radtke et al. |
| 10,054,581 | B1 | 8/2018 | Radtke et al. |
| 11,472,771 | B2 | 10/2022 | Bauer et al. |
| 2003/0176438 | A1 | 9/2003 | Arienti et al. |
| 2005/0101521 | A1 | 5/2005 | Miyachi et al. |
| 2005/0171328 | A1 | 8/2005 | Harris |
| 2006/0002924 | A1 | 1/2006 | Bodmer et al. |
| 2006/0074024 | A1 | 4/2006 | Bunting et al. |
| 2007/0265264 | A1 | 11/2007 | Battista et al. |
| 2008/0161366 | A1 | 7/2008 | McComas et al. |
| 2008/0269265 | A1 | 10/2008 | Miller et al. |
| 2009/0081238 | A1 | 3/2009 | Siebel et al. |
| 2009/0105266 | A1 | 4/2009 | Glatthar et al. |
| 2010/0120869 | A1 | 5/2010 | Ajioka et al. |
| 2010/0234463 | A1 | 9/2010 | Churcher et al. |
| 2010/0292193 | A1 | 11/2010 | McBride et al. |
| 2012/0202785 | A1 | 8/2012 | Heald et al. |
| 2014/0323519 | A1 | 10/2014 | Siddiqui et al. |
| 2015/0246938 | A1 | 9/2015 | Matsumura et al. |

(Continued)

FOREIGN PATENT DOCUMENTS

| | | | |
|---|---|---|---|
| CN | 103784460 | A | 5/2014 |
| CN | 109134336 | A | 1/2019 |
| EP | 1820795 | A1 | 8/2007 |

(Continued)

OTHER PUBLICATIONS

STN/CAS Registry: RN 1942689-46-4 Registry Entered STN: Jun. 30, 2016; RN 1942689-46-4 Registry Entered STN: Jun. 30, 2016; RN 1216050-09-7 Registry Entered STN: Apr. 4, 2010; RN 1215960-99-8 Registry Entered STN: Apr. 4, 2010.*

(Continued)

*Primary Examiner* — Paul V Ward

(74) *Attorney, Agent, or Firm* — Fenwick & West LLP

(57) ABSTRACT

The present invention relates to new inhibitors of Notch signalling pathway and its use in the treatment and/or prevention of cancers.

(I)

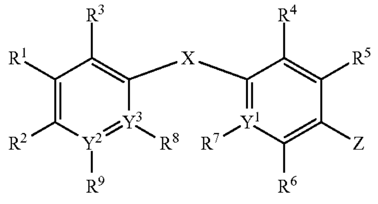

17 Claims, 10 Drawing Sheets

(56) References Cited

U.S. PATENT DOCUMENTS

2020/0022990 A1 1/2020 Sidransky

FOREIGN PATENT DOCUMENTS

| | | | |
|---|---|---|---|
| JP | H07048251 | A | 2/1995 |
| JP | H11152277 | A | 6/1999 |
| JP | 2001089412 | A | 4/2001 |
| JP | 2022-525186 | A | 3/2020 |
| WO | WO 93/25225 | A1 | 12/1993 |
| WO | WO 98/41525 | A1 | 9/1998 |
| WO | WO 00/42012 | A1 | 7/2000 |
| WO | WO 2003/051825 | A1 | 6/2003 |
| WO | WO 2004/087195 | A2 | 10/2004 |
| WO | WO 2005/047366 | A1 | 5/2005 |
| WO | WO 2006/020951 | A1 | 2/2006 |
| WO | WO 2009/060209 | A1 | 5/2009 |
| WO | WO 2009/146875 | A1 | 12/2009 |
| WO | WO 2010/033655 | A1 | 3/2010 |
| WO | WO2013/093885 | * | 6/2013 |
| WO | WO 2013/093885 | A1 | 6/2013 |
| WO | WO 2013/192274 | A2 | 12/2013 |
| WO | WO 2014/039994 | A2 | 3/2014 |
| WO | WO 2019/243523 | A1 | 12/2019 |
| WO | WO 2020/208139 | A1 | 10/2020 |
| WO | WO 2020/209933 | A1 | 10/2020 |

OTHER PUBLICATIONS

STN/CAS Registry: RN 1082154-71-9 Registry/ Entered STN: Dec. 9, 2008; RN 1040009-65-1 Registry Entered STN: Aug. 10, 2008.*

McMahon et al.(2000) Pinedo et al. (2000).*

Vippagunta et al. (2001).*

PCT International Search Report and Written Opinion, PCT/EP2020/060153, May 29, 2020, 14 Pages.

Hammad, I., et al., "Synthesis, Characterization, and Pharmacological Evaluation of Selected Aromatic Amines," Journal of Chemistry, Jan. 1, 2015, vol. 2015, pp. 1-9.

Khim, S. K., et al., "Discovery of Novel and Potent Aryl Diamines as Leukotriene $A_4$ Hydrolase Inhibitors," Bioorganic & Medicinal Chemistry Letters, Jul. 15, 2008, vol. 18, No. 14, pp. 3895-3898, Pergamon, Amsterdam, NL.

Mehdi, T., et al., "A Quick and Green lonic Liquid-Mediated Approach for the Synthesis of High-Performance, Organosoluble and Thermally Stable Polyimides," Chinese Journal of Polymer Science, Mar. 9, 2013, vol. 31, No. 4, pp. 679-690.

Sun, M. et al., "Design, Synthesis, and In Vitro Antitumor Evaluation of Novel Diaryl Ureas Derivatives," European Journal of Medicinal Chemistry, Jun. 1, 2010, vol. 45, No. 6, Elsevier, Amsterdam, NL.

Astudillo, L., et al. "the small molecule IMR-1 inhibits the Notch transcriptional activation complex to suppress tumorigenesis," Cancer Research, vol. 76, Issue 12, Jun. 14, 2016, pp. 3593-3603.

Brown, N. "Bicisosterism in Medicinal Chemistry," First Edition, Aug. 3, 2012, pp. 1-237.

Dastur, A. et al. "NOTCH1 Represses MCL-1 Levels in GSI-Resistant T-ALL, Making them Susceptible to ABT-263." Clinical Cancer Research, vol. 25, No. 1, Jan. 1, 2019, pp. 312-324.

Ismail, H., et al., "Synthesis, Characterization, and Pharmacological Evaluation of Selected Aromatic Amines," Journal of Chemistry, Jan. 1, 2015, vol. 2015, pp. 1-9.

Jiao, Z., et al. "Modulating Notch pathway using γ-secretase inhibitors for the immunotherapy of rheumatoid arthritis," Bioscience Hypotheses, vol. 1, Issue 6, Jan. 1, 2008, pp. 332-333.

Kang, J. H. et al. "Regulation of Th1 and Th2 Phenotypes by y-Secretase Inhibitor in an Animal Model for Asthma (79.10)." The Journal of Immunology, Abstract, vol. 182, No. 1, Apr. 2009, pp. 1-4.

Kleinjan, A., et al. "The Notch pathway inhibitor stapled α-helical peptide derived from mastermind-like 1 (SAHM1) abrogates the hallmarks of allergic asthma," Journal of Allergy and Clinical Immunology, vol. 142, Issue 1, Jul. 2018, pp. 76-85.

Lehal, R., et al. "Pharmacological activity of CB-103—An oral pan-NOTCH inhibitor with a novel mode of action" Haematologica, vol. 102, Jun. 22-25, 2017, p. 29.

Lehal, R. et al. "Pharmacological Disruption of the Notch Transcription Factor Complex." PNAS, vol. 117, No. 28, Jul. 14, 2020, pp. 16292-16301.

Li, M. et al. "Combined Inhibition of Notch Signaling and Bcl-2/Bcl-xL Results in Synergistic Antimyeloma Effect." Molecular Cancer Therapeutics, vol. 9, No. 12, Dec. 1, 2010, pp. 3200-3209.

Linder, B. et al. "Arsenic Trioxide and (−)-Gossypol Synergistically Target Glioma Stem-Like Cells via Inhibition of Hedgehog and Notch Signaling." Cancers, vol. 11, No. 3, Mar. 12, 2019, pp. 1-22.

Ma, L., et al. "Effect of γ-secretase Inhibitor on Th17 cell differentiation and function of mouse psoriasis-like skin inflammation," Journal of Translational Medicine, vol. 16, Mar. 10, 2018, pp. 1-10.

Minter, L., et al. "Inhibitors of γ-secretase block in vivo and in vitro T helper type 1 polarization by preventing Notch upregulation of Tbx21," Nature Immunology, vol. 6, Issue 7, May 29, 2005, pp. 680-688.

Mukherjee, N. et al. "Combining a GSI and BCL-2 Inhibitor to Overcome Melanoma's Resistance to Current Treatments." Oncotarget, vol. 7, No. 51, Dec. 20, 2016, pp. 84594-84607.

PCT International Search Report and Written Opinion, PCT Application No. PCT/EP2021/084426, Mar. 2, 2022, 19 pages.

PCT International Search Report and Written Opinion, PCT Application No. PCT/EP2021/075466, Dec. 20, 2021, 18 Pages.

PCT International Search Report and Written Opinion, PCT Application No. PCT/EP2022/064684, Jan. 2, 2023, 19 pages.

Sakakibara-Konishi, J. et al. "Combined Antitumor Effect of γ-Secretase Inhibitor and ABT-737 in Notch-Expressing Non-Small Cell Lung Cancer." International Journal of Clinical Oncology, vol. 22, Apr. 2017, pp. 257-268.

Seveno, C. et al. "γ-Secretase Inhibition Promotes Cell Death, Noxa Upregulation, and Sensitization to BH3 Mimetic ABT-737 in Human Breast Cancer Cells." Breast Cancer Research, vol. 14, No. R96, Jun. 15, 2012, pp. 1-15.

Taghavi, M., et al., "A Quick and Green lonic Liquid-Mediated Approach for the Synthesis of High-Performance, Organosoluble and Thermally Stable Polyimides," Chinese Journal of Polymer Science, Mar. 9, 2013, vol. 31, No. 4, pp. 679-690.

Timme, C. R. et al. "Gamma-Secretase Inhibition Attenuates Oxaliplatin-Induced Apoptosis Through Increased Mcl-1 and/or Bcl-xL in Human Colon Cancer Cells." Apoptosis, vol. 18, No. 10, Jul. 2013, pp. 1163-1174.

Tse, C. et al. "ABT-263: A Potent and Orally Bioavailable Bcl-2 Family Inhibitor." Cancer Research, vol. 68, No. 9, May 1, 2008, pp. 3421-3428.

United States Office Action, U.S. Appl. No. 17/882,432, filed Aug. 22, 2023, seven pages.

United States Office Action, U.S. Appl. No. 17/882,432, Feb. 1, 2024, seven pages.

United States Office Action, U.S. Appl. No. 17/354,521, Feb. 14, 2024, 18 pages.

United States Office Action, U.S. Appl. No. 17/354,521, Aug. 15, 2024, 23 pages.

Zhou, M., et al. "Blockade of Notch Signalling by y-secretase Inhibitor in Lung T Cells of Asthmatic Mice Affects T Cell Differentiation and Pulmonary Inflammation," Inflammation, vol. 38, Issue 3, Jun. 2015, pp. 1281-1288.

3-Pyridinamine, 6-[3-(1, 1-dimethylethyl)phenoxy]—, Feb. 1, 2009, CAS Registry No. 1098366-43-8 (3 pages).

3-Pyridinamine, 6-[4-(1, 1-dimethylpropyl)phenoxy]—, Jul. 27, 2008, CAS Registry No. 1036533-91-1 (3 pages).

Artavanis-Tsakonas et al., "Notch signalling: cell fate control and signal integration in development", Science 284(5415): 770-776.

Benzenamine, 4-[4-(I,I-dimethylethyl)phenoxy]-3-fluoro—, Sep. 12, 2007, CAS Registry No. 946785-77-9 (3 pages).

Benzenamine, 4-[4-(I,I-dimethylpropyl)phenoxy]-3-fluoro—, Sep. 12, 2007, CAS Registry No. 946742-50-3 (3 pages).

(56) References Cited

OTHER PUBLICATIONS

Bharate, S. S. "Recent Developments in Pharmaceutical Salts: FDA Approvals from 2015 to 2019." Drug Discovery Today, vol. 26, No. 2, Feb. 2021, pp. 384-398.
Bhatia, N. et al., Identification of novel small molecules that inhibit protein-protein interactions between MAGE and KAP-1:, Arch Biochem Biophys., 2011, vol. 508, No. 2, pp. 217-221.
Bray, S.J., "Notch signalling: a simple becomes complex", Nature Rev Molec Cell Biol 7: 678-689, 2006.
Clinton, R. O. et al. "A Structure Proof for 4-(4-Diethylamino-1-methylbutylamino)-7-phenoxyquinoline." Journal of the American Chemical Society, vol. 69, No. 3, Mar. 1, 1947, pp. 704-706.
De Houwer, J. et al. "Synthesis of Aryl(di)azinyl Ketones through Copper- and Iron-catalyzed Oxidation of the Methylene Group of Aryl(di)azinylmethanes." Angewandte Chemie International Edition, vol. 51, No. 11, Mar. 12, 2012, pp. 2745-2748.
Desbordes, S. G. et al., "High-Throughput Screening Assay for the Identification of Compounds Regulating Self-Renew AI and Differentation in Human Embryonic Stem Cells", Cell Stem Cell. Jun. 5, 2008; 2(6): 602-612.
Dittmer, D. P. et al. "Kaposi Sarcoma-Associated Herpesvirus: Immunobiology, Oncogenesis, and Therapy." The Journal of Clinical Investigation, vol. 126, No. 9, Sep. 1, 2016, pp. 3165-3175.
Emuss et al., "KSHV manipulates Notch sigrialing by DLL4 and JAGI to alter cell cycle genes in lymphatic endothelia", PLoS Pathog 5(10): eI000616, 2009 (12 total pages).
European Extended Search Report, European Application No. 11010130.0, Jun. 6, 2012, 6 pages.
Friedman, H. L. et al. "Tuberculostatic Compounds. I. Ethers of 2-Hydroxy-5-Aminopyridine." J. Amer. Chem. Soc., vol. 69, 1947, pp. 1204-1206.
Harvard Medical School. "Comparison of Chemical Libraries." ICCB—Longwood Screening Facility, Aug. 2006, 1 page.
Hsiao, S-H. et al., "Electroactive aromatic polyamides and polyimides with adamantylphenoxy-substituted triphenylamine units", European Polymer Journal, vol. 45, Issue 8, 2009, pp. 2234-2248.
Huang, X. et al. "Late Stage Benzylic C—H Fluorination with [18F]fluoride for PET Imaging." Journal of the American Chemical Society, vol. 136, No. 19, May 14, 20174, pp. 6842-6845.
Jaleco et al., "Differential effects of Notch ligands Delta-1 and Jagged-1 in human lymphoid differentiation", J Exp Med 194(7): 991-1001, 2001.
Kavian, N. et al., "New insights into the mechanism of Notch signalling in fibrosis", Open Rheumatol J 6(Suppl 1: M5): 96-102, 2012.
King, H. "254. Curare Alkaloids. Part IV. Bebeerine and Tubocurarine. Orientation of Phenolic Groups." Journal of the Chemical Society, 1939, pp. 1157-1164.
Krug, M. et al. "Discovery and Selectivity-profiling of 4-benzylamino 1-aza-9-oxafluorene Derivatives as Lead Structures for IGF-1R Inhibitors." Bioorganic & Medicinal Chemistry Letters, vol. 20, No. 23, Dec. 1, 2010, pp. 6915-6919.
Laemmler, G., et al., "Chemotherapy of Fascioliases. IV. Action of Aromatic Amines Against Liver Flukes. 2," [Retrieved Online] Chemical Abstracts Service, Columbus, Ohio, US.
Lange, N. A. et al. "Some Para-Phenoxy-Ureas and Thio-Ureas Derived from Para-Phenoxy-Aniline. The Effect of the Phenoxy Group on the Taste." Journal of the American Chemical Society, vol. 48, No. 4, Apr. 1, 1926, pp. 1069-1074.
Langer, R. "New Methods of Drug Delivery." Science, vol. 249, No. 4976, Sep. 28, 1990, pp. 1527-1533.
Maybridge. "Browse HIT Finder." Plate 1 to 40, 1 page, [Online] [Retrieved Nov. 16, 2020], Retrieved from the internet <URL:http://www.chem.maybridge.com/hitfinder/>.
Maybridge. "Browse HIT Finder." Plate 121-160, 1 page, [Online] [Retrieved Nov. 16, 2020], Retrieved from the internet <URL:http://www.chem.maybridge.com/hitfinder/>.
Maybridge. "Browse HIT Finder." Plate 161-180, 1 page, [Online] [Retrieved Nov. 16, 2020], Retrieved from the internet <URL:http://www.chem.maybridge.com/hitfinder/>.
Maybridge. "Browse HIT Finder." Plate 41-80, 1 page, [Online] [Retrieved Nov. 16, 2020], Retrieved from the internet <URL:http://www.chem.maybridge.com/hitfinder/>.
Maybridge. "Browse HIT Finder." Plate 81-120, 1 page, [Online] [Retrieved Nov. 16, 2020], Retrieved from the internet <URL:http://www.chem.maybridge.com/hitfinder/>.
Maybridge. "Diversity Matters: Target Your Research with the HitFinger™ Collection of Screening Compounds." J. Chem. Inf. Comput. Sci., vol. 39, 1999, 1 page.
Mesri, E. A. et al. "Human Viral Oncogenesis: A Cancer Hallmark Analysis." Cell Host & Microbe, vol. 15, No. 3, Mar. 12, 2014, pp. 266-282.
Miele, L., "Transcription factor RBPJ/CSL: A genome-wide look at transcriptional regulation", Proc Natl Acad Sci USA 108(39): 14715-14716, 2011.
Oberbek et al., "Generation of stable, high-producing CHO cell lines by lentiviral vector-mediated gene transfer in serum-free suspension culture", Biotechnol Bioeng 108: 600-610, 2011.
PCT International Search Report and Written Opinion, PCT Application No. PCT/IB2012/057622, Apr. 26, 2013, 11 pages.
PCT International Search Report and Written Opinion, PCT Application No. PCT/EP2019/066381, Nov. 19, 2019, 17 pages.
PCT International Search Report and Written Opinion, PCT Application No. PCT/EP2020/060149, Jun. 19, 2020, 11 Pages.
Rosen, A. et al. "Lymphoblastoid Cell Line with B1 Cell Characteristics Established from a Chronic Lymphocytic Leukemia Clone by in Vitro EBV Infection." OncoImmunology, vol. 1, No. 1, Jan. 1, 2012, pp. 18-27.
Sarmento, L. M. et al., "Therapeutic potential of Notch inhibition in T-cell acute lymphoblastic leukemia: rationale, caveats and promises", Expert Review of Anticancer Therapy, 2011, vol. 11, No. 9, pp. 1403-1415.
Schroeter et al., "Notch-1 signalling requires ligand-induced proteolytic release of intracelluar domain", Nature 3 93: 3 82-386, 1998.
Shih, I-M. et al. "Notch Signaling, y-Secretase Inhibitors, and Cancer Therapy." Cancer Research, vol. 67, No. 5, Mar. 1, 2007, pp. 1879-1882.
Silverman, R. "The Organic Chemistry of Drug Design and Drug Action," 2004, Elsevier, excerpt, pp. 29-32.
Stahl, P. H. et al. "Appendix." Handbook of Pharmaceutical Salts: Properties, Selection, and Use, Wiley-VCH, 2002, pp. 329-331.
Szajnman, S. H. et al. "Design and Synthesis of Aryloxyethyl Thiocyanate Derivatives as Potent Inhibitors of Trypanosoma cruzi Proliferation." Journal of Medical Chemistry, vol. 43, No. 9, Apr. 14, 2000, pp. 1826-1840.
Technology Networks. "Thermo Scientific Introduces Maybridge HitFinder-Plus Screening Compound Library." Technologynetworks.com, Dec. 16, 2011, 8 pages, [Online] [Retrieved Nov. 16, 2020], Retrieved from the internet <URL:https://www.technologynetworks.com/drug-discovery/product-news/thermo-scientific-introduces-maybridge-hitfinderplus-screening-compound-library-224110>.
Udeh, C. U. et al. "Tuning Structure and Function in Tetra(aniline)-based rod-coil-rod Architectures." Journal of Materials Chemistry C, vol. 1, No. 39, Aug. 30, 2013, pp. 6428-6437.
United States Office Action, U.S. Appl. No. 14/366,917, Mar. 3, 2015, seven pages.
United States Office Action, U.S. Appl. No. 15/017,986, Aug. 18, 2017, 16 pages.
United States Office Action, U.S. Appl. No. 15/017,986, Jun. 13, 2018, six pages.
United States Office Action, U.S. Appl. No. 16/363,336, Aug. 27, 2020, five pages.
United States Office Action, U.S. Appl. No. 16/363,336, Dec. 1, 2020, nine pages.
Written Opinion of International Search Authority issued Jun. 21, 2014, in International Application No. PCT/IB2012/057622.
Anusha, G. et. al., "SingaCycle™—A1-catalyzed successive Suzuki-Miyaura and Buchwald couplings for the synthesis of various new pyridine analogues," ChemistrySelect, vol. 3, No. 46, Dec. 13, 2018, pp. 13182-13190.

(56) References Cited

OTHER PUBLICATIONS

Chern, Y et. al., "High Tg and high organosolubility of novel unsymmetric polyimides polyimides," Journal of Polymer Science, Part A: Polymer Chemistry, vol. 47, No. 9, May 1, 2009, pp. 2443-2452.

Dilthey, W. et. al., "Heteropolar compounds. XVI. Biphenyl green dyes," Journal fuer Praktische Chemie (Leipzig), 19321932, vol. 134, pp. 188-208.

Fabbro, D., et al. "Notch inhibition in cancer: challenges and opportunities," Chimia, vol. 74, Issue 10, Oct. 28, 2020, pp. 779-783.

Kuettel, S. et. al., "Synthesis and Evaluation of Antiparasitic Activities of New 4-[5-(4-Phenoxyphenyl)-2H-pyrazol-3-yl]morpholine Derivatives," Journal of Medicinal Chemistry, vol. 50, No. 23, Oct. 20, 2007, pp. 5833-5839.

Liang, X. et.al., "One-pot propagation of (Hetero) Arylamines: Modular synthesis of diverse Amino-di(hetero)arylamines," Tetrahedron, vol. 75, No. 6, Feb. 8, 2019, pp. 721-731.

PCT International Search Report and Written Opinion, PCT Application No. PCT/EP2022/080933, Jan. 30, 2023, 14 pages.

STN Registry, "Cas Registration Nos. 2108917-91-3, 2108210-57-5, 1216050-09-7, 1215960-99-8, and 900721-11-1," 2017, pp. 1-3.

Yang, S. et al., "Iridium-Catalyzed Highly Efficient and Site-Selective Deoxygenation of Alcohols," ACS Catalysis, vol. 8, No. 10, Aug. 27, 2018, pp. 9320-9326.

Yao, J., et al. "Combination treatment of PD98059 and DAPT in gastric cancer through induction of apoptosis and downregulation of WNT/β-catenin," Cancer Biology & Therapy, vol. 14, Issue 9, Sep. 19, 2013, pp. 833-839.

CAS Registry No. 2108792-48-7 (entered Aug. 6, 2017).

CAS Registry No. 2108267-00-9 (entered Aug. 4, 2017).

CAS Registry No. 6628-69-9 (entered Nov. 16, 1984).

* cited by examiner 6-(4-(tert-butyl)phenoxy)pyridin-3-amine 4-([1,1'-biphenyl]-4-yloxy)aniline 6-([1,1'-biphenyl]-4-yloxy)-N-methylpyridin-3-amine 4-([1,1'-biphenyl]-4-yloxy)-3-fluoro-N-methylaniline 6-((4'-fluoro-[1,1'-biphenyl]-4-yl)oxy)pyridin-3-amine

6-([1,1'-Biphenyl]-4-yloxy)-4-methylpyridin-3-amine

6-([1,1'-biphenyl]-4-yloxy)-2-methylpyridin-3-amine

N-methyl-6-((6-phenylpyridin-3-yl)oxy)pyridin-3-amine 6-((2-(2-(4-aminophenoxy)ethyl)-[1,1'-biphenyl]-4-yl)oxy)pyridin-3-amine 6-((4'-fluoro-[1,1'-biphenyl]-4-yl)oxy)-2-methylpyridin-3-amine 6-((4'-fluoro-[1,1'-biphenyl]-4-yl)oxy)-N-methylpyridin-3-amine 2-methyl-6-(4-(thiazol-2-yl)phenoxy)pyridin-3-amine 4-methyl-6-(4-(thiazol-2-yl)phenoxy)pyridin-3-amine 2-methyl-6-(4-(thiazol-5-yl)phenoxy)pyridin-3-amine 4-methyl-6-(4-(thiazol-5-yl)phenoxy)pyridin-3-amine

INHIBITORS OF NOTCH SIGNALING PATHWAY AND USE THEREOF IN TREATMENT OF CANCERS

CROSS-REFERENCE TO RELATED APPLICATIONS

This application is a national phase of International Application No. PCT/EP2020/060153, titled "Inhibitors of Notch Signalling Pathway and Use Thereof in Treatment of Cancers," filed on Apr. 9, 2020, which claims priority to European Patent Application No. 19168508.0, filed on Apr. 10, 2019.

FIELD OF THE INVENTION

The present invention relates to new inhibitors of Notch signalling pathway and its use in the treatment and/or prevention of cancers.

BACKGROUND OF THE INVENTION

The Notch signalling pathway represents a critical component in the molecular circuits that control cell fate during development, cell survival and cell proliferation (Shih IeM, Wang T L in Cancer Res 2007; 67(5):1879-82). Aberrant activation of this pathway contributes to tumorigenesis. The Notch family members are being revealed as oncogenes in an ever-increasing number of cancers. The role of Notch in human cancer has been highlighted recently by the presence of activating mutations and amplification of Notch genes in human cancer and by the demonstration that genes/proteins in the Notch signalling pathway could be potential therapeutic targets. It has become clear that one of the major therapeutic targets in the Notch pathway are the Notch receptors, in which γ-secretase inhibitors prevent the generation of the oncogenic (intracellular) domain of Notch molecules and suppress the Notch activity.

Though significant progress has been made in dissecting the complex workings of this signalling pathway, there are very limited options available for developing novel Notch inhibitors. However, the pioneering class of Notch inhibitors is already in clinical trials for few cancer types, such as γ-secretase inhibitors AL101 from Ayala Pharma (formerly BMS 906024), LY3039478 from Eli Lilly and Nirogacestat from Springworks Therapeutics, a synthetic small molecule, inhibits the Notch signalling pathway, which may result in induction of growth arrest in tumor cells in which the Notch signalling pathway is overactivated.

One of the drawbacks of use of γ-secretase inhibitors to block Notch signaling, as currently under investigation, is their wide range of additional targets such as amyloid precursor protein. Due to their ability to block Notch signalling via all four receptors γ-secretase inhibitors are known to cause goblet cell metaplasia in the intestine. In addition, some of the hematological malignancies and solid tumors harbor mutations in the Notch receptors (such as chromosomal translocations) resulting in constitutive expression of dominant active form of NICD independent of cleavage by γ-secretase complex. Therefore these tumors will fail to respond to γ-secretase inhibitors treatment.

WO2013/093885 discloses several Notch inhibiting compounds among them 6-(4-tert-butylphenoxy)pyridin-3-amine as particular preferred compound. Notch inhibition measured varies significantly among the disclosed compounds. Therefore, there is still a need to identify and develop further specific and selective inhibitors of Notch signaling pathway with improved properties useful for treating and/or preventing cancers.

SUMMARY OF THE INVENTION

The present invention provides compounds of formula (I)

Formula (I)

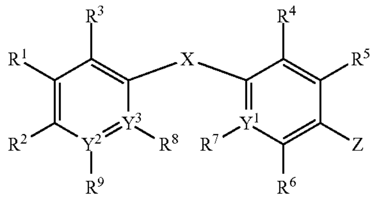

pharmaceutically-acceptable salts, hydrates, solvates, or stereoisomers thereof, wherein X is selected from $CH_2$, $CF_2$, CHF, CO, CHOH, $CHO(C_1\text{-}C_3)$ alkyl, NH, $N(C_1\text{-}C_3$ alkyl), S, SO and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1\text{-}C_6$ alkyl;

wherein $R^1$ is selected from H, halogen, $C_1\text{-}C_6$ alkyl, $C_3\text{-}C_{12}$ cycloalkyl, $C_3\text{-}C_{12}$ heterocyclyl, $C_1\text{-}C_6$ alkoxy, $C_1\text{-}C_6$ heteroalkyl, $C_0\text{-}C_3$ alkyl$OC_0\text{-}C_3$ alkyl aryl wherein the aryl is optionally substituted by $NH_2$, $OC_1\text{-}C_6$ alkyl, $C_1\text{-}C_6$ alkyl, $C_1\text{-}C_6$ heteroalkyl, halogen, CN, $C_3\text{-}C_{12}$ cycloalkyl, $C_3\text{-}C_{12}$ heterocyclyl; $C_0\text{-}C_3$ alkyl$OC_0\text{-}C_3$ alkyl heteroaryl wherein the heteroaryl is optionally substituted by $NH_2$, $OC_1\text{-}C_6$ alkyl, $C_1\text{-}C_6$ alkyl, $C_1\text{-}C_6$ heteroalkyl, halogen, CN, $C_3\text{-}C_{12}$ cycloalkyl, $C_3\text{-}C_{12}$ heterocyclyl; and $C_1\text{-}C_6$ alkyl substituted by aryl or heteroaryl wherein the aryl and the heteroaryl are optionally substituted by $NH_2$, $OC_1\text{-}C_6$ alkyl, $C_1\text{-}C_6$ alkyl, $C_1\text{-}C_6$ heteroalkyl, halogen, CN, $C_3\text{-}C_{12}$ cycloalkyl, $C_3\text{-}C_{12}$ heterocyclyl;

wherein $R^2$ is selected from aryl and heteroaryl wherein the aryl and the heteroaryl are optionally substituted by $NH_2$, $OC_1\text{-}C_6$ alkyl, $C_1\text{-}C_6$ alkyl, $C_1\text{-}C_6$ heteroalkyl, halogen, CN, $C_3\text{-}C_{12}$ cycloalkyl, $C_3\text{-}C_{12}$ heterocyclyl, $C(O)R^{12}$, $C_1\text{-}C_6$ alkyl $C(O)R^{12}$;

wherein $R^3$ is selected from H, halogen, $C_1\text{-}C_6$ alkyl, $C_1\text{-}C_6$ heteroalkyl, $C_3\text{-}C_{12}$ cycloalkyl, $C_3\text{-}C_{12}$ heterocyclyl and $C_1\text{-}C_6$ alkoxy;

wherein $R^4$, $R^5$ and $R^6$ are each independently selected from H, halogen, CN, $C_1\text{-}C_6$ alkoxy, $C_1\text{-}C_6$—S-alkyl, $C_1\text{-}C_6$ alkyl, $C_1\text{-}C_6$ heteroalkyl, $C_3\text{-}C_{12}$ cycloalkyl and $C_3\text{-}C_{12}$ heterocyclyl;

wherein $R^7$ is absent when $Y^1$ is N or is selected from H, halogen, $C_1\text{-}C_6$ alkyl, $C_1\text{-}C_6$ heteroalkyl, $C_3\text{-}C_{12}$ cycloalkyl, $C_3\text{-}C_{12}$ heterocyclyl and $C_1\text{-}C_6$ alkoxy when $Y^1$ is C;

wherein $R^8$ is absent when $Y^3$ is N or is selected from H, halogen, $C_1\text{-}C_6$ alkyl, $C_1\text{-}C_6$ heteroalkyl, $C_3\text{-}C_{12}$ cycloalkyl, $C_3\text{-}C_{12}$ heterocyclyl and $C_1\text{-}C_6$ alkoxy when $Y^3$ is C;

wherein $R^9$ is absent when $Y^2$ is N or is selected from H, halogen, $C_1\text{-}C_6$ alkyl, $C_3\text{-}C_{12}$ cycloalkyl, $C_3\text{-}C_{12}$ heterocyclyl, $C_1\text{-}C_6$ alkoxy, $C_1\text{-}C_6$ heteroalkyl, $C_0\text{-}C_3$ alkyl$OC_0\text{-}C_3$ alkyl aryl wherein the aryl is optionally substituted by $NH_2$, $OC_1\text{-}C_6$ alkyl, $C_1\text{-}C_6$ alkyl, $C_1\text{-}C_6$ heteroalkyl, halogen, CN, $C_3\text{-}C_{12}$ cycloalkyl, $C_3\text{-}C_{12}$ heterocyclyl; $C_0\text{-}C_3$ alkyl$OC_0\text{-}C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^{12}$ is selected from H, $NH_2$, $NHC_1$-$C_6$ alkyl, $C_1$-$C_6$ alkyl, $C_1$-$C_6$ heteroalkyl, $C_2$-$C_6$ alkenyl, $C_2$-$C_6$ alkynyl, $C_3$-$C_{12}$ cycloalkyl and $C_3$-$C_{12}$ heterocyclyl;

with the proviso that the compound of formula (I) is not 6-([1,1'-Biphenyl]-4-yloxy)-pyridine-3-amine, 4-([1, 1'-Biphenyl]-4-yloxy)-aniline, 6-([1,1'-Biphenyl]-4-yloxy)-2-methylpyridin-3-amine and 6-([1,1'-Biphenyl]-4-yloxy)-4-methylpyridin-3-amine.

The present invention also provides compounds of formula (I)

Formula (I)

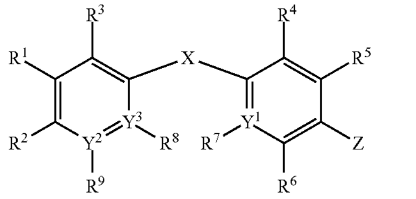

pharmaceutically-acceptable salts, hydrates, solvates, or stereoisomers thereof, wherein X is selected from $CH_2$, $CF_2$, CHF, CO, CHOH, $CHO(C_1$-$C_3)$ alkyl, NH, $N(C_1$-$C_3$ alkyl), S, SO and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy;

wherein $R^4$, $R^5$ and $R^6$ are each independently selected from H, halogen, CN, $C_1$-$C_6$ alkoxy, $C_1$-$C_6$—S-alkyl, $C_1$-$C_6$ alkyl, $C_1$-$C_6$ heteroalkyl, $C_3$-$C_{12}$ cycloalkyl and $C_3$-$C_{12}$ heterocyclyl;

wherein $R^7$ is absent when $Y^1$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^1$ is C;

wherein $R^8$ is absent when $Y^3$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^3$ is C;

wherein $R^9$ is absent when $Y^2$ is N or is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^{12}$ is selected from H, $NH_2$, $NHC_1$-$C_6$ alkyl, $C_1$-$C_6$ alkyl, $C_1$-$C_6$ heteroalkyl, $C_2$-$C_6$ alkenyl, $C_2$-$C_6$ alkynyl, $C_3$-$C_{12}$ cycloalkyl and $C_3$-$C_{12}$ heterocyclyl, for use in a method for the prevention or treatment of cancer, preferably for use in a method for the prevention or treatment of a Notch dependent cancer. The present invention also provides a pharmaceutical composition comprising a compound of formula (I) and a pharmaceutically acceptable carrier, and a kit comprising a compound of formula (I), optionally with reagents and/or instructions. The present invention also provides the use of compounds of formula (I), for inhibiting in vitro or in vitro the Notch signalling pathway in cells.

It has been surprisingly found by the inventors of the present application that compounds which differ with respect to their chemical structure substantially from the compounds specifically disclosed in WO2013/093885 show unrivalled biological properties in Notch inhibition like high potency against NOTCH driven human cancers and high potency in downregulating NOTCH target genes.

Figure 1:
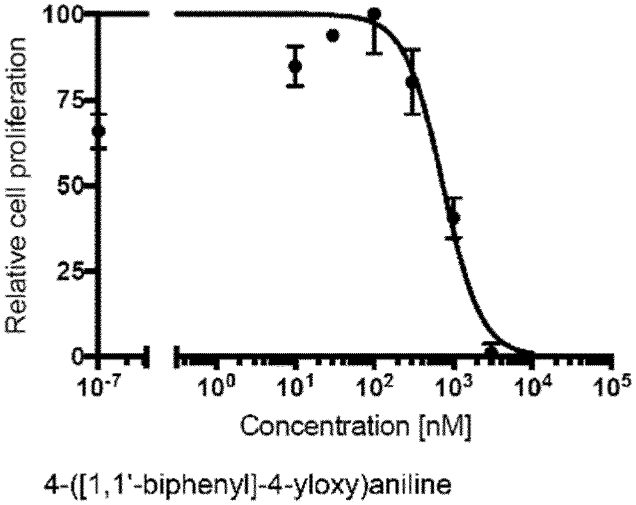
FIG. 1 shows anti-proliferative effect of compounds on NOTCH positive and NOTCH dependent human leukemic cell lines (RPMI8402). Cells were treated with compounds for 72 hours and effect on proliferation was quantified using Alamar blue readout.
Figure 1:
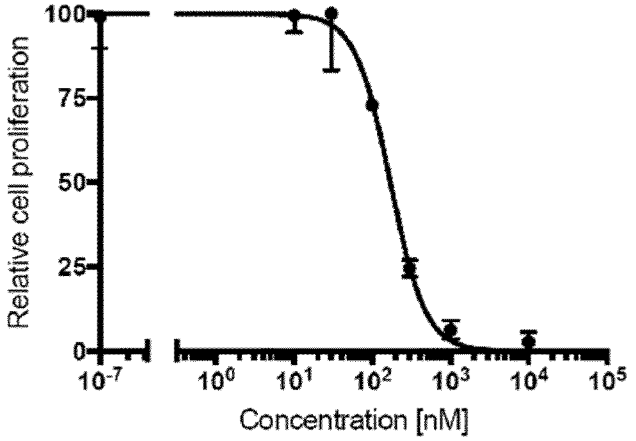
Figure 1:
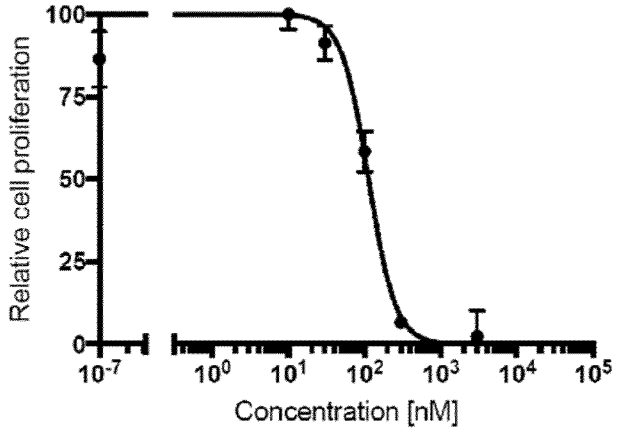
Figure 1:
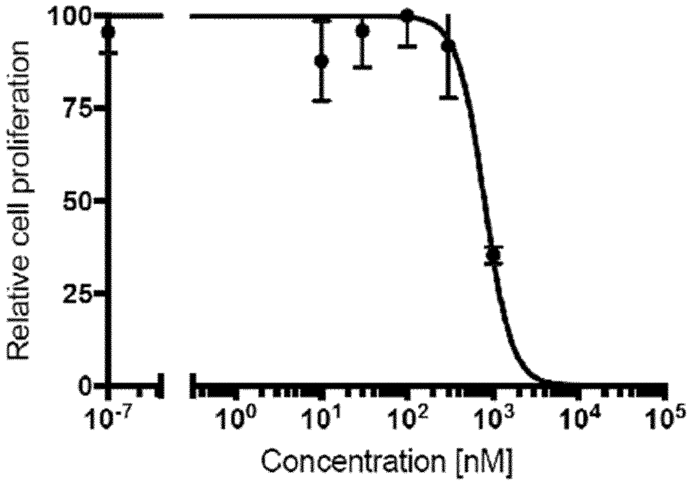
Figure 1:
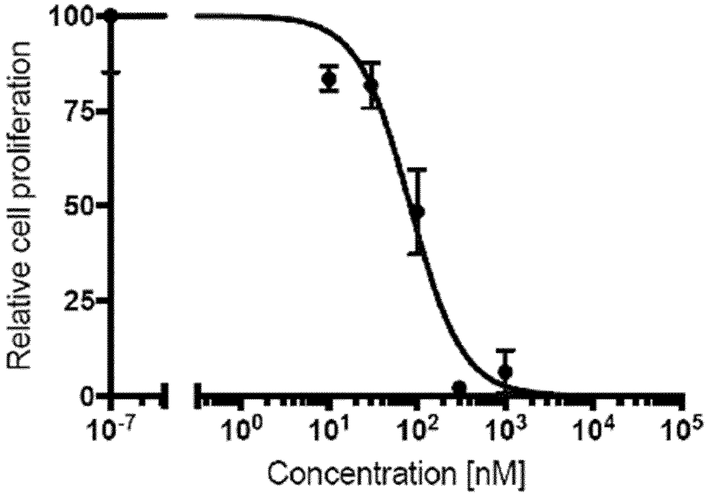
Figure 1:
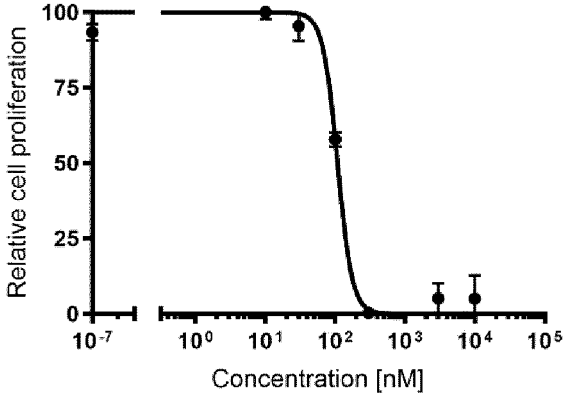
Figure 1:
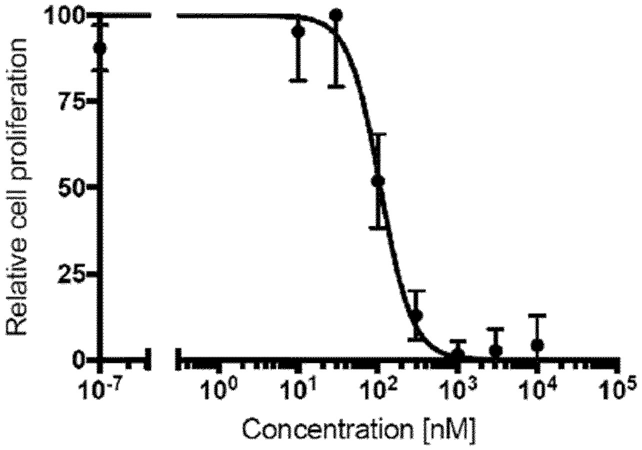
Figure 1:
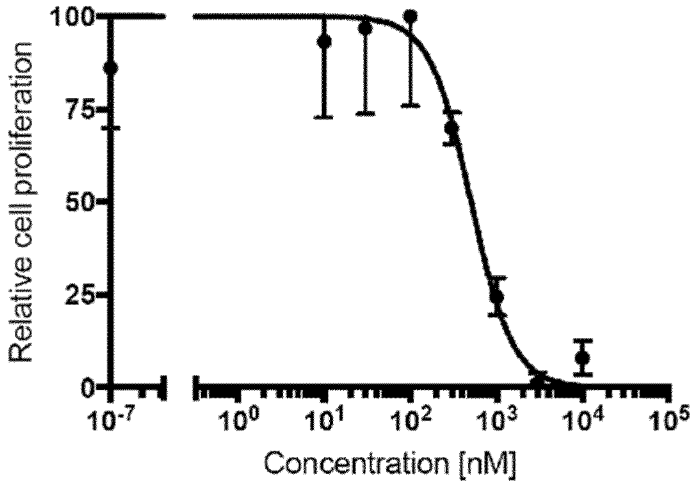
Figure 1:
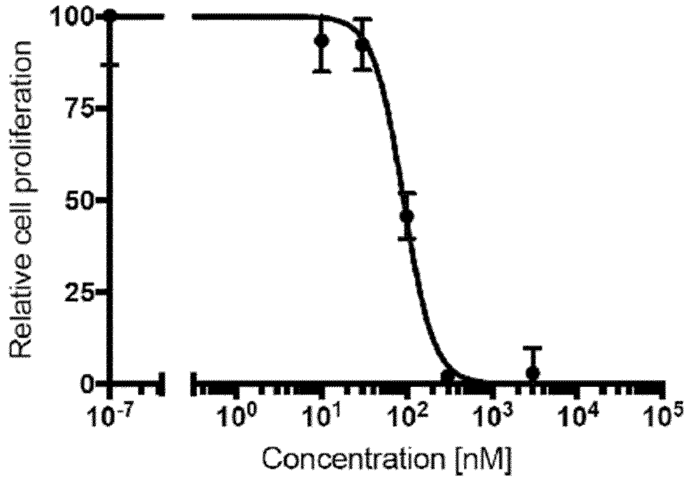
Figure 1:
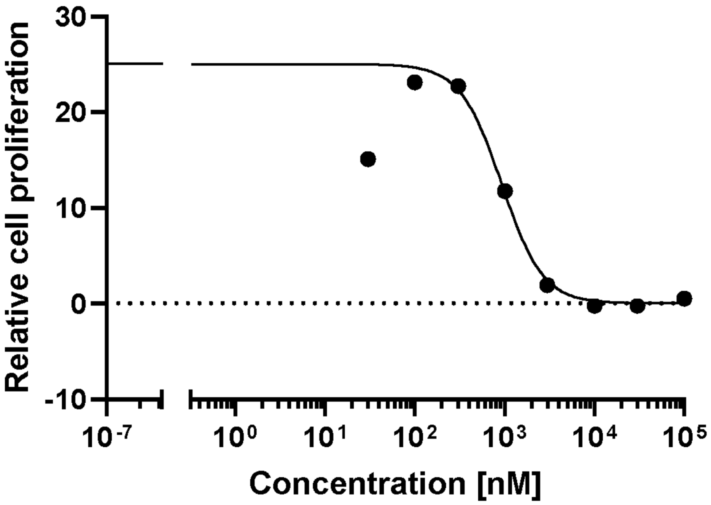
Figure 1:
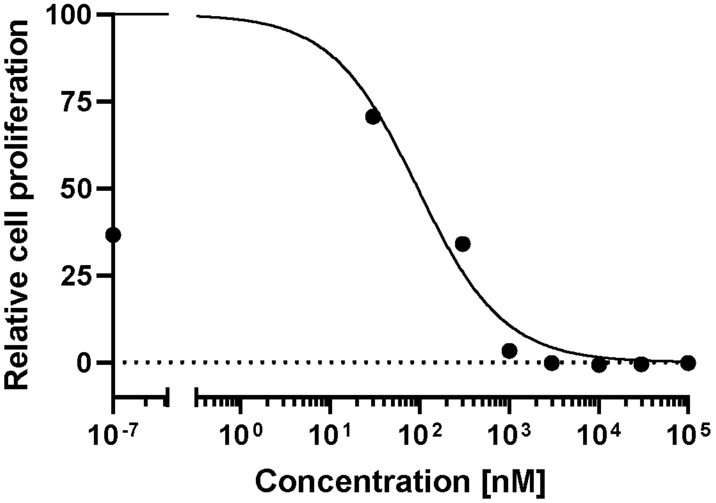
Figure 1:
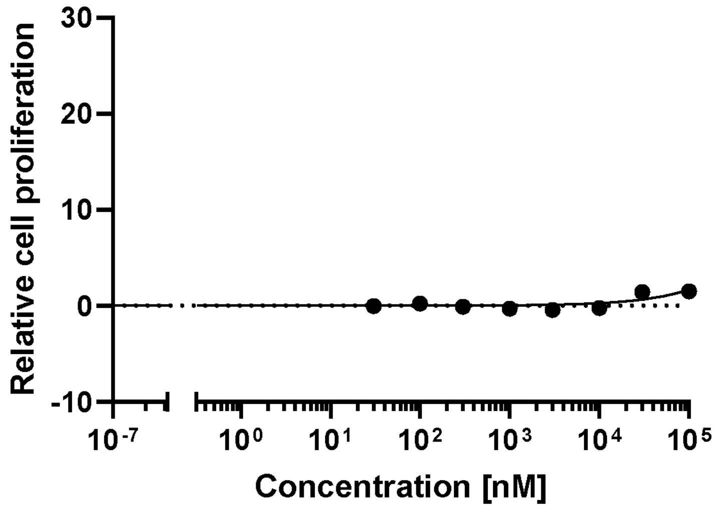
Figure 1:
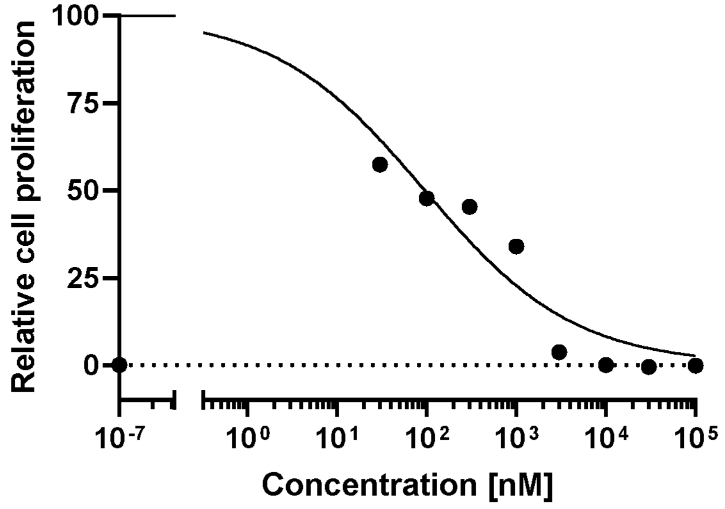
Figure 1:
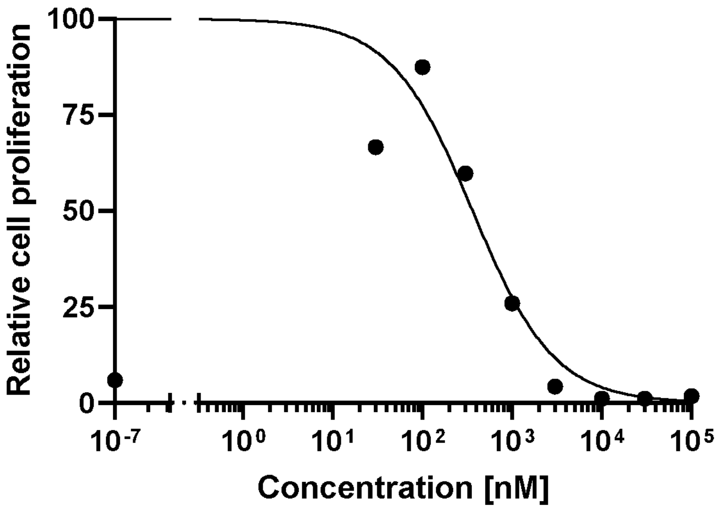
Figure 1:
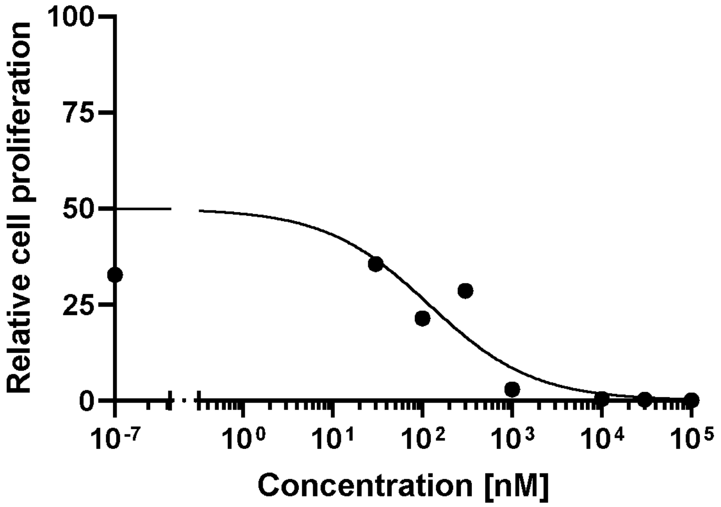
Figure 1:
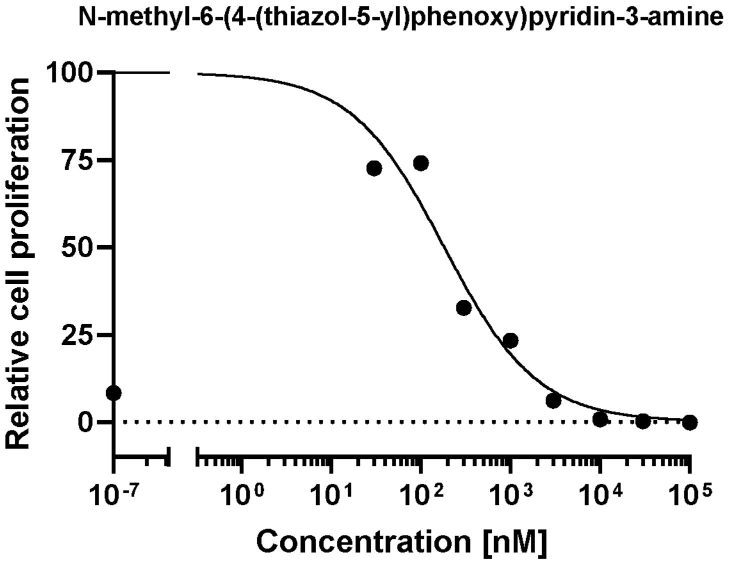
Figure 1:
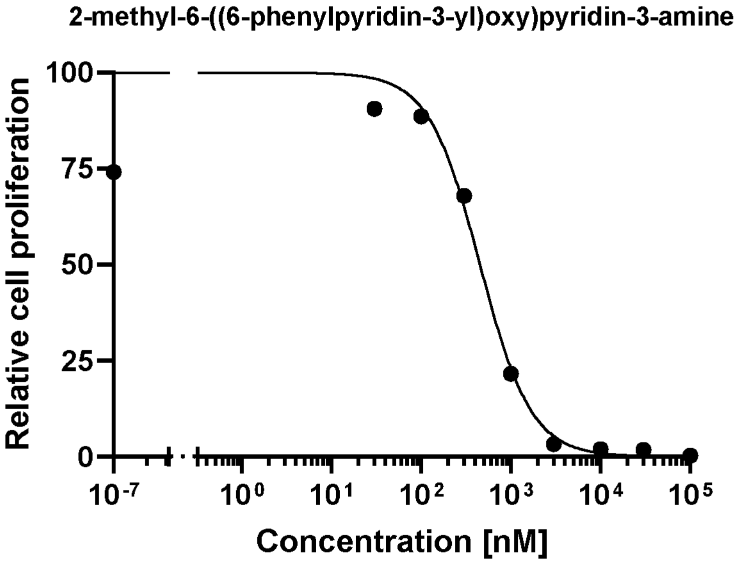

[1,1'-biphenyl]-4-yl)oxy)pyridin-3-amine, 6-([1,1'-Biphenyl]-4-yloxy)-4-methylpyridin-3-amine, 6-([1,1'-Biphenyl]-4-yloxy)-2-methylpyridin-3-amine and N-Methyl-6-((6-phenylpyridin-3-yl)oxy)pyridin-3-amine for 24 hours. Following treatment, total protein lysates were extracted and protein expression analysed by western blot. Data shows that 6-((4'-Fluoro-[1,1'-biphenyl]-4-yl)oxy)pyridin-3-amine, 6-([1,1'-Biphenyl]-4-yloxy)-4-methylpyridin-3-amine, 6-([1,1-Biphenyl]-4-yloxy)-2-methylpyridin-3-amine and N-Methyl-6-((6-phenylpyridin-3-yl)oxy)pyridin-3-amine has enhanced potency in downregulating NOTCH pathway in human cancer cells compared with 6-(4-tert-butylphenoxy)pyridin-3-amine.

DETAILED DESCRIPTION OF THE INVENTION

All publications, patent applications, patents, and other references mentioned herein are incorporated by reference in their entirety. The publications and applications discussed herein are provided solely for their disclosure prior to the filing date of the present application. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term "comprise/comprising" is generally used in the sense of include/including, that is to say permitting the presence of one or more features or components. The terms "comprise" and "comprising" also encompass the more restricted terms "consist" and "consisting".

As used herein, the singular form "a", "an" and "the" include plural references unless the context clearly dictates otherwise.

As used herein the terms "subject" is well-recognized in the art, and, refers to a mammal, including dog, cat, rat, mouse, monkey, cow, horse, goat, sheep, pig, camel, and, most preferably, a human. In some embodiments, the subject is a subject in need of treatment or a subject with a disease or disorder, such as cancer. However, in other embodiments, the subject can be a normal subject or a subject who has already undergone a treatment against cancer. The term does not denote a particular age or sex. Thus, adult, children and newborn subjects, whether male or female, are intended to be covered.

The terms "cancer", "cancer cells", "cell proliferative diseases" and "cell proliferative disorders" as used herein refer to or describe the physiological condition in mammals that is typically characterized by unregulated cell growth. According to the present invention, cancer refers preferably to solid tumors, such as salivary, liver, brain, breast, prostate, colorectum, kidney, lung, sarcoma, or melanoma and liquid tumors, affecting the blood, such as leukemia. More preferably according to the present invention, cancers are Notch dependent cancers selected from the group comprising adenoid cystic carcinoma (ACC), T cell-Acute lymphoblastic leukemia (T-ALL), chronic myeloid leukemia (CIVIL), chronic lymphocytic leukemia (CLL), Mantle cell lymphoma, breast cancer, pancreatic cancer, prostate cancer, melanoma, brain tumors, tumor angiogenesis, liver cancer and colorectal cancer. Even more preferably, the Notch dependent cancer is resistant to γ-secretase inhibitor treatment. Examples of γ-secretase inhibitor treatment comprise 1) Gamma secretase inhibitor RO4929097 and Cediranib Maleate in treating patients with advanced solid tumors (NCT01131234), 2) Gamma-Secretase Inhibitor RO4929097 in Treating Young Patients With Relapsed or Refractory Solid Tumors, CNS Tumors, Lymphoma, or T-Cell Leukemia (NCT01088763), 3) Study of MK-0752 in combination with Tamoxifen or Letrozole to treat early stage breast cancer (NCT00756717), 4) GDC-0449 and RO4929097 in treating patients with Advances or metastatic sarcoma (NCT01154452) 5) RO4929097 and Erlotinib Hydrochloride in treating patients with stage IV or recurrent Non-Small Cell Lung Cancer (NCT01193881), 6) Bicalutamide and RO4929097 in treating patients with previously treated prostate cancer (NCT01200810), 7) RO4929097 in treating patients with recurrent invasive Gliomas (NCT01269411), 8) A Notch signaling pathway inhibitor for patients with T-cell Acute Lymphoblastic Leukemia/Lymphoma (ALL) (NCT00100152) and 9) RO4929097 in treating patients with metastatic colorectal cancer (NCT01116687).

The term "alkyl" as used herein refers to a saturated straight or branched chain group of carbon atoms derived from an alkane by the removal of one hydrogen atom. $C_1$-$C_3$ alkyl comprises for example methyl, ethyl, n-propyl, i-propyl and comprises preferably non-branched $C_1$-$C_3$ alkyl. $C_1$-$C_4$ alkyl comprises for example methyl, ethyl, n-propyl, i-propyl, n-butyl, i-butyl, tert-butyl and comprises preferably non-branched $C_1$-$C_4$ alkyl. $C_1$-$C_6$ alkyl comprises for example methyl, ethyl, n-propyl, i-propyl, n-butyl, i-butyl, tert-butyl, n-pentyl, and n-hexyl and comprises preferably non-branched $C_1$-$C_6$ alkyl. $C_1$-$C_{10}$ alkyl comprises for example methyl, ethyl, n-propyl, i-propyl, n-butyl, i-butyl, tert-butyl, n-pentyl, n-hexyl, n-heptyl, n-octyl, n-nonyl or n-decyl and comprises preferably non-branched $C_1$-$C_{10}$ alkyl. The term "$C_0$ alkyl" as used herein refers to a covalent bond. Thus e.g. the term "$C_0$ alkylO$C_0$ alkyl aryl" refers to Oaryl.

The term "$C_0$-$C_3$ alkylO$C_0$-$C_3$ alkyl aryl" as used herein refers to Oaryl as defined herein when both $C_0$-$C_3$ alkyl groups are $C_0$ alkyl. The term refers to O$C_0$-$C_3$ alkyl aryl when the first $C_0$-$C_3$ alkyl group is $C_0$ alkyl. The term refers to $C_0$-$C_3$ alkylOaryl when the second $C_0$-$C_3$ alkyl group is $C_0$ alkyl. Preferably $C_0$-$C_3$ alkylO$C_0$-$C_3$ alkyl aryl is $C_0$-$C_3$ alkylOaryl, more preferably Oaryl or $C_1$-$C_3$ alkylOaryl. The term "$C_0$-$C_3$ alkylO$C_0$-$C_3$ alkyl heteroaryl" as used herein refers to Oheteroaryl as defined herein when both $C_0$-$C_3$ alkyl groups are $C_0$ alkyl. The term refers to O$C_0$-$C_3$ alkyl heteroaryl when the first $C_0$-$C_3$ alkyl group is $C_0$ alkyl. The term refers to $C_0$-$C_3$ alkylOheteroaryl when the second $C_0$-$C_3$ alkyl group is $C_0$ alkyl. Preferably $C_0$-$C_3$ alkylO$C_0$-$C_3$ alkyl heteroaryl is $C_0$-$C_3$ alkylOheteroaryl, more preferably Oheteroaryl or $C_1$-$C_3$ alkylOheteroaryl, most preferably Oheteroaryl. The aryl and the heteroaryl of $C_0$-$C_3$ alkylO$C_0$-$C_3$ alkyl aryl and $C_0$-$C_3$ alkylO$C_0$-$C_3$ alkyl heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably are optionally substituted by $NH_2$.

The term "heteroalkyl" as used herein refers to an alkyl radical as defined herein wherein one, two, three or four hydrogen atoms have been replaced with a substituent independently selected from the group consisting of $OR^a$, $C(O)OR^a$, $NR^bR^c$, $C(O)NR^bR^c$, $S(O)_nR^d$ (where n is an integer from 0 to 2) and halogen, with the understanding that the point of attachment of the heteroalkyl radical is through a carbon atom, wherein $R^a$ is H, $C_1$-$C_3$ alkylcarbonyl, $C_1$-$C_3$ alkyl, or $C_{3-7}$ cycloalkyl; $R^b$ and $R^c$ are each independently H, $C_1$-$C_3$ alkylcarbonyl, $C_1$-$C_3$ alkyl, $C_{3-7}$ cycloalkyl or $NR^bR^c$ is guanidinyl; and when n is O, $R^d$ is H, $C_1$-$C_3$ alkyl or $C_{3-7}$ cycloalkyl, and when n is 1 or 2, $R^d$ is $C_1$-$C_3$ alkyl or $C_{3-7}$ cycloalkyl. Preferably. the term "heteroalkyl" or "heteroalkanediyl" as used herein refers to an alkyl radical or an alkanediyl radical as defined herein wherein one, two, three or four hydrogen atoms have been replaced with a substituent independently selected from the group consisting of OH, $NH_2$, guanidinyl and halogen, more preferably wherein one or two hydrogen atoms have been replaced with a substituent independently selected from the group consisting of OH, $NH_2$ and halogen. Representative examples include, but are not limited to, 2-hydroxyethyl, 2-hydroxypropyl, 3-hydroxypropyl, 2-hydroxy-1-hydroxymethylethyl, 2-hydroxy-1-methylethyl, 2,3-dihydroxypropyl, 1-hydroxymethylethyl, 3-hydroxybutyl, 2,3-dihydroxybutyl, 1-hydroxy-2-methylpropyl, 3-hydroxy-1-(2-hydroxyethyl)-propyl, 2-hydroxy-1-methylpropyl, 1,1,1-trifluoroethyl, 1,1,1-trifluoromethyl, 2,2,3,3-tetrafluoropropyl.

The term "$C_{3-12}$ cycloalkyl" and "$C_{3-7}$ cycloalkyl" as used herein refers to a monovalent saturated monocyclic or bicyclic hydrocarbon group, preferably a monovalent saturated monocyclic group of 3-12 or 3-7 carbons, respectively derived from a cycloalkane by the removal of a single hydrogen atom. "$C_{3-7}$ cycloalkyl" includes cyclopropyl, cyclobutyl, cyclopentyl, cyclohexyl and cycloheptyl. The term "$C_{3-12}$ cycloalkyl" and "$C_{3-7}$ cycloalkyl" as used herein also includes cycloalkyl groups that comprise a $C_{1-3}$ alkyl radical. Examples of such "$C_{3-7}$ cycloalkyl" groups comprise cyclopropylmethyl, 2-cyclopropylethyl, cyclobutylmethyl, 2-cyclobutylethyl, cyclopentylmethyl, 2-cyclopentylethyl. Cycloalkyl groups of this invention can be optionally substituted.

The term "aryloxy" or "Oaryl" which are used interchangeably herein refers to a radical —OR where R is an aryl as defined herein, e.g. phenoxy.

The term "$C_1$-$C_6$ alkoxy" or "$OC_1$-$C_6$ alkyl" which are used interchangeably herein refers to a radical —OR where R is a $C_1$-$C_6$ alkyl as defined herein. Examples are methoxy, ethoxy, propoxy, butoxy.

The term "aryl" as used herein refers to a mono- or bicyclic carbocyclic ring system having one or two aromatic rings, and is preferably a monocyclic carbocyclic ring system. The aryl group can also be fused to a cyclohexane, cyclohexene, cyclopentane, or cyclopentene ring or to a cyclohexane, cyclohexene, cyclopentane, or cyclopentene ring comprising a carbonyl group. The aryl groups of this invention can be optionally substituted as further described below. A preferred aryl group and optionally substituted aryl group, respectively of this invention is a phenyl group or substituted phenyl group. Substituents can be e.g. $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$.

The term "heteroaryl" as used herein refers to substituted and unsubstituted aromatic 5-, or 6-membered monocyclic groups and 9- or 10-membered bicyclic groups, preferably a substituted and unsubstituted aromatic 5-, or 6-membered monocyclic group, which have at least one heteroatom (O, S or N) in at least one of the ring(s). Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated.

Heteroaryl groups must include at least one fully aromatic ring but the other fused ring or rings may be aromatic or non-aromatic. The heteroaryl group may be attached at any available nitrogen or carbon atom of any ring. Heteroaryl groups of this invention can be optionally substituted as further described below. Usually, a heteroaryl group and optionally substituted heteroaryl group, respectively of this invention is selected from the group consisting of substituted and/or unsubstituted aromatic 5-, or 6-membered monocyclic groups, which have at least one heteroatom (O, S or N), preferably one or two heteroatoms selected from S and N in the ring, more preferably one S and one N in the ring, or one or two N in the ring. A preferred heteroaryl group is an optionally substituted heteroaryl group, selected from the group consisting of an optionally substituted pyridinyl group, an optionally substituted pyrimidinyl group, an optionally substituted di- or triazine group, an optionally substituted thiazole group, an optionally substituted oxazole group, and an optionally substituted imidazole group. An even more preferred heteroaryl group is an optionally substituted pyridinyl group, an optionally substituted pyrimidinyl group, an optionally substituted imidazole group or an optionally substituted thiazole group. Most preferably an optionally substituted pyridinyl group, an optionally substituted imidazole group or an optionally substituted thiazole group, is used as heteroaryl group in the present invention. Optional substituents can be e.g. $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$, or $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl.

The term "heterocyclyl" as used herein means a saturated, monocyclic ring with 3 to 12, preferably with 3 to 7, more preferably 5 to 6 ring atoms which contains up to 3, preferably 1 or 2 heteroatoms selected independently from nitrogen, oxygen or sulfur, and wherein the remaining ring atoms being carbon atoms. Examples of such saturated heterocycles include [1,3]dioxanyl, [1,3]dioxolanyl, pyrrolidinyl, morpholinyl, piperazinyl, piperidinyl, oxazolidinyl, thiazolidinyl, azepanyl and the like. Preferably such heterocyclyl groups are unsubstituted.

The terms "halo" or "halogen" as used herein refers to F, Cl, Br, or I and is preferably F, Cl, or Br, more preferably F.

The term "optionally substituted" or "substituted" means that the referenced group is substituted with one or more additional group(s), preferably with one additional group, individually and independently selected from the listed groups.

The compound 6-([1,1'-Biphenyl]-4-yloxy)-pyridine-3-amine which is excluded from the compounds of formula (I) in some aspects or embodiments of the present invention has the following chemical structure:

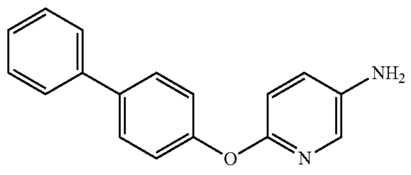 [SMILES: Nc1ccc(Oc2ccc(-c3ccccc3)cc2)nc1]

The compound 4-([1,1'-Biphenyl]-4-yloxy)-aniline which is excluded from the compounds of formula (I) in some aspects or embodiments of the present invention has the following chemical structure:

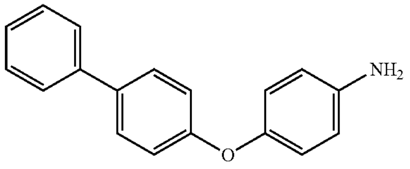

The compound 6-([1,1'-Biphenyl]-4-yloxy)-2-methylpyridin-3-amine which is excluded from the compounds of formula (I) in some aspects or embodiments of the present invention has the following chemical structure:

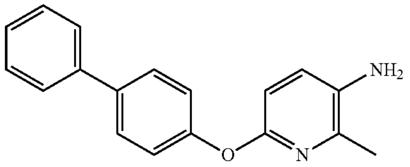

The compound 6-([1,1'-Biphenyl]-4-yloxy)-4-methylpyridin-3-amine which is excluded from the compounds of formula (I) in some aspects or embodiments of the present invention has the following chemical structure:

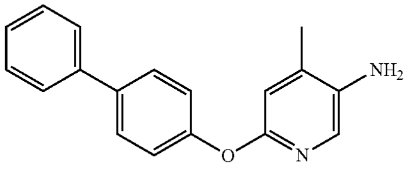

The compound 4-(4'-Methoxy-biphenyl-4-yloxy)phenylamine which is excluded from the compounds of formula (I) in some aspects or embodiments of the present invention has the following chemical structure:

4-(4'-Methoxy-biphenyl-4-yloxy)-phenylamine

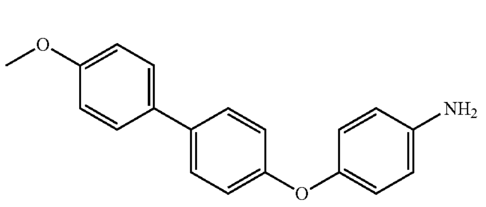 [SMILES: COc1ccc(-c2ccc(Oc3ccc(N)cc3)cc2)cc1]

The compound 4-(4'-Chloro-biphenyl-4-yloxy)phenylamine which is excluded from the compounds of formula (I) in some aspects or embodiments of the present invention has the following chemical structure:

4-(4'-Chloro-biphenyl-4-yloxy)-phenylamine

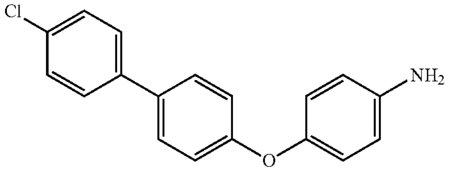

The compound 4-(4'-tert-Butyl-biphenyl-4-yloxy)phenylamine which is excluded from the compounds of formula (I) in some aspects or embodiments of the present invention has the following chemical structure:

4-(4'-tert-Butyl-biphenyl-4-yloxy)-phenylamine

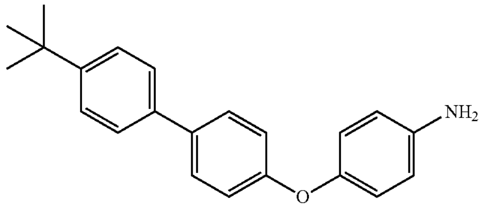 [SMILES: CC(C)(C)c1ccc(-c2ccc(Oc3ccc(N)cc3)cc2)cc1]

The compound 4-(4-(thiazol-2-yl)phenoxy)aniline which is excluded from the compounds of formula (I) in some aspects or embodiments of the present invention has the following chemical structure:

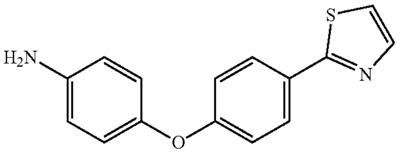

4-(4-(thiazol-2-yl)phenoxy)aniline

The compound 4-(4-(1H-imidazol-2-yl)phenoxy)aniline which is excluded from the compounds of formula (I) in some aspects or embodiments of the present invention has the following chemical structure:

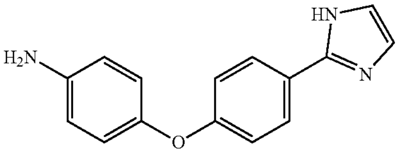

4-(4-(1H-imidazol-2-yl)phenoxy)aniline

The compound 4-(4-(oxazol-2-yl)phenoxy)aniline which is excluded from the compounds of formula (I) in some aspects or embodiments of the present invention has the following chemical structure:

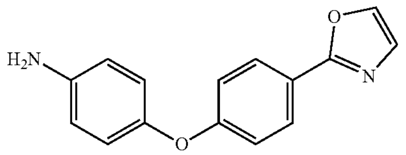

4-(4-(oxazol-2-yl)phenoxy)aniline

The compound 4-(4-(1H-pyrrol-1-yl)phenoxy)aniline which is excluded from the compounds of formula (I) in some aspects or embodiments of the present invention has the following chemical structure:

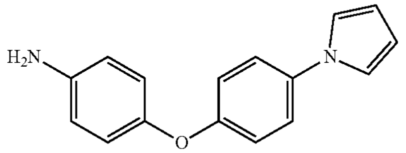

4-(4-(1H-pyrrol-1-yl)phenoxy)aniline

Thus, in a first aspect the present invention provides a compound of formula (I)

Formula (I)

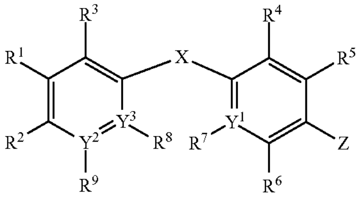

pharmaceutically-acceptable salts, hydrates, solvates, or stereoisomers thereof, wherein X is selected from $CH_2$, $CF_2$, CHF, CO, CHOH, CHO($C_1$-$C_3$) alkyl, NH, N($C_1$-$C_3$ alkyl), S, SO and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, C(O)$R^{12}$, $C_1$-$C_6$ alkyl C(O)$R^{12}$;

wherein $R^3$ is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy;

wherein $R^4$, $R^5$ and $R^6$ are each independently selected from H, halogen, CN, $C_1$-$C_6$ alkoxy, $C_1$-$C_6$—S-alkyl, $C_1$-$C_6$ alkyl, $C_1$-$C_6$ heteroalkyl, $C_3$-$C_{12}$ cycloalkyl and $C_3$-$C_{12}$ heterocyclyl;

wherein $R^7$ is absent when $Y^1$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^1$ is C;

wherein $R^8$ is absent when $Y^3$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^3$ is C;

wherein $R^9$ is absent when $Y^2$ is N or is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^{12}$ is selected from H, $NH_2$, NH$C_1$-$C_6$ alkyl, $C_1$-$C_6$ alkyl, $C_1$-$C_6$ heteroalkyl, $C_2$-$C_6$ alkenyl, $C_2$-$C_6$ alkynyl, $C_3$-$C_{12}$ cycloalkyl and $C_3$-$C_{12}$ heterocyclyl;

with the proviso that the compound of formula (I) is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine and 6-([1,1'-Biphenyl]-4-yloxy)-4-methylpyridin-3-amine, preferably with the proviso that the compound of formula (I) is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, and 4-(4'-tert-Butyl-biphenyl-4-yloxy)phenylamine, more preferably with the proviso that the compound of formula (I) is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, 4-(4'-tert-Butyl-biphenyl-4-yloxy)phenylamine, 4-(4-(thiazol-2-yl)phenoxy)aniline, 4-(4-(1H-imidazol-2-yl)phenoxy)aniline, 4-(4-(oxazol-2-yl)phenoxy)aniline and 4-(4-(1H-pyrrol-1-yl)phenoxy)aniline.

The Notch signalling pathway is evolutionarily conserved and the basic molecular players in this pathway are ligands (Delta and Jagged), Notch receptors, and the transcription factors (Shih IeM, Wang T L in Cancer Res 2007; 67(5): 1879-82). Notch is a transmembrane heterodimeric receptor and there are four distinct members (Notch1, Notch2, Notch3 and Notch4) in humans and rodents. In a physiologic condition, binding of the Notch ligand to its receptor initiates Notch signalling by releasing the intracellular domain of the Notch receptor (Notch-ICD) through a cascade of proteolytic cleavages by both α-secretase (also called tumor necrosis factor-α-converting enzyme) and γ-secretase. The released intracellular Notch-ICD then translocates into the nucleus where it modulates gene expression primarily by binding to a ubiquitous transcription factor, CBF1, suppressor of hairless, Lag-1 (CSL). This binding recruits transcription activators to the CSL complex and converts it from a transcriptional repressor into an activator, which turns on several downstream effectors. The physiologic functions of Notch signalling are multifaceted, including maintenance of stem cells, specification of cell fate, and regulation of differentiation in development as well as in oncogenesis.

In cancers, molecular genetic alterations, such as chromosomal translocation, point mutations, and chromosomal amplification at the Notch receptor loci, are the known mechanisms for constitutive activation of Notch pathway. Despite the different mechanisms, they all result in increased levels of intracellular Notch-IC. The oncogenic potential of Notch was first discovered in human T-cell acute lymphoblastic leukemia (T-ALL), adenoid cystic carcinoma (ACC), breast cancer and chronic lymphocytic leukemia (CLL). While Notch1 signalling is essential for normal development of T-cell progenitors, constitutive activation of Notch1 signalling due to molecular genetic alterations is associated with T-ALL. For example, interstitial deletions of the extracellular portion of human Notch1 due to chromosomal translocation are associated with ~1% of T-ALL cases and activating point mutations of Notch1 are present in about 50% of T-ALL cases. Formation of T-cell leukemia/lymphoma was observed in a Notch-ICD transgenic mouse model, which indicates a causal role of Notch activation in T-ALL development. In nonsmall cell lung cancer, chromosomal translocation has been identified in a subset of tumors, and the translocation is thought to elevate Notch3 transcription in tumors. In ovarian cancer, Notch3 gene amplification was found to occur in about 19% of tumors, and overexpression of Notch3 was found in more than half of the ovarian serous carcinomas. Similarly, Notch signalling activation has been shown in the development of breast cancer. In animal models, constitutively active Notch4 expression causes mammary tumors in mice and Notch1-activating mutations contribute to the development of T-ALL. A recent study further shows that overexpression of activated Notch1 and Notch3 in transgenic mice blocks mammary gland development and induces mouse breast tumors. Notch signalling activation has also been implicated in lung and bone metastasis of breast cancer cells. Overexpression of Notch3 is sufficient to induce choroid plexus tumor formation in a mouse model, suggesting a role of Notch3 in the development of certain types of brain tumors.

The present invention also encompasses chemical modifications of the compounds of the present invention to prolong their circulating lifetimes. Non-limiting examples of methods for transiently, or reversibly, pegylating drugs, including polypeptide-based drugs, are provided in U.S. Pat. No. 4,935,465 (issued in Jun. 19, 1990) and U.S. Pat. No. 6,342,244 (issued Jan. 29, 2002); and in U.S. published applications number US2006/0074024. One skilled in the art would typically find more details about PEG-based reagents in, for example, published applications WO2005047366, US2005171328, and those listed on the NEKTAR PEG Reagent Catalog® 2005-2006 (Nektar Therapeutics, San Carlos, Calif.).

The invention also relates to salts, hydrates or solvates of the compounds of formula (I). Preferably, these salts, hydrates and/or solvates are pharmaceutically acceptable. According to the present invention, pharmaceutically acceptable salts are produced from acidic inorganic or organic compounds, or alkaline inorganic or organic compounds. As used herein, the phrase "pharmaceutically acceptable salt" refers to a salt that retains the biological effectiveness of the free acids and bases of a specified compound and that is not biologically or otherwise undesirable.

The invention also relates to stereoisomers of the compounds of formula (I). "Stereoisomer" or "stereoisomers" refer to compounds that differ in the chirality of one or more stereocentres. Stereoisomers include enantiomers and diastereomers. A compound of formula (I) may exist in stereoisomeric form if they possess one or more asymmetric centres or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of Advanced Organic Chemistry, 4th ed., J. March, John Wiley and Sons, New York, 1992).

A skilled person will know that, if the compounds of the present invention contain charged group, a suitable counterion will be derived from an organic or inorganic acid. Such counterions include halide (such as chloride, bromide, fluoride, iodide), sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. If the polar moiety is a negatively charged group, a suitable counterion will be selected from sodium, ammonium, barium, calcium, copper, iron, lithium, potassium and zinc, and the like.

In a further aspect the present invention provides a pharmaceutical composition comprising the compounds of the present invention, pharmaceutically acceptable salts, hydrates, or stereoisomers thereof, and a pharmaceutically acceptable carrier.

Thus in a further aspect the present invention provides a pharmaceutical composition comprising a compound of formula (I)

Formula (I)

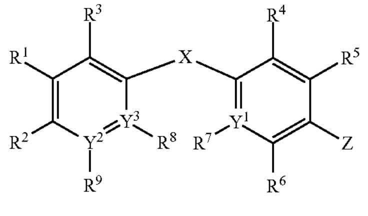

pharmaceutically-acceptable salts, hydrates, solvates, or stereoisomers thereof, wherein X is selected from $CH_2$, $CF_2$, CHF, CO, CHOH, CHO($C_1$-$C_3$) alkyl, NH, N($C_1$-$C_3$ alkyl), S, SO and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, C(O)$R^{12}$, $C_1$-$C_6$ alkyl C(O)$R^{12}$;

wherein $R^3$ is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy;

wherein $R^4$, $R^5$ and $R^6$ are each independently selected from H, halogen, CN, $C_1$-$C_6$ alkoxy, $C_1$-$C_6$—S-alkyl, $C_1$-$C_6$ alkyl, $C_1$-$C_6$ heteroalkyl, $C_3$-$C_{12}$ cycloalkyl and $C_3$-$C_{12}$ heterocyclyl;

wherein $R^7$ is absent when $Y^1$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^1$ is C;

wherein $R^8$ is absent when $Y^3$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^3$ is C;

wherein $R^9$ is absent when $Y^2$ is N or is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^{12}$ is selected from H, $NH_2$, NH$C_1$-$C_6$ alkyl, $C_1$-$C_6$ alkyl, $C_1$-$C_6$ heteroalkyl, $C_2$-$C_6$ alkenyl, $C_2$-$C_6$ alkynyl, $C_3$-$C_{12}$ cycloalkyl and $C_3$-$C_{12}$ heterocyclyl; and a pharmaceutically acceptable carrier. Preferably the compound of formula (I) comprised by the pharmaceutical composition is not 4-([1,1'-Biphenyl]-4-yloxy)-aniline, more preferably is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine and 6-([1,1'-Biphenyl]-4-yloxy)-4-methylpyridin-3-amine. Even more preferably the compound of formula (I) comprised by the pharmaceutical composition is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, and 4-(4'-tert-Butyl-biphenyl-4-yloxy)phenylamine. In particular the compound of formula (I) comprised by the pharmaceutical composition is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, 4-(4'-tert-Butyl-biphenyl-4-yloxy)phenylamine, 4-(4-(thiazol-2-yl)phenoxy)aniline, 4-(4-(1H-imidazol-2-yl)phenoxy)aniline, 4-(4-(oxazol-2-yl)phenoxy)aniline and 4-(4-(1H-pyrrol-1-yl)phenoxy)aniline.

In a further aspect the present invention provides a compound of formula (I)

Formula (I)

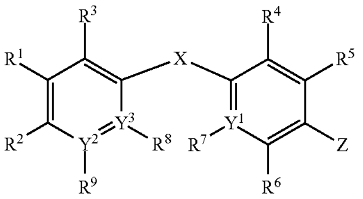

pharmaceutically-acceptable salts, hydrates, solvates, or stereoisomers thereof, wherein X is selected from $CH_2$, $CF_2$, CHF, CO, CHOH, CHO($C_1$-$C_3$) alkyl, NH, N($C_1$-$C_3$ alkyl), S, SO and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, C(O)$R^{12}$, $C_1$-$C_6$ alkyl C(O)$R^{12}$;

wherein $R^3$ is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy;

wherein $R^4$, $R^5$ and $R^6$ are each independently selected from H, halogen, CN, $C_1$-$C_6$ alkoxy, $C_1$-$C_6$—S-alkyl, $C_1$-$C_6$ alkyl, $C_1$-$C_6$ heteroalkyl, $C_3$-$C_{12}$ cycloalkyl and $C_3$-$C_{12}$ heterocyclyl; wherein $R^7$ is absent when $Y^1$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^1$ is C; wherein $R^8$ is absent when $Y^3$ is N or is selected from H, halogen, $C_1$-$C_6$ alkyl, $C_1$-$C_6$ heteroalkyl, $C_3$-$C_{12}$ cycloalkyl, $C_3$-$C_{12}$ heterocyclyl and $C_1$-$C_6$ alkoxy when $Y^3$ is C; wherein $R^9$ is absent when $Y^2$ is N or is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^{12}$ is selected from H, $NH_2$, NH$C_1$-$C_6$ alkyl, $C_1$-$C_6$ alkyl, $C_1$-$C_6$ heteroalkyl, $C_2$-$C_6$ alkenyl, $C_2$-$C_6$ alkynyl, $C_3$-$C_{12}$ cycloalkyl and $C_3$-$C_{12}$ heterocyclyl, for use in a method for the prevention or treatment of cancer. Preferably the compound of formula (I) for use in a method for the prevention or treatment of cancer is not 4-([1,1'-Biphenyl]-4-yloxy)-aniline, more preferably is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine and 6-([1,1'-Biphenyl]-4-yloxy)-4-methylpyridin-3-amine. Even more preferably the compound of formula (I) for use in a method for the prevention or treatment of cancer is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, and 4-(4'-tert-Butyl-biphenyl-4-yloxy)phenylamine. In particular the compound of formula (I) for use in a method for the prevention or treatment of cancer is not 6-([1,1'-Biphenyl]-4-yloxy)-pyridine-3-amine, 4-([1,1'-Biphenyl]-4-yloxy)-aniline, 6-([1,1'-Biphenyl]-4-yloxy)-2-methylpyridin-3-amine, 6-([1,1'-Biphenyl]-4-yloxy)-4-methylpyridin-3-amine, 4-(4'-Methoxy-biphenyl-4-yloxy)phenylamine, 4-(4'-Chloro-biphenyl-4-yloxy)phenylamine, 4-(4'-tert-Butyl-biphenyl-4-yloxy)phenylamine, 4-(4-(thiazol-2-yl)phenoxy)aniline, 4-(4-(1H-imidazol-2-yl)phenoxy)aniline, 4-(4-(oxazol-2-yl)phenoxy)aniline and 4-(4-(1H-pyrrol-1-yl)phenoxy)aniline.

When $R^1$ is $C_0$-$C_3$ alkylO$C_0$-$C_3$ alkyl aryl or $C_0$-$C_3$ alkylO$C_0$-$C_3$ alkyl heteroaryl, the optional substitutions of the aryl and the heteroaryl group are preferably in para position.

When $R^2$ is aryl or heteroaryl, the optional substitutions are preferably in ortho or meta position, provided that the substitutents are not halogen, O$C_1$-$C_6$ alkyl or methyl and are in para position when the substituents are halogen, O$C_1$-$C_6$ alkyl or methyl.

When $R^9$ is $C_0$-$C_3$ alkylO$C_0$-$C_3$ alkyl aryl or $C_0$-$C_3$ alkylO$C_0$-$C_3$ alkyl heteroaryl the optional substitutions of the aryl and the heteroaryl group are preferably in para position.

In one embodiment X is selected from $CH_2$, $CF_2$, CHF, NH, N($C_1$-$C_3$ alkyl), S, SO and O. In a further embodiment X is selected from CO, CHOH, CHO($C_1$-$C_3$) alkyl, S, SO and O. In a preferred embodiment X is selected from $CH_2$, NH, and O. In a more preferred embodiment X is selected from $CH_2$, CO, CHOH, CHO($C_1$-$C_3$) alkyl, NH, and O. In an even more preferred embodiment X is selected from $CH_2$, CO, CHOH, CHO($C_1$-$C_3$) alkyl, and O. In a particular preferred embodiment X is selected from $CH_2$, CO, CHOH, $CHOCH_3$, and O. In a more particular preferred embodiment X is selected from $CH_2$ and O. In an even more particular preferred embodiment X is O.

In one embodiment $R^1$ is selected from H, halogen, $C_1$-$C_6$ alkyl, $C_1$-$C_6$ heteroalkyl, $C_0$-$C_3$ alkylO$C_0$-$C_3$ alkyl aryl wherein the aryl is optionally substituted by $NH_2$, $C_1$-$C_6$ alkyl, $C_1$-$C_6$ heteroalkyl, halogen, CN, preferably is optionally substituted by $NH_2$; and $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further embodiment $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl. In a preferred embodiment $R^1$ is selected from H, halogen and $C_1$-$C_4$ alkyl, $C_0$-$C_3$ alkylO$C_0$-$C_3$ alkyl aryl wherein the aryl is optionally substituted by $NH_2$, $C_1$-$C_6$ alkyl, $C_1$-$C_6$ heteroalkyl, halogen, CN, preferably is optionally substituted by $NH_2$; and $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further preferred embodiment $R^1$ is selected from H, halogen, $C_1$-$C_6$ alkyl and $C_1$-$C_6$ heteroalkyl. In a more preferred embodiment $R^1$ is selected from H, $C_1$-$C_6$ alkyl, $C_0$-$C_3$ alkylO$C_0$-$C_3$ alkyl aryl wherein the aryl is optionally substituted by $NH_2$, $C_1$-$C_6$ alkyl, $C_1$-$C_6$ heteroalkyl, halogen, CN, preferably is optionally substituted $NH_2$; $C_0$-$C_3$ alkylO$C_0$-$C_3$ alkyl heteroaryl wherein the heteroaryl is optionally substituted by $NH_2$, $C_1$-$C_6$ alkyl, $C_1$-$C_6$ heteroalkyl, halogen, CN, preferably is optionally substituted by $NH_2$. In an even more preferred embodiment $R^1$ is selected from H, $C_1$-$C_4$ alkyl and $C_0$-$C_3$ alkylO$C_0$-$C_3$ alkyl aryl wherein the aryl is optionally substituted by $NH_2$, $C_1$-$C_6$ alkyl, $C_1$-$C_6$ heteroalkyl, halogen, CN, preferably is optionally substituted by $NH_2$; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further more preferred embodiment $R^1$ is selected from H, halogen and $C_1$-$C_4$ alkyl. In an even more preferred embodiment $R^1$ is selected from H, methyl, $C_0$-$C_3$ alkylO$C_0$-$C_3$ alkyl aryl wherein the aryl is optionally substituted by $NH_2$, $C_1$-$C_6$ alkyl, $C_1$-$C_6$ heteroalkyl, halogen, CN, preferably is optionally substituted by $NH_2$; and $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further even more preferred embodiment $R^1$ is selected from $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further even more preferred embodiment $R^1$ is selected from $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$. In a further even more preferred embodiment $R^1$ is selected from H and methyl.

In one embodiment $R^2$ is selected from aryl and heteroaryl wherein the aryl and the heteroaryl is substituted by a substituent selected from $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$ and $C_1$-$C_6$ alkyl $C(O)R^{12}$. In a further embodiment $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C(O)R^{12}$, $C_1$-$C_6$ alkyl $C(O)R^{12}$.

In a preferred embodiment $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$ and $C_1$-$C_6$ alkyl $C(O)R^{12}$. In a more preferred embodiment $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$. In a further more preferred embodiment $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C_3$-$C_{12}$ cycloalkyl, $C_3$-$C_{12}$ heterocyclyl. In a particular preferred embodiment $R^2$ is selected from aryl and heteroaryl wherein the aryl and the heteroaryl are optionally substituted by $C_1$-$C_6$ alkyl, halogen, $C_1$-$C_6$ heteroalkyl, $C(O)R^{12}$, $C_1$-$C_6$ alkyl $C(O)R^{12}$. In a further particular preferred embodiment $R^2$ is selected from aryl and heteroaryl wherein the aryl and the heteroaryl are optionally substituted by $C_1$-$C_6$ alkyl, halogen. In a further particular preferred embodiment $R^2$ is selected from aryl and heteroaryl wherein the aryl and the heteroaryl are optionally substituted by $NH_2$, halogen, CN. In a further particular preferred embodiment $R^2$ is selected from aryl and heteroaryl wherein the aryl and the heteroaryl are optionally substituted by $C(O)R^{12}$, $C_1$-$C_6$ alkyl $C(O)R^{12}$. Among the particular preferred embodiments the embodiment wherein $R^2$ is selected from aryl and heteroaryl wherein the aryl and the heteroaryl are optionally substituted by $C_1$-$C_6$ alkyl, halogen, $C_1$-$C_6$ heteroalkyl, $C(O)R^{12}$, $C_1$-$C_6$ alkyl $C(O)R^{12}$ is preferred. In an even more particular preferred embodiment $R^2$ is selected from aryl and heteroaryl wherein the aryl and the heteroaryl are optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$.

In an even more particular preferred embodiment $R^2$ is selected from phenyl, pyridyl, imidazole and thiazole each optionally substituted by $NH_2$, $OC_1$-$C_6$ alkyl, $C_1$-$C_6$ alkyl, $C_1$-$C_6$ heteroalkyl, halogen, CN, $C(O)R^{12}$, $C_1$-$C_6$ alkyl $C(O)R^{12}$. In a further even more particular preferred embodiment $R^2$ is selected from phenyl, thiazole, pyridyl, imidazole and thiazole each optionally substituted by $NH_2$, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$. In a further even more particular preferred embodiment $R^2$ is selected from phenyl, pyridyl, imidazole and thiazole each optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$. In a further even more particular preferred embodiment $R^2$ is selected from phenyl, pyridyl, imidazole and thiazole each optionally substituted by $C_1$-$C_6$ alkyl, halogen, $C_1$-$C_6$ heteroalkyl, $C(O)R^{12}$, $C_1$-$C_6$ alkyl $C(O)R^{12}$. In a further even more particular preferred embodiment $R^2$ is selected from phenyl, pyridyl, imidazole and thiazole each optionally substituted by $C_1$-$C_6$ alkyl, halogen. In a further even more particular preferred embodiment $R^2$ is selected from phenyl, pyridyl, imidazole and thiazole each optionally substituted by $NH_2$, halogen, CN. In a further even more particular preferred embodiment $R^2$ is selected from phenyl, pyridyl, imidazole and thiazole each optionally substituted by $C(O)R^{12}$, $C_1$-$C_6$ alkyl $C(O)R^{12}$. Among the even more particular preferred embodiments the embodiment wherein $R^2$ is selected from phenyl, pyridyl, imidazole and thiazole each optionally substituted by $C_1$-$C_6$ alkyl, halogen, $C_1$-$C_6$ heteroalkyl, $C(O)R^{12}$, $C_1$-$C_6$ alkyl $C(O)R^{12}$ is preferred. In a further even more particular preferred embodiment $R^2$ is selected from phenyl, pyridyl, imidazole and thiazole each optionally substituted by $C_1$-$C_6$ alkyl, halogen. In a further even more particular preferred embodiment $R^2$ is selected from phenyl, pyridyl, imidazole and thiazole each optionally substituted by $C(O)R^{12}$, $C_1$-$C_6$ alkyl $C(O)R^{12}$.

In a most particular preferred embodiment $R^2$ is selected from phenyl, pyridyl, imidazole and thiazole each optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$.

In a preferred embodiment $R^2$ is selected from aryl and heteroaryl wherein the heteroaryl is an optionally substituted aromatic 5-, or 6-membered monocyclic group.

In a further preferred embodiment $R^2$ is selected from aryl and heteroaryl, with the proviso that the heteroaryl is not unsubstituted thiazole, oxazole, imidazole and pyrrole. In a further more preferred embodiment $R^2$ is selected from aryl and heteroaryl, with the proviso that the heteroaryl is not thiazole, oxazole, imidazole and pyrrole.

In one embodiment $R^3$ is selected from H, halogen, $C_1$-$C_6$ alkyl, and $C_3$-$C_{12}$ cycloalkyl. In a preferred embodiment $R^3$ is selected from H, halogen, $C_1$-$C_4$ alkyl, and $C_3$-$C_7$ cycloalkyl. In a more preferred embodiment $R^3$ is selected from H, halogen and $C_1$-$C_4$ alkyl. In an even more preferred embodiment $R^3$ is H.

In one embodiment $R^4$, $R^5$ and $R^6$ are each independently selected from H, halogen, CN, $C_1$-$C_6$ alkyl and $C_1$-$C_6$ heteroalkyl. In a preferred embodiment $R^4$, $R^5$ and $R^6$ are each independently selected from H, halogen, CN, $C_1$-$C_4$ alkyl and $C_1$-$C_4$ heteroalkyl. In an even more preferred embodiment $R^4$, $R^5$ and $R^6$ are each independently selected from H, halogen, and $C_1$-$C_4$ alkyl. In a particular preferred embodiment $R^4$, $R^5$ and $R^6$ are each independently selected from H, halogen, and methyl. In an more particular preferred embodiment $R^4$ is selected from H and halogen and/or $R^5$ and/or $R^6$ are selected from H and $C_1$-$C_6$ alkyl, in particular from H and $C_1$-$C_4$ alkyl, more particular from H and methyl.

In one embodiment $R^7$ is absent when $Y^1$ is N or is selected from H, halogen, $C_1$-$C_6$ alkyl and $C_3$-$C_{12}$ cycloalkyl when $Y^1$ is C. In a preferred embodiment $R^7$ is absent when $Y^1$ is N or is selected from H, halogen, $C_1$-$C_4$ alkyl and $C_3$-$C_7$ cycloalkyl when $Y^1$ is C. In a more preferred embodiment $R^7$ is absent when $Y^1$ is N or is selected from H, halogen and $C_1$-$C_4$ alkyl, preferably selected from H, halogen, and methyl when $Y^1$ is C. In an even more preferred embodiment $R^7$ is absent when $Y^1$ is N or is selected from H, halogen, and methyl when $Y^1$ is C. In a particular preferred embodiment $R^7$ is absent when $Y^1$ is N or is selected from H and halogen when $Y^1$ is C. In a more particular preferred embodiment $R^7$ is absent.

In one embodiment $R^8$ is absent when $Y^3$ is N or is selected from H, halogen, $C_1$-$C_6$ alkyl and $C_3$-$C_{12}$ cycloalkyl when $Y^3$ is C. In a preferred embodiment $R^8$ is absent when $Y^3$ is N or is selected from H, halogen, $C_1$-$C_4$ alkyl and $C_3$-$C_7$ cycloalkyl when $Y^3$ is C. In a more preferred embodiment $R^8$ is absent when $Y^3$ is N or is selected from H, halogen and $C_1$-$C_4$ alkyl preferably selected from H, halogen, and methyl when $Y^3$ is C. In an even more preferred embodiment $R^8$ is absent when $Y^3$ is N or is selected from H, halogen, and methyl when $Y^3$ is C. In a particular preferred embodiment $R^8$ is absent when $Y^3$ is N or is selected from H and halogen when $Y^3$ is C. In a particular preferred embodiment $R^8$ is H.

In one embodiment $R^9$ is absent when $Y^2$ is N or is selected from H, halogen, $C_1$-$C_6$ alkyl and $C_3$-$C_{12}$ cycloalkyl when $Y^2$ is C. In a preferred embodiment $R^9$ is absent when $Y^2$ is N or is selected from H, halogen, $C_1$-$C_4$ alkyl and $C_3$-$C_7$ cycloalkyl when $Y^2$ is C. In a more preferred embodiment $R^9$ is absent when $Y^2$ is N or is selected from H and $C_1$-$C_4$ alkyl preferably selected from H, halogen, and methyl when $Y^2$ is C. In an even more preferred embodiment $R^9$ is absent when $Y^2$ is N or is selected from H, halogen, and methyl when $Y^2$ is C. In a particular preferred embodiment $R^9$ is absent when $Y^2$ is N or is selected from H and halogen, preferably H, when $Y^2$ is C.

In one embodiment $R^7$ is absent when $Y^1$ is N or is selected from H, halogen, $C_1$-$C_6$ alkyl and $C_3$-$C_{12}$ cycloalkyl when $Y^1$ is C, preferably selected from H, halogen, and methyl when $Y^1$ is C, $R^8$ is absent when $Y^3$ is N or is selected from H, halogen, $C_1$-$C_6$ alkyl and $C_3$-$C_{12}$ cycloalkyl, preferably selected from H, halogen, and methyl when $Y^3$ is C, and $R^9$ is absent when $Y^2$ is N or is selected from H, halogen, $C_1$-$C_6$ alkyl and $C_3$-$C_{12}$ cycloalkyl, preferably selected from H, halogen, and methyl when $Y^2$ is C.

In a preferred embodiment $R^7$ is absent when $Y^1$ is N or is selected from H and halogen when $Y^1$ is C, $R^8$ is absent when $Y^3$ is N or is H when $Y^3$ is C, and $R^9$ is absent when $Y^2$ is N or is selected from H and methyl when $Y^2$ is C.

In one embodiment at least one of $R^{10}$ and $R^{11}$ is $C_1$-$C_6$ alkyl, preferably $C_1$-$C_4$ alkyl, more preferably methyl. In a preferred embodiment $R^{10}$ and $R^{11}$ are independently selected from H and methyl. In a more preferred embodiment $R^{10}$ is H and $R^{11}$ is selected from H and $C_1$-$C_4$ alkyl. In an even more preferred embodiment $R^{10}$ is H and $R^{11}$ is H or methyl. In a particular preferred embodiment $R^{10}$ is H and $R^{11}$ is $C_1$-$C_6$ alkyl. In a more particular preferred embodiment $R^{10}$ is H and $R^{11}$ is $C_1$-$C_4$ alkyl. In an even more particular preferred embodiment $R^{10}$ is H and $R^{11}$ is methyl.

In one embodiment $R^{12}$ is selected from $NH_2$, $NHC_1$-$C_6$ alkyl, $C_1$-$C_6$ alkyl, and $C_1$-$C_6$ heteroalkyl. In a preferred embodiment $R^{12}$ is selected from $NH_2$, $C_1$-$C_6$ alkyl, and $C_1$-$C_6$ heteroalkyl. In a more preferred embodiment $R^{12}$ is $NH_2$.

In one embodiment $Y^1$ is N. In a preferred embodiment $Y^1$ and $Y^2$ are each independently selected from N and C and $Y^3$ is C. In a more preferred embodiment $Y^1$ is selected from N and C and $Y^2$ and $Y^3$ are selected from N and C with the proviso that one of $Y^2$ and $Y^3$ is C. In a particular preferred embodiment $Y^1$ is N and $R^7$ is absent, $Y^2$ is selected from N and C and $Y^3$ is C. In a more particular preferred embodiment $Y^1$ is N and $R^7$ is absent.

In one embodiment at least one of the substituents selected from $R^1$, $R^3$, $R^4$, $R^5$, $R^6$, $R^7$, $R^8$, and $R^9$ is not H. In a further embodiment at least one of the substituents selected from $R^1$, $R^3$, $R^8$, and $R^9$ is not H.

Preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O, preferably selected from $CH_2$, CO, CHOH, $CHO(C_1$-$C_3)$ alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O, preferably selected from $CH_2$, CO, CHOH, $CHO(C_1$-$C_3)$ alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl; with the proviso that when $R^1$ is selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $R^2$ is selected from aryl and heteroaryl wherein the aryl and the heteroaryl are optionally substituted by $NH_2$, halogen, CN, preferably wherein the aryl and the heteroaryl are not substituted.

More preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C; and wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl, with the proviso that when $R^2$ is selected from aryl and heteroaryl wherein the aryl and the heteroaryl are substituted by $C_1$-$C_6$ alkyl, halogen, $C_1$-$C_6$ heteroalkyl, $C(O)R^{12}$, $C_1$-$C_6$ alkyl $C(O)R^{12}$, $R^1$ is selected from H, halogen, $C_1$-$C_6$ alkyl and $C_1$-$C_6$ heteroalkyl, preferably is H or methyl.

Further more preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C; and wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O, preferably selected from $CH_2$, CO, CHOH, $CHO(C_1$-$C_3)$ alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkylOC$_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylOC$_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkylOC$_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_0$-$C_3$ alkylOC$_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, halogen, CN;

wherein $R^3$ is selected from H, halogen and $C_1$-$C_4$ alkyl;

wherein $R^4$, $R^5$ and $R^6$ are each independently selected from H, halogen, and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C; and wherein $R^9$ is absent when $Y^2$ is N or is selected from H, halogen and $C_1$-$C_4$ alkyl when $Y^2$ is C.

Even more preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O, preferably selected from $CH_2$, CO, CHOH, $CHO(C_1$-$C_3)$ alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_4$ alkyl and $C_1$-$C_4$ heteroalkyl;

wherein $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$;

wherein $R^3$ is selected from H, halogen, $C_1$-$C_4$ alkyl and $C_3$-$C_7$ cycloalkyl;

wherein $R^4$, $R^5$ and $R^6$ are each independently selected from H, halogen, CN, $C_1$-$C_4$ alkyl and $C_1$-$C_4$ heteroalkyl;

wherein $R^7$ is absent when $Y^1$ is N or is selected from H, halogen, $C_1$-$C_4$ alkyl and $C_3$-$C_7$ cycloalkyl when $Y^1$ is C;

wherein $R^8$ is absent when $Y^3$ is N or is selected from H, halogen, $C_1$-$C_4$ alkyl and $C_3$-$C_7$ cycloalkyl when $Y^3$ is C;

wherein $R^9$ is absent when $Y^2$ is N or is selected from H, halogen, $C_1$-$C_4$ alkyl and $C_3$-$C_7$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O, preferably selected from $CH_2$, CO, CHOH, $CHO(C_1$-$C_3)$ alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, more preferably $R^{19}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ alkyl, $C_1$-$C_6$ heteroalkyl, halogen, $C(O)R^{12}$, $C_1$-$C_6$ alkyl $C(O)R^{12}$;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ heteroalkyl;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ alkyl, halogen;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C(O)R^{12}$, $C_1$-$C_6$ alkyl $C(O)R^{12}$;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O, preferably selected from $CH_2$, CO, CHOH, CHO($C_1$-$C_3$) alkyl, and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$, wherein $R^1$ is preferably selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$;

wherein $R^2$ is selected from aryl and heteroaryl wherein the aryl and the heteroaryl are optionally substituted by $NH_2$, halogen, $C_1$-$C_6$ alkyl, CN, preferably optionally substituted by halogen, $C_1$-$C_6$ alkyl;

wherein $R^3$ is selected from H, halogen and $C_1$-$C_4$ alkyl;

wherein $R^4$, $R^5$ and $R^6$ are each independently selected from H, halogen, and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C; and wherein $R^9$ is absent when $Y^2$ is N or is selected from H, halogen and $C_1$-$C_4$ alkyl when $Y^2$ is C.

Preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, C(O)$R^{12}$, $C_1$-$C_6$ alkyl C(O)$R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, NH$C_1$-$C_6$ alkyl, $C_1$-$C_6$ alkyl, and $C_1$-$C_6$ heteroalkyl.

Further preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl $C_3$-$C_{12}$ heterocyclyl, C(O)$R^{12}$, $C_1$-$C_6$ alkyl C(O)$R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, NH$C_1$-$C_6$ alkyl, $C_1$-$C_6$ alkyl, and $C_1$-$C_6$ heteroalkyl; with the proviso that when $R^1$ is selected from $C_0$-$C_3$ alkylO$C_0$-$C_3$ alkyl aryl wherein the aryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkylO$C_0$-$C_3$ alkyl heteroaryl wherein the heteroaryl is optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, O$C_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $R^2$ is selected from aryl and heteroaryl wherein the aryl and the heteroaryl are optionally substituted by $NH_2$, halogen, CN, preferably wherein the aryl and the heteroaryl are not substituted.

More preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C; and wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl, with the proviso that when $R^2$ is selected from aryl and heteroaryl wherein the aryl and the heteroaryl are substituted by $C_1$-$C_6$ alkyl, halogen, $C_1$-$C_6$ heteroalkyl, $C(O)R^{12}$, $C_1$-$C_6$ alkyl $C(O)R^{12}$, $R^1$ is selected from H, halogen, $C_1$-$C_6$ alkyl and $C_1$-$C_6$ heteroalkyl, preferably is H or methyl.

Further more preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C; and wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more preferred compounds of formula (I) pharmaceutically-acceptable salts, hydrates, solvates, or stereoisomers thereof are those, wherein X is selected from $CH_2$, NH and O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy; $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, halogen, CN;

wherein $R^3$ is selected from H, halogen and $C_1$-$C_4$ alkyl;

wherein $R^4$, $R^5$ and $R^6$ are each independently selected from H, halogen, and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C; and wherein $R^9$ is absent when $Y^2$ is N or is selected from H, halogen and $C_1$-$C_4$ alkyl when $Y^2$ is C.

Even more preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_4$ alkyl and $C_1$-$C_4$ heteroalkyl;

wherein $R^2$ is selected from aryl and heteroaryl wherein the aryl and the heteroaryl are optionally substituted by $NH_2$, $C_1$-$C_6$ alkyl, $C_1$-$C_6$ heteroalkyl, halogen, CN, $C(O)R^{12}$, $C_1$-$C_6$ alkyl $C(O)R^{12}$;

wherein $R^3$ is selected from H, halogen, $C_1$-$C_4$ alkyl and $C_3$-$C_7$ cycloalkyl;

wherein $R^4$, $R^5$ and $R^6$ are each independently selected from H, halogen, CN, $C_1$-$C_4$ alkyl and $C_1$-$C_4$ heteroalkyl;

wherein $R^7$ is absent when $Y^1$ is N or is selected from H, halogen, $C_1$-$C_4$ alkyl and $C_3$-$C_7$ cycloalkyl when $Y^1$ is C;

wherein $R^8$ is absent when $Y^3$ is N or is selected from H, halogen, $C_1$-$C_4$ alkyl and $C_3$-$C_7$ cycloalkyl when $Y^3$ is C;

wherein $R^9$ is absent when $Y^2$ is N or is selected from H, halogen, $C_1$-$C_4$ alkyl and $C_3$-$C_7$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Particular preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, more preferably $R^{19}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ alkyl, $C_1$-$C_6$ heteroalkyl, halogen, $C(O)R^{12}$, $C_1$-$C_6$ alkyl $C(O)R^{12}$;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ heteroalkyl;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C_1$-$C_6$ alkyl, halogen;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from H, halogen and $C_1$-$C_4$ alkyl;

wherein $R^2$ is selected from aryl and heteroaryl wherein the aryl and the heteroaryl are optionally substituted by $C(O)R^{12}$, $C_1$-$C_6$ alkyl $C(O)R^{12}$;

wherein $R^3$ is selected from H, halogen and $C_1$-$C_4$ alkyl;

wherein $R^4$, $R^5$ and $R^6$ are each independently selected from H, halogen and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C;

wherein $R^9$ is absent when $Y^2$ is N or is selected from H, halogen and $C_1$-$C_4$ alkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further particular preferred compounds of formula (I) pharmaceutically-acceptable salts, hydrates, solvates, or stereoisomers thereof are those, wherein X is selected from $CH_2$, NH and O, and is preferably O;

wherein $Y^1$, $Y^2$, and $Y^3$ are each independently selected from N and C, preferably $Y^1$ and $Y^2$ are each independently selected from N and C and $Y^3$ is C, more preferably $Y^1$ is N and $R^7$ is absent, $Y^2$ is selected from N and C and $Y^3$ is C;

wherein Z is $NR^{10}R^{11}$ wherein $R^{10}$ and $R^{11}$ are each independently selected from H and $C_1$-$C_6$ alkyl, preferably independently selected from H and methyl, preferably $R^{10}$ is H and $R^{11}$ is H or methyl;

wherein $R^1$ is selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$, wherein $R^1$ is preferably selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$; and $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, preferably is optionally substituted by $NH_2$;

wherein $R^2$ is selected from aryl and heteroaryl wherein the aryl and the heteroaryl are optionally substituted by $NH_2$, halogen, $C_1$-$C_6$ alkyl, CN, preferably optionally substituted by halogen, $C_1$-$C_6$ alkyl;

wherein $R^3$ is selected from H, halogen and $C_1$-$C_4$ alkyl;

wherein $R^4$, $R^5$ and $R^6$ are each independently selected from H, halogen, and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C; and wherein $R^9$ is absent when $Y^2$ is N or is selected from H, halogen and $C_1$-$C_4$ alkyl when $Y^2$ is C.

Further particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy and $C_1$-$C_6$ heteroalkyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

More particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^7$ is absent when $Y^1$ is N or is selected from H, halogen, $C_1$-$C_6$ alkyl and $C_3$-$C_{12}$ cycloalkyl when $Y^1$ is C;

wherein $R^8$ is absent when $Y^3$ is N or is selected from H, halogen, $C_1$-$C_6$ alkyl and $C_3$-$C_{12}$ cycloalkyl when $Y^3$ is C;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, halogen, $C_1$-$C_6$ alkyl, $C_3$-$C_{12}$ cycloalkyl, $C_3$-$C_{12}$ heterocyclyl, $C_1$-$C_6$ alkoxy, $C_1$-$C_6$ heteroalkyl, $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_1$-$C_6$ alkyl substituted by aryl or heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl, $C(O)R^{12}$, $C_1$-$C_6$ alkyl $C(O)R^{12}$;

wherein $R^3$ is selected from H, halogen, $C_1$-$C_6$ alkyl and $C_3$-$C_{12}$ cycloalkyl;

wherein $R^4$, $R^5$ and $R^6$ are each independently selected from H, halogen, CN, $C_1$-$C_6$ alkyl and $C_1$-$C_6$ heteroalkyl;

wherein $R^8$ is selected from H, halogen, $C_1$-$C_6$ alkyl and $C_3$-$C_{12}$ cycloalkyl;

wherein $R^9$ is absent when $Y^2$ is N or is selected from H, halogen, $C_1$-$C_6$ alkyl and $C_3$-$C_{12}$ cycloalkyl when $Y^2$ is C; and wherein $R^{12}$ is selected from $NH_2$, $NHC_1$-$C_6$ alkyl, $C_1$-$C_6$ alkyl, and $C_1$-$C_6$ heteroalkyl.

Further more particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H, $C_1$-$C_6$ alkyl, $C_0$-$C_3$ alkyl$OC_0$-$C_3$ alkyl aryl wherein the aryl is optionally substituted by $NH_2$; $C_0$-$C_3$ alkyl$OC_0$-$C_3$ alkyl heteroaryl wherein the heteroaryl is optionally substituted by $NH_2$;

wherein $R^2$ is selected from aryl and heteroaryl wherein the aryl and the heteroaryl are optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$;

wherein $R^3$ is H;

wherein $R^4$ is selected from H and halogen;

wherein $R^5$ and $R^6$ are each independently selected from H and $C_1$-$C_6$ alkyl;

wherein $R^7$ is absent when $Y^1$ is N or is H when $Y^1$ is C;

wherein $R^8$ is absent when $Y^3$ is N or is H when $Y^3$ is C;

wherein $R^9$ is absent when $Y^2$ is N or is H when $Y^2$ is C; and wherein $R^{12}$ is $NH_2$.

Further more particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H, $C_1$-$C_6$ alkyl, $C_0$-$C_3$ alkyl$OC_0$-$C_3$ alkyl aryl wherein the aryl is optionally substituted by $NH_2$; $C_0$-$C_3$ alkyl$OC_0$-$C_3$ alkyl heteroaryl wherein the heteroaryl is optionally substituted by $NH_2$;

wherein $R^2$ is selected from aryl and heteroaryl wherein the aryl and the heteroaryl are optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$;

wherein $R^3$ is H;

wherein $R^4$ is selected from H and halogen;

wherein $R^5$ and $R^6$ are each independently selected from H and $C_1$-$C_6$ alkyl;

wherein $R^8$ is H;

wherein $R^9$ is absent when $Y^2$ is N or is H when $Y^2$ is C; and wherein $R^{12}$ is $NH_2$.

Further more particular preferred compounds of formula (I) pharmaceutically-acceptable salts, hydrates, solvates, or stereoisomers thereof are those, wherein X is selected from $CH_2$, CO, CHOH, $CHO(C_1$-$C_3)$ alkyl, NH, and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from H and $C_1$-$C_6$ alkyl;

wherein $R^2$ is selected from aryl and heteroaryl wherein the aryl and the heteroaryl are optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$;

wherein $R^3$ is H;

wherein $R^4$ is selected from H and halogen;

wherein $R^5$ and $R^6$ are each independently selected from H and $C_1$-$C_6$ alkyl;

wherein $R^7$ is absent when $Y^1$ is N or is H when $Y^1$ is C;

wherein $R^8$ is absent when $Y^3$ is N or is H when $Y^3$ is C;

wherein $R^9$ is absent when $Y^2$ is N or is H when $Y^2$ is C; and wherein $R^{12}$ is $NH_2$.

Further more particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O;

wherein $Y^1$ is N and $R^7$ is absent, $Y^2$ is selected from N and C and $Y^3$ is C;

wherein Z is $NR^{10}R^{11}$, wherein $R^{10}$ and $R^{11}$ are each independently selected from H and $C_1$-$C_6$ alkyl;

wherein $R^1$ is selected from H and $C_1$-$C_6$ alkyl;

wherein $R^2$ is selected from aryl and heteroaryl wherein the aryl and the heteroaryl are optionally substituted by $OC_1$-$C_6$ alkyl, $C_1$-$C_6$ alkyl, $C_1$-$C_6$ heteroalkyl, halogen, $C_1$-$C_6$ alkyl $C(O)R^{12}$;

wherein $R^3$ is H;

wherein $R^4$ is selected from H and halogen;

wherein $R^5$ and $R^6$ are each independently selected from H and $C_1$-$C_6$ alkyl;

wherein $R^8$ is H;

wherein $R^9$ is absent when $Y^2$ is N or is H when $Y^2$ is C; and wherein $R^{12}$ is $NH_2$.

Further more particular preferred compounds of formula (I) pharmaceutically-acceptable salts, hydrates, solvates, or stereoisomers thereof are those, wherein X is selected from $CH_2$, CO, CHOH, CHO($C_1$-$C_3$) alkyl, NH, and O;

wherein $Y^1$, $Y^2$, and $Y^3$ are each independently selected from N and C;

wherein Z is $NR^{10}R^{11}$, wherein $R^{10}$ and $R^{11}$ are each independently selected from H and $C_1$-$C_6$ alkyl;

wherein $R^1$ is selected from $C_0$-$C_3$ alkyl$OC_0$-$C_3$ alkyl aryl wherein the aryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl; and $C_0$-$C_3$ alkyl$OC_0$-$C_3$ alkyl heteroaryl wherein the heteroaryl is optionally substituted by $NH_2$, $OC_1$-$C_6$ alkyl, $C_1$-$C_6$ alkyl, $C_1$-$C_6$ heteroalkyl, halogen, CN, $C_3$-$C_{12}$ cycloalkyl, $C_3$-$C_{12}$ heterocyclyl;

wherein $R^2$ is selected from aryl and heteroaryl wherein the aryl and the heteroaryl are optionally substituted by $NH_2$, halogen, $C_1$-$C_6$ alkyl, CN;

wherein $R^3$ is selected from H, halogen and $C_1$-$C_4$ alkyl;

wherein $R^4$, $R^5$ and $R^6$ are each independently selected from H, halogen, and $C_1$-$C_4$ alkyl;

wherein $R^7$ is absent when $Y^1$ is N or is selected from H, halogen and $C_1$-$C_4$ alkyl when $Y^1$ is C;

wherein $R^8$ is absent when $Y^3$ is N or is selected from H, halogen and $C_1$-$C_4$ alkyl when $Y^3$ is C; and wherein $R^9$ is absent when $Y^2$ is N or is selected from H, halogen and $C_1$-$C_4$ alkyl when $Y^2$ is C.

Even more particular preferred compounds of the compound of formula (I) are selected from the group consisting of

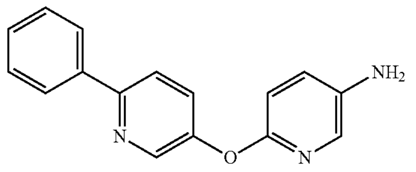

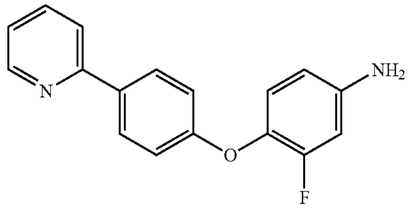

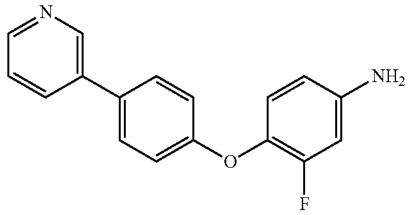

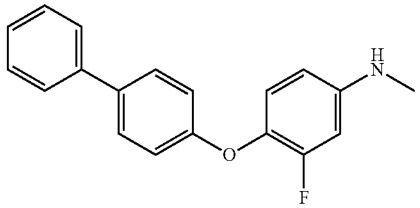

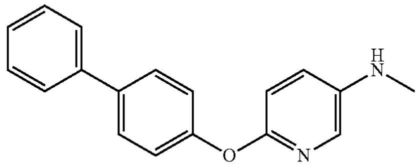

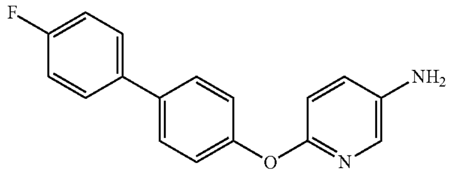

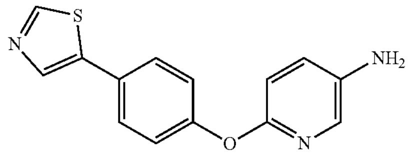

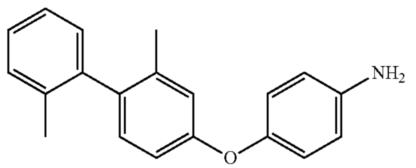

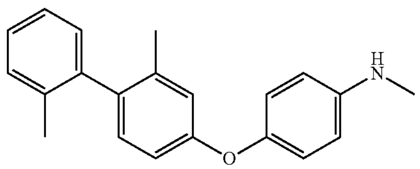

-continued
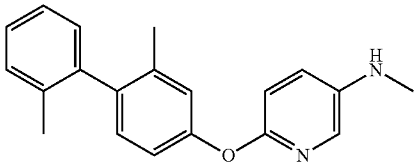
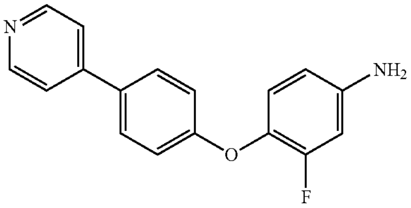
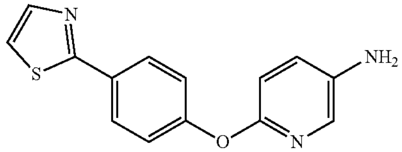
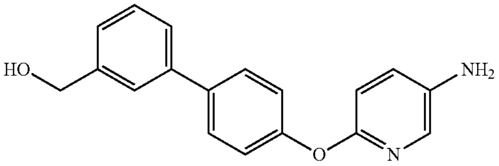
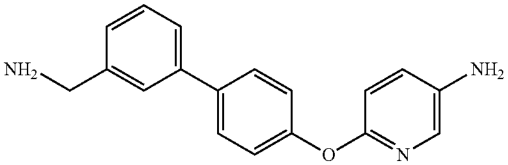
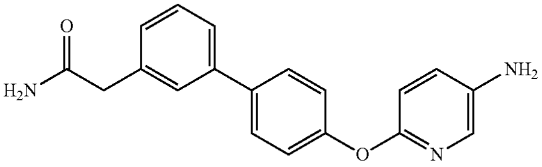
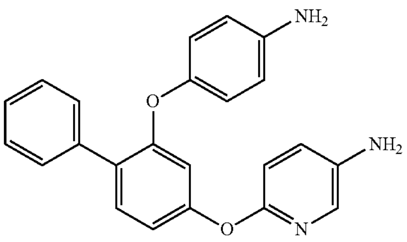
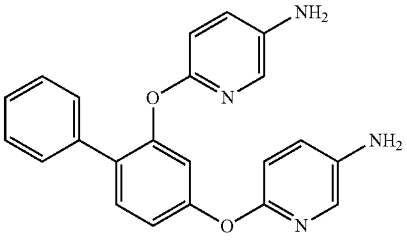
-continued
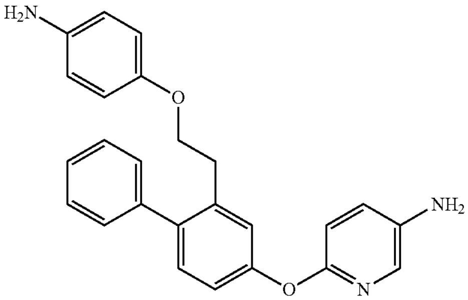
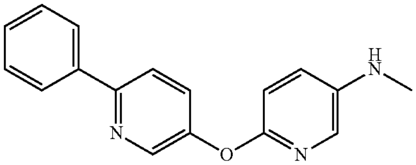
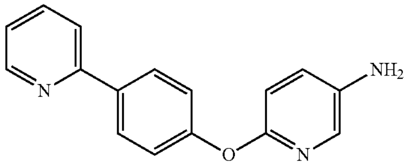
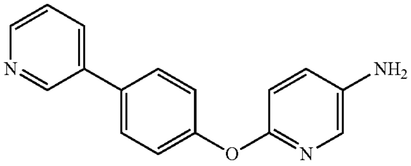
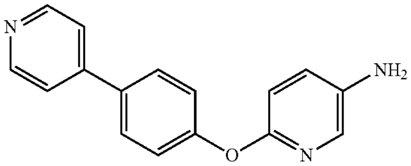
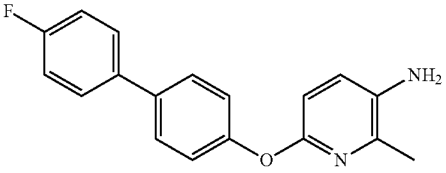
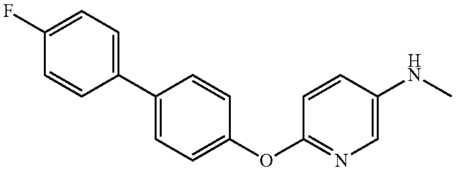
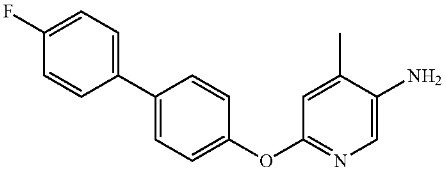
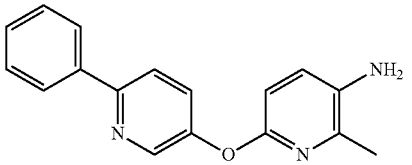

-continued
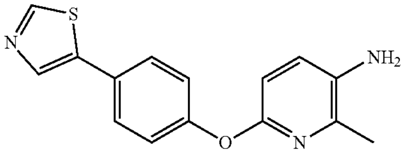
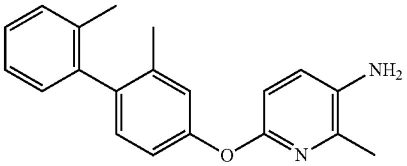
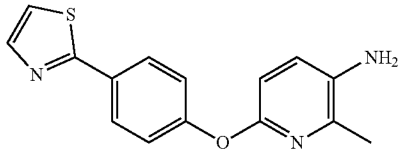
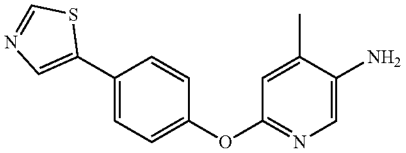
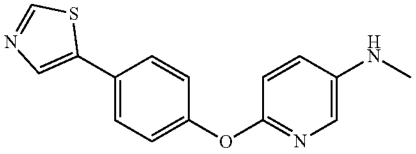
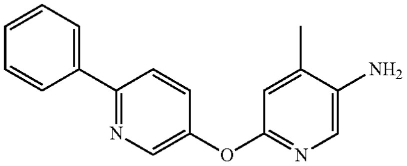
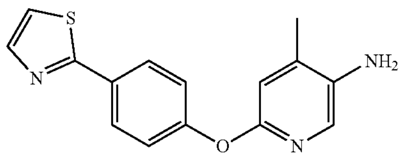
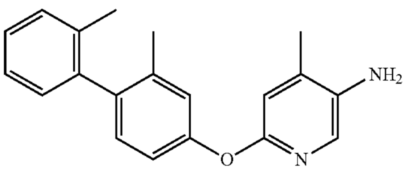
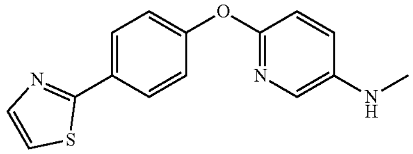
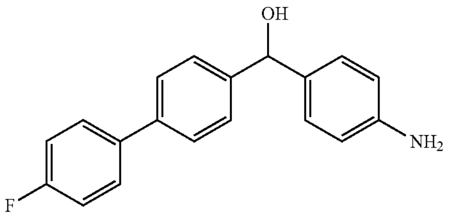
-continued
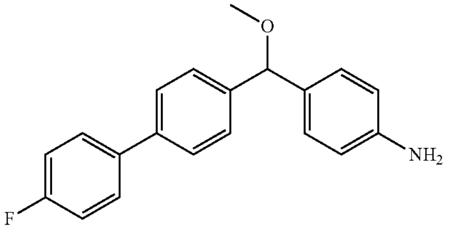
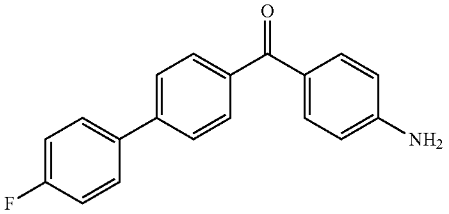
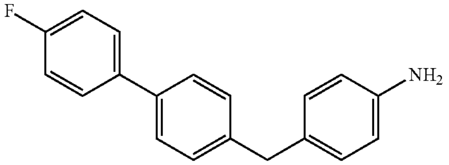
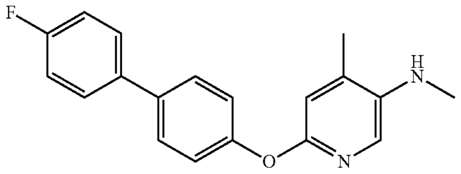
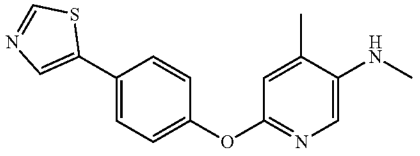
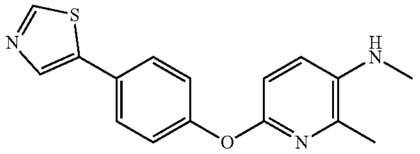
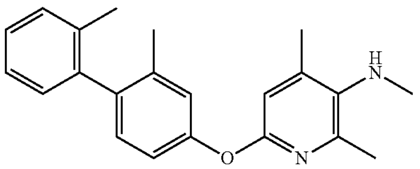
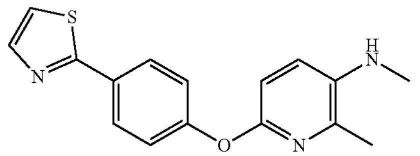
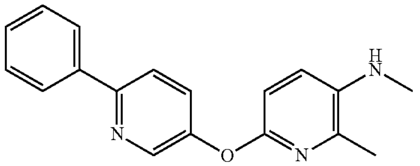

-continued
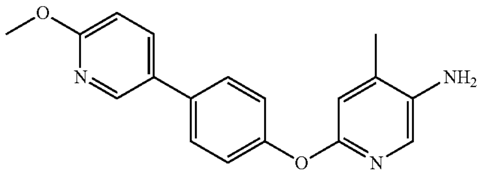
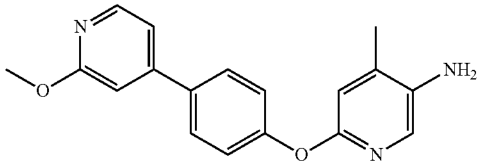
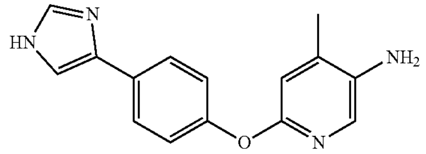
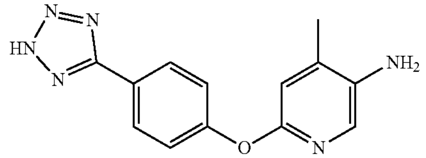
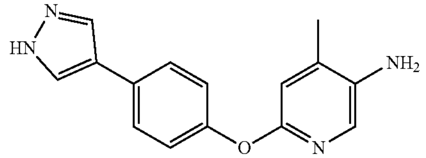
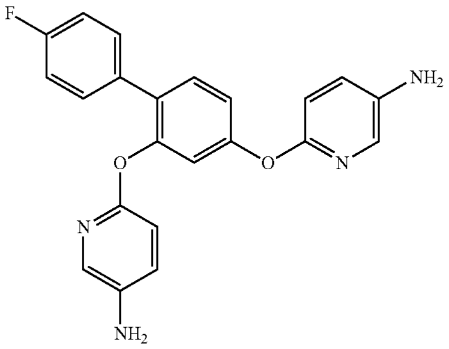
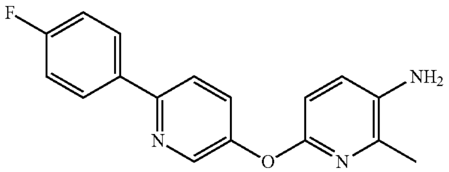
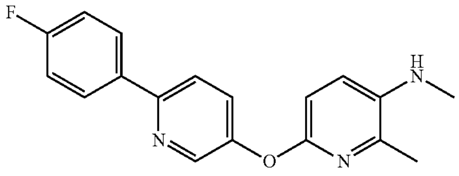
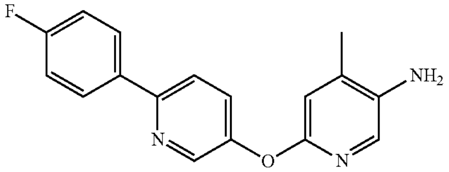
-continued
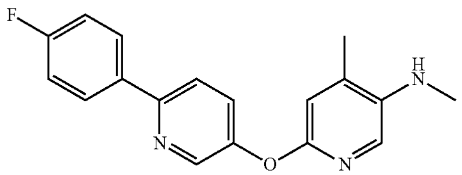
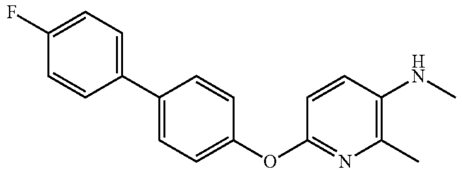
Further even more particular preferred compounds of the compound of formula (I) are selected from the group consisting of
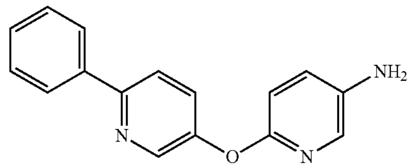
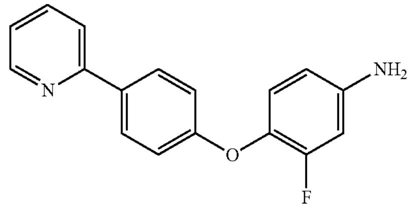
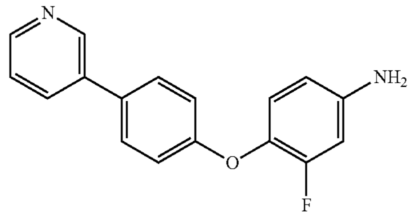
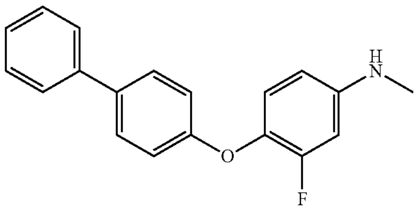
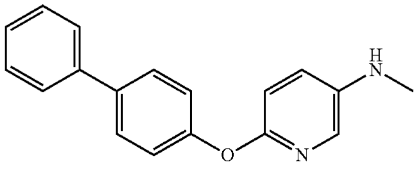
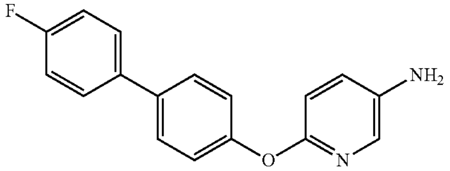

-continued
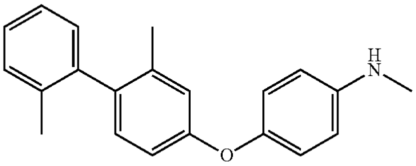
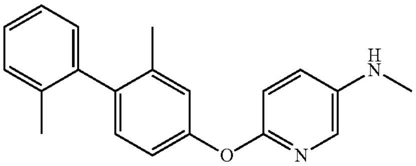
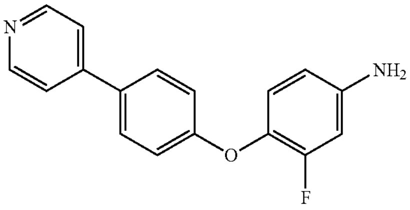
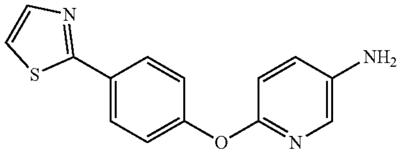
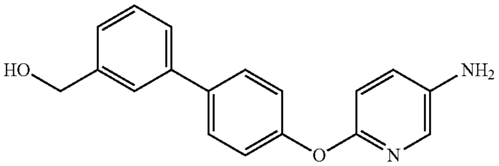
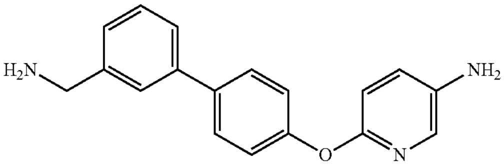
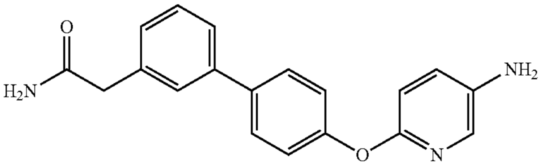
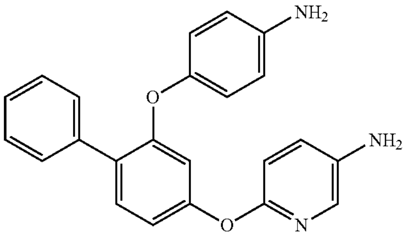
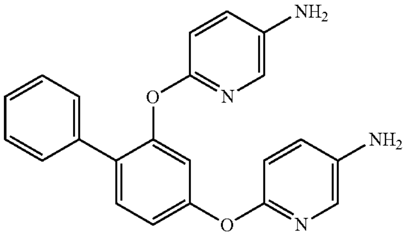
-continued
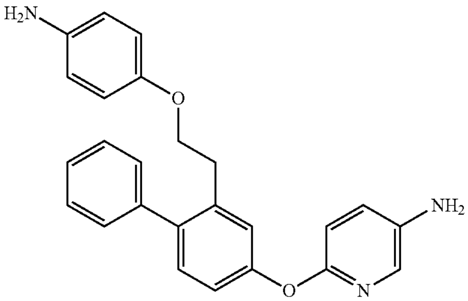
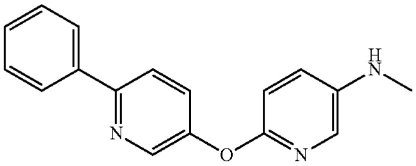
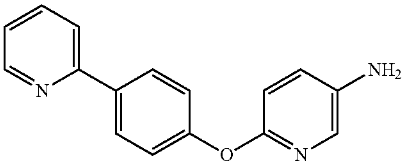
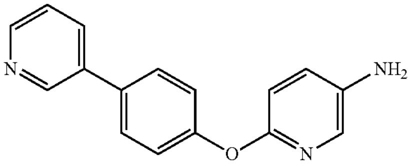
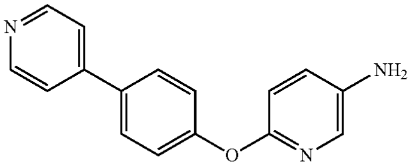
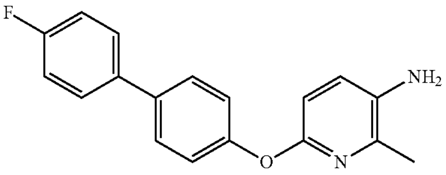
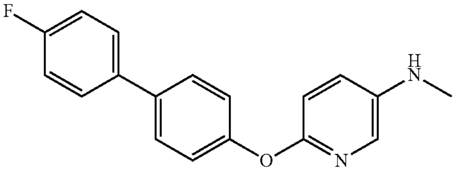
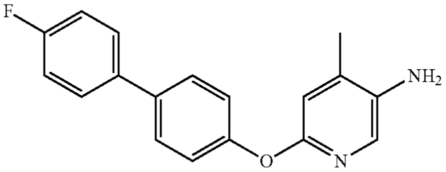
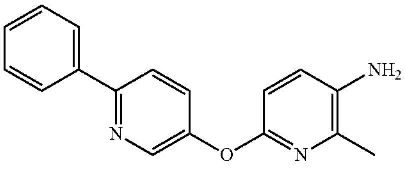

-continued
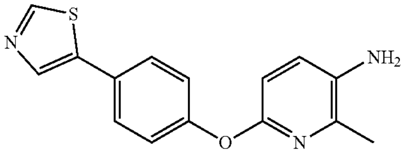
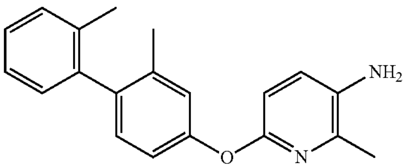
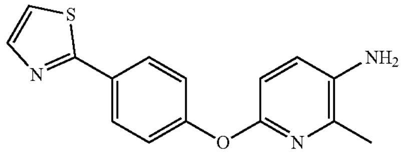
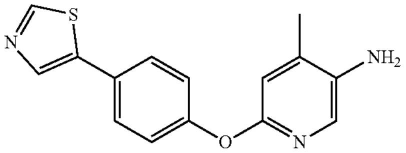
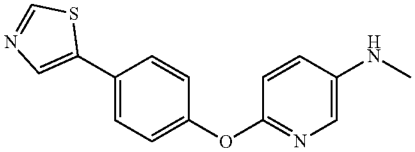
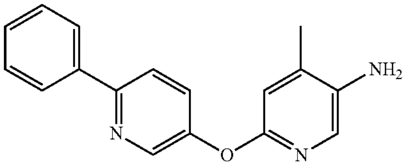
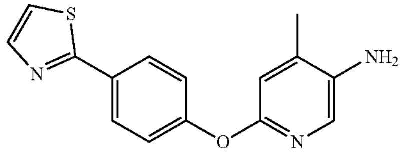
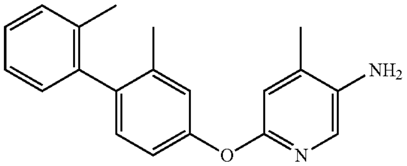
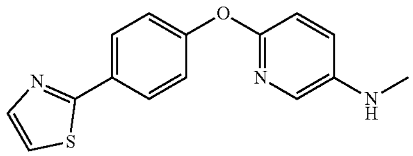
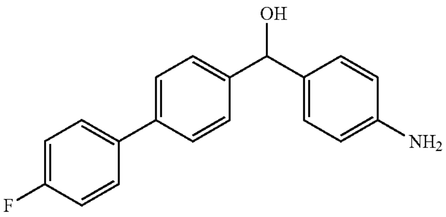
-continued
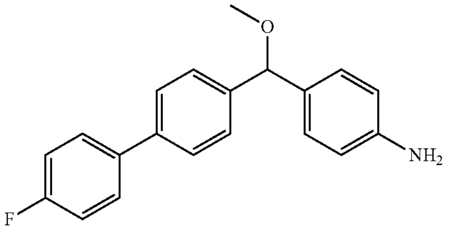
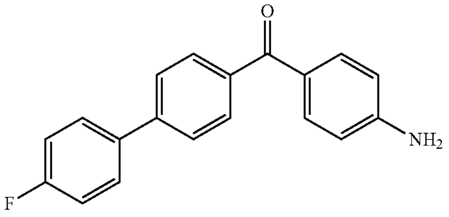
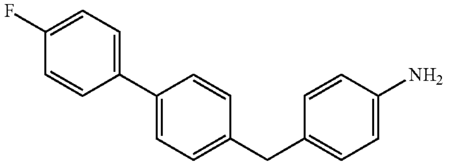
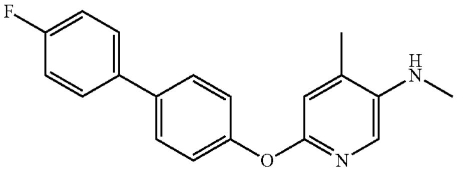
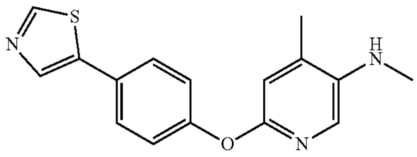
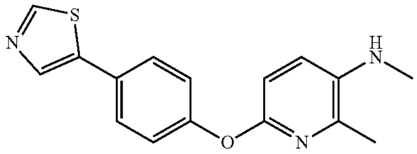
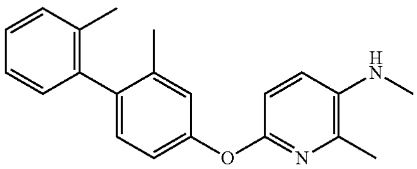
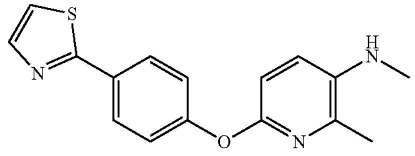
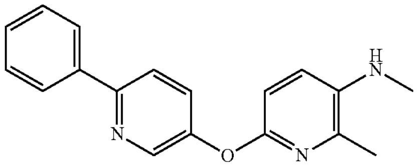

-continued
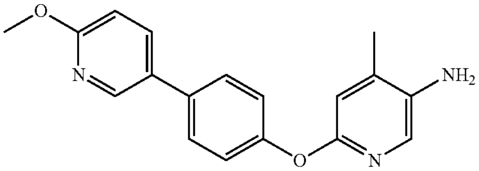
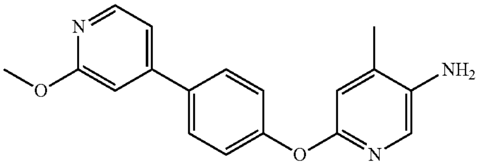
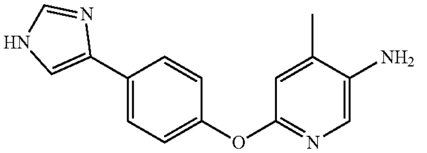
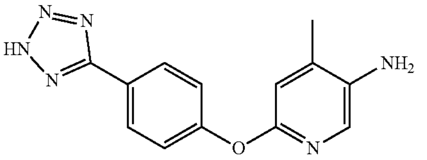
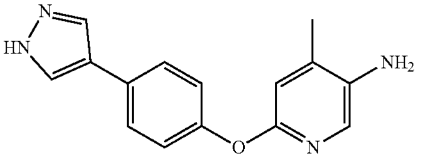
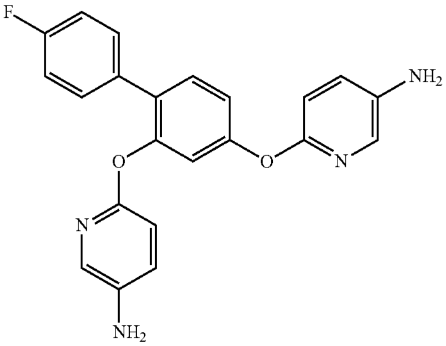
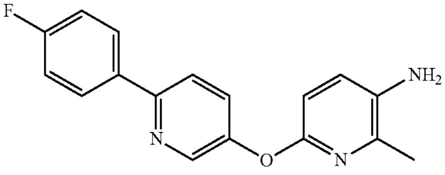
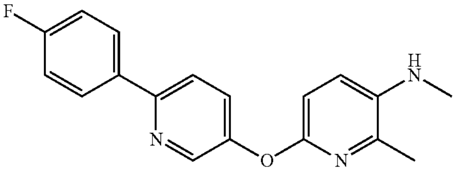
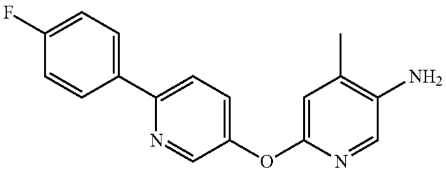
-continued
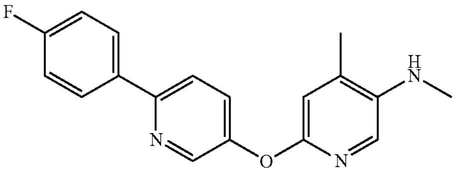
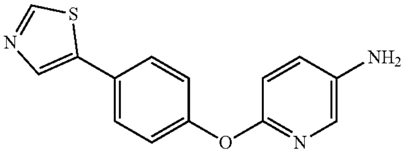
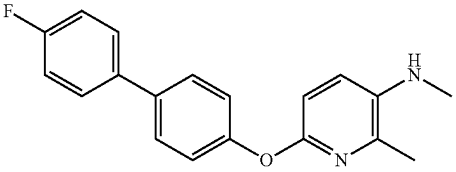
Further even more particular preferred compounds of the compound of formula (I) are selected from the group consisting of
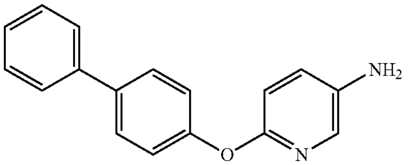 [SMILES: O=[N+]([O-])c1ccc(Oc2ccc(-c3ccccc3)cc2)nc1]
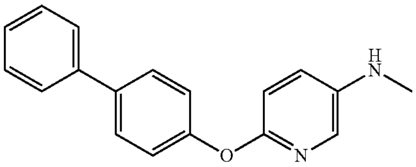 [SMILES: CNc1ccc(Oc2ccc(-c3ccccc3)cc2)nc1]
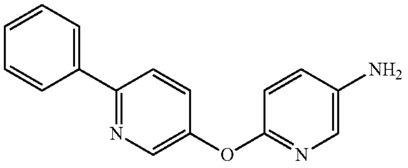 [SMILES: O=[N+]([O-])c1ccc(Oc2ccc(-c3ccccc3)nc2)nc1]
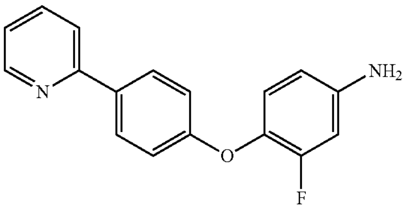 [SMILES: Nc1ccc(Oc2ccc(-c3ccccn3)cc2)c(F)c1]
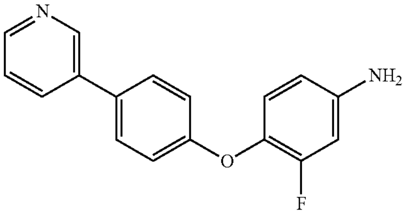

-continued
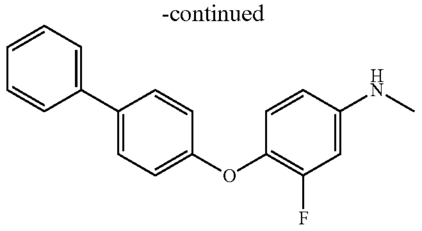
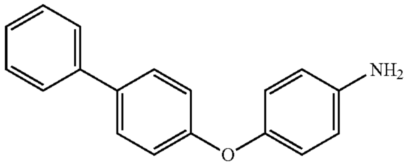
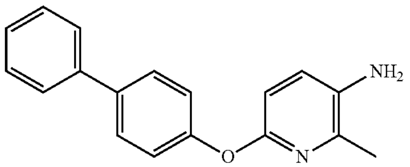
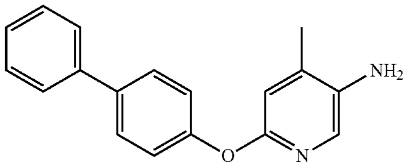
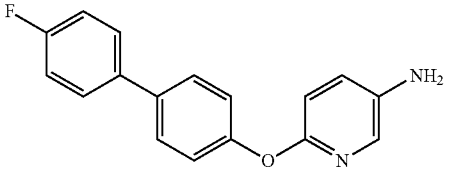
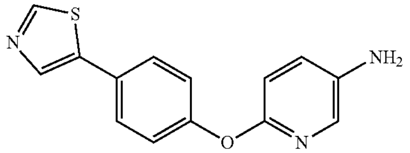
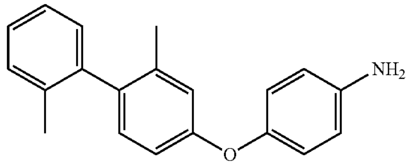
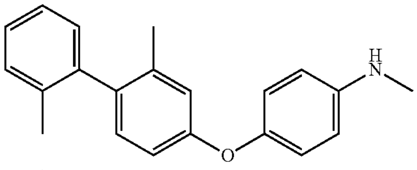
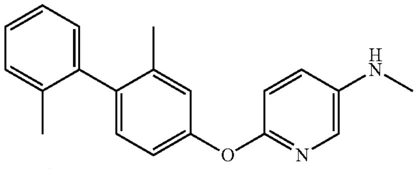
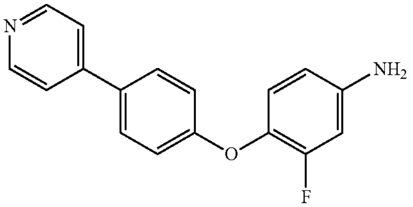
-continued
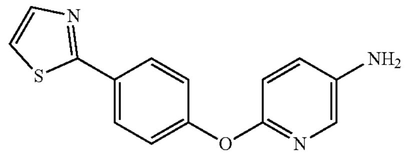
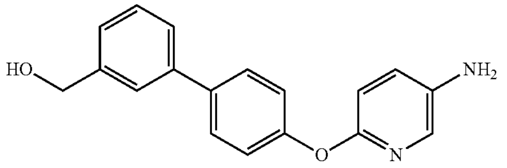
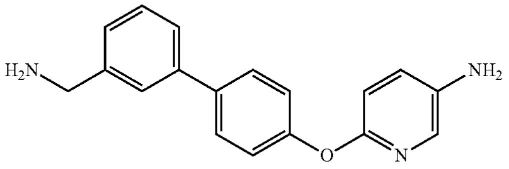
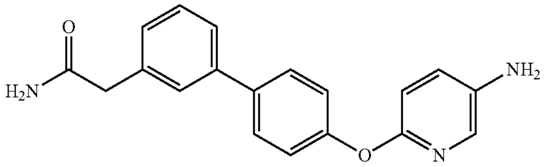
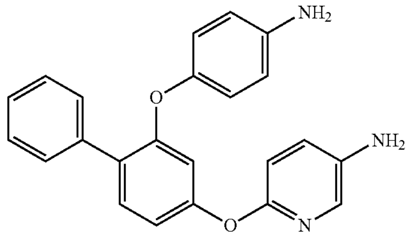
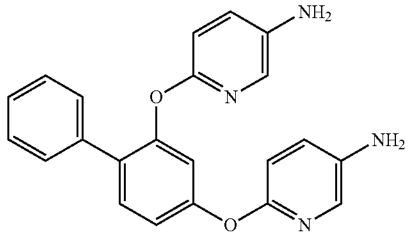
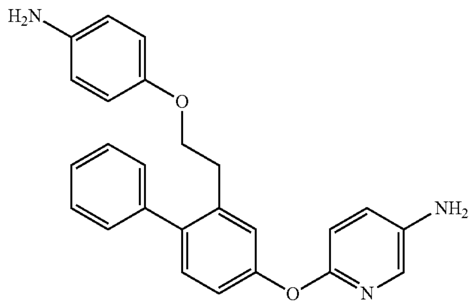
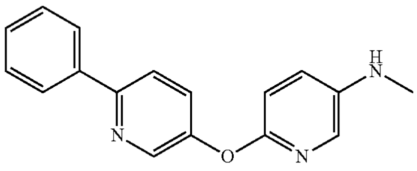

-continued
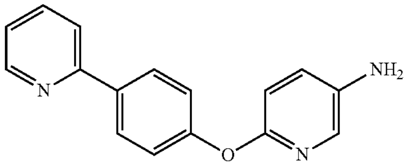
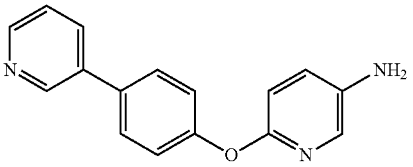
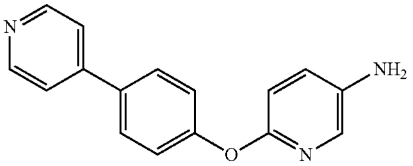
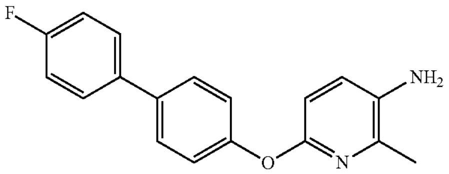
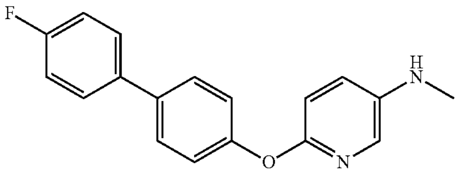
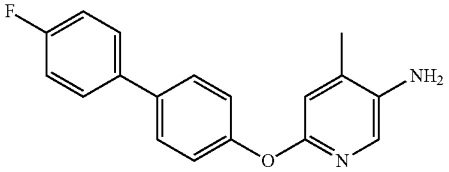
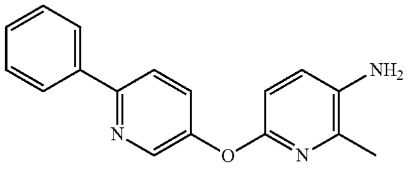
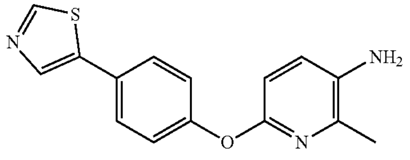
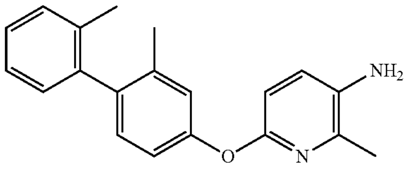
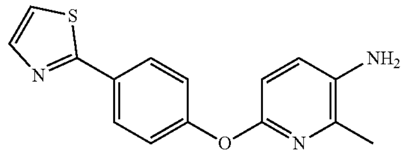
-continued
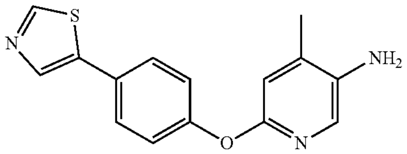
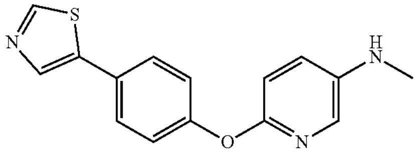
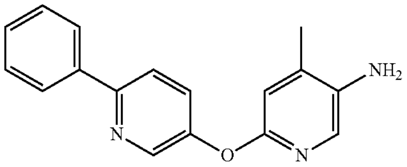
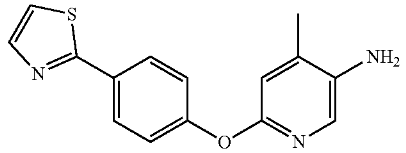
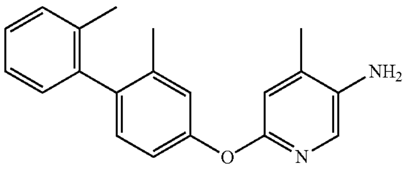
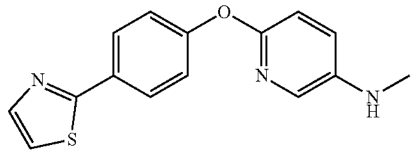
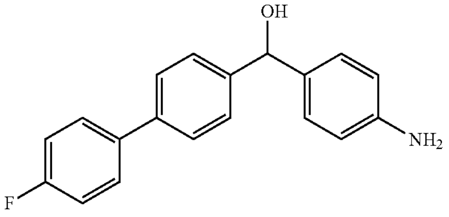
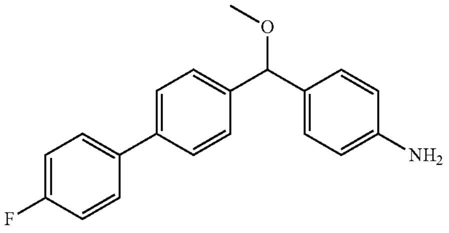
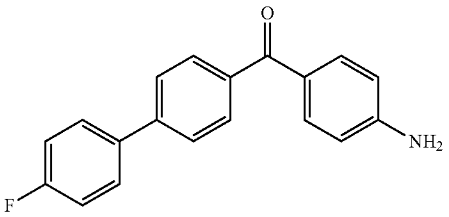

-continued
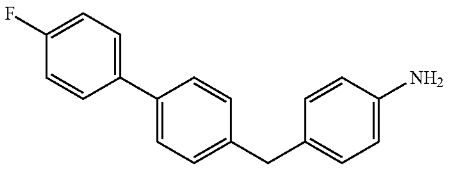
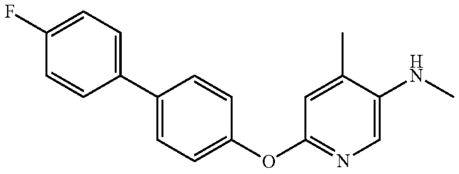
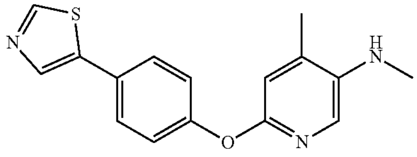
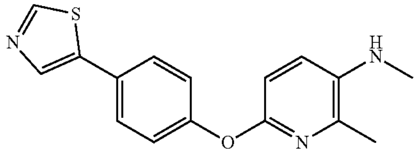
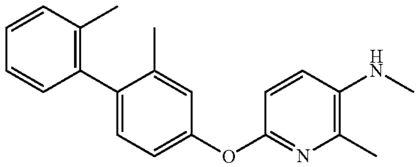
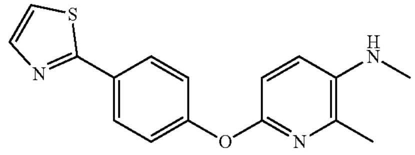
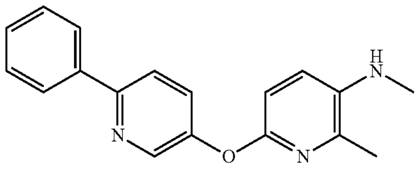
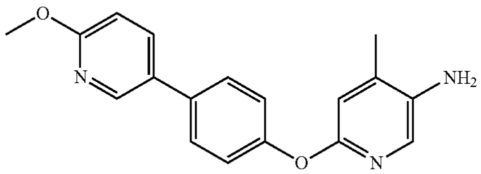
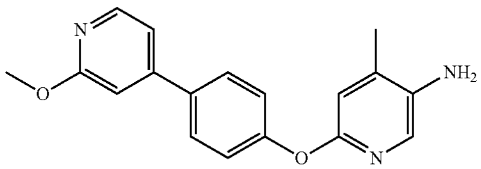
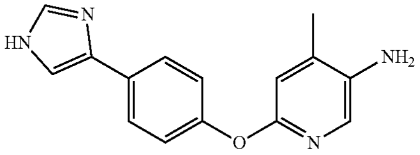
-continued
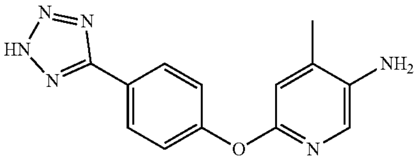
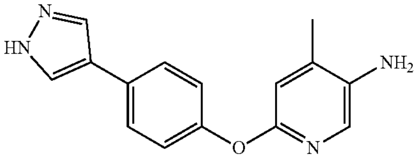
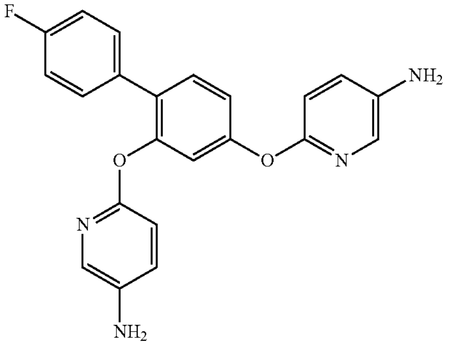
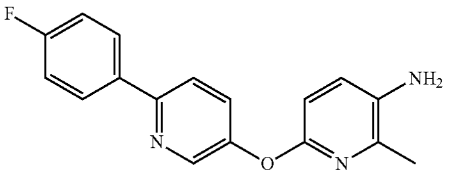
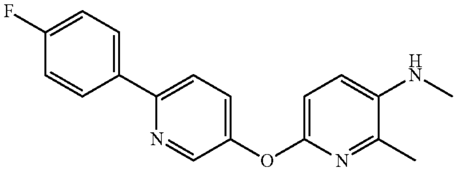
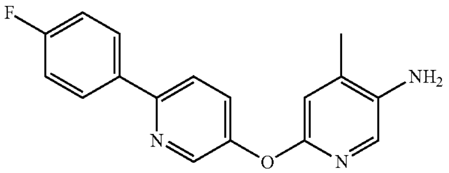
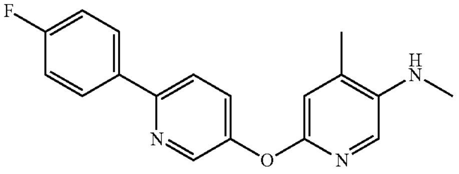
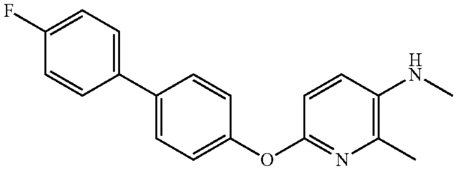
Further even more particular preferred compounds of the compound of formula (I) are selected from the group consisting of

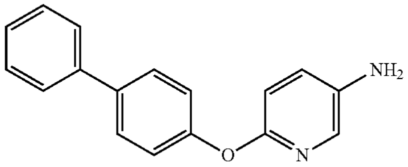
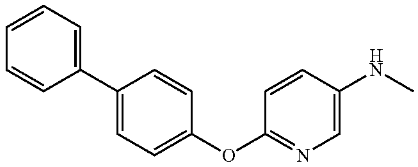
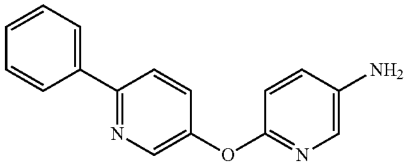
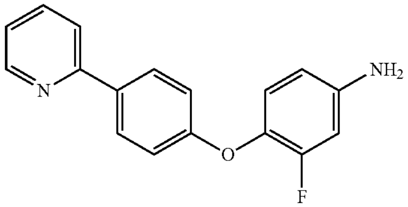
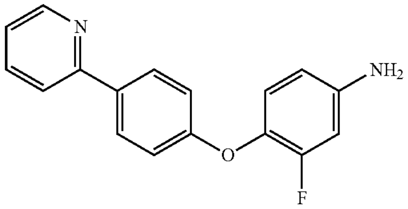
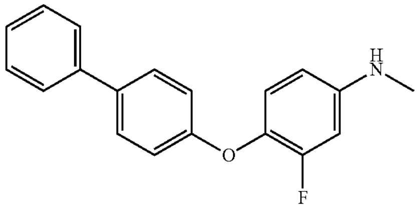
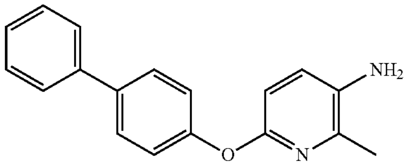
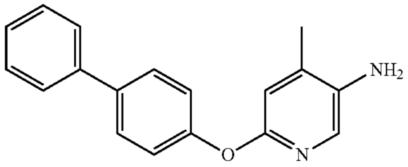
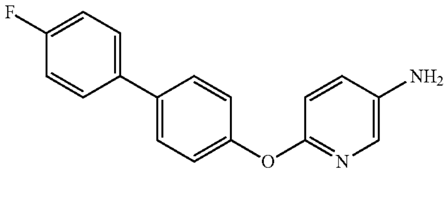
-continued
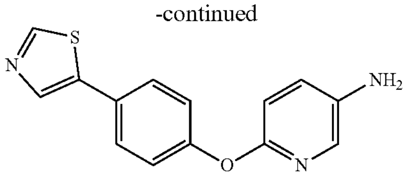
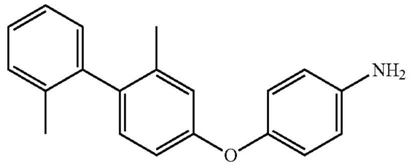
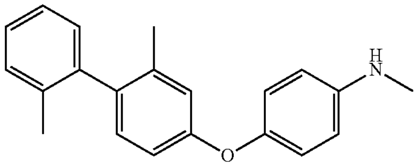
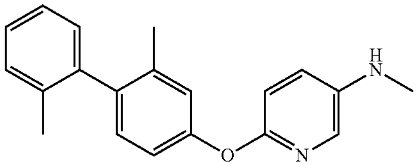
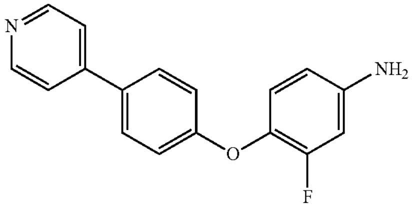
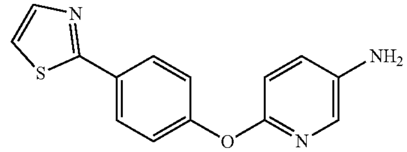
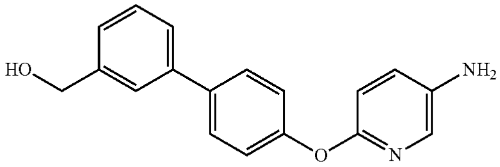
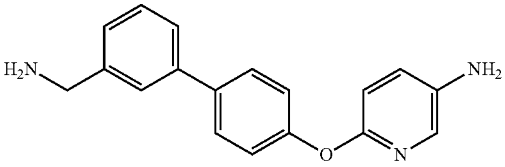
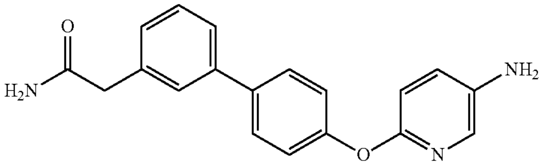
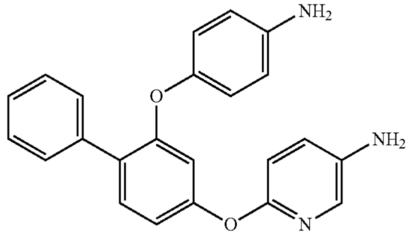

-continued
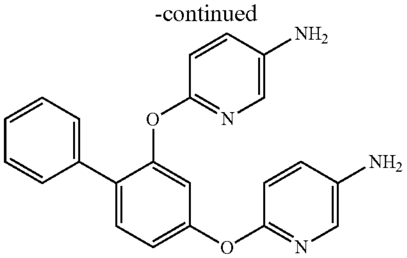
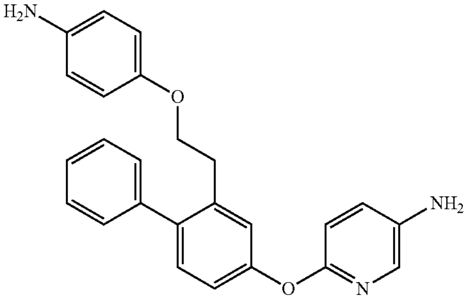
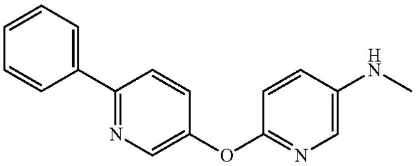
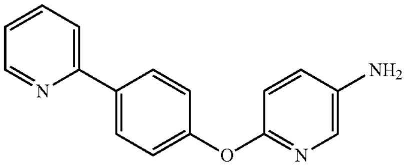
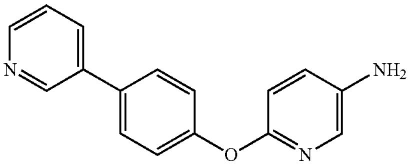
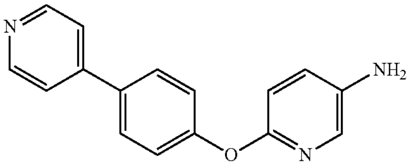
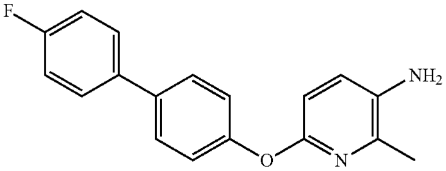
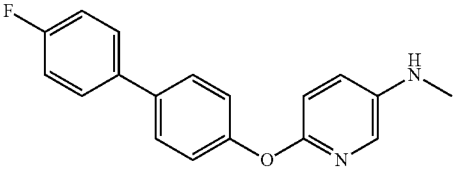
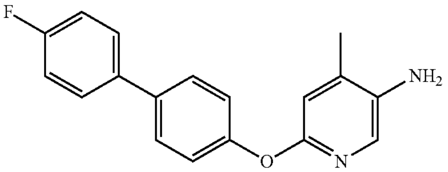
-continued
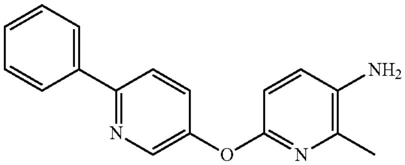
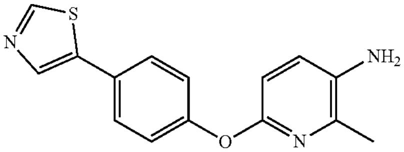
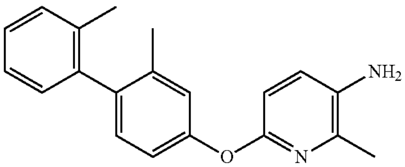
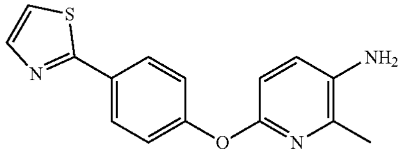
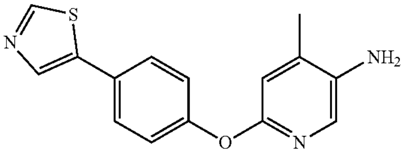
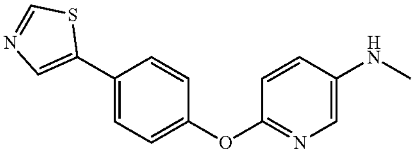
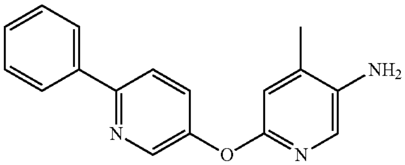
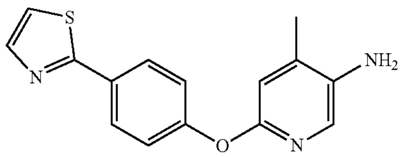
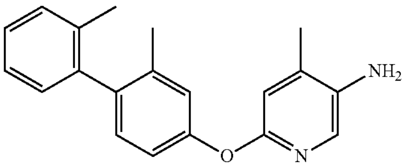
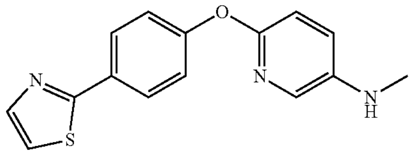

-continued
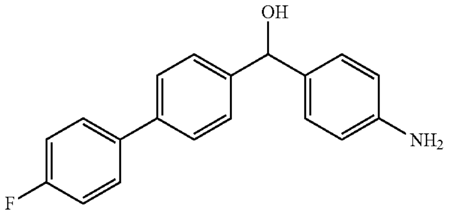
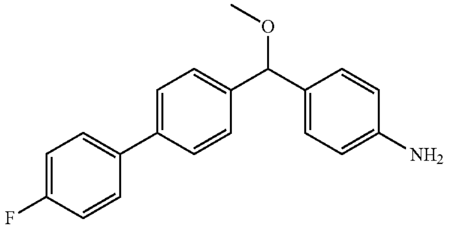
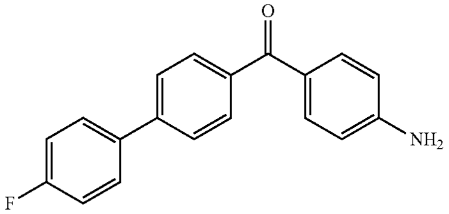
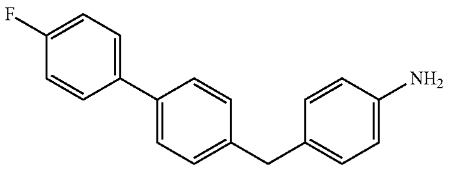
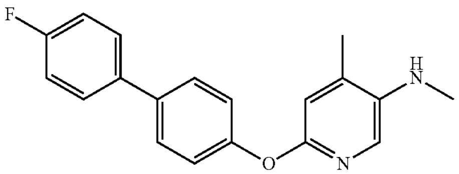
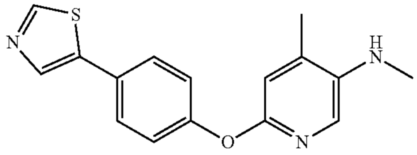
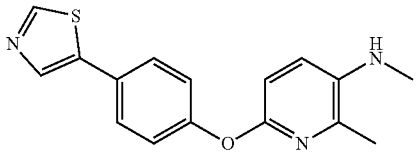
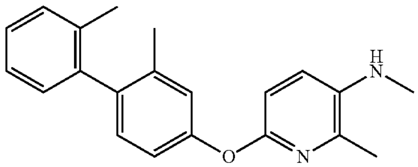
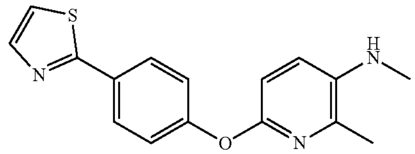
-continued
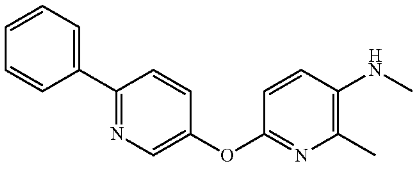
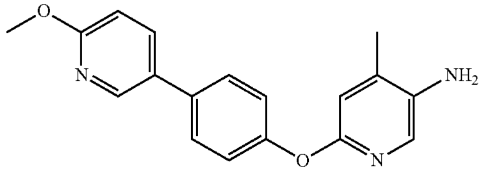
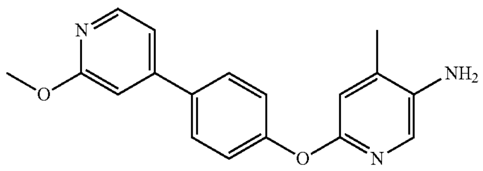
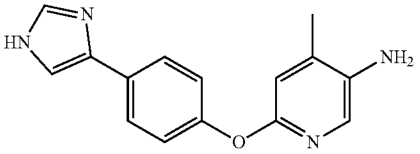
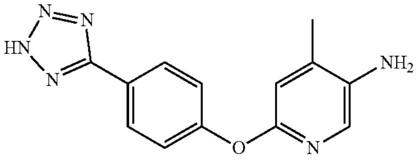
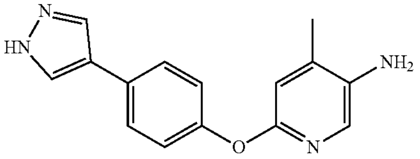
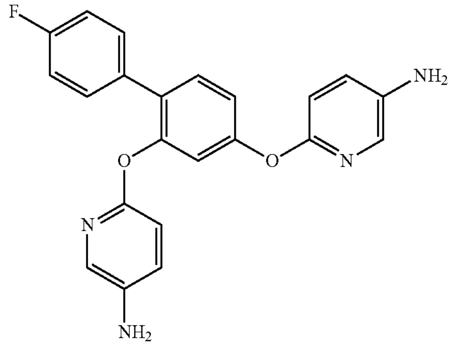
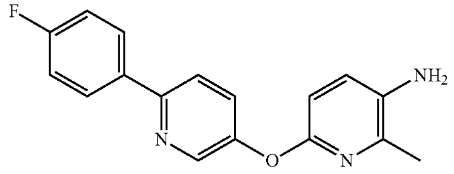
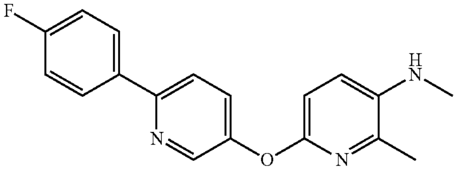

-continued
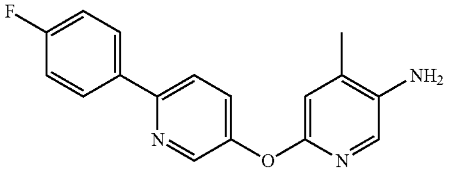
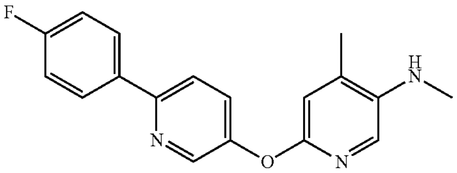
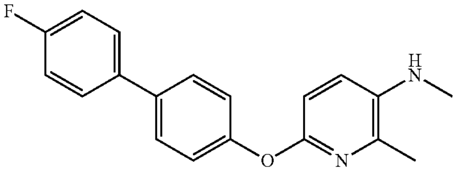
Further even more particular preferred compounds of the compound of formula (I) are selected from the group consisting of
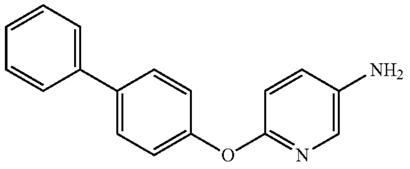
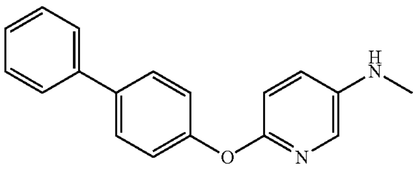
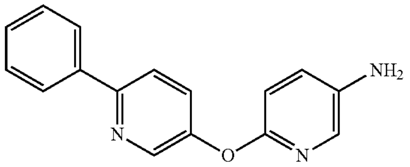
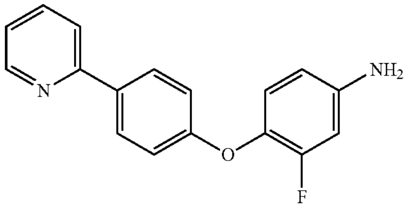
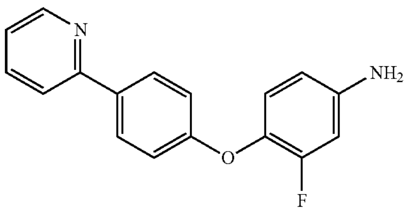
-continued
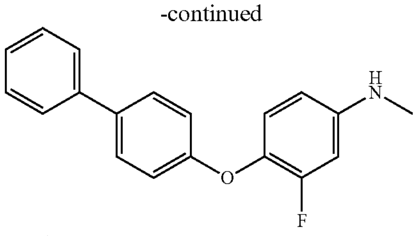
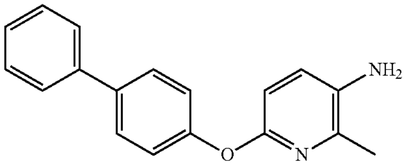
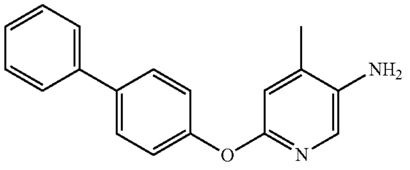
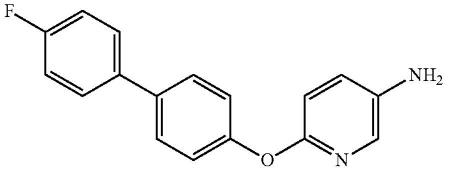
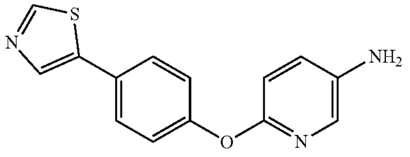
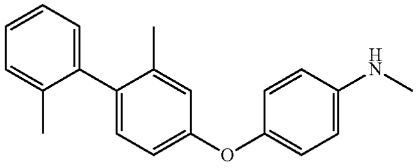
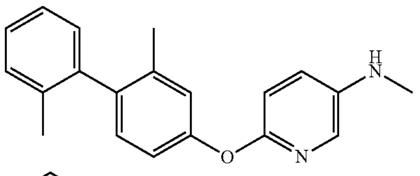
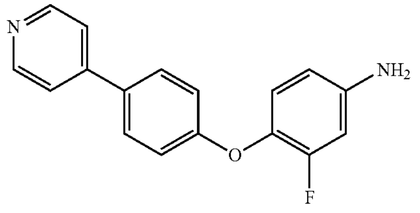
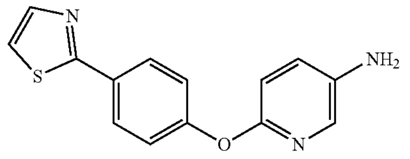
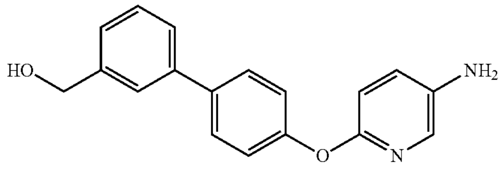

-continued
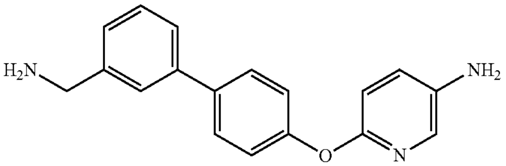
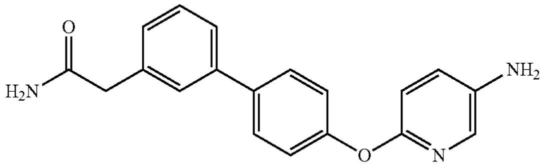
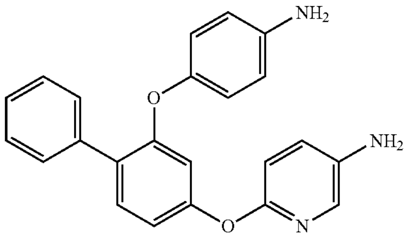
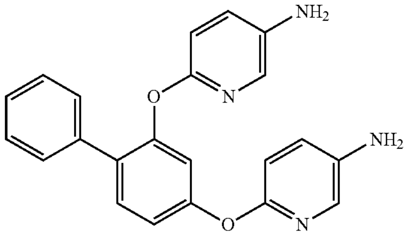
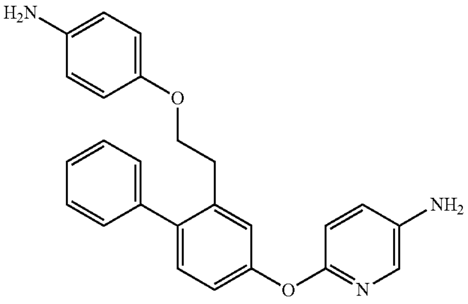
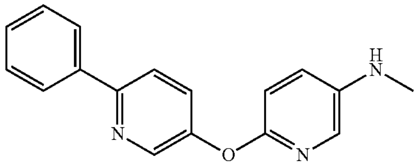
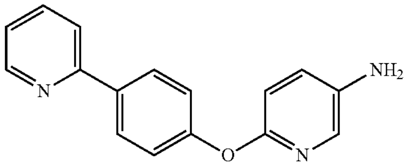
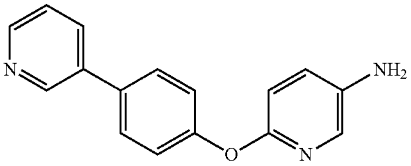
-continued
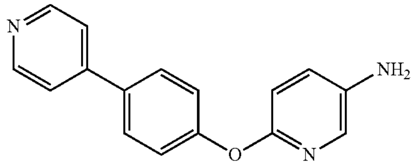
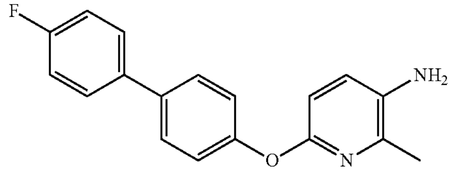
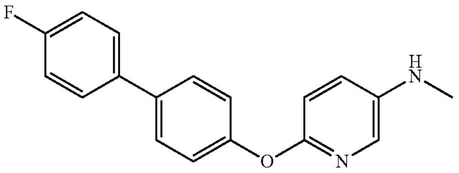
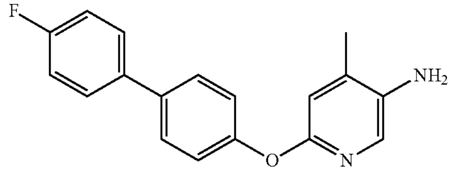
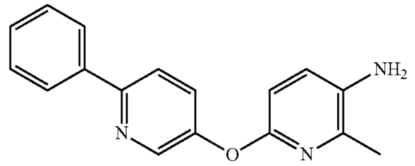
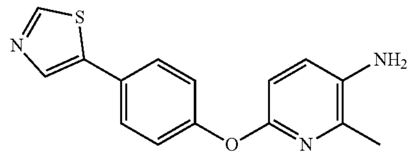
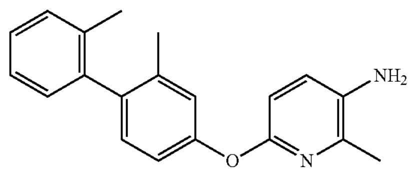
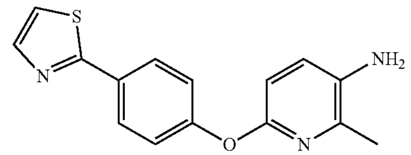
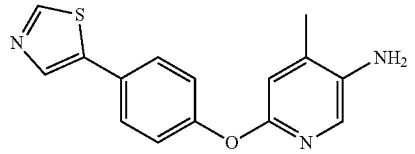
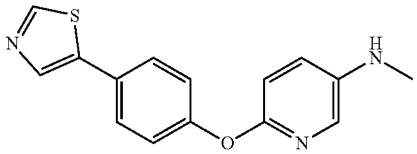

-continued
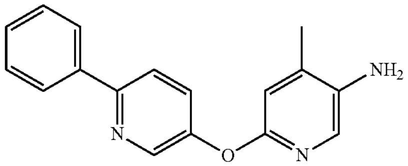
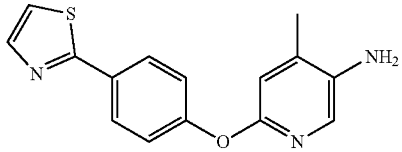
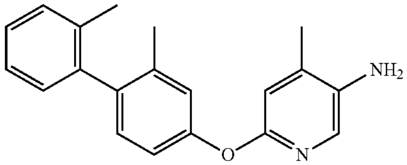
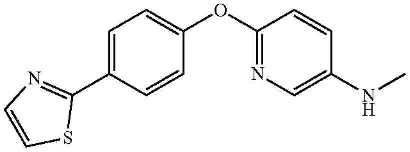
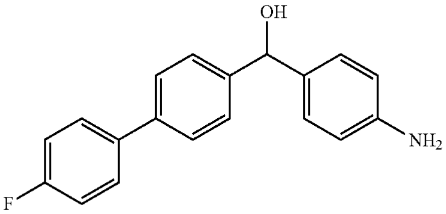
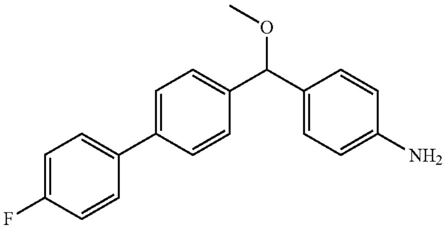
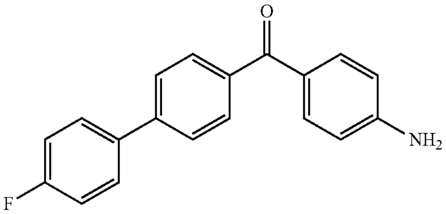
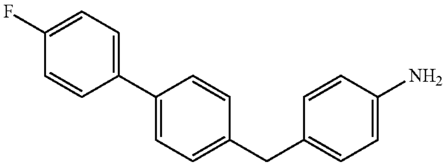
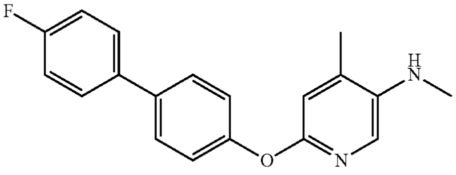
-continued
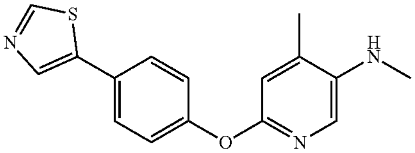
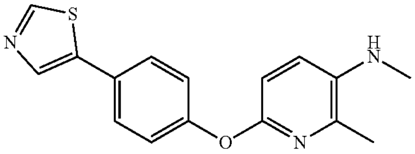
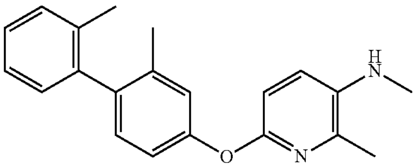
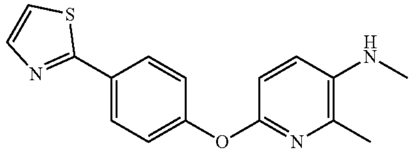
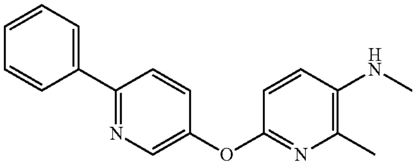
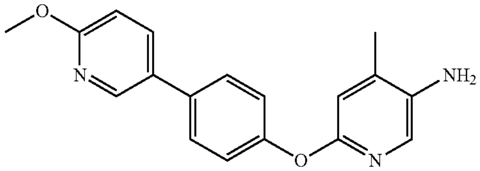
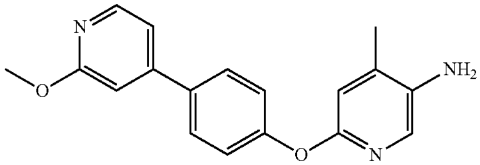
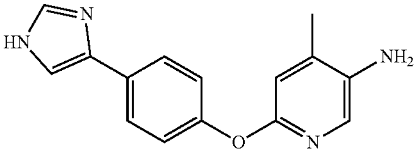
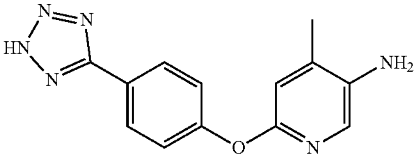
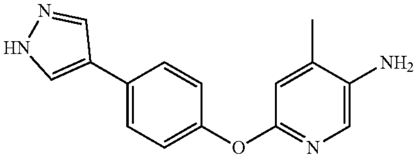

-continued
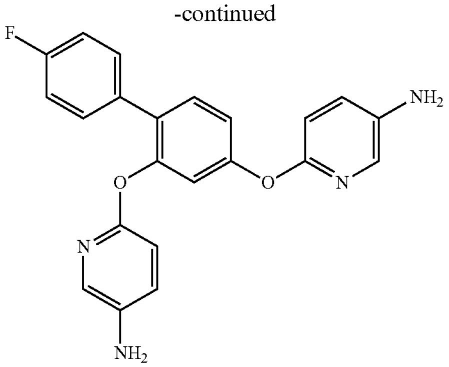
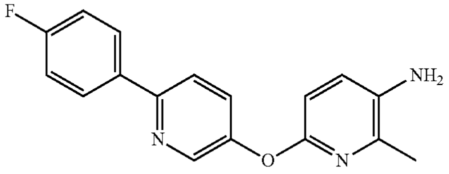
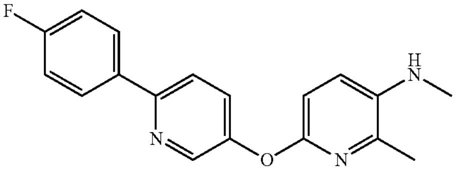
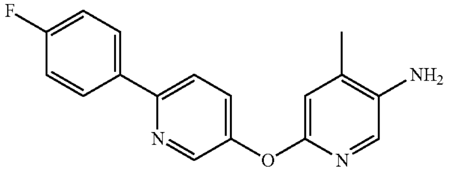
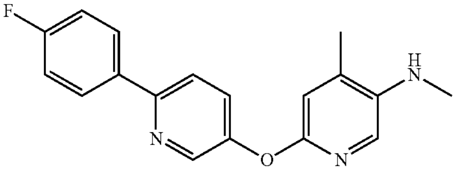
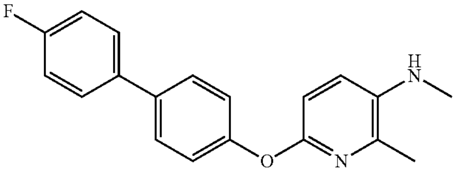
Further even more particular preferred compounds of the compound of formula (I) are selected from the group consisting of
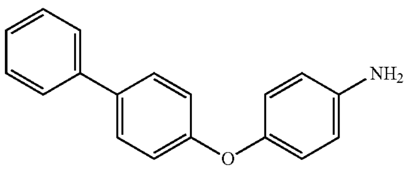
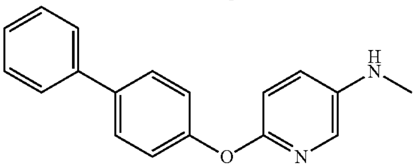
-continued
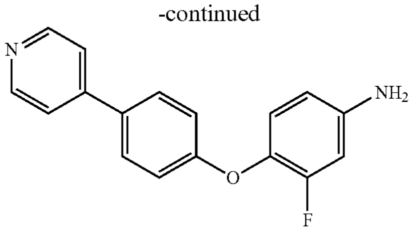
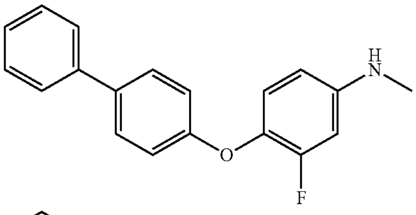
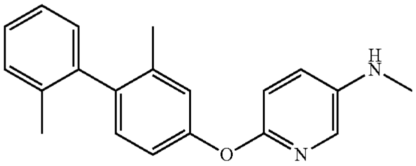
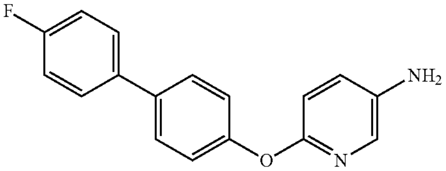
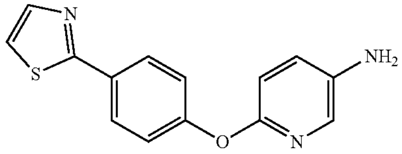
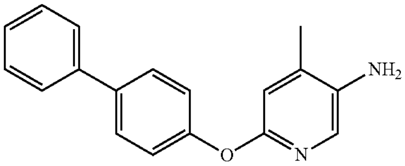
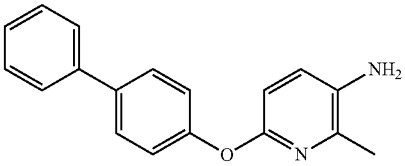
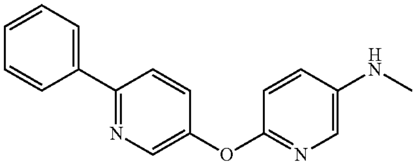
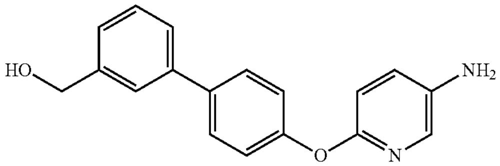
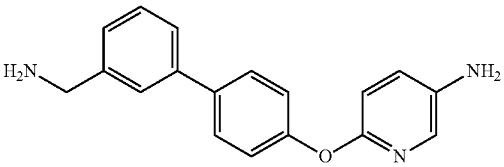

-continued
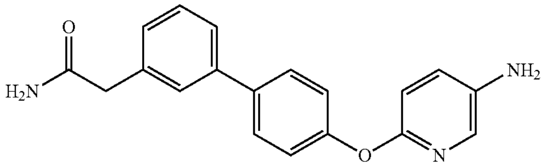
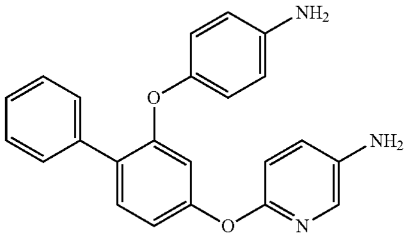
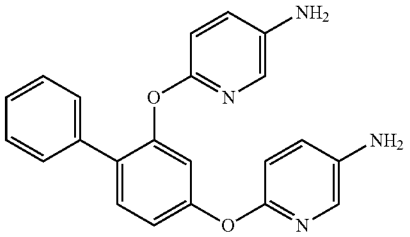
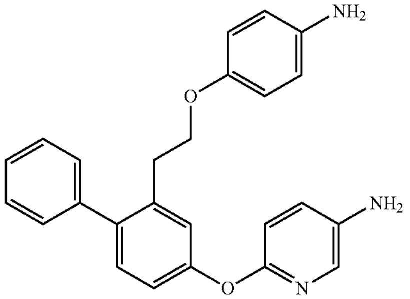
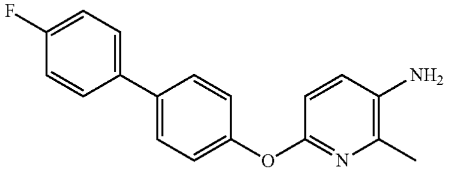
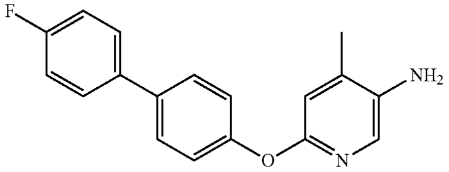
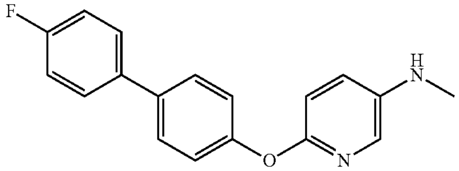
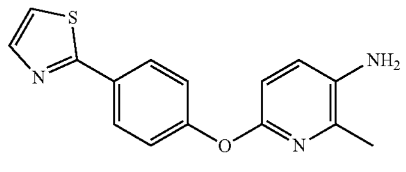
-continued
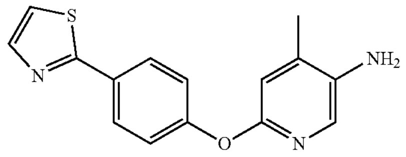
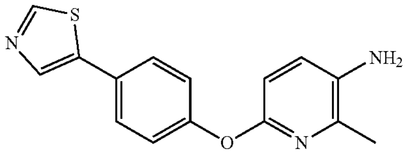
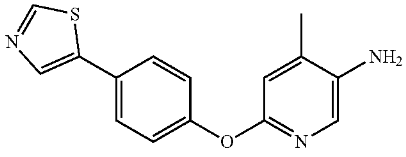
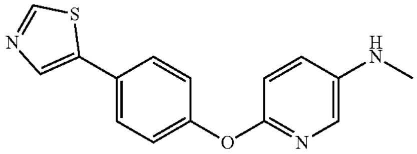
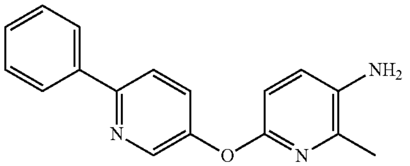
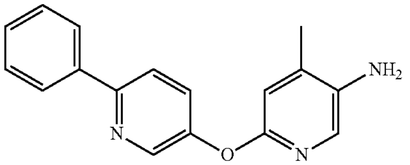
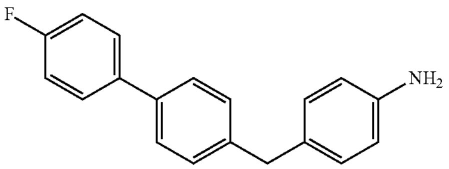
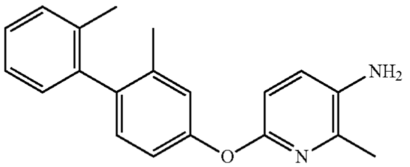
Most particular preferred compounds of the compound of formula (I) are selected from the group consisting of
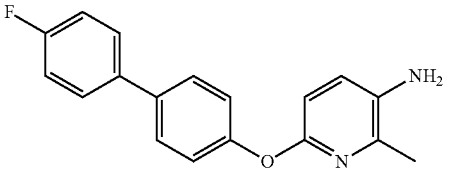

-continued
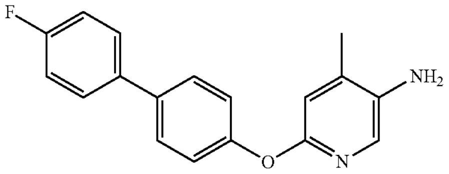
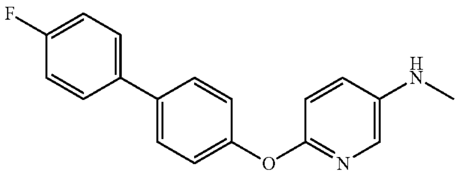
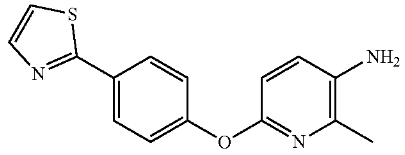
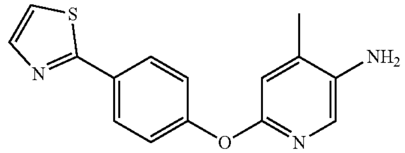
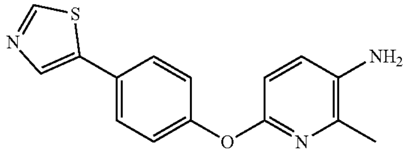
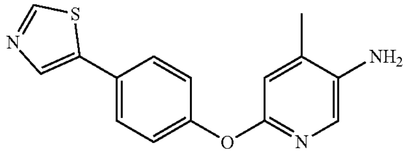
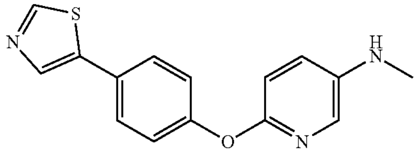
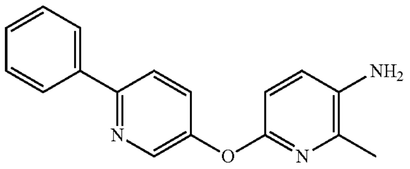
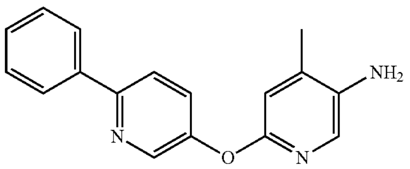
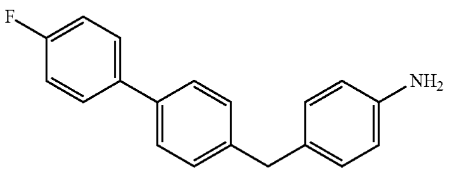
-continued
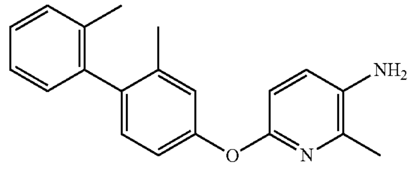
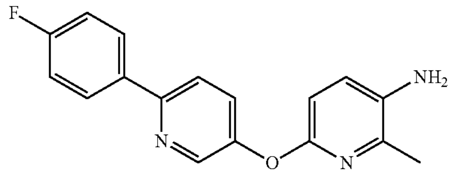
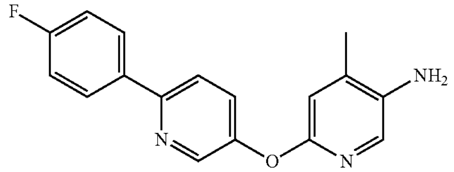
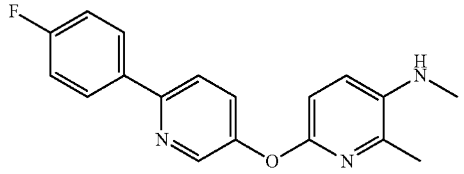
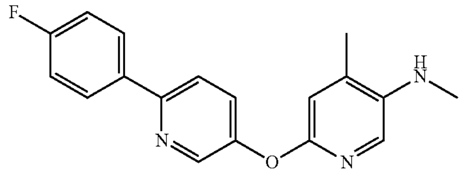
More particular preferred compounds of formula (I), pharmaceutically-acceptable salts, hydrates, solvates, or stereoisomers thereof are selected from the group consisting of
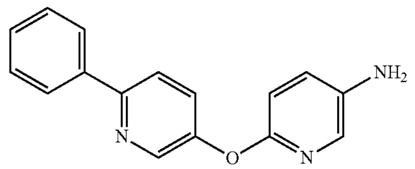
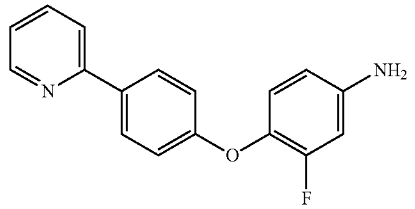 [SMILES: O=[N+]([O-])c1ccc(Oc2ccc(-c3ccccn3)cc2)c(F)c1]
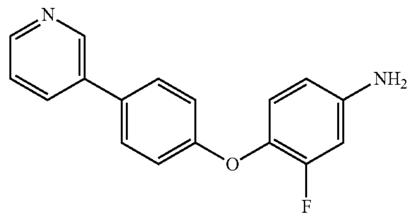

-continued
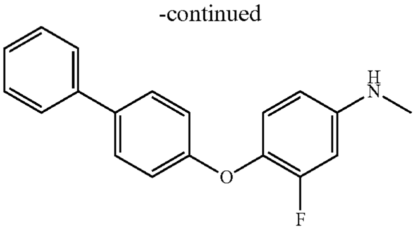
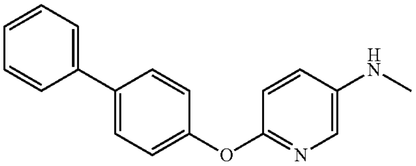
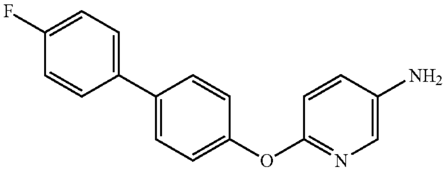
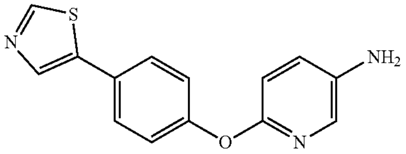
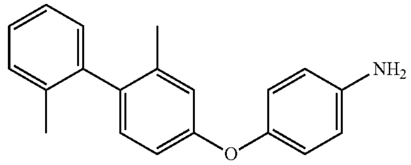
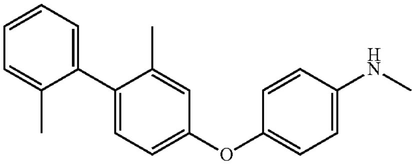
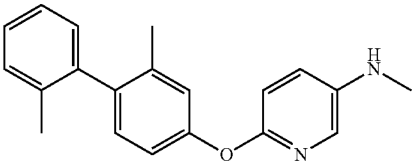
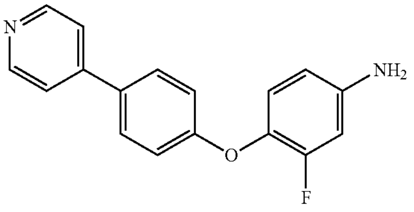
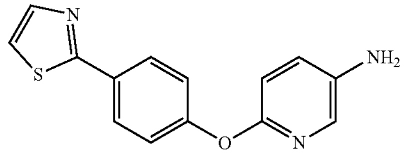
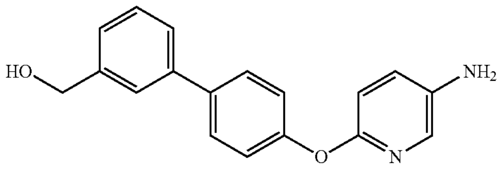
-continued
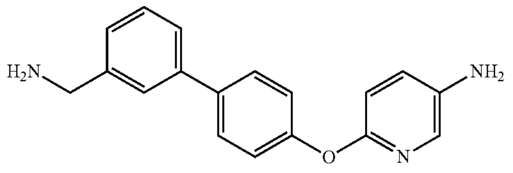
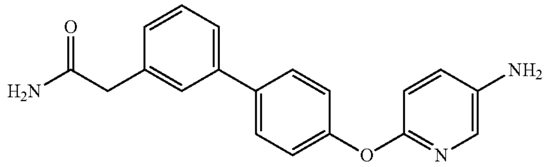
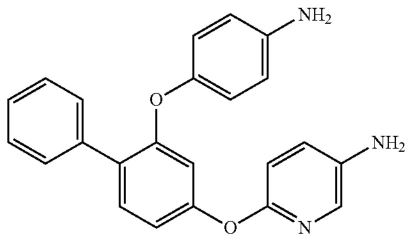
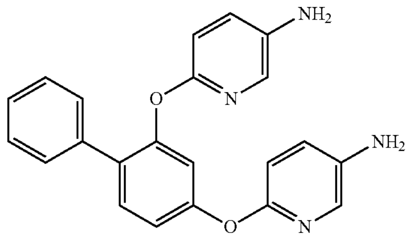
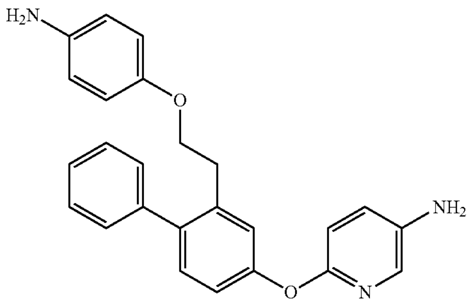
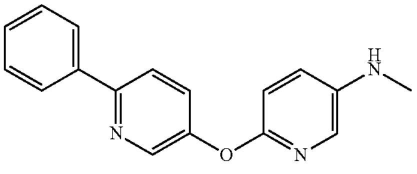
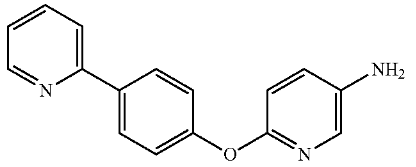
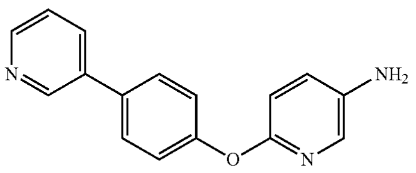

-continued

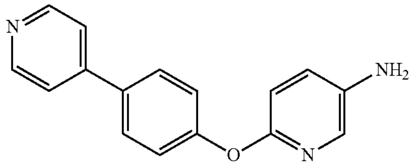

Further more particular preferred compounds of formula (I), pharmaceutically-acceptable salts, hydrates, solvates, or stereoisomers thereof are selected from the group consisting of

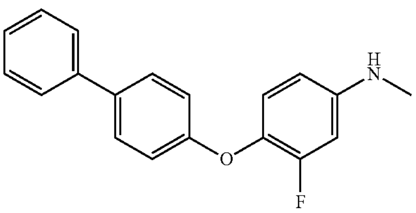

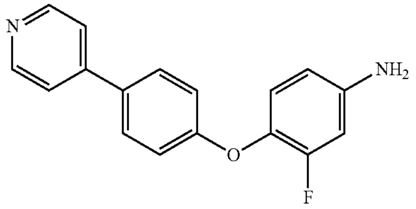

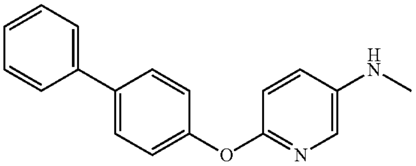

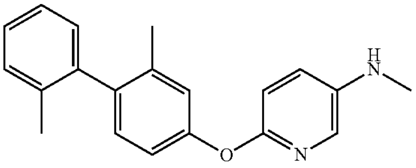

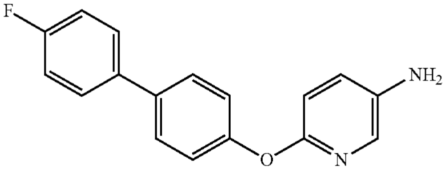

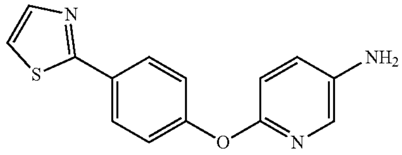

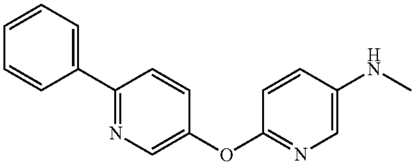

-continued

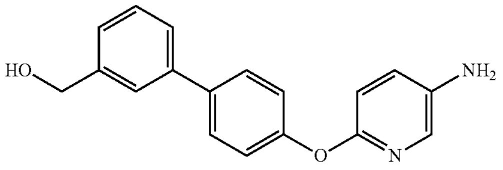

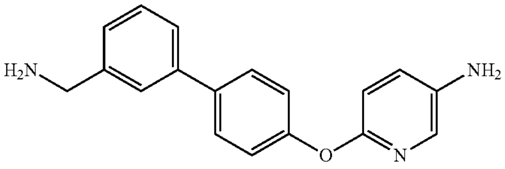

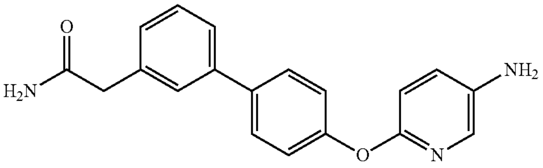

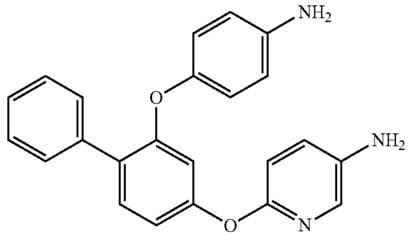

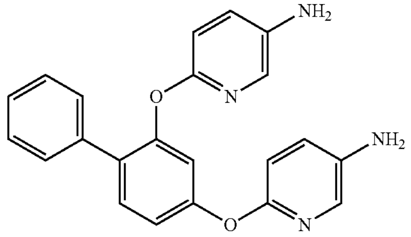

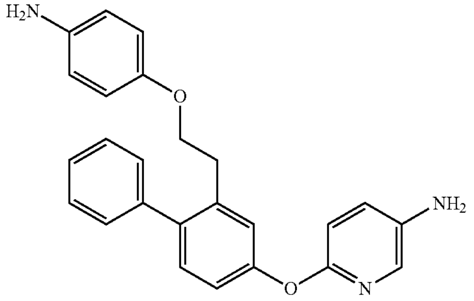

Further more particular preferred compounds of the compound of formula (I) for use, and the pharmaceutical composition comprising a compound of formula (I) are selected from the group consisting of

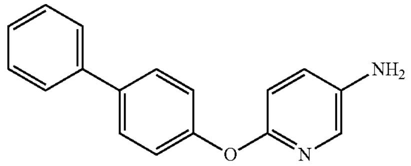

-continued
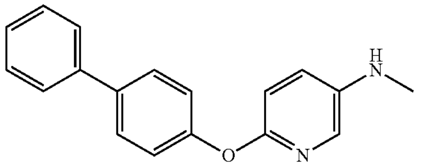
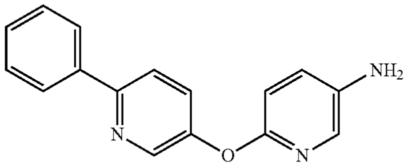
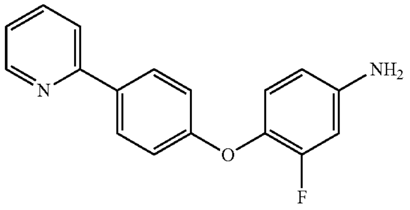
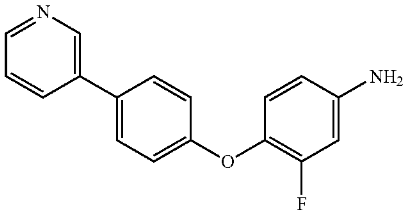
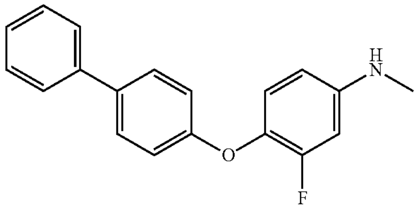
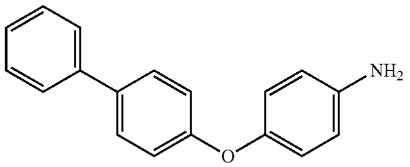
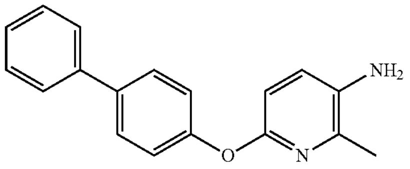
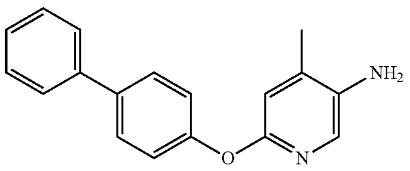
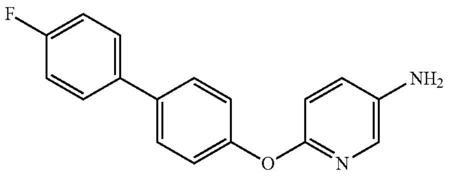
-continued
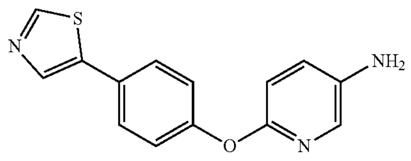
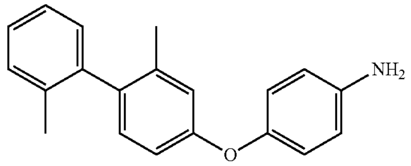
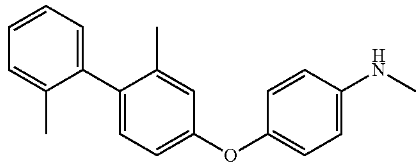
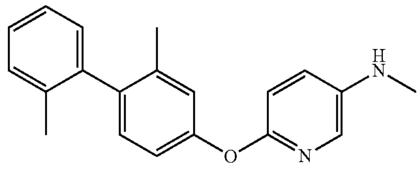
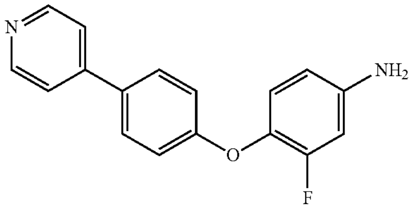
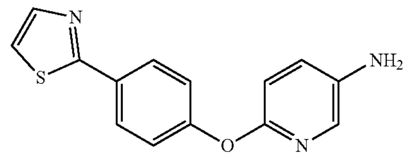
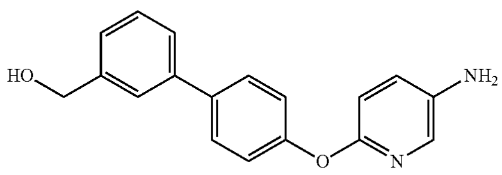
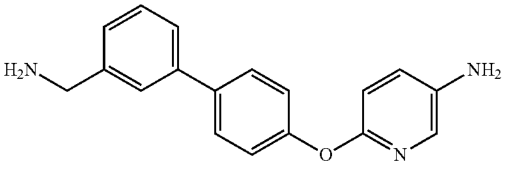
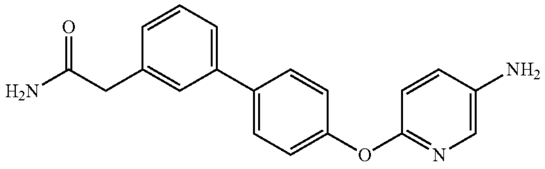

-continued
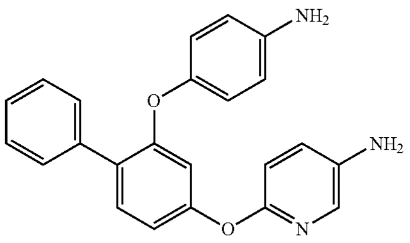
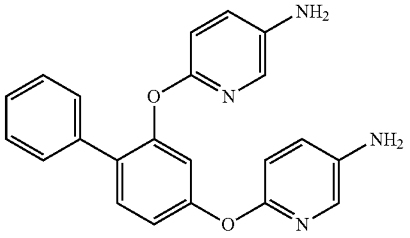
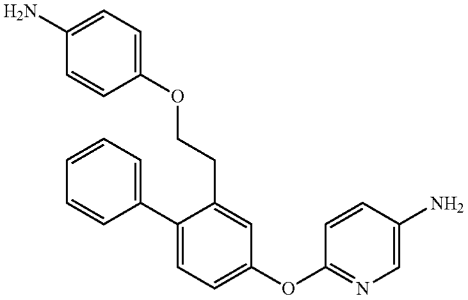
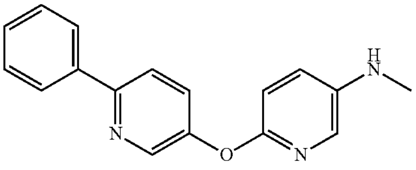
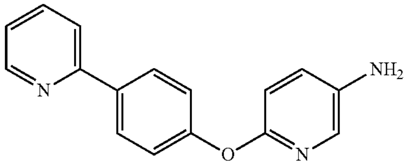
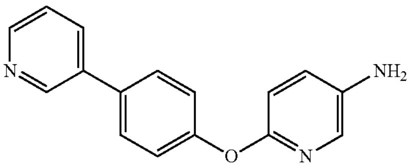
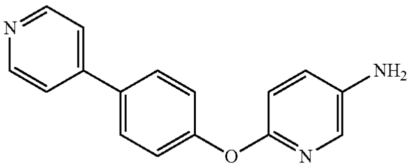
Further more particular preferred compounds of the compound of formula (I) for use, and the pharmaceutical composition comprising a compound of formula (I) are selected from the group consisting of
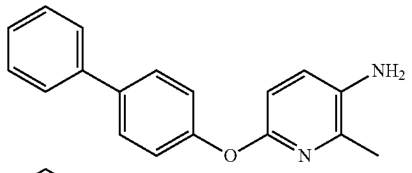
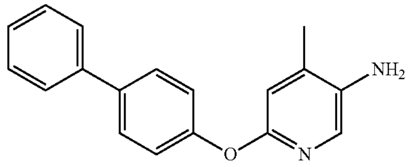
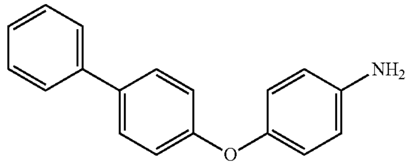
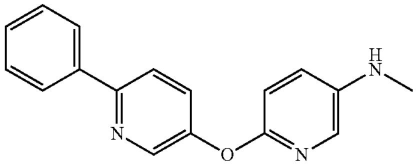
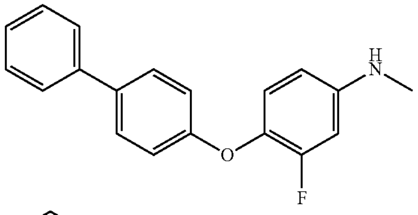
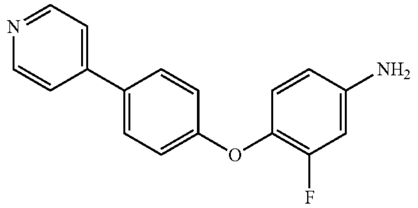
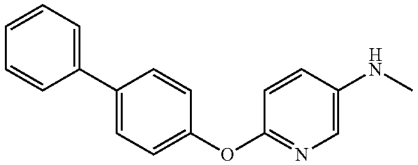
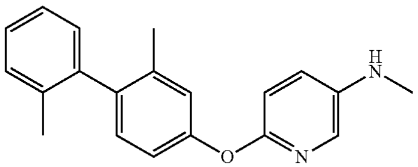
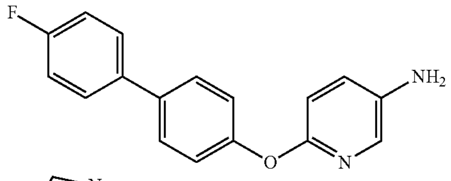
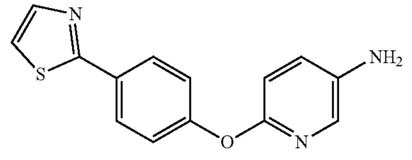

-continued

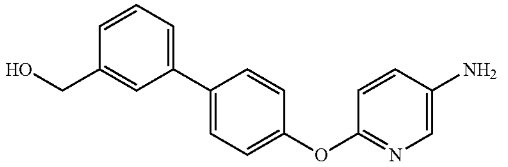

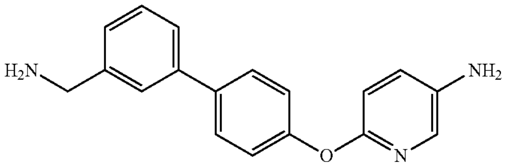

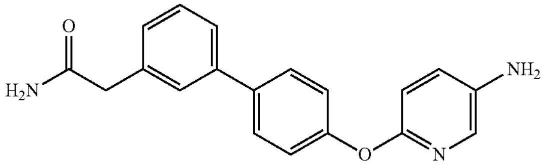

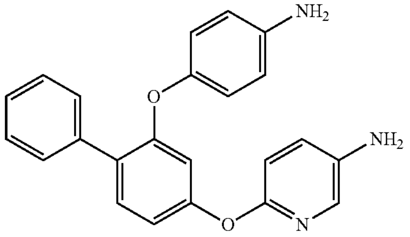

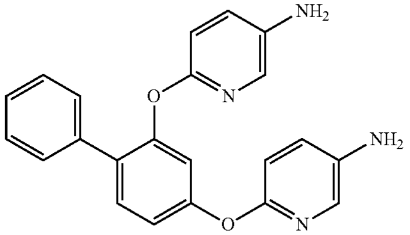

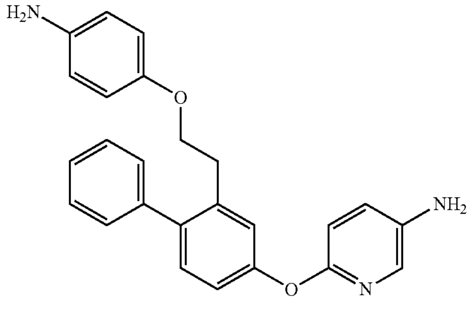

Preparation of the Compounds

The compounds of the invention may be prepared by the exemplary processes described in the following reaction schemes or by the processes described in the examples. Exemplary reagents and procedures for these reactions appear hereinafter. Starting materials can be purchased or readily prepared by one of ordinary skilled in the art.

Scheme 1: X = NH, N(C1-C3-alkyl), S and O

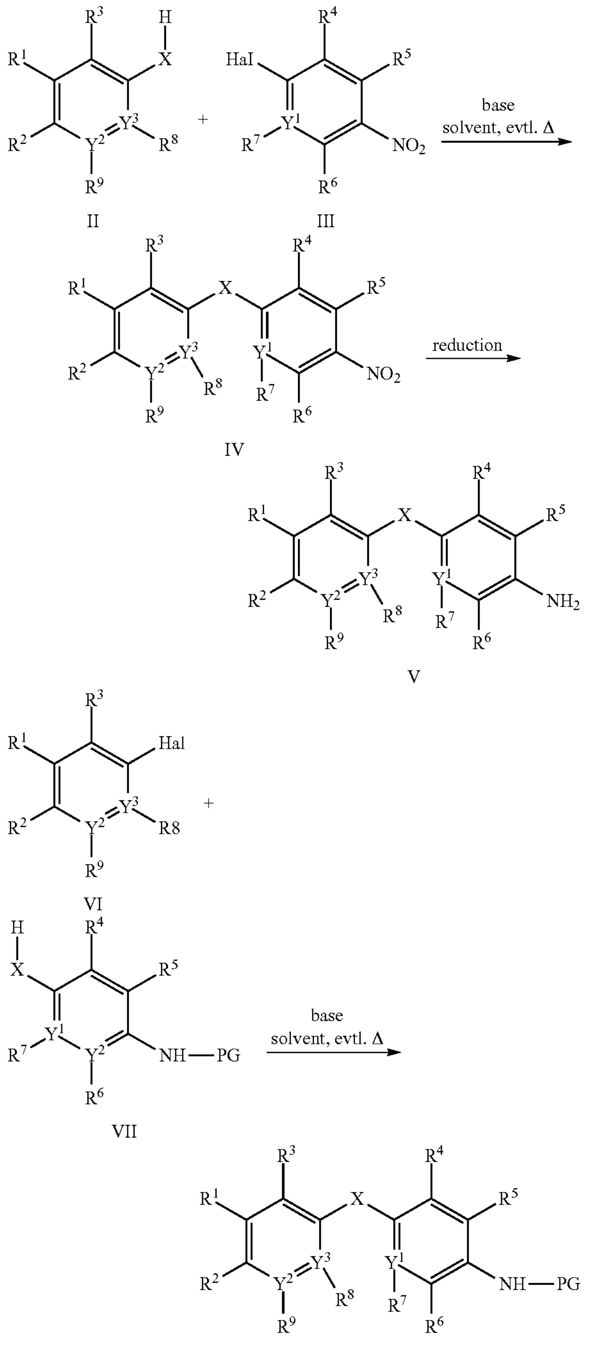

II III IV V VI VII VIII

The syntheses of the di-arylamino, di-arylether and di-arylthioether analogs is depicted in Scheme 1: The respective amino-aryl moiety of formula (II) (X═NH, eventually monoalkylated) is reacted with the halogenated nitro-aryl precursor of formula (III) in a polar solvent in presence of a base at elevated temperatures. Preferably the solvent is a mixture of DMSO and an alcohol like tBuOH. As a base an alcoholate like tBuOK can be used. Reaction temperatures are between room temperature and 150° C., preferably between 60 and 110° C. The respective hydroxy- or mercapto-aryl moiety of formula (II) (X═O, S) is reacted with the halogenated nitro-aryl precursor of formula (III) in a polar solvent in presence of a base. A preferred reaction condition is carbonate as base in DMF at room temperature. Finally, the nitro function of formula (IV) can be reduced to the respective amine of formula (V) under Bèchamp conditions or via catalytic hydrogenation. Preferred Bèchamp conditions are Fe powder in a mixture of EtOH, $H_2O$ and AcOH under sonication. Catalytic hydrogenation can be performed in presence of Pd/C in a polar solvent like an alcohol. Alternatively, target compounds of formula (VIII) ($Y^3$=N) can be obtained via substitution of the halogene of formula (VI) by the X-containing aryl moiety of formula (VII), eventually in presence of a protection group (PG). Preferred conditions are phosphate as a base in an unpolar aromatic solvent at 100 to 150° C. under ferrocenyl catalysis [see: *Advanced Synthesis & Catalysis* 353 (2011), 3403].

Scheme 2

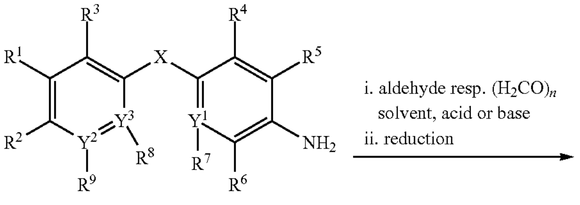

V

-continued

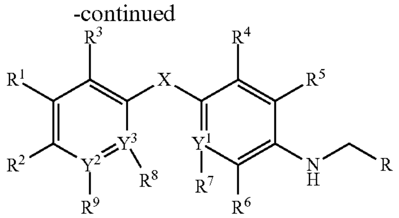

IX

R: H, $C_1$-$C_5$ alkyl

Scheme 2 depicts the reductive alkylation of amino-derivatives of formula (V): A preferred method is stirring the amine of formula (V) and the respective aldehyde in a polar solvent like an alcohol in presence of a weak acid like acetic acid. Then a reducing reagent like $NaBH_3CN$ is added. Basic work-up finally yields compounds of formula (IX). Alternatively, the amine of formula (V) and the aldehyde are mixed in an unpolar solvent like dichloromethane in presence of a base like triethylamine. Then a reducing reagent like $NaBH(OAc)_3$ is added. Aqueous work-up finally yields compounds of formula (IX). The N-methylated derivatives of formula (IX; R=H) are obtained from compounds of formula (V) and paraformaldehyde in MeOH with MeONa as a base followed by reduction with $NaBH_4$ and aqueous work-up.

Scheme 3: X = $CH_2$, $CF_2$, CHF, CHOH, CHOAlk, CO

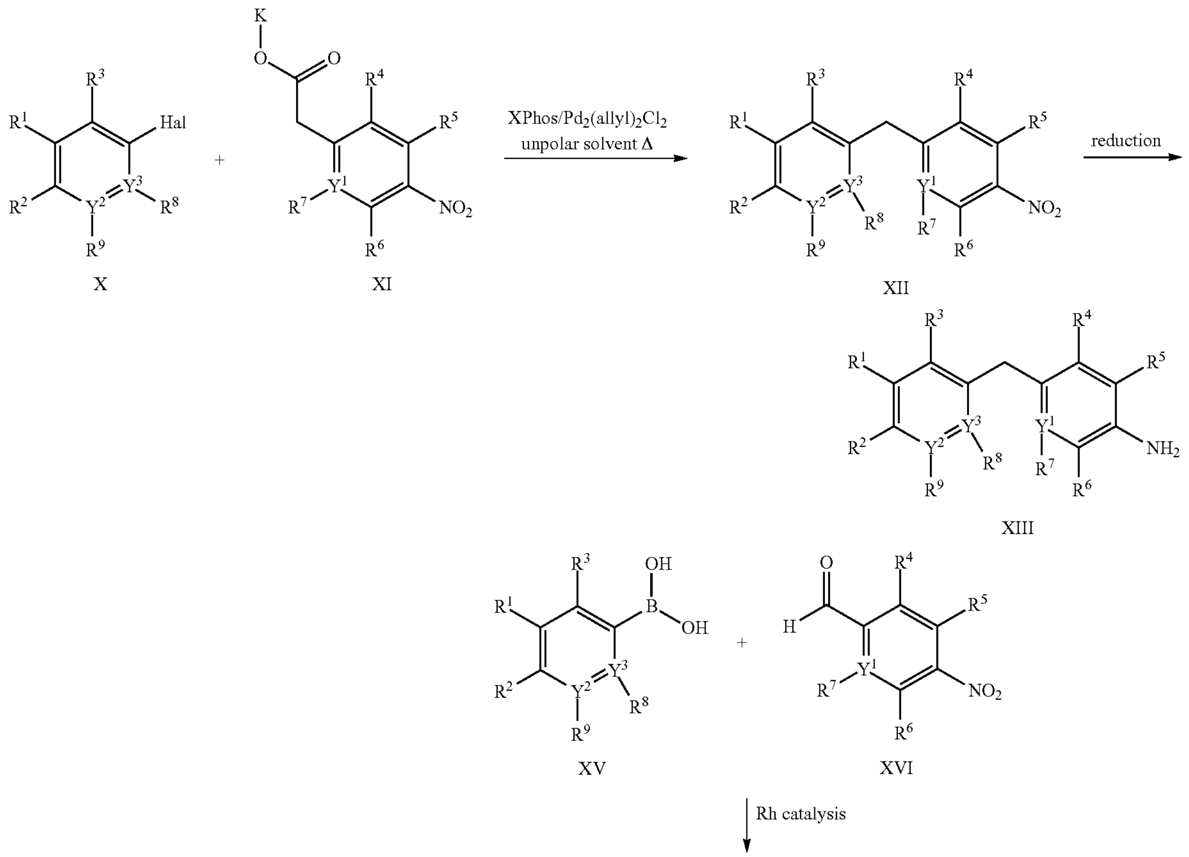

X XI XII XIII XV XVI

-continued

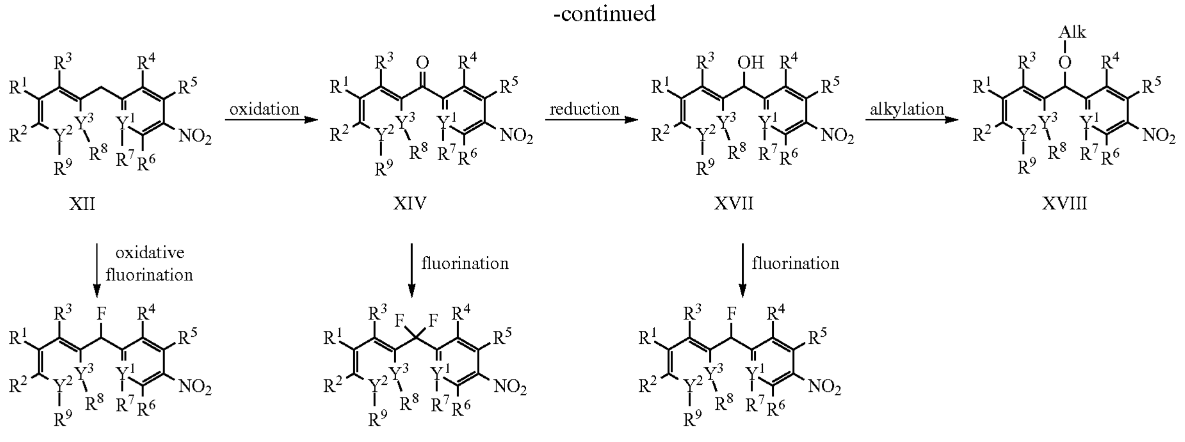

XII XIV XVII XVIII XIX XX XIX

Scheme 3 illustrates the syntheses of carbon-bridged analogs (X=$CH_2$, $CF_2$, CHF, CHOH, CHOAlk, CO): The halogen-aryl moiety of formula (X) is decarboxylatively coupled to the aryl-acetate of formula (XI), catalyzed by a transition metal complex, yielding the nitro derivative of formula (XII). Preferred conditions are XPhos/$Pd_2$(allyl)$_2$ $Cl_2$ as the catalyst in a unpolar solvent at elevated temperatures. The methylene bridge (X=$CH_2$) of formula (XII) can be oxidized to the respective di-aryl-ketone of formula (XIV). Preferred conditions are oxygen as the reagent in a mixture of acetic acid and DMSO at elevated temperature, catalyzed by $FeCl_2$.($H_2O$)$_4$ [analogously to: *Angew. Chem. Int. Ed.* 51 (2012), 2745].

Reduction of the carbonyl group of formula (XIV) leads to the benzylic alcohol of formula (XVII). A preferred reducing reagent could be sodium borohydride. Alternatively, the benzylic alcohol of formula (XVII) can be obtained via cross coupling of a boronate of formula (XV) with an aryl-aldehyde of formula (XVI). Alkylation of the compound of formula (XVII) with an alkyl-iodide in presence of a strong base (e.g. NaH) in an aprotic polar solvent yields the alkoxy-derivative of formula (XVIII) [analogously to: Example 2 in U.S. Pat. No. 5,965,740]. The mono-fluoro derivative of formula (XIX) can be obtained either by oxidative fluorination of the compound of formula (XII) or hydroxy-substitution in a compound of formula (XVII). The oxidative fluorination can be done under conditions as Jacobsen salene complex, iodosylbenzene, base, tris(hydrogen fluoride) in a polar solvent at elevated temperatures [*J. Am. Chem. Soc.* 136 (2014), 6842]. Substitution of the benzylic hydroxy group by fluoride can be achieved by applying conditions like activation with trichloroacetimidate, 1,8-diazabicyclo[5.4.0]undec-7-ene in dichloromethane in presence of bis(1,5-cyclooctadiene)rhodium(I) tetrafluoroborate followed by triethylamine tris(hydrogen fluoride) in a mixture of $F_3C—C_6H_5$ and tetrahydrofurane at slightly elevated temperatures [Tetrahedron 71 (2015), 5932]. The keto-derivative of formula (XIV) can be converted to the difluoromethylen derivative of formula (XX) with [bis(2-methoxyethyl)amino]-sulfur trifluoride at elevated temperatures [analogously to: US2015246938; Step 2, Preparation of Compound 76; page 55]. Finally, the nitro-groups of compounds of formula (XII), (XIV) and (XVII)-(XX) can be reduced to the respective amino derivatives as described in Scheme 1.

Stereoisomers

Compounds of the present invention can exist as stereoisomers wherein asymmetric or chiral centers are present. These compounds are designated by the symbols "R" or "S", depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring.

Compounds of the present invention can also exist as racemates which is given the descriptor "rac". The term racemate, as used herein, means an equimolar mixture of a pair of enantiomers. A racemate is usually formed when synthesis results in the generation of a stereocenter. As used herein, the term racemic mixture means racemate. Compounds of the present invention can also exist as diastereomeric meso forms which is given the descriptor "rel". The term diastereomeric meso form as used herein means achiral forms with a pseudostereogenic C-atom, which is given the descriptor "r" or "s", respectively.

Salts

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. The salts may be prepared in situ during the final isolation and purification of the compounds of the invention or separately by reacting a free base function with a suitable acid.

Representative acid addition salts include, but are not limited to trifluoroacetic acid (TFA), acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Solvates/Hydrates

It should be appreciated that solvates and hydrates of the compound according to formula (I) are also within the scope of the present application. Methods of solvation are generally known in the art. A further embodiment of the present invention may also include compounds, which are identical to the compounds of formula (I) except that one or more atoms are replaced by an atom having an atomic mass number or mass different from the atomic mass number or mass usually found in nature, e.g. compounds enriched in $^{2}H$ (D), $^{3}H$, $^{13}C$, $^{127}I$ etc. These isotopic analogs and their pharmaceutical salts and formulations are considered useful agents in therapy and/or diagnosis, for example, but not limited to, where a fine-tuning of in vivo half-life time could lead to an optimized dosage regimen.

Pharmaceutical Compositions

In a further aspect the present invention provides a pharmaceutical composition comprising a compound of formula (I) according to the invention and a pharmaceutically acceptable diluent, excipient or carrier.

In one embodiment the pharmaceutical composition further comprises another pharmaceutical active agent.

In one embodiment, the invention provides a pharmaceutical composition comprising a compound of formula (I) according to the invention and a pharmaceutically acceptable diluent, excipient or carrier, wherein said compound of formula (I) is present in a therapeutically effective amount.

Formulations and Modes of Administration:

The compounds of the present invention may, in accordance with the invention, be administered in single or divided doses by oral, parenteral, inhalatory, rectal or topical administration including cutaneous, ophthalmic, mucosal scalp, sublingual, buccal and intranasal routes of administration; further, the compounds provided by the invention may be formulated to be used for the treatment of leukocyte populations ex vivo and in vitro.

When the compounds of the present invention are to be administered e.g. by the oral route, they may be administered as medicaments in the form of pharmaceutical compositions which contain them in association with a pharmaceutically acceptable diluent, excipient or carrier material. Thus the present invention also provides a pharmaceutical composition comprising the compounds according to the invention as described supra and one or more pharmaceutically acceptable diluent, excipient or carrier. The pharmaceutical compositions can be prepared in a conventional manner and finished dosage forms can be solid dosage forms, for example, tablets, dragees, capsules, and the like, or liquid dosage forms, for example solutions, suspensions, emulsions and the like. Pharmaceutically acceptable diluent, excipient or carrier include sterile aqueous solutions or dispersions and sterile powders for the extemporaneous preparation of sterile injectable solutions or dispersion. The use of such media and agents for pharmaceutically active substances is known in the art. In one embodiment, the invention provides a pharmaceutical composition comprising a compound of formula (I) according to the invention and at least one pharmaceutically acceptable diluent, excipient or carrier, wherein the composition is a tablet or a capsule, preferably a tablet.

Dosing Regimen

An exemplary treatment regime entails administration once daily, twice daily, three times daily, every second day, twice per week, once per week. The composition of the invention is usually administered on multiple occasions. Intervals between single dosages can be, for example, less than a day, daily, every second day, twice per week, or weekly. The composition of the invention may be given as a continuous uninterrupted treatment. In an exemplary treatment regime the compound of formula (I) according to the invention can be administered from 0.1-100 mg per day.

Therapeutic Use

The compounds according to the invention as described supra have preventive and therapeutic utility in human and veterinary diseases.

Thus, in a further aspect the present invention provides the use of the compounds as described herein and the use of the pharmaceutical composition described herein for preventive and/or therapeutic purposes. In one embodiment of the present invention, the compounds according to the invention as described herein or the pharmaceutical composition as described herein may be used as a medicament, preferably for use in human medicine and/or veterinarian medicine. Accordingly the present invention provides the compounds according to the invention as described herein or a pharmaceutical composition as described herein, for use as a medicament.

In a further aspect the present invention also provides the compounds of the present invention, or the pharmaceutical composition of the invention for use in a method for the prevention or treatment of cancer. Also provided is a method for treating and/or preventing cancers, said method comprising administering the compounds of the present invention, or the pharmaceutical composition of the invention to a subject in need thereof. Also provided is the use of the compounds of the present invention, or the pharmaceutical composition of the invention for the manufacture of a medicament for treating and/or preventing cancers in a subject. Also provided is the use of the compounds of the present invention, or the pharmaceutical composition of the invention for treating and/or preventing cancers in a subject.

Cancers to be prevented or treated are preferably Notch dependent cancers, more preferably, Notch dependent cancers selected from the group consisting of adenoid cystic carcinoma (ACC), T cell-Acute lymphoblastic leukemia (T-ALL), chronic myeloid leukemia (CIVIL), chronic lymphocytic leukemia (CLL), Mantle cell lymphoma (MCL), breast cancer, pancreatic cancer, prostate cancer, melanoma, brain tumors, tumor angiogenesis, liver cancer and colorectal cancer. Preferably, the compounds of the present invention can be also used in the treatment of cancers where Notch dependent cancers are resistant to γ-secretase inhibitor treatment. Notch signalling dependent human tumors resistant to γ-secretase inhibitor treatment can be determined by the levels of NICD, Notch target genes as well as by mutation status of Notch receptor and other components of the Notch pathway.

In a further aspect the present invention provides a method of treatment of a disease associated with an up-regulated Notch signaling pathway activity, said method comprising administering the compounds of the present invention, or the pharmaceutical composition of the invention to a subject in need thereof.

The daily dose of compounds of the present invention will necessarily be varied depending upon the host treated, the particular route of administration, and the severity and kind of the illness being treated. Accordingly the optimum dosage may be determined by the practitioner who is treating any particular patient. Further, it is noted that the clinician or treating physician will know how and when to start, interrupt, adjust, or terminate therapy in conjunction with individual patient response. For any compound used in the methods of the present invention, a therapeutically effective dose can be estimated initially from cell culture assays, animal models, or microdosing of human subjects.

"Treatment" as used herein, refers to both therapeutic treatment and prophylactic or preventative measures. Subjects in need of treatment include those already with the disorder, such as cancer, as well as those in which the disorder, such as cancer, is to be prevented. Hence, the mammal, preferably human, to be treated herein may have been diagnosed as having the disorder, such as cancer, or may be predisposed or susceptible to the disorder, such as cancer.

"Prevention" as used herein comprise prophylactic treatments. In preventive applications, the pharmaceutical combination of the invention is administered to a subject suspected of having, or at risk for developing cancer. In therapeutic applications, the pharmaceutical combination is administered to a subject such as a patient already suffering from cancer, in an amount sufficient to cure or at least partially arrest the symptoms of the disease. Amounts effective for this use will depend on the severity and course of the disease, previous therapy, the subject's health status and response to the drugs, and the judgment of the treating physician.

The term "therapeutically effective amount" refers to an amount of a drug effective to treat a disease or disorder in a mammal. In the case of cancer, the therapeutically effective amount of the drug may reduce the number of tumor or cancer cells, reduce the tumor size; inhibit (i.e., slow to some extent and preferably stop) cancer cells infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compounds of the present invention may prevent growth and/or kill existing cancer cells, it may be cytostatic and/or cytotoxic. The phrase "therapeutically effective amount" is used herein to mean an amount sufficient to prevent, or preferably reduce by at least about 30 percent, preferably by at least 50 percent, preferably by at least 70 percent, preferably by at least 80 percent, preferably by at least 90%, a clinically significant change in the growth or progression or mitotic activity of a target cellular mass, group of cancer cells, or other feature of pathology.

In one embodiment the compounds of the present invention may be used against cell proliferate diseases in combination (for example either at the same time, or almost at the same time, or one after the other) with conventional treatments such as standard radiotherapy and/or standard chemotherapy. The standard radiotherapy and chemotherapy can be also the concomitant chemo-radiotherapy. The standard radiotherapy and/or chemotherapy can be performed before, simultaneously or after the administration of a therapeutically effective amount of the compound of the present invention, or pharmaceutical compositions containing thereof.

The term "concomitant chemo-radiotherapy" is used when these two treatments (chemotherapy and radiotherapy) are given either at the same time, or almost at the same time, for instance one after the other, or on the same day, etc.

The term "standard radiotherapy" refers to the use of ionizing radiation as part of cancer treatment to control malignant cells. Preferably the ionizing radiation is γ-irradiation. It is also common to combine radiotherapy with surgery, chemotherapy, hormone therapy, or combinations thereof. Most common cancer types can be usually treated with radiotherapy. The precise treatment intent (curative, adjuvant, neoadjuvant or palliative) will depend on the tumor type, location, and stage, as well as the general health of the subject in need thereof.

The term "standard chemotherapy" generally refers to a treatment of a cancer using specific chemotherapeutic/chemical agents. A chemotherapeutic agent refers to a pharmaceutical agent generally used for treating cancer. The chemotherapeutic agents for treating cancer include, for example, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide, Tioguanine/Thioguanine, Thiotepa, Topotecan, Treosulfan, Vinblastine, Vincristine, Vindesine or Vinorelbine.

When a chemotherapeutic agent is used in combination with a compound according to the present invention, then this may be used in the form of a medicament containing a combination of these two agents, for simultaneous administration, or they may be used in the form of separate dosage forms, each containing one of the agents, and in the latter case the individual dosage forms may be used e.g. sequentially, i.e. one dosage form with the compound of the invention, followed by a dosage form containing the chemotherapeutic agent (or vice versa). This embodiment of two separate dosage forms may be conceived and provided in the form of a kit.

Also optionally the compounds of the present invention may be used against cell proliferate diseases, such as cancers, in combination with conventional removal of a tumor bulk, by for example segmental resection (biopsy or gross resection).

The term "removal of a tumor bulk" refers to any removal, ablation or resection of a tumor bulk from a subject. The removal can be chemical, radiation or surgical. Preferably said removal is surgical, such as ablation or resection. Resection can be "segmental resection" (or segmentectomy), a surgical procedure to remove part of an organ or gland from a subject. It may also be used to remove a tumor and normal tissue around it. Debulking agent may be also used to remove tumor bulk. The term "debulking agent" includes any molecule (e.g. chemical, biological) or any external/environmental agent (e.g. γ-irradiation) or traditional surgery that would allow killing cancer cells from the tumor bulk (e.g. $FL1^0$ and $FL1^-$ cells as mentioned above).

As to the appropriate carriers, reference may be made to the standard literature describing these, e.g. to chapter 25.2 of Vol. 5 of "Comprehensive Medicinal Chemistry", Pergamon Press 1990, and to "Lexikon der Hilfsstoffe für Pharmazie, Kosmetik and angrenzende Gebiete", by H. P. Fiedler, Editio Cantor, 2002. The term "pharmaceutically acceptable carrier" means a carrier or excipient that is useful in preparing a pharmaceutical composition that is generally safe, and possesses acceptable toxicities. Acceptable carriers include those that are acceptable for veterinary use as well as human pharmaceutical use. A "pharmaceutically acceptable carrier" as used in the specification and claims includes both one and more than one such carrier.

Optionally, the pharmaceutical composition of the present invention further comprises one or more additional active agents selected among the non limiting group comprising chemotherapeutic agents for treating cancer. Such chemotherapeutic agents may be selected among the group comprising, for example, Altretamine, Bleomycin, Busulphan, Capecitabine, Carboplatin, Carmustine, Chlorambucil, Cisplatin, Cladribine, Crisantaspase, Cyclophosphamid, Cytarabine, Dacarbazine, Daunorubicin, Doxorubicin, Epirubicin, Etoposide, Fludarabine, Fluorouracil, Gemcitabine, Idarubicin, Ifosfamide, Irinotecan, Lomustine, Melphalan, Mercaptopurine, Methotrexate, Mitomycin, Mitoxantrone, Oxaliplatin, Pentostatin, Procarbazine, Streptozocin, Taco, Temozolomide Tioguanine/Thioguanine, Thiotepa, Topotecan, Treosulfan, Vinblastine, Vincristine, Vindesine and Vinorelbine.

The compounds of the invention that can be used in the treatment and/or prevention of cancers can be incorporated into a variety of formulations and medicaments for therapeutic administration. More particularly, one or more compound(s) as provided herein can be formulated into pharmaceutical compositions by combination with appropriate, pharmaceutically acceptable carriers, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracranial and/or intratracheal administration. Moreover, the compound can be administered in a local rather than systemic manner, in a depot or sustained release formulation. The compounds can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. The compounds can be administered alone, in combination with each other, or they can be used in combination with other known compounds. Suitable formulations for use in the present invention are found in Remington's Pharmaceutical Sciences (Mack Publishing Company (1985) Philadelphia, PA, 17th ed.), which is incorporated herein by reference. Moreover, for a brief review of methods for drug delivery, see, Langer, Science (1990) 249:1527-1533, which is incorporated herein by reference.

The amount of a compound as provided herein that can be combined with a carrier material to produce a single dosage form will vary depending upon the disease treated, the subject in need thereof, and the particular mode of administration. However, as a general guide, suitable unit doses for the compounds of the present invention can, for example, preferably contain between 0.1 mg to about 1000 mg, between 1 mg to about 500 mg, and between 1 mg to about 300 mg of the active compound. In another example, the unit dose is between 1 mg to about 100 mg. Such unit doses can be administered more than once a day, for example, 2, 3, 4, 5 or 6 times a day, but preferably 1 or 2 times per day, so that the total dosage for a 70 kg human adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area. A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release. It can be necessary to use dosages outside these ranges in some cases as will be apparent to those skilled in the art.

A further object of the present invention is a kit comprising a container and a package insert, wherein the container comprises at least one dose of a medicament comprising a compound of formula (I) and optionally one or more pharmaceutically acceptable diluents, excipients or carrier, and the package insert comprises instructions for treating a subject for cancer using the medicament. The kit can further comprise one or more doses of a chemotherapeutic agent. Optionally, the kit may also comprise reagents and/or instructions for use.

Generally, the kit comprises a container and a label or package insert on or associated with the container. Suitable containers include, for example, bottles, vials, syringes, etc. The containers may be formed from a variety of materials such as glass or plastic. The container holds the pharmaceutical composition that is effective for treating the condition and may have a sterile access port (for example the container may be an intravenous solution bag or a vial having a stopper pierceable by a hypodermic injection needle). The label or package insert indicates that the composition is used for treating the condition of choice, such as cancer.

In a further object the present invention provides the use of the compounds of the invention for inhibiting in vitro or in vivo the Notch signalling pathway in cells. Usually, said cells are cancer cells.

In a further object the present invention provides a method of treating a subject for Notch dependent cancer, comprising i) determining in cancer cells obtained from a biological sample of said subject whether the cancer is Notch signalling pathway dependent, ii) and treating said subject based upon whether the cancer is Notch dependent cancer by administering a therapeutically effective amount of the compounds of the invention, or a pharmaceutical composition of the invention.

Usually, the Notch signalling pathway dependency in cancer cells is determined by any method known in the art. As an example, this method can consist in an in vitro γ-secretase complex activity assays as described herein.

This method of treating may further comprise administering at least one conventional cancer treatment. The conventional cancer treatment is administered before, simultaneously or after the administration of the therapeutically effective amount of compounds of the invention, or the pharmaceutical composition of the invention.

Usually, the conventional cancer treatment consists in radiotherapy and/or chemotherapy.

In a further object the present invention provides the use of the compounds of the invention in a method for provoking apoptosis in a cell, either in vitro or in vivo, by inducing G0/G1 cell cycle arrest.

In a further object the present invention provides the use of the compounds of the invention in diagnosing, predicting, and/or monitoring of Notch dependent cancer in a subject.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Chemical Synthesis of Compounds

Abbreviations

AcOH acetic acid
brine saturated aqueous NaCl solution
CV column volumes
DCM dichloromethane
DME 1,2-dimethoxyethane
DMF dimethylformamide
DMSO-d6 deuterated dimethyl sulfoxide
equiv equivalent(s)
EtOAc ethyl acetate
$Et_2O$ diethyl ether
EtOH ethanol
expl. example
Fe iron
h hour(s)
M molar concentration
MeOH methanol
$MgSO_4$ magnesium sulfate
min minute(s)
mL milliliter(s)
Mw molecular weight
$NaHCO_3$ sodium bicarbonate
$Na_2SO_4$ sodium sulfate
Pd/C palladium on carbon
pTSA p-toluenesulfonic acid
RT room temperature
tBuOH tert.-butanol
tBuOK potassium tert.-butylate
TEA triethylamine
THF tetrahydrofurane
TLC thin layer chromatography ($R_f$: retention factor)

The following general procedure were used for the synthesis of the compounds reported:

General procedure A: Aromatic nucleophilic substitution with substituted phenol (refers to Scheme 1)

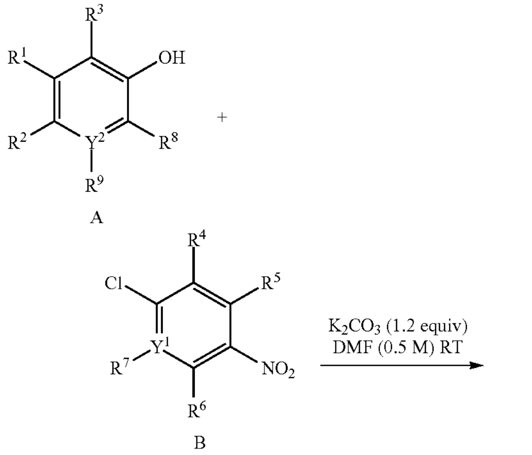

-continued

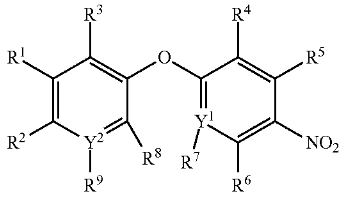

C

To the desired aryl alcohol A (1.1 equiv) and the corresponding 4-halo-nitroaryl B (1.0 equiv) in DMF (0.5 M), was added $K_2CO_3$ (1.2 equiv). The reaction was stirred at RT. After completion (monitored by TLC with EtOAc/hexanes or EtOAc/cyclohexane as eluent and stained with $KMnO_4$), usually observed after 14 h, the reaction mixture was poured into a mixture of $Et_2O$ and a saturated aqueous solution of $NaHCO_3$. The layers were separated and the aqueous phase extracted twice with $Et_2O$. The combined organic layers were washed with a saturated aqueous solution of $NaHCO_3$, dried over $Na_2SO_4$ or $MgSO_4$, filtered-off and concentrated under reduced pressure. The crude product was purified by combi flash column chromatography using EtOAc/hexanes or EtOAc/cyclohexane as the eluent, to afford the corresponding nitro compound C.

General procedure B: Nitro-aromatic reduction (refers to Scheme 1)

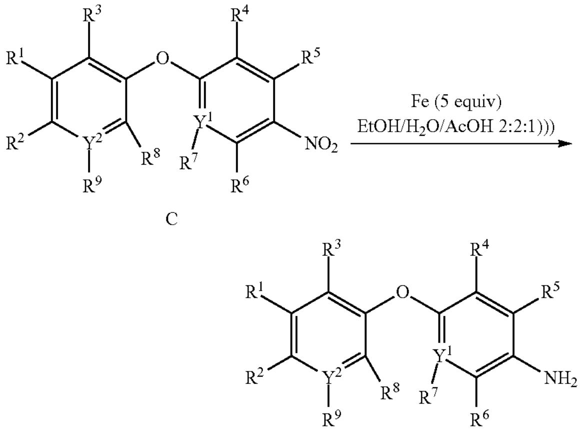

C

D

To the nitro compound C (1.0 equiv) were added Fe powder (5.0 equiv) and EtOH/$H_2O$/AcOH 2:2:1 (0.1 M). The reaction was sonicated until completion (monitored by TLC, with EtOAc/hexanes or EtOAc/cyclohexane as eluent and stained with $KMnO_4$). The obtained brown slurry was filtered through filter paper, rinsed with EtOAc and the organic solvents were evaporated. EtOAc was added followed by careful addition of a saturated aqueous solution of $NaHCO_3$. Layers were separated and the aqueous layer was extracted three times with EtOAc. The combined organic layers were dried over $MgSO_4$ or $Na_2SO_4$, filtered-off and the solvent was evaporated. The crude product was purified by combi flash column chromatography using EtOAc/hexanes or EtOAc/cyclohexane as the eluent, to afford the corresponding title compound D.

General procedure C: Aminoaryl methylation (refers to Scheme 2)

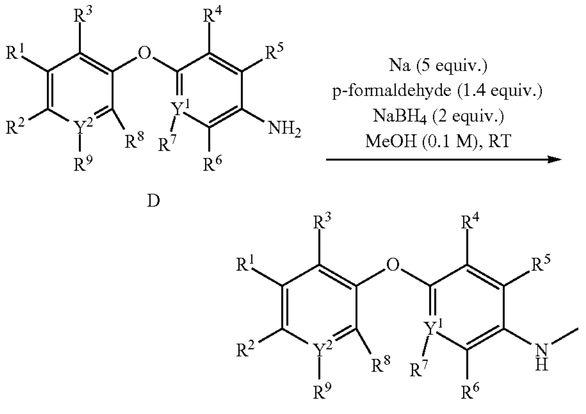

D

E

To a freshly prepared solution of sodium methoxide (Na 5.0 equiv, MeOH 0.1M) under inert atmosphere, the aminoaryl derivative D (1.0 equiv) was added. The reaction was stirred at RT (1 h). Then, para-formaldehyde (1.4 equiv) was added followed, after 16 h, by $NaBH_4$ (2.0 equiv). The mixture was stirred until completion (monitored by TLC). MeOH was evaporated and EtOAc followed by saturated aqueous $NaHCO_3$ were added. The layers were separated and the organic layer was washed with brine, dried over $MgSO_4$ or $Na_2SO_4$, filtered and evaporated under vacuum. The crude residue was purified by column chromatography using EtOAc/hexanes or EtOAc/cyclohexane as the eluent, to afford the target compound E.

General procedure D: Suzuki coupling

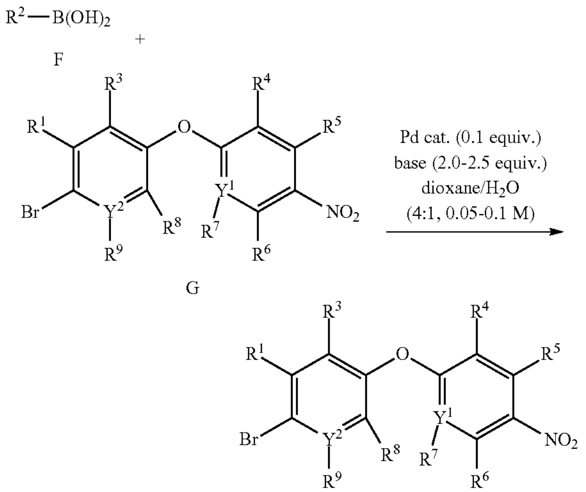

F

G

C

To a suspension of the desired boronic acid F (1.2 equiv), the desired bromoaryl G (1.0 equiv) and the accurate base (2.0-2.5 equiv) in dioxane/$H_2O$ 4:1 (0.05-0.1 M), the palladium catalyst (10% mol) was added. The reaction mixture was stirred at reflux. After 16 h, EtOAc and $H_2O$ were added. The layers were separated and the aqueous layer was extracted with EtOAc (2×). The combined organic layers were washed with brine, dried over $MgSO_4$ or $Na_2SO_4$, filtered through a pad of celite and concentrated under reduced pressure. The residue was purified by column chromatography using EtOAc/hexanes or EtOAc/cyclohexane as the eluent, to afford the target compound C.

N.B.: This procedure was also applied to Suzuki couplings between F as a bromoaryl derivative and G as aryl boronic acid/ester.

General procedure E: Suzuki coupling

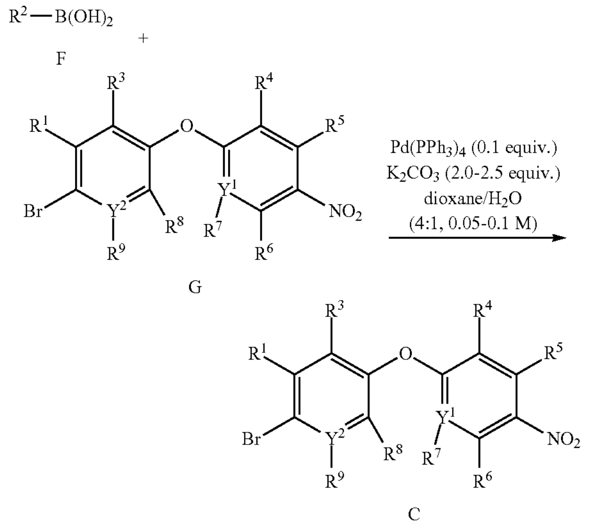

To a suspension of the desired boronic acid F (1.2 equiv), the desired bromoaryl G (1.0 equiv) and $K_2CO_3$ (2.0-2.5 equiv) in dioxane:$H_2O$ 4:1 (0.05-0.1 M), tetrakis(triphenylphosphine)palladium(0) (10% mol) was added. The reaction mixture was stirred at reflux. After 16 h, EtOAc and $H_2O$ were added. The layers were separated and the aqueous layer was extracted with EtOAc (2×). The combined organic layers were washed with brine, dried over $MgSO_4$ or $Na_2SO_4$, filtered through a pad of celite and concentrated under reduced pressure. The residue was purified by column chromatography using EtOAc/hexanes or EtOAc/cyclohexane as the eluent, to afford the target compound C.

General procedure F: Nitro-aromatic reduction (refers to Scheme 1)

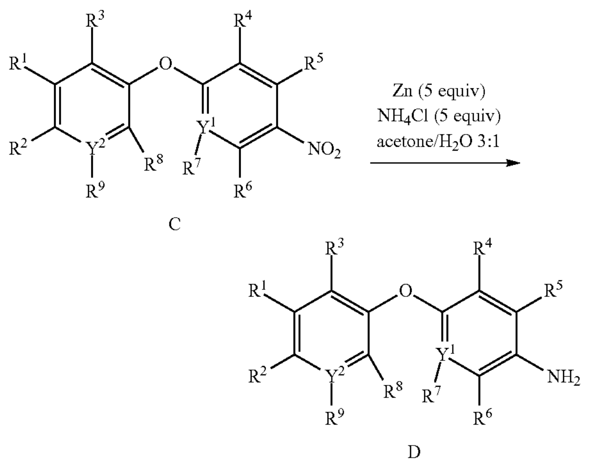

To a solution of the nitro compound C (1.0 equiv), at RT, in a 3:1 mixture of acetone/$H_2O$ was added $NH_4Cl$ (5 equiv). To this stirring solution Zn (5.0 equiv) was added in portions. The reaction mixture was stirred for 1 h (monitored by TLC, with EtOAc/hexanes or EtOAc/cyclohexane as eluent and stained with $KMnO_4$) and then concentrated under reduced pressure. The residue was suspended in EtOAc and filtered through a pad of celite which was washed with EtOAc. The filtrate was washed with $NaHCO_3$ (2×), dried over $MgSO_4$ or $Na_2SO_4$, filtered-off and the solvent was evaporated to afford the corresponding title compound D.

General procedure G: Aminoaryl methylation (refers to Scheme 2)

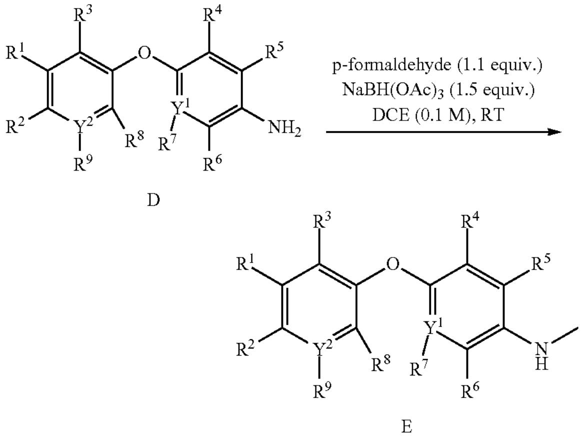

To a solution of the aminoaryl derivative D (1.0 equiv), in DCE (0.25M), at RT, was added para-formaldehyde (1.1 equiv). The mixture was stirred for 5 min before NaBH$(OAc)_3$ (1.5 equiv) was added followed by AcOH (1 equiv) addition. The reaction was stirred at RT overnight. The reaction mixture was quenched by adding 1M NaOH and diluted with $H_2O$ and $CH_2Cl_2$. The two layers were separated and the aqueous layer was extracted with $CH_2Cl_2$ (2×). The combined organic layers were washed with brine, dried over $MgSO_4$ or $Na_2SO_4$, filtered and evaporated under vacuum. The crude residue was purified by column chromatography using EtOAc/hexanes or EtOAc/cyclohexane as the eluent, to afford the target compound E.

Example 1: 6-([1,1'-Biphenyl]-4-yloxy)pyridin-3-amine

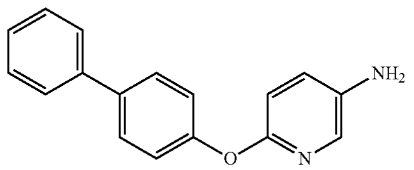

Following the General procedure B, 6-([1,1'-biphenyl]-4-yloxy)pyridin-3-amine was obtained in 97% yield (1.66 mmol, 434 mg) from 2-([1,1'-biphenyl]-4-yloxy)-5-nitropyridine (1.71 mmol, 500 mg).

$C_{17}H_{14}N_2O$; Mw=262.31 g·mol$^{-1}$; $^1$H NMR (400 MHz, $CDCl_3$) δ 7.75 (dd, J=3.0, 0.6 Hz, 1H), 7.61-7.52 (m, 4H), 7.47-7.39 (m, 2H), 7.36-7.29 (m, 1H), 7.17-7.06 (m, 3H), 6.82 (dd, J=8.6, 0.6 Hz, 1H); $^{13}$C NMR (101 MHz, $CDCl_3$)

δ 156.60, 155.34, 140.87, 138.96, 136.84, 134.28, 128.85, 128.45, 127.11, 127.09, 127.01, 120.20, 112.77, 77.48, 77.16, 76.84.

The starting material was prepared as follows:

Step 1: 2-([1,1'-Biphenyl]-4-yloxy)-5-nitropyridine

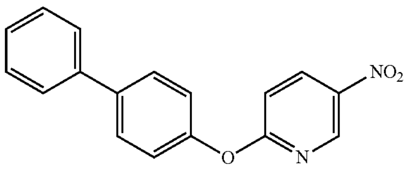

Following the General procedure A, 2-([1,1'-biphenyl]-4-yloxy)-5-nitropyridine was obtained in 99% yield without purification (4.65 mmol, 1.36 g) from [1,1'-biphenyl]-4-ol (4.70 mmol, 800 mg) and 2-chloro-5-nitropyridine (4.70 mmol, 745 mg).

$C_{17}H_{12}N_2O_3$; Mw=292.29 g·mol$^{-1}$; $^1$H NMR (400 MHz, $CDCl_3$) δ 9.08 (d, J=2.8 Hz, 1H), 8.50 (dd, J=9.1, 2.8 Hz, 1H), 7.67 (d, J=8.8 Hz, 2H), 7.60 (dd, J=8.3, 1.2 Hz, 2H), 7.46 (dd, J=8.2, 6.8 Hz, 2H), 7.40-7.33 (m, 1H), 7.26-7.20 (m, 2H), 7.08 (dd, J=9.1, 0.5 Hz, 1H).

Example 2: 6-([1,1'-Biphenyl]-4-yloxy)-N-methylpyridin-3-amine

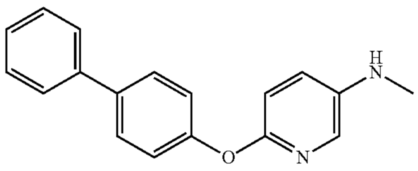

Following the General procedure C, 6-([1,1'-biphenyl]-4-yloxy)-N-methylpyridin-3-amine was obtained in 86% yield (3.98 mmol, 1.10 g) from 6-([1,1'-biphenyl]-4-yloxy)pyridin-3-amine (4.61 mmol, 1.21 g).

$C_{18}H_{16}N_2O$; Mw=276.34 g·mol$^{-1}$; $^1$H NMR (400 MHz, $CDCl_3$) δ 7.69 (d, J=3.0 Hz, 1H), 7.59-7.53 (m, 4H), 7.42 (t, J=7.6 Hz, 2H), 7.35-7.29 (m, 1H), 7.15-7.09 (m, 2H), 7.05 (dd, J=8.7, 3.1 Hz, 1H), 6.86 (d, J=8.7 Hz, 1H), 2.86 (s, 3H).

Example 3: 6-((6-Phenylpyridin-3-yl)oxy)pyridin-3-amine

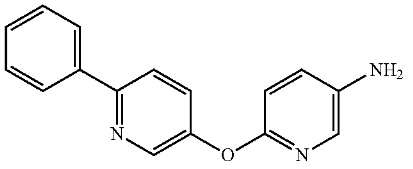

Following the General procedure B, 6-((6-phenylpyridin-3-yl)oxy)pyridin-3-amine was obtained in 93% yield (2.43 mmol, 0.64 g) from 5-nitro-2-((6-phenylpyridin-3-yl)oxy)pyridine (2.63 mmol, 0.77 g).

$C_{16}H_{13}N_3O$; Mw=263.30 g·mol$^{-1}$; Solid; $^1$H NMR (400 MHz, $CDCl_3$) δ 8.53 (d, J=2.7 Hz, 1H), 7.96 (d, J=7.3 Hz, 2H), 7.71 (dd, J=7.9, 5.9 Hz, 2H), 7.51 (dd, J=8.6, 2.7 Hz, 1H), 7.46 (t, J=7.5 Hz, 2H), 7.39 (t, J=7.3 Hz, 1H), 7.13 (dd, J=8.6, 2.9 Hz, 1H), 6.86 (d, J=8.6 Hz, 1H), 3.63 (s, 2H).

The starting material was prepared as follows:

Step 1: 5-Nitro-2-((6-phenylpyridin-3-yl)oxy)pyridine

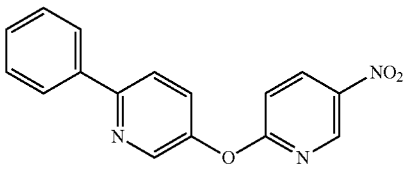

Following the General procedure A, 5-nitro-2-((6-phenylpyridin-3-yl)oxy)pyridine was obtained in 93% yield (2.63 mmol, 0.77 g) from 6-phenylpyridin-3-ol (2.92 mmol, 0.51 g) and 2-chloro-5-nitropyridine (2.84 mmol, 0.45 g).

$C_{16}H_{11}N_3O_3$; Mw=293.28 g·mol$^{-1}$; Solid; $^1$H NMR (400 MHz, $CDCl_3$) δ 9.04 (d, J=2.7 Hz, 1H), 8.59 (d, J=2.6 Hz, 1H), 8.54 (dd, J=9.0, 2.8 Hz, 1H), 8.04-7.97 (m, 2H), 7.83 (d, J=8.6 Hz, 1H), 7.62 (dd, J=8.6, 2.8 Hz, 1H), 7.52-7.47 (m, 2H), 7.45 (dd, J=4.9, 3.6 Hz, 1H), 7.16 (d, J=9.0 Hz, 1H).

Example 4: 3-Fluoro-4-(4-(pyridin-2-yl)phenoxy)aniline

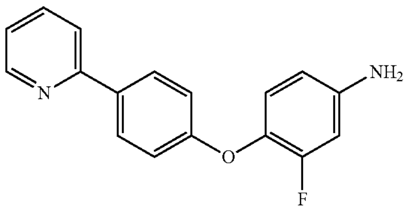

Following the General procedure B, 3-fluoro-4-(4-(pyridin-2-yl)phenoxy)aniline was obtained in 42% yield (1.8 mmol, 0.51 g) from 2-(4-(2-fluoro-4-nitrophenoxy)phenyl)pyridine (4.38 mmol, 1.36 g).

$C_{17}H_{13}FN_2O$; Mw=280.30 g·mol$^{-1}$; $^1$H NMR (400 MHz, $CDCl_3$) δ 8.63 (d, J=5.0 Hz, 1H), 7.90 (d, J=8.5 Hz, 2H), 7.75 (s, 1H), 7.66 (d, J=8.0 Hz, 1H), 7.28 (m, 1H), 7.02-6.94 (m, 2H), 6.90 (t, J=8.8 Hz, 1H), 6.46 (dd, J=12.0, 2.7 Hz, 1H), 6.39 (ddd, J=8.6, 2.7, 1.3 Hz, 1H).

The starting material was prepared as follows:

Step 1: 2-(4-(2-Fluoro-4-nitrophenoxy)phenyl)pyridine

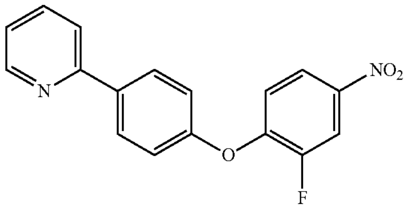

Following the General procedure A, 2-(4-(2-fluoro-4-nitrophenoxy)phenyl)pyridine was obtained in 30% yield (4.38 mmol, 1.36 g) from 4-(pyridin-2-yl)phenol (14.6 mmol, 2.50 g) and 1,2-difluoro-4-nitrobenzene (14.3 mmol, 2.28 g).

$C_{17}H_{11}FN_2O_3$; Mw=310.28 g·mol$^{-1}$; $^1$H NMR (400 MHz, $CDCl_3$) δ 8.71 (ddd, J=4.9, 1.8, 0.9 Hz, 1H), 8.12 (dd, J=10.2, 2.6 Hz, 1H), 8.10-8.04 (m, 2H), 8.01 (ddd, J=9.0, 2.6, 1.5 Hz, 1H), 7.84-7.76 (m, 1H), 7.76-7.71 (m, 1H), 7.29 (s, 1H), 7.23-7.16 (m, 2H), 7.06 (dd, J=9.1, 7.9 Hz, 1H).

Example 5:
3-Fluoro-4-(4-(pyridin-3-yl)phenoxy)aniline

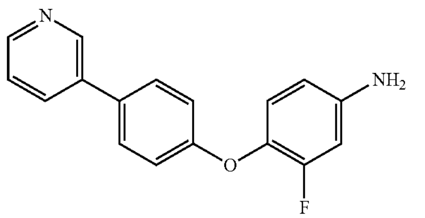

Following the General procedure B, 3-fluoro-4-(4-(pyridin-3-yl)phenoxy)aniline was obtained in 63% yield (11.1 mmol, 3.1 g) from 3-(4-(2-fluoro-4-nitrophenoxy)phenyl) pyridine (17.7 mmol, 5.48 g).

$C_{17}H_{13}FN_2O$; Mw=280.30 g·mol$^{-1}$; $^1$H NMR (400 MHz, $CDCl_3$) δ 8.82 (d, J=2.4 Hz, 1H), 8.57 (dd, J=5.0, 1.5 Hz, 1H), 7.95 (s, 1H), 7.52-7.47 (m, 2H), 7.45 (s, 1H), 7.06-7.00 (m, 2H), 6.97 (t, J=8.7 Hz, 1H), 6.54 (dd, J=12.0, 2.7 Hz, 1H), 6.46 (ddd, J=8.6, 2.7, 1.2 Hz, 1H).

The starting material was prepared as follows:

Step 1:
3-(4-(2-Fluoro-4-nitrophenoxy)phenyl)pyridine

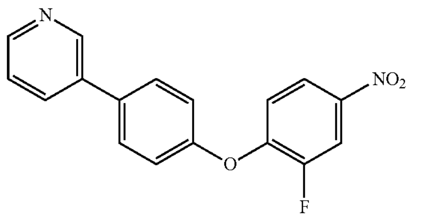 [SMILES: O=[N+]([O-])c1ccc(Oc2ccc(-c3cccnc3)cc2)c(F)c1]

Following the General procedure A, 3-(4-(2-fluoro-4-nitrophenoxy)phenyl)pyridine was obtained in 79% yield (17.7 mmol, 5.48 g) from 4-(pyridin-3-yl)phenol (22.4 mmol, 3.84 g) and 1,2-difluoro-4-nitrobenzene (22.0 mmol, 3.50 g).

$C_{17}H_{11}FN_2O_3$; Mw=310.28 g·mol$^{-1}$; $^1$H NMR (400 MHz, $CDCl_3$) δ 8.88 (s, 1H), 8.64 (d, J=5.0 Hz, 1H), 8.13 (dd, J=10.2, 2.7 Hz, 1H), 8.09-7.98 (m, 2H), 7.69-7.61 (m, 2H), 7.55-7.48 (m, 1H), 7.23-7.17 (m, 2H), 7.11 (dd, J=9.0, 7.8 Hz, 1H).

Example 6: 4-([1,1'-Biphenyl]-4-yloxy)-3-fluoro-N-methylaniline

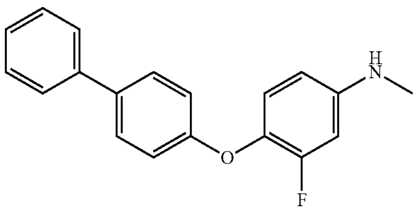 [SMILES: CNc1ccc(Oc2ccc(-c3ccccc3)cc2)c(F)c1]

Following the General procedure C, 4-([1,1'-biphenyl]-4-yloxy)-3-fluoro-N-methylaniline was obtained in 77% yield (3.2 mmol, 0.93 g) from 4-([1,1'-biphenyl]-4-yloxy)-3-fluoroaniline (4.1 mmol, 1.15 g).

$C_{19}H_{16}FNO$; Mw=293.34 g·mol$^{-1}$; $^1$H NMR (400 MHz, $CDCl_3$) δ 7.57-7.52 (m, 2H), 7.52-7.47 (m, 2H), 7.41 (t, J=7.6 Hz, 2H), 7.31 (t, J=7.4 Hz, 1H), 7.03-6.95 (m, 3H), 6.46 (dd, J=12.7, 2.7 Hz, 1H), 6.39 (dd, J=8.7, 1.7 Hz, 1H), 4.04 (s, 1H), 2.85 (s, 3H).

The starting material was prepared as follows:

Step 1:
1-(4-Bromophenoxy)-2-fluoro-4-nitrobenzene

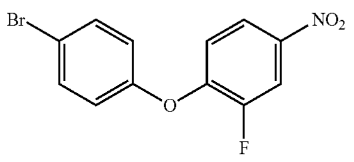 [SMILES: O=[N+]([O-])c1ccc(Oc2ccc(Br)cc2)c(F)c1]

Following the General procedure A, 1-(4-bromophenoxy)-2-fluoro-4-nitrobenzene was obtained in 96% yield (12.0 mmol, 3.73 g) from 4-bromophenol (12.8 mmol, 2.21 g) and 1,2-difluoro-4-nitrobenzene (12.5 mmol, 1.99 g).

$C_{12}H_7BrFNO_3$; Mw=312.09 g·mol$^{-1}$; $^1$H NMR (400 MHz, $CDCl_3$) δ 8.10 (dd, J=10.2, 2.7 Hz, 1H), 8.01 (ddd, J=9.1, 2.7, 1.6 Hz, 1H), 7.57-7.51 (m, 2H), 7.05-7.00 (m, 1H), 7.00-6.94 (m, 2H).

Step 2: 4-(2-Fluoro-4-nitrophenoxy)-1,1'-biphenyl

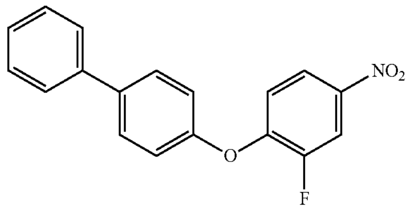

Following the General procedure E, a mixture of phenylboronic acid (12.1 mmol, 1.48 g), 1-(4-bromophenoxy)-2-fluoro-4-nitrobenzene (9.9 mmol, 3.10 g), $K_2CO_3$ (21.5 mmol, 2.97 g) and $Pd(PPh_3)_4$ (10% mol) in dioxane/$H_2O$ 4:1 (0.05-0.1 M) was converted to 4-(2-fluoro-4-nitrophenoxy)-1,1'-biphenyl in 56% yield (5.6 mmol, 1.72 g).

$C_{18}H_{12}FNO_3$; Mw=309.30 g·mol$^{-1}$; $^1$H NMR (400 MHz, $CDCl_3$) δ 8.11 (dd, J=10.2, 2.6 Hz, 1H), 8.01 (ddd, J=9.1, 2.6, 1.5 Hz, 1H), 7.67-7.62 (m, 2H), 7.61-7.56 (m, 2H), 7.46 (t, J=7.5 Hz, 2H), 7.37 (t, J=7.3 Hz, 1H), 7.19-7.14 (m, 2H), 7.06 (dd, J=9.0, 8.0 Hz, 1H).

Step 3: 4-([1,1'-Biphenyl]-4-yloxy)-3-fluoroaniline

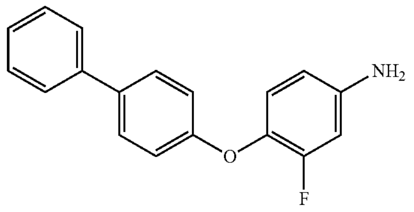 [SMILES: O=[N+]([O-])c1ccc(Oc2ccc(-c3ccccc3)cc2)c(F)c1]

Following the General procedure B, 4-([1,1'-biphenyl]-4-yloxy)-3-fluoroaniline was obtained in 85% yield (4.7 mmol, 1.31 g) from 4-(2-fluoro-4-nitrophenoxy)-1,1'-biphenyl (5.5 mmol, 1.70 g).

$C_{18}H_{14}FNO$; Mw=279.31 g $mol^{-1}$; $^{1}H$ NMR (400 MHz, $CDCl_3$) δ 7.58-7.52 (m, 2H), 7.52-7.48 (m, 2H), 7.41 (t, J=7.6 Hz, 2H), 7.31 (t, J=7.4 Hz, 1H), 7.01-6.93 (m, 3H), 6.53 (dd, J=12.0, 2.7 Hz, 1H), 6.48-6.42 (m, 1H), 3.70 (br s, 2H).

Example 7: 4-([1,1'-Biphenyl]-4-yloxy)aniline

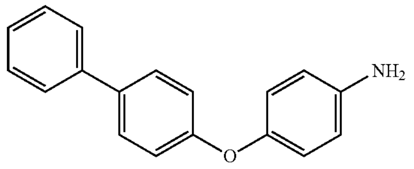 [SMILES: O=[N+]([O-])c1ccc(Oc2ccc(-c3ccccc3)cc2)cc1]

Following the General procedure B, 4-([1,1'-biphenyl]-4-yloxy)aniline was obtained in 33% yield (2.4 mmol, 0.62 g) from 4-(4-nitrophenoxy)-1,1'-biphenyl (7.1 mmol, 2.08 g). $C_{18}H_{15}NO$; Mw=261.32 g·$mol^{-1}$; $^{1}H$ NMR (400 MHz, $CDCl_3$) δ 7.57-7.53 (m, 2H), 7.53-7.47 (m, 2H), 7.45-7.39 (m, 2H), 7.34-7.28 (m, 1H), 7.03-6.97 (m, 2H), 6.95-6.89 (m, 2H), 6.74-6.66 (m, 2H), 3.61 (br s, 2H).

The starting material was prepared as follows:

Step 1: 4-(4-Nitrophenoxy)-1,1'-biphenyl

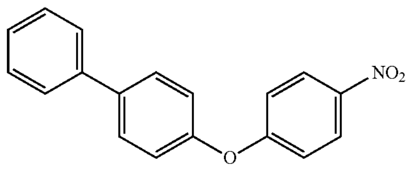

Following the General procedure A, 4-(4-nitrophenoxy)-1,1'-biphenyl was obtained in 61% yield (7.1 mmol, 2.08 g) from [1,1'-biphenyl]-4-ol (11.8 mmol, 2.00 g) and 4-fluoronitrobenzene (11.5 mmol, 1.63 g).

$C_{18}H_{13}NO_3$; Mw=291.31 g·$mol^{-1}$; $^{1}H$ NMR (400 MHz, $CDCl_3$) δ 8.26-8.20 (m, 2H), 7.69-7.63 (m, 2H), 7.62-7.57 (m, 2H), 7.50-7.43 (m, 2H), 7.41-7.34 (m, 1H), 7.19-7.14 (m, 2H), 7.11-7.05 (m, 2H).

Example 8: 6-([1,1'-Biphenyl]-4-yloxy)-2-methylpyridin-3-amine

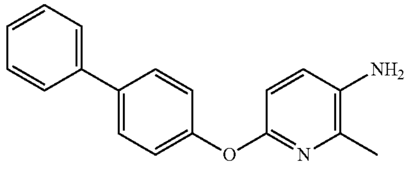 [SMILES: Cc1nc(Oc2ccc(-c3ccccc3)cc2)ccc1N]

Following the General procedure B, 6-([1,1'-biphenyl]-4-yloxy)-2-methylpyridin-3-amine was obtained in 90% yield (4.7 mmol, 1.31 g) from 6-([1,1'-biphenyl]-4-yloxy)-2-methyl-3-nitropyridine (5.3 mmol, 1.61 g).

$C_{18}H_{16}N_2O$; Mw=276.34 g·$mol^{-1}$; $^{1}HNMR$ (400 MHz, $CDCl_3$) δ 7.59-7.52 (m, 4H), 7.42 (t, J=7.6 Hz, 2H), 7.32 (ddd, J=7.4, 3.9, 1.2 Hz, 1H), 7.10 (d, J=8.7 Hz, 2H), 7.02 (d, J=8.4 Hz, 1H), 6.63 (d, J=8.4 Hz, 1H), 3.49 (s, 2H), 2.37 (s, 3H).

The starting material was prepared as follows:

Step 1: 6-([1,1'-Biphenyl]-4-yloxy)-2-methyl-3-nitropyridine

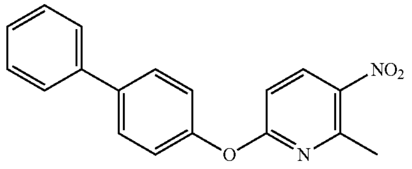 [SMILES: Cc1nc(Oc2ccc(-c3ccccc3)cc2)ccc1[N+](=O)[O-]]

Following the General procedure A, 6-([1,1'-biphenyl]-4-yloxy)-2-methyl-3-nitropyridine was obtained in 89% yield (5.3 mmol, 1.63 g) from [1,1'-biphenyl]-4-ol (5.9 mmol, 1.00 g) and 6-chloro-2-methyl-3-nitropyridine (5.8 mmol, 1.00 g).

$C_{18}H_{14}N_2O_3$; Mw=306.32 g·$mol^{-1}$; $^{1}HNMR$ (400 MHz, $CDCl_3$) δ 8.38 (d, J=8.9 Hz, 1H), 7.63 (dd, J=16.5, 7.9 Hz, 4H), 7.46 (t, J=7.6 Hz, 2H), 7.37 (dd, J=8.3, 6.4 Hz, 1H), 7.24 (d, J=8.7 Hz, 2H), 6.84 (d, J=8.9 Hz, 1H), 2.78 (s, 3H).

Example 9: 6-([1,1'-Biphenyl]-4-yloxy)-4-methylpyridin-3-amine

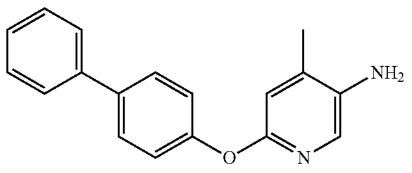 [SMILES: Cc1cc(Oc2ccc(-c3ccccc3)cc2)ncc1N]

Following the General procedure B, 6-([1,1'-biphenyl]-4-yloxy)-4-methylpyridin-3-amine was obtained in 74% yield (1.5 mmol, 410 mg) from 6-([1,1'-biphenyl]-4-yloxy)-4-methyl-3-nitropyridine (2.0 mmol, 600 mg).

$C_{18}H_{16}N_2O$; Mw=276.34 g·$mol^{-1}$; $^{1}HNMR$ (400 MHz, $CDCl_3$) δ 7.69 (s, 1H), 7.61-7.52 (m, 4H), 7.42 (t, J=7.6 Hz, 2H), 7.33 (dt, J=9.2, 4.3 Hz, 1H), 7.12 (d, J=8.7 Hz, 2H), 6.72 (s, 1H), 3.03 (s, 2H), 2.21 (d, J=0.5 Hz, 3H).

The starting material was prepared as follows:

Step 1: 6-([1,1'-Biphenyl]-4-yloxy)-4-methyl-3-nitropyridine

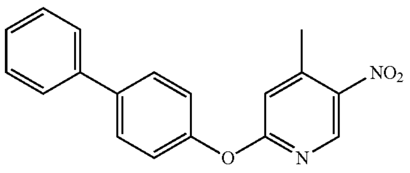 [SMILES: Cc1cc(Oc2ccc(-c3ccccc3)cc2)ncc1[N+](=O)[O-]]

Following the General procedure A, 6-([1,1'-biphenyl]-4-yloxy)-4-methyl-3-nitropyridine was obtained in 38% yield (2.3 mmol, 0.71 g) from [1,1'-biphenyl]-4-ol (5.9 mmol, 1.00 g) and 6-chloro-4-methyl-3-nitropyridine (5.8 mmol, 1.00 g).

$C_{18}H_{14}N_2O_3$; Mw=306.32 g·mol$^{-1}$; $^1$H NMR (400 MHz, $CDCl_3$) δ 8.92 (s, 1H), 7.69-7.63 (m, 2H), 7.63-7.57 (m, 2H), 7.49-7.42 (m, 2H), 7.40-7.34 (m, 1H), 7.25-7.20 (m, 2H), 6.88 (d, J=0.9 Hz, 1H), 2.69 (d, J=0.8 Hz, 3H).

Example 10: 6-((4'-Fluoro-[1,1'-biphenyl]-4-yl)oxy) pyridin-3-amine

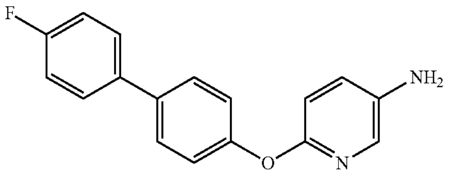

Following the General procedure B, 6-((4'-fluoro-[1,1'-biphenyl]-4-yl)oxy)pyridin-3-amine was obtained in 58% yield (3.9 mmol, 1.10 g) from 2-((4'-fluoro-[1,1'-biphenyl]-4-yl)oxy)-5-nitropyridine (6.8 mmol, 2.10 g).

$C_{17}H_{13}FN_2O$; Mw=280.30 g·mol$^{-1}$; $^1$H NMR (400 MHz, $CDCl_3$) δ 7.75 (d, J=3.0 Hz, 1H), 7.51 (m, 4H), 7.16-7.07 (m, 5H), 6.82 (d, J=8.6 Hz, 1H). $^{19}$F NMR (376 MHz, Chloroform-d) δ 116.54.

The starting materials were prepared as followed:

Step 1: 2-(4-Bromophenoxy)-5-nitropyridine

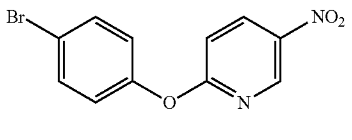 [SMILES: O=[N+]([O-])c1ccc(Oc2ccc(Br)cc2)nc1]

Following the General procedure A, 2-(4-bromophenoxy)-5-nitropyridine was obtained in 89% yield (37.2 mmol, 10.97 g) from 4-bromophenol (42.8 mmol, 7.40 g) and 2-chloro-5-nitropyridine (41.6 mmol, 6.60 g).

$C_{11}H_7BrN_2O_3$; Mw=295.09 g·mol$^{-1}$; $^1$H NMR (400 MHz, $CDCl_3$) δ 9.03 (d, J=2.6 Hz, 1H), 8.49 (dd, J=9.0, 2.8 Hz, 1H), 7.57 (d, J=8.8 Hz, 2H), 7.06 (m, 3H).

Step 2: 2-((4'-Fluoro-[1,1'-biphenyl]-4-yl)oxy)-5-nitropyridine

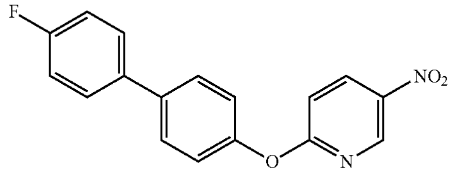

Following the General procedure E, a mixture of 4-fluorophenylboronic acid (8.9 mmol, 1.25 g), 2-(4-bromophenoxy)-5-nitropyridine (7.8 mmol, 2.30 g), $K_2CO_3$ (19.5 mmol, 2.70 g) and $Pd(PPh_3)_4$ (10% mol) in dioxane/$H_2O$ 4:1 (0.05-0.1 M) was converted to 24(4'-fluoro-[1,1'-biphenyl]-4-yl)oxy)-5-nitropyridine in 87% yield (6.8 mmol, 2.10 g).

$C_{17}H_{11}FN_2O_3$; Mw=310.28 g·mol$^{-1}$; $^1$H NMR (400 MHz, $CDCl_3$) δ 9.07 (d, J=2.7 Hz, 1H), 8.50 (dd, J=9.0, 2.7 Hz, 1H), 7.62 (d, J=8.5 Hz, 2H), 7.55 (dd, J=8.5, 5.4 Hz, 2H), 7.23 (d, J=8.6 Hz, 2H), 7.14 (t, J=8.6 Hz, 2H), 7.09 (d, J=9.0 Hz, 1H).

Example 11: 6-(4-(Thiazol-5-yl)phenoxy)pyridin-3-amine

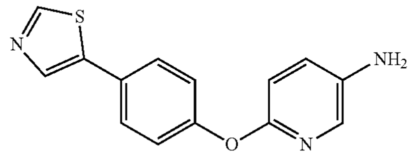

Following the General procedure B, 6-(4-(thiazol-5-yl) phenoxy)pyridin-3-amine was obtained in 46% yield (1.8 mmol, 0.48 g) from 5-(4-((5-nitropyridin-2-yl)oxy)phenyl) thiazole (3.8 mmol, 1.15 g).

$C_{14}H_{11}N_3OS$; Mw=269.32 g·mol$^{-1}$; $^1$H NMR (400 MHz, $CDCl_3$) δ 8.67 (s, 1H), 7.95 (s, 1H), 7.67 (d, J=3.0 Hz, 1H), 7.49 (d, J=8.7 Hz, 2H), 7.05 (m, 3H), 6.76 (d, J=8.6 Hz, 1H).

The starting material was prepared as follows:

Step 1: 5-Nitro-2-(4-(4,4,5,5-tetramethyl-1,3,2-dioxaborolan-2-yl)phenoxy)pyridine

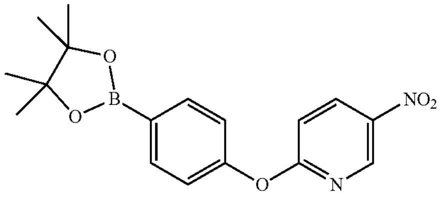 [SMILES: CC1(C)OB(c2ccc(Oc3ccc([N+](=O)[O-])cn3)cc2)OC1(C)C]

To a suspension of 2-(4-bromophenoxy)-5-nitropyridine (20.6 mmol, 6.08 g), $CH_3COOK$ (61.1 mmol, 6.00 g) and bis(pinacolato)diboron (30.5 mmol, 7.75 g) in dioxane (0.1 M, 150 mL) under inert atmosphere, $Pd(dppf)Cl_2CH_2Cl_2$ (5% mol) was added. The red mixture was stirred 16 h at 105° C. The reaction mixture was filtered through a pad of celite. Water was added to the filtrate and the mixture was extracted with EtOAc (2×). The organic layer was washed with sat. aq. $NaHCO_3$, brine, dried over $Na_2SO_4$, filtered-off and concentrated. The crude product was purified by combi flash column chromatography using EtOAc/cyclohexane (1% to 20%) as the eluent, to afford 5-nitro-2-(4-(4,4,5,5-tetramethyl-1,3,2-dioxaborolan-2-yl)phenoxy)pyridine (15.6 mmol, 5.93 g, 76% yield).

$C_{17}H_{19}BN_2O_5$; Mw=342.16 g·mol$^{-1}$; $^1$H NMR (400 MHz, $CDCl_3$) δ 9.04 (d, J=2.5 Hz, 1H), 8.47 (dd, J=9.1, 2.8 Hz, 1H), 7.94-7.88 (m, 2H), 7.20-7.13 (m, 2H), 7.06-7.01 (m, 1H), 1.35 (s, 12H).

Step 2: 5-(4-((5-Nitropyridin-2-yl)oxy)phenyl)thiazole

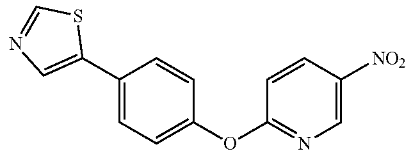 [SMILES: O=[N+]([O-])c1ccc(Oc2ccc(-c3cncs3)cc2)nc1]

Following the General procedure D, a mixture of 5-nitro-2-(4-(4,4,5,5-tetramethyl-1,3,2-dioxaborolan-2-yl)phenoxy) pyridine (9.2 mmol, 3.50 g), 5-bromothiazole (7.4 mmol, 1.25 g), $Cs_2CO_3$ (15.0 mmol, 4.90 g) and $PdCl_2(PPh_3)_2$ (10% mol) in dioxane/$H_2O$ 4:1 (0.05-0.1 M) was converted to 5-(4-((5-nitropyridin-2-yl)oxy)phenyl)thiazole in 52% yield (3.8 mmol, 1.15 g).

$C_{14}H_9N_3O_3S$; Mw=299.30 g·mol$^{-1}$; $^1$H NMR (400 MHz, $CDCl_3$) δ 9.05 (d, J=2.6 Hz, 1H), 8.78 (s, 1H), 8.51 (dd, J=9.1, 2.8 Hz, 1H), 8.08 (s, 1H), 7.67 (d, J=8.2 Hz, 2H), 7.23 (d, J=8.4 Hz, 2H), 7.10 (d, J=9.0 Hz, 1H).

Example 12: 4-((2,2'-Dimethyl-[1,1'-biphenyl]-4-yl) oxy)aniline

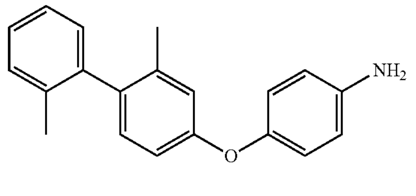 [SMILES: Cc1ccccc1-c1ccc(Oc2ccc(N)cc2)cc1C]

Following the General procedure B, 4-((2,2'-dimethyl-[1,1'-biphenyl]-4-yl)oxy)aniline was obtained in 88% yield (21.9 mmol, 6.33 g) from 2,2'-dimethyl-4-(4-nitrophenoxy)-1,1'-biphenyl (24.9 mmol, 7.96 g).

$C_{20}H_{19}NO$; Mw=289.38 g·mol$^{-1}$; $^1$H NMR (400 MHz, $CDCl_3$) δ 7.26-7.24 (m, 2H), 7.23-7.18 (m, 1H), 7.10 (d, J=6.8 Hz, 1H), 7.00 (d, J=8.3 Hz, 1H), 6.96-6.91 (m, 2H), 6.84 (d, J=2.5 Hz, 1H), 6.77 (dd, J=8.4, 2.6 Hz, 1H), 6.75-6.71 (m, 2H), 2.07 (s, 3H), 2.00 (s, 3H).

The starting material was prepared as follows:

Step 1: 1-Bromo-2-methyl-4-(4-nitrophenoxy)benzene

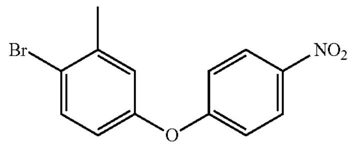 [SMILES: Cc1cc(Oc2ccc([N+](=O)[O-])cc2)ccc1Br]

Following the General procedure A, 1-bromo-2-methyl-4-(4-nitrophenoxy)benzene was obtained in 91% yield (27.1 mmol, 8.34 g) from 4-bromo-3-methyl-phenol (31.5 mmol, 6.01 g) and 4-fluoro-nitrobenzene (29.9 mmol, 4.22 g).

$C_{13}H_{10}BrNO_3$; Mw=308.13 g·mol$^{-1}$; $^1$H NMR (400 MHz, $CDCl_3$) δ 8.24-8.18 (m, 2H), 7.57 (d, J=8.6 Hz, 1H), 7.05-6.96 (m, 3H), 6.80 (dd, J=8.6, 2.9 Hz, 1H), 2.41 (s, 3H).

Step 2: 2,2'-Dimethyl-4-(4-nitrophenoxy)-1,1'-biphenyl

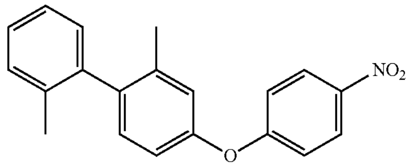

Following the General procedure E, a mixture of o-tolylboronic acid (30.9 mmol, 4.20 g), 1-bromo-2-methyl-4-(4-nitrophenoxy)benzene (27.1 mmol, 8.34 g), $K_2CO_3$ (55.0 mmol, 7.60 g) and $Pd(PPh_3)_4$ (10% mol) in dioxane/$H_2O$ 4:1 (0.05-0.1 M) was converted to 2,2'-dimethyl-4-(4-nitrophenoxy)-1,1'-biphenyl in 92% yield (24.9 mmol, 7.96 g).

$C_{20}H_{17}NO_3$; Mw=319.36 g·mol$^{-1}$; $^1$H NMR (400 MHz, $CDCl_3$) δ 8.26-8.21 (m, 2H), 7.31-7.27 (m, 2H), 7.24 (d, J=4.8 Hz, 1H), 7.14 (dd, J=14.2, 7.6 Hz, 2H), 7.11-7.04 (m, 2H), 7.00 (d, J=2.5 Hz, 1H), 6.95 (dd, J=8.2, 2.2 Hz, 1H), 2.09 (s, 3H), 2.07 (s, 3H).

Example 13: 4-((2,2'-Dimethyl-[1,1'-biphenyl]-4-yl) oxy)-N-methylaniline

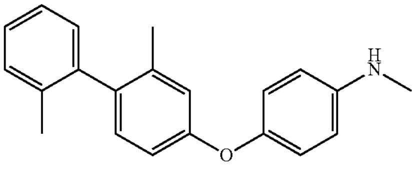 [SMILES: CNc1ccc(Oc2ccc(-c3ccccc3C)c(C)c2)cc1]

Following the General procedure C, 4-((2,2'-dimethyl-[1,1'-biphenyl]-4-yl)oxy)-N-methylaniline was obtained in 86% yield (8.9 mmol, 2.70 g) from 4-((2,2'-dimethyl-[1,1'-biphenyl]-4-yl)oxy)aniline (10.4 mmol, 3.00 g).

$C_{21}H_{21}NO$; Mw=303.41 g·mol$^{-1}$; $^1$H NMR (400 MHz, $CDCl_3$) δ 7.26-7.23 (m, 2H), 7.20 (ddd, J=9.0, 5.8, 3.7 Hz, 1H), 7.10 (d, J=6.8 Hz, 1H), 7.04-6.95 (m, 3H), 6.84 (s, 1H), 6.77 (dd, J=8.2, 2.1 Hz, 1H), 6.64 (d, J=7.9 Hz, 2H), 3.78 (s, 1H), 2.86 (s, 3H), 2.07 (s, 3H), 2.00 (s, 3H).

Example 14: 6-((2,2'-Dimethyl-[1,1'-biphenyl]-4-yl) oxy)-N-methylpyridin-3-amine

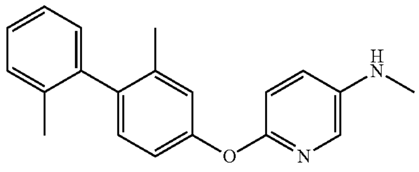 [SMILES: CNc1ccc(Oc2ccc(-c3ccccc3C)c(C)c2)nc1]

Following the General procedure C, 6-((2,2'-dimethyl-[1, 1'-biphenyl]-4-yl)oxy)-N-methylpyridin-3-amine was obtained in 78% yield (0.2 mmol, 53 mg) from 6-((2,2'-dimethyl-[1,1'-biphenyl]-4-yl)oxy)pyridin-3-amine (0.2 mmol, 65 mg).

$C_{20}H_{20}N_2O$; Mw=304.39 g·mol$^{-1}$; $^1$H NMR (400 MHz, $CDCl_3$) δ 7.72 (d, J=3.0 Hz, 1H), 7.26-7.24 (m, 2H), 7.21 (m, 1H), 7.11 (d, J=6.8 Hz, 1H), 7.08-7.02 (m, 2H), 6.95 (d, J=2.5 Hz, 1H), 6.89 (dd, J=8.2, 2.6 Hz, 1H), 6.86 (d, J=8.7 Hz, 1H), 2.87 (s, 3H), 2.08 (s, 3H), 2.02 (s, 3H).

The starting material was prepared as follows:

Step 1: 2-(4-Bromo-3-methylphenoxy)-5-nitropyridine

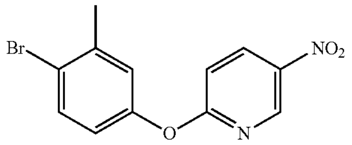 [SMILES: Cc1cc(Oc2ccc([N+](=O)[O-])cn2)ccc1Br]

Following the General procedure A, 2-(4-bromo-3-methylphenoxy)-5-nitropyridine was obtained in 98% yield (6.2 mmol, 1.93 g) from 4-bromo-3-methyl-phenol (6.8 mmol, 1.28 g) and 2-chloro-5-nitropyridine (6.4 mmol, 1.01 g).

$C_{12}H_9BrN_2O_3$; Mw=309.12 g·mol$^{-1}$; $^1$H NMR (400 MHz, $CDCl_3$) δ 9.04 (d, J=2.7 Hz, 1H), 8.49 (dd, J=9.0, 2.9 Hz, 1H), 7.59 (d, J=8.6 Hz, 1H), 7.10-7.01 (m, 2H), 6.88 (dd, J=8.6, 2.8 Hz, 1H), 2.42 (s, 3H).

Step 2: 2-((2,2'-Dimethyl-[1,1'-biphenyl]-4-yl)oxy)-5-nitropyridine

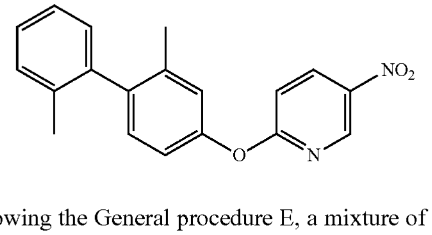

Following the General procedure E, a mixture of o-tolylboronic acid (1.9 mmol, 264 mg), 2-(4-bromo-3-methylphenoxy)-5-nitropyridine (1.3 mmol, 400 mg), $K_2CO_3$ (2.6 mmol, 358 mg) and $Pd(PPh_3)_4$ (10% mol) in dioxane/$H_2O$ 4:1 (0.05-0.1 M) was converted to 2-((2,2'-dimethyl-[1,1'-biphenyl]-4-yl)oxy)-5-nitropyridine in 95% yield (1.2 mmol, 392 mg). $C_{19}H_{16}N_2O_3$; Mw=320.35 g·mol$^{-1}$; $^1$H NMR (400 MHz, $CDCl_3$) δ 9.11 (d, J=2.8 Hz, 1H), 8.49 (dd, J=9.1, 2.8 Hz, 1H), 7.35-7.31 (m, 1H), 7.29 (m, 1H), 7.25-7.22 (m, 1H), 7.18 (d, J=8.2 Hz, 1H), 7.15 (dt, J=7.0, 1.2 Hz, 1H), 7.09-7.00 (m, 3H), 2.10 (s, 3H), 2.09 (s, 3H).

Step 3: 6-((2,2'-Dimethyl-[1,1'-biphenyl]-4-yl)oxy) pyridin-3-amine

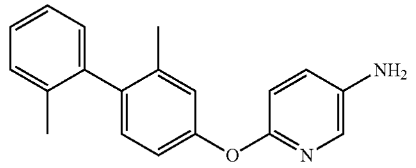 [SMILES: Cc1ccccc1-c1ccc(Oc2ccc([N+](=O)[O-])cn2)cc1C]

Following the General procedure B, 6-((2,2'-dimethyl-[1, 1'-biphenyl]-4-yl)oxy)pyridin-3-amine was obtained in 37% yield (0.5 mmol, 132 mg) from 2-((2,2'-dimethyl-[1,1'-biphenyl]-4-yl)oxy)-5-nitropyridine (1.2 mmol, 392 mg).

$C_{19}H_{18}N_2O$; Mw=290.37 g·mol$^{-1}$; $^1$H NMR (400 MHz, $CDCl_3$) δ 7.79 (d, J=2.8 Hz, 1H), 7.25 (s, 2H), 7.23-7.18 (m, 1H), 7.12 (t, J=6.2 Hz, 2H), 7.06 (d, J=8.2 Hz, 1H), 6.96 (d, J=1.9 Hz, 1H), 6.90 (dd, J=8.3, 2.3 Hz, 1H), 6.82 (d, J=8.6 Hz, 1H), 2.85 (s, 2H), 2.08 (s, 3H), 2.02 (s, 3H).

Example 15: 3-Fluoro-4-(4-(pyridin-4-yl)phenoxy)aniline

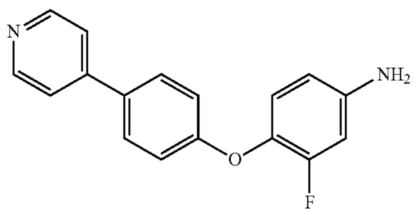 [SMILES: Nc1ccc(Oc2ccc(-c3ccncc3)cc2)c(F)c1]

Following the General procedure B, 3-fluoro-4-(4-(pyridin-4-yl)phenoxy)aniline was obtained in 71% yield (211 mg, 0.752 mmol) from 4-(4-(2-fluoro-4-nitrophenoxy)phenyl)pyridine (330 mg, 1.06 mmol).

$C_{17}H_{13}FN_2O$; Mw=280.30 g·mol$^{-1}$; $^1$H NMR (400 MHz, DMSO-d6) δ 8.59 (dd, J=4.5, 1.6 Hz, 2H), 7.80-7.74 (m, 2H), 7.65 (dd, J=4.5, 1.6 Hz, 2H), 7.01-6.93 (m, 3H), 6.51 (dd, J=13.3, 2.5 Hz, 1H), 6.44-6.39 (m, 1H), 5.39 (s, 2H).

The starting material was prepared as follows:

Step 1: 4-(4-(2-Fluoro-4-nitrophenoxy)phenyl)pyridine

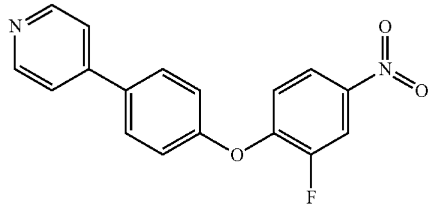 [SMILES: O=[N+]([O-])c1ccc(Oc2ccc(-c3ccncc3)cc2)c(F)c1]

Following the General procedure E, 4-(4-(2-fluoro-4-nitrophenoxy)phenyl)pyridine was obtained in 75% yield (300 mg, 0.967 mmol) from 1-(4-bromophenoxy)-2-fluoro-4-nitrobenzene (400 mg, 1.28 mmol; Example 6: Step 1).

$C_{17}H_{11}FN_2O_3$; Mw=310.28 g·mol$^{-1}$; $^1$H NMR (400 MHz, $CDCl_3$) δ 8.68 (d, J=6.1 Hz, 2H), 8.13 (dd, J=10.2, 2.7 Hz, 1H), 8.04 (ddd, J=9.0, 2.6, 1.5 Hz, 1H), 7.70 (d, J=8.8 Hz, 2H), 7.49 (d, J=6.2 Hz, 2H), 7.19 (d, J=8.8 Hz, 2H), 7.10 (dd, J=9.0, 7.9 Hz, 1H).

Example 16: 6-(4-(Thiazol-2-yl)phenoxy)pyridin-3-amine

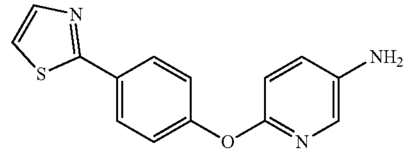 [SMILES: Nc1ccc(Oc2ccc(-c3nccs3)cc2)nc1]

Following the General procedure B, 6-(4-(thiazol-2-yl) phenoxy)pyridin-3-amine was obtained in 21% yield (15 mg, 0.057 mmol) from 2-(4-((5-nitropyridin-2-yl)oxy)phenyl)thiazole (100 mg, 0.300 mmol).

$C_{14}H_{11}N_3OS$; Mw=269.32 g·mol$^{-1}$; $^1$H NMR (400 MHz, $CDCl_3$) δ 8.00-7.95 (m, 2H), 7.85 (d, J=3.3 Hz, 1H), 7.77 (d, J=3.0 Hz, 1H), 7.31 (d, J=3.3 Hz, 1H), 7.16-7.11 (m, 3H), 6.84 (d, J=8.5 Hz, 1H).

The starting material was prepared as follows:

Step 1: 2-(4-((5-Nitropyridin-2-yl)oxy)phenyl)thiazole

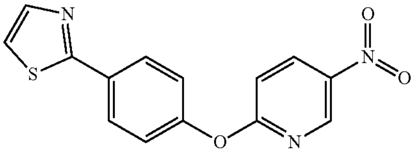 [SMILES: O=[N+]([O-])c1ccc(Oc2ccc(-c3nccs3)cc2)nc1]

Following the General procedure A, 2-(4-((5-nitropyridin-2-yl)oxy)phenyl)thiazole was obtained in 61% yield (206 mg, 0.688 mmol) from 4-(thiazol-2-yl)phenol (0.23 g, 1.30 mmol) and 2-chloro-5-nitropyridine (0.18 g, 1.10 mmol).

$C_{14}H_9N_3SO_3$; Mw=299.30 g·mol$^{-1}$; $^1$H NMR (400 MHz, $CDCl_3$) δ 9.06 (d, J=2.8 Hz, 1H), 8.51 (dd, J=9.0, 2.8 Hz, 1H), 8.10-8.04 (m, 2H), 7.88 (d, J=3.3 Hz, 1H), 7.36 (d, J=3.3 Hz, 1H), 7.29-7.23 (m, 2H), 7.10 (d, J=9.0 Hz, 1H).

Example 17: (4'((5-Aminopyridin-2-yl)oxy)-[1,1'-biphenyl]-3-yl)methanol

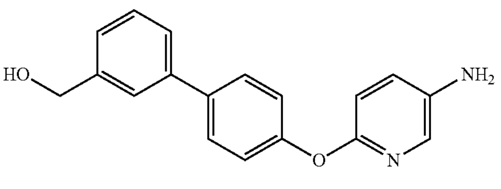 [SMILES: Nc1ccc(Oc2ccc(-c3cccc(CO)c3)cc2)nc1]

Following the General procedure B, (4'-((5-aminopyridin-2-yl)oxy)-[1,1'-biphenyl]-3-yl)methanol was obtained in 44% yield (20 mg, 0.044 mmol) from (4'-((5-nitropyridin-2-yl)oxy)[1,1'-biphenyl]-3-yl)methanol (50 mg, 0.16 mmol).

$C_{18}H_{16}N_2O_2$; Mw=292.34 g·mol$^{-1}$; $^1$H NMR (400 MHz, $CDCl_3$) δ 7.75 (d, J=2.9 Hz, 1H), 7.57 (dd, J=6.5, 2.1 Hz, 3H), 7.50 (d, J=7.7 Hz, 1H), 7.42 (t, J=7.6 Hz, 1H), 7.33 (d, J=7.6 Hz, 1H), 7.18-7.06 (m, 3H), 6.82 (d, J=8.6 Hz, 1H), 4.76 (s, 2H), 3.49 (s, 2H).

The starting material was prepared as follows:

Step 1: (4'((5-Nitropyridin-2-yl)oxy)-[1,1'-biphenyl]-3-yl)methanol

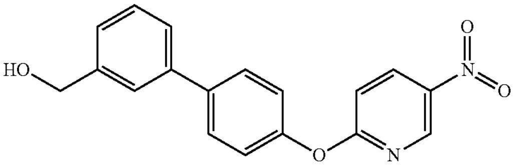 [SMILES: O=[N+]([O-])c1ccc(Oc2ccc(-c3cccc(CO)c3)cc2)nc1]

Following the General procedure E, (4'-((5-nitropyridin-2-yl)oxy)-[1,1'-biphenyl]-3-yl)methanol was obtained in 65% yield (281 mg, 0.872 mmol) from 2-(4-bromophenoxy)-5-nitropyridine (400 mg, 1.36 mmol; Example 10: Step 1) and (3-(hydroxymethyl)phenyl)boronic acid (240 mg, 1.60 mmol).

$C_{18}H_{14}N_2O_4$; Mw=322.32 g·mol$^{-1}$; $^1$H NMR (400 MHz, DMSO-d6) δ 9.07 (dd, J=2.8, 0.6 Hz, 1H), 8.50 (dd, J=9.1, 2.8 Hz, 1H), 7.71-7.65 (m, 2H), 7.62 (td, J=1.8, 0.7 Hz, 1H), 7.54 (dt, J=7.6, 1.6 Hz, 1H), 7.46 (t, J=7.5 Hz, 1H), 7.37 (dt, J=7.6, 1.4 Hz, 1H), 7.26-7.22 (m, 2H), 7.08 (dd, J=9.1, 0.6 Hz, 1H), 4.79 (d, J=5.9 Hz, 2H), 1.72 (t, J=5.9 Hz, 1H).

Example 18: 6-((3'-(Aminomethyl)-[1,1'-biphenyl]-4-yl)oxy)pyridin-3-amine

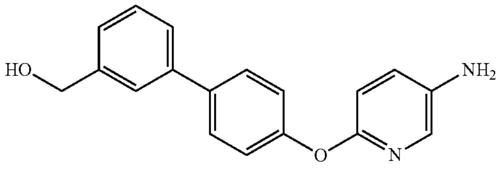 [SMILES: Nc1ccc(Oc2ccc(-c3cccc(CO)c3)cc2)nc1]

2-((4'-((5-Aminopyridin-2-yl)oxy)-[1,1'-biphenyl]-3-yl) methyl)isoindoline-1,3-dione (51 mg, 0.121 mmol) was suspended in methanol (1 mL, 0.1M) (poor solubility at RT) under $N_2$.

Hydrazine hydrate (15 mg, 0.30 mmol) was added. The yellow solution was refluxed overnight. When allowing to RT, a white solid precipitated. The reaction mixture was filtered and the filtrate was concentrated. The crude residue was purified with the Biotage Isolera Four (KP-sil 25 g column, DCM/MeOH, MeOH 1-15%; 28 CV), yielding 6-((3'-(aminomethyl)-[1,1'-biphenyl]-4-yl)oxy)pyridin-3-amine as a pale yellow solid (20 mg, 0.07 mmol, 57%).

$C_{18}H_{17}N_3O$; Mw=291.35 g·mol-1; $^1$H NMR (400 MHz, DMSO-d6) δ 7.66 (d, J=1.8 Hz, 1H), 7.65-7.61 (m, 2H), 7.57 (d, J=2.9 Hz, 1H), 7.52 (dt, J=7.7, 1.5 Hz, 1H), 7.41 (t, J=7.6 Hz, 1H), 7.33 (d, J=7.7 Hz, 1H), 7.10 (dd, J=8.6, 3.0 Hz, 1H), 7.06-7.02 (m, 2H), 6.81 (d, J=8.6 Hz, 1H), 5.13 (s, 2H), 3.88 (s, 2H).

The starting material was prepared as follows:

Step 1: 2-((4'-((5-Nitropyridin-2-yl)oxy)-[1,1'-biphenyl]-3-yl)methyl)isoindoline-1,3-dione

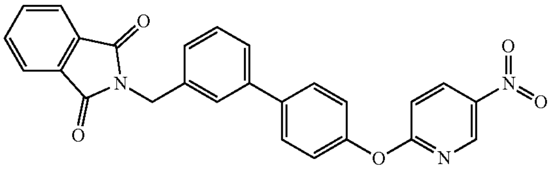 [SMILES: O=C1c2ccccc2C(=O)N1Cc1cccc(-c2ccc(Oc3ccc([N+](=O)[O-])cn3)cc2)c1]

To a 25-mL round-bottom flask, (4'((5-nitropyridin-2-yl)oxy)-[1,1'-biphenyl]-3-yl)methanol (0.117 g, 0.363 mmol), triphenylphosphine (0.115 g, 0.438 mmol) and phthalimide (0.068 g, 0.46 mmol) were added under $N_2$, followed by THF (2 mL). Diisopropyl azodicarboxylate (0.075 mL, 0.39 mmol) was added dropwise at 0° C. The yellow solution was stirred at RT (2 d). The mixture was concentrated and the crude was purified with the Biotage Isolera Four (KP-sil 25 g column, cyclohexane/EtOAc, EtOAc 0-40%, 15 CV), yielding 2-((4'-((5-nitropyridin-2-yl)oxy)-[1,1'-biphenyl]-3-yl)methyl)isoindoline-1,3-dione (158 mg, 0.350 mmol, 96%) as a yellow foam.

$C_{26}H_{17}N_3O_5$; Mw=451.44 g·mol$^{-1}$; $^1$H NMR (400 MHz, $CDCl_3$) δ 9.07 (dd, J=2.8, 0.6 Hz, 1H), 8.49 (dd, J=9.0, 2.8 Hz, 1H), 7.87-7.84 (m, 2H), 7.72 (dd, J=5.5, 3.0 Hz, 2H), 7.66 (d, J=1.8 Hz, 1H), 7.66-7.62 (m, 2H), 7.50 (dt, J=7.3, 1.7 Hz, 1H), 7.47-7.43 (m, 1H), 7.40 (t, J=7.5 Hz, 1H), 7.24-7.20 (m, 2H), 7.07 (dd, J=9.0, 0.6 Hz, 1H), 4.92 (s, 2H). TLC (cyclohexane/EtOAc 7:3) $R_f$=0.42.

Step 2: 2-((4'-((5-Aminopyridin-2-yl)oxy)-[1,1'-biphenyl]-3-yl)methyl)isoindoline-1,3-dione

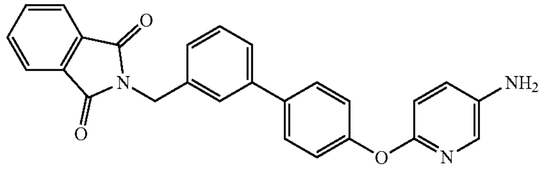 [SMILES: Nc1ccc(Oc2ccc(-c3cccc(CN4C(=O)c5ccccc5C4=O)c3)cc2)nc1]

2-((4'-((5-Nitropyridin-2-yl)oxy)-[1,1'-biphenyl]-3-yl)methyl)isoindoline-1,3-dione (158 mg, 0.350 mmol) was suspended in EtOAc (3 mL) under $N_2$. Pd/C (10%, 16 mg) was added resulting in a black suspension which was stirred overnight under a $H_2$ atmosphere (1 atm). The reaction mixture was filtered through celite and the filtrate concentrated, giving 170 mg of crude product as a yellow oil. The crude product was purified with the Biotage Isolera Four (KP-sil 25 g column, cyclohexane/EtOAc, EtOAc 12-100%, 18 CV), yielding 2-((4'-((5-aminopyridin-2-yl)oxy)-[1,1'-biphenyl]-3-yl)methyl)isoindoline-1,3-dione as a yellow gum (100 mg, 0.200 mmol, 67%).

$C_{26}H_{19}N_3O_3$; Mw=421.46 g·mol$^{-1}$; $^1$H NMR (400 MHz, $CDCl_3$) δ 7.85 (dd, J=5.4, 3.1 Hz, 2H), 7.75 (dd, J=3.0, 0.7 Hz, 1H), 7.71 (dd, J=5.5, 3.0 Hz, 2H), 7.63 (s, 1H), 7.56-7.52 (m, 2H), 7.47 (dt, J=7.0, 1.8 Hz, 1H), 7.43-7.34 (m, 2H), 7.14-7.09 (m, 3H), 6.81 (dd, J=8.7, 0.6 Hz, 1H), 4.90 (s, 2H).

Example 19: 2-(4'((5-Aminopyridin-2-yl)oxy)-[1,1'-biphenyl]-3-yl)acetamide

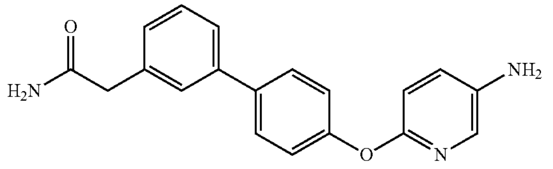 [SMILES: NC(=O)Cc1cccc(-c2ccc(Oc3ccc(N)cn3)cc2)c1]

Following the General procedure B, 2-(4'-((5-aminopyridin-2-yl)oxy)-[1,1'-biphenyl]-3-yl)acetamide was obtained in 89% yield (17 mg, 0.053 mmol) from 2-(4'-((5-nitropyridin-2-yl)oxy)-[1,1'-biphenyl]-3-yl)acetamide (21 mg, 0.060 mmol).

$C_{19}H_{17}N_3O_2$; Mw=319.36 g·mol$^{-1}$; $^1$H NMR (400 MHz, $CDCl_3$) δ 7.74 (d, J=2.9 Hz, 1H), 7.56 (d, J=8.6 Hz, 2H), 7.53-7.46 (m, 2H), 7.42 (t, J=7.6 Hz, 1H), 7.24 (s, 1H), 7.17-7.06 (m, 3H), 6.82 (d, J=8.6 Hz, 1H), 5.37 (d, J=24.0 Hz, 2H), 3.66 (s, 2H).

The starting material was prepared as follows:

Step 1: 2-(4'-((5-Nitropyridin-2-yl)oxy)-[1,1'-biphenyl]-3-yl)acetonitrile

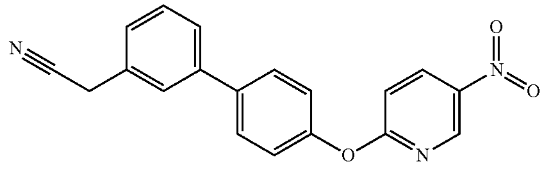 [SMILES: N#CCc1cccc(-c2ccc(Oc3ccc([N+](=O)[O-])cn3)cc2)c1]

Following the General procedure E 2-(4'-((5-nitropyridin-2-yl)oxy)-[1,1'-biphenyl]-3-yl)acetonitrile was obtained in 99% yield (432 mg, 1.7 mmol) from 2-(4-bromophenoxy)-5-nitropyridine (500 mg, 1.69 mmol; Example 10: Step 1) and 2-(3-(4,4,5,5-tetramethyl-1,3,2-dioxaborolan-2-yl)phenyl)acetonitrile (536 mg, 2.20 mmol).

$C_{19}H_{13}N_3O_3$; Mw=331.33 g·mol$^{-1}$; $^1$H NMR (400 MHz, $CDCl_3$) δ 9.07 (d, J=2.7 Hz, 1H), 8.51 (dd, J=9.1, 2.8 Hz, 1H), 7.69-7.63 (m, 2H), 7.57 (d, J=6.7 Hz, 2H), 7.47 (t, J=8.0 Hz, 1H), 7.33 (d, J=7.9 Hz, 1H), 7.28-7.24 (d, 2H), 7.10 (d, J=9.0 Hz, 1H), 3.84 (s, 2H).

Step 2: 2-(4'((5-Nitropyridin-2-yl)oxy)-[1,1'-biphenyl]-3-yl)acetamide

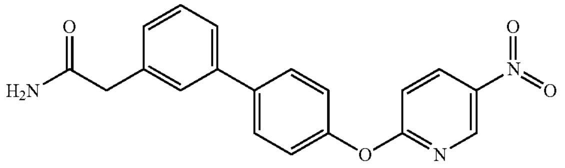 [SMILES: NC(=O)Cc1cccc(-c2ccc(Oc3ccc([N+](=O)[O-])cn3)cc2)c1]

$H_2SO_4$ (500 ul; 9.0 mmol) was slowly added, at 0° C., to 2-(4'-((5-nitropyridin-2-yl)oxy)-[1,1'-biphenyl]-3-yl)acetonitrile (50 mg, 0.18 mmol). The mixture was stirred at RT overnight. The solution was poured into ice water and neutralized with 2M aqueous solution of NaOH. Then a 2M aqueous solution of HCl was used to get a solution at pH=6. The aqueous layer was washed 3 times with EtOAc. The crude product was purified with the Biotage Isolera Four (KP-sil 25 g column, cyclohexane/EtOAc, EtOAc 0 to 100%, 18 CV), yielding 2-(4'-((5-nitropyridin-2-yl)oxy)-[1,1'-biphenyl]-3-yl)acetamide as a yellow gum (30 mg, 0.100 mmol, 57%).

$C_{19}H_{15}N_3O_4$; Mw=349.35 g·mol$^{-1}$; $^1$H NMR (400 MHz, $CDCl_3$) δ 9.07 (d, J=2.8 Hz, 1H), 8.51 (dd, J=9.1, 2.8 Hz, 1H), 7.66 (d, J=8.6 Hz, 2H), 7.57-7.51 (m, 2H), 7.46 (t, J=7.7 Hz, 1H), 7.30 (d, 1H), 7.24 (d, 2H), 7.09 (d, J=9.0 Hz, 1H), 5.43-5.32 (m, 2H), 3.67 (s, 2H)

Example 20: 6-((2-(4-Aminophenoxy)-[1,1'-biphenyl]-4-yl)oxy)pyridin-3-amine

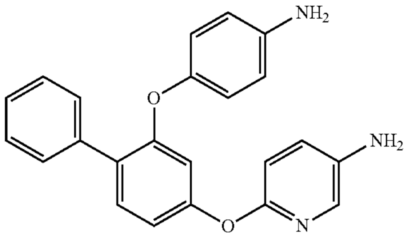 [SMILES: Nc1ccc(Oc2cc(Oc3ccc(N)cn3)ccc2-c2ccccc2)cc1]

Following the General procedure B, 6-((2-(4-nitrophenoxy)-[1,1'-biphenyl]-4-yl)oxy)pyridin-3-amine was obtained in 32% yield (50 mg, 0.13 mmol) from 5-nitro-2-((2-(4-nitrophenoxy)-[1,1'-biphenyl]-4-yl)oxy)pyridine (166 mg, 0.387 mmol). Then 6-((2-(4-nitrophenoxy)-[1,1'-biphenyl]-4-yl)oxy)pyridin-3-amine (50 mg, 0.130 mmol) was suspended in MeOH (1.5 mL, 0.08M). Pd/C (10%, 6.7 mg) was added resulting in a black suspension. The mixture was stirred overnight under $H_2$ atmosphere (1 atm). The reaction mixture was filtered through celite pad. The filtrate was concentrated. The crude product was purified with the Biotage Isolera Four (KP-sil 10 g column, cyclohexane/EtOAc, EtOAc 50-100%, 22 CV), yielding 6-((2-(4-aminophenoxy)-[1,1'-biphenyl]-4-yl)oxy)pyridin-3-amine as an orange solid (40 mg, 0.110 mmol, 86%).

$C_{23}H_{19}N_3O_2$; Mw=369.42 g·mol$^{-1}$; $^1$H NMR (400 MHz, $CDCl_3$) δ 7.72 (d, J=2.9 Hz, 1H), 7.57 (d, J=7.1 Hz, 2H), 7.40-7.34 (m, 4H), 7.07 (dd, J=8.6, 3.0 Hz, 1H), 6.84 (d, J=8.8 Hz, 2H), 6.80-6.74 (m, 2H), 6.64-6.60 (m, 3H).

The starting material was prepared as follows:

Step 1: 4-Methoxy-[1,1'-biphenyl]-2-ol

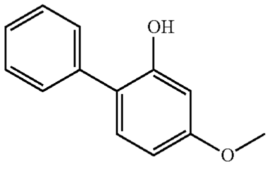

To a 500-mL round-bottom flask phenylboronic acid (310 mg, 2.50 mmol), 2-bromo-5-methoxyphenol (0.41 g, 2.00 mmol), potassium carbonate (0.66 g, 4.70 mmol), water (4 mL) and 2-propanol (16 mL) were added under $N_2$. Bis(triphenylphosphine)palladium(II) chloride (140 mg, 0.20 mmol) was then added and the yellow suspension was stirred at RT for 20 min before being heated to reflux (16 h). The mixture was filtered through a pad of celite and the filtrate was concentrated under vacuum. Water and EtOAc were added to the residue. The layers were separated and the aqueous layer was washed with EtOAc (twice). All the organic layers were combined, dried ($Na_2SO_4$), filtered and concentrated under vacuum. The crude product was purified with the Biotage Isolera Four (KP-sil 50 g column, hexane/EtOAc, EtOAc 2-20%, 16 CV) yielding 4-methoxy-[1,1'-biphenyl]-2-ol as a brown oil (0.87 g, 84%). $C_{13}H_{12}O_2$; Mw=200.24 g·mol$^{-1}$; $^1$H NMR (400 MHz, $CDCl_3$) δ 7.51-7.41 (m, 4H), 7.38 (d, J=7.1 Hz, 1H), 7.19-7.12 (m, 1H), 6.57 (d, J=7.1 Hz, 2H), 5.25 (s, 1H), 3.83 (s, 3H).

Step 2: 4-Methoxy-2-(4-nitrophenoxy)-1,1'-biphenyl

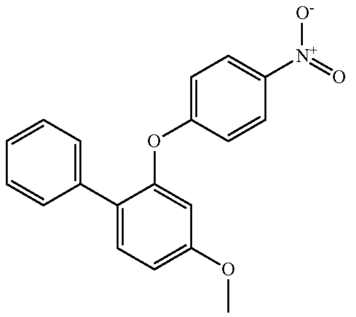 [SMILES: COc1ccc(-c2ccccc2)c(Oc2ccc([N+](=O)[O-])cc2)c1]

Following the General procedure A, 4-methoxy-2-(4-nitrophenoxy)-1,1'-biphenyl was obtained in 66% yield (0.255 g, 0.794 mmol) from 4-methoxy-[1,1'-biphenyl]-2-ol (0.244 g, 1.20 mmol) and 1-fluoro-4-nitrobenzene (0.200 g, 1.40 mmol).

$C_{19}H_{15}NO_4$; Mw=321.33 g·mol$^{-1}$; $^1$H NMR (400 MHz, $CDCl_3$) δ 8.11-8.05 (m, 2H), 7.43 (d, J=8.6 Hz, 1H), 7.41-7.37 (m, 2H), 7.29 (t, J=7.4 Hz, 2H), 7.24-7.20 (m, 1H), 6.92 (dd, J=8.6, 2.6 Hz, 1H), 6.90-6.85 (m, 2H), 6.68 (d, J=2.6 Hz, 1H), 3.84 (s, 3H).

TLC (cyclohexane/EtOAc 9:1) $R_f$=0.39.

Step 3: 2-(4-Nitrophenoxy)-[1,1'-biphenyl]-4-ol

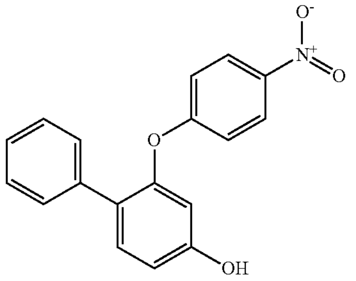 [SMILES: O=[N+]([O-])c1ccc(Oc2cc(O)ccc2-c2ccccc2)cc1]

In a 100-mL round-bottom flask, 4-methoxy-2-(4-nitrophenoxy)-1,1'-biphenyl (255 mg, 0.794 mmol) was dissolved in $CH_2Cl_2$ (10 mL, 0.06M) under $N_2$. The brown solution was cooled down to 0° C. A $CH_2Cl_2$ solution of $BBr_3$ (0.5 M, 2.38 mL, 1.19 mmol) was added dropwise during 1 h with a syringe pump. The solution was allowed to reach RT and then stirred for 4 h. The mixture was quenched at 0° C. with water, then neutralized with a 6M aqueous solution of NaOH. The layers were separated and the aqueous layer was washed with $CH_2Cl_2$ (twice), the combined organic layers were washed with brine, dried ($Na_2SO_4$), filtered and concentrated. The crude product was purified with the Biotage Isolera Four (KP-sil 25 g column, cyclohexane/EtOAc, EtOAc 0-15%, 22 CV) yielding 139 mg of 2-(4-nitrophenoxy)-[1,1'-biphenyl]-4-ol as a yellow solid (51%).

$C_{18}H_{13}NO_4$; Mw=307.31 g·mol$^{-1}$; $^1$H NMR (400 MHz, $CDCl_3$) δ 8.12-8.06 (m, 2H), 7.41-7.35 (m, 3H), 7.29 (t, J=7.5 Hz, 2H), 7.25-7.22 (m, 1H), 6.91-6.86 (m, 2H), 6.84 (dd, J=8.4, 2.5 Hz, 1H), 6.64 (d, J=2.5 Hz, 1H), 4.94 (s, 1H).

Step 4: 5-Nitro-2-((2-(4-nitrophenoxy)-[1,1'-biphenyl]-4-yl)oxy)pyridine

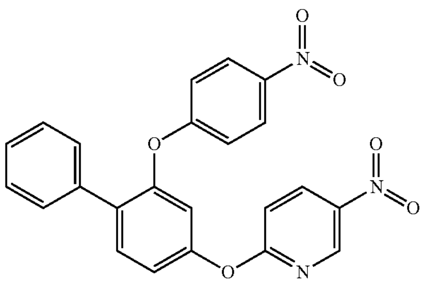 [SMILES: O=[N+]([O-])c1ccc(Oc2cc(Oc3ccc([N+](=O)[O-])cn3)ccc2-c2ccccc2)cc1]

Following the General procedure A, 5-nitro-24(2-(4-nitrophenoxy)-[1,1'-biphenyl]-4-yl)oxy)pyridine was obtained in 86% yield (166 mg, 0.387 mmol) from 2-(4-nitrophenoxy)-[1,1'-biphenyl]-4-ol (139 mg, 0.452 mmol) and 2-chloro-5-nitropyridine (72 mg, 0.452 mmol).

$C_{23}H_{15}N_3O_6$; Mw=429.39 g·mol$^{-1}$; $^1$H NMR (400 MHz, $CDCl_3$) δ 9.07 (d, J=2.8 Hz, 1H), 8.52 (dd, J=9.0, 2.8 Hz, 1H), 8.14-8.09 (m, 2H), 7.58 (d, J=8.5 Hz, 1H), 7.49-7.44 (m, 2H), 7.38-7.28 (m, 3H), 7.19 (dd, J=8.5, 2.4 Hz, 1H), 7.11 (d, J=9.0 Hz, 1H), 7.00 (d, J=2.4 Hz, 1H), 6.97-6.93 (m, 2H).

Example 21: 6,6'-([1,1'-Biphenyl]-2,4-diylbis(oxy))bis(pyridin-3-amine)

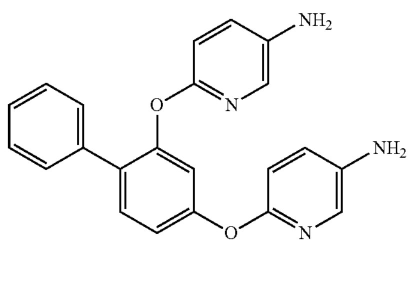

Following the General procedure B, 6,6'-([1,1'-biphenyl]-2,4-diylbis(oxy))bis(pyridin-3-amine) was obtained in 13% yield (10 mg, 0.021 mmol) from 6,6'-([1,1'-biphenyl]-2,4-diylbis(oxy))bis(3-nitropyridine) (90 mg, 0.31 mmol).

$C_{22}H_{18}N_4O_2$; Mw=370.41 g·mol$^{-1}$; $^1$H NMR (400 MHz, $CDCl_3$) δ 7.75 (d, J=2.9 Hz, 1H), 7.66 (d, J=2.9 Hz, 1H), 7.53-7.48 (m, 2H), 7.38 (d, J=8.5 Hz, 1H), 7.32 (t, J=7.4 Hz, 3H), 7.09 (dd, J=8.7, 2.9 Hz, 1H), 7.01-6.96 (m, 1H), 6.92 (dd, J=8.4, 2.3 Hz, 1H), 6.82-6.78 (m, 2H), 6.62 (d, J=8.7 Hz, 1H).

The starting material was prepared as follows:

Step 1: 6,6'-((4-Bromo-1,3-phenylene)bis(oxy))bis(3-nitropyridine)

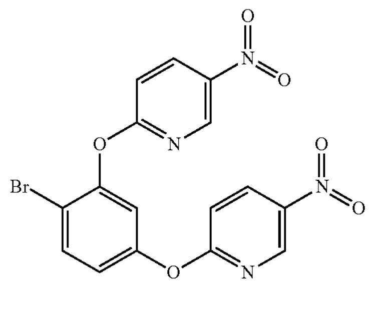 [SMILES: O=[N+]([O-])c1ccc(Oc2ccc(Br)c(Oc3ccc([N+](=O)[O-])cn3)c2)nc1]

Following the General procedure A, 6,6'-((4-bromo-1,3-phenylene)bis(oxy))bis(3-nitropyridine) was obtained in 97% yield (320 mg, 0.74 mmol) from 4-bromoresorcinol (150 mg, 0.78 mmol) and 2-chloro-5-nitropyridine (260 mg, 1.60 mmol).

$C_{16}H_9BrN_4O_6$; Mw=433.17 g·mol$^{-1}$; $^1$H NMR (400 MHz, $CDCl_3$) δ 9.05 (dd, J=2.8, 0.6 Hz, 1H), 9.02 (dd, J=2.8, 0.6 Hz, 1H), 8.52 (ddd, J=9.0, 8.3, 2.8 Hz, 2H), 7.73 (d, J=8.7 Hz, 1H), 7.18-7.05 (m, 4H).

Step 2: 6,6'-([1,1'-Biphenyl]-2,4-diylbis(oxy))bis(3-nitropyridine)

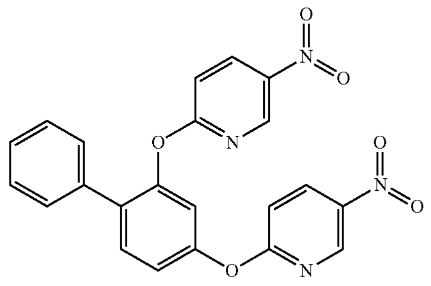 [SMILES: O=[N+]([O-])c1ccc(Oc2ccc(-c3ccccc3)c(Oc3ccc([N+](=O)[O-])cn3)c2)nc1]

To a 250-mL round-bottom flask was added phenylboronic acid (120 mg, 0.96 mmol), 6,6'-((4-bromo-1,3-phenylene)bis(oxy))bis(3-nitropyridine) (320 mg, 0.74 mmol), potassium carbonate (210 mg, 1.50 mmol), water (1 mL) and 2-propanol (6 mL) under $N_2$. Bis(triphenylphosphine)palladium(II) chloride (51 mg, 0.071 mmol) was then added and the yellow suspension was stirred at RT for 5 min before being heated to reflux (16 h). The mixture was filtered through a pad of celite and the filtrate was concentrated under vacuum. Water and EtOAc were added to the residue. The layers were separated and the aqueous layer was washed with EtOAc (twice). All the organic layers were combined, dried ($Na_2SO_4$), filtered and concentrated under vacuum. The crude product was purified with the Biotage Isolera Four (KP-sil 50 g column, cyclohexane/EtOAc, EtOAc 0-25%, 22 CV) yielding 6,6'-([1,1'-biphenyl]-2,4-diylbis(oxy))bis(3-nitropyridine) as a colorless oil (90 mg, 28%). $C_{22}H_{14}N_4O_6$; Mw=430.38 g·mol$^{-1}$; $^1$H NMR (400 MHz, $CDCl_3$) δ 9.09 (dd, J=2.8, 0.6 Hz, 1H), 8.92 (dd, J=2.8, 0.6 Hz, 1H), 8.52 (dd, J=9.0, 2.8 Hz, 1H), 8.34 (dd, J=9.0, 2.8 Hz, 1H), 7.56 (d, J=8.4 Hz, 1H), 7.45-7.40 (m, 2H), 7.35-

7.27 (m, 3H), 7.23 (dd, J=8.5, 2.4 Hz, 1H), 7.16-7.10 (m, 2H), 6.90 (dd, J=9.0, 0.6 Hz, 1H).

Example 22: 6-((2-(2-(4-Aminophenoxy)ethyl)-[1,1'-biphenyl]-4-yl)oxy)pyridin-3-amine

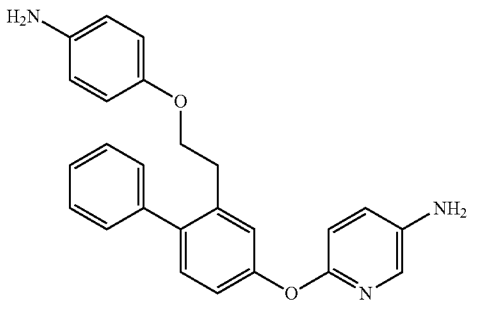 [SMILES: Nc1ccc(OCCc2cc(Oc3ccc(N)cn3)ccc2-c2ccccc2)cc1]

Following the General procedure B, 6-((2-(2-(4-aminophenoxy)ethyl)-[1,1'-biphenyl]-4-yl)oxy)pyridin-3-amine was obtained in 12% yield (5 mg, 0.012 mmol) from 5-nitro-2-((2-(2-(4-nitrophenoxy)ethyl)-[1,1'-biphenyl]-4-yl)oxy)pyridine (48 mg, 0.10 mmol).

$C_{25}H_{23}N_3O_2$; Mw=397.48 g·mol$^{-1}$; $^1$H NMR (400 MHz, $CDCl_3$) δ 7.75 (d, J=3.0 Hz, 1H), 7.42-7.38 (m, 2H), 7.37-7.31 (m, 3H), 7.20 (d, J=8.3 Hz, 1H), 7.13-7.07 (m, 2H), 6.96 (dd, J=8.3, 2.5 Hz, 1H), 6.82 (d, J=8.6 Hz, 1H), 6.59-6.51 (m, 4H), 3.92 (t, J=7.4 Hz, 2H), 3.01 (t, J=7.4 Hz, 2H).

The starting material was prepared as follows:

Step 1: 2-(2-Bromo-5-methoxyphenyl)acetic acid

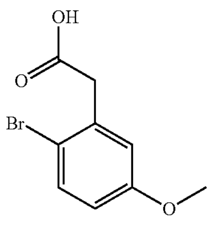

In a 250-mL round-bottom flask, 2-(3-methoxyphenyl) acetic acid (1.50 g, 9.00 mmol) was dissolved in $CH_2Cl_2$ (25 mL, 0.36M). N-Bromsuccinimid (1.80 g, 9.90 mmol) was added portionwise at 0° C. and under $N_2$. The colorless solution was stirred at RT for 3 h. Water was added to the mixture and the layers were separated. The aqueous layer was washed with $CH_2Cl_2$. All the organic layers were combined and washed with brine, dried ($Na_2SO_4$), filtered and concentrated yielding 2-(2-bromo-5-methoxyphenyl) acetic acid as an orange solid (2.22 g, 100%).

$C_9H_9BrO_3$; Mw=245.07 g·mol$^{-1}$; $^1$H NMR (400 MHz, $CDCl_3$) δ 7.46 (d, J=8.8 Hz, 1H), 6.86 (d, J=3.0 Hz, 1H), 6.73 (dd, J=8.8, 3.0 Hz, 1H), 3.81 (s, 2H), 3.79 (s, 3H).

Step 2: 2-(2-Bromo-5-methoxyphenyl)ethan-1-ol

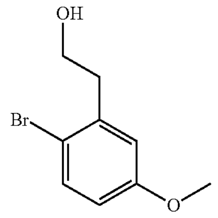

In a 250-mL round-bottom flask, 2-(2-bromo-5-methoxyphenyl)acetic acid (2.22 g, 9.06 mmol) was dissolved in in dry THF (16 mL, 0.55M). The yellow solution was cooled down to 0° C. and a 2.4M THF solution of $LiAlH_4$ (2.30 ml, 5.5 mmol) was added dropwise. The yellow solution was stirred at RT (2 h). The reaction mixture was quenched at 0° C. with 1M NaOH (10 mL). THF was evaporated, $CH_2Cl_2$ and water were added. The cloudy mixture was stirred for 1 h. The layers were separated and the aqueous layer was washed with $CH_2Cl_2$. All the organic layers were combined and washed with 1M HCl, brine, dried ($Na_2SO_4$), filtered and concentrated, yielding 2-(2-bromo-5-methoxyphenyl) ethan-1-ol as a pale yellow oil (1.35 g, 65%).

$C_9H_{11}BrO_2$; Mw=231.09 g·mol$^{-1}$; $^1$H NMR (400 MHz, $CDCl_3$) δ 7.43 (d, J=8.8 Hz, 1H), 6.83 (d, J=3.0 Hz, 1H), 6.67 (dd, J=8.8, 3.1 Hz, 1H), 3.88 (t, J=6.6 Hz, 2H), 3.78 (s, 3H), 2.99 (t, J=6.6 Hz, 2H).

Step 3: 1-Bromo-4-methoxy-2-(2-(4-nitrophenoxy)ethyl)benzene

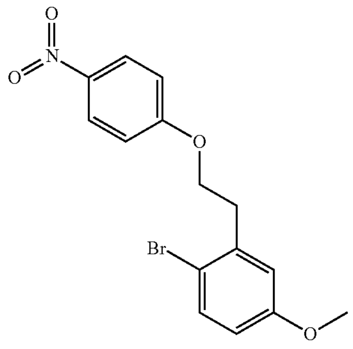 [SMILES: COc1ccc(Br)c(CCOc2ccc([N+](=O)[O-])cc2)c1]

In a 25-mL round-bottom flask, 2-(2-bromo-5-methoxyphenyl)ethan-1-ol (190 mg, 0.82 mmol) was dissolved in dry DMF (3 mL, 0.3M). NaH (60%, 42 mg, 1.00 mmol) was added portionwise resulting in a dark yellow suspension. The solution was stirred at RT (15 min), then 1-fluoro-4-nitrobenzene (110 mg, 0.78 mmol) was added. The dark green suspension was stirred overnight at RT. Water was added to quench the mixture, followed by EtOAc. The layers are separated. The aqueous layer was washed with EtOAc. All organic layers were combined, washed with brine, dried ($Na_2SO_4$), filtered and concentrated. The crude product was purified with the Biotage Isolera Four (KP-sil 25 g column, cyclohexane/EtOAc, EtOAc 0-20%, 16 CV) yielding 1-bromo-4-methoxy-2-(2-(4-nitrophenoxy)ethyl)benzene as a yellow solid (150 mg, 60%).

$C_{15}H_{14}BrNO_4$; Mw=352.18 g·mol$^{-1}$; $^1$H NMR (400 MHz, $CDCl_3$) δ 8.22-8.16 (m, 2H), 7.45 (d, J=8.8 Hz, 1H), 6.98-6.93 (m, 2H), 6.88 (d, J=3.0 Hz, 1H), 6.70 (dd, J=8.8, 3.0 Hz, 1H), 4.28 (t, J=7.0 Hz, 2H), 3.79 (s, 3H), 3.23 (t, J=7.0 Hz, 2H). TLC (cyclohexane/EtOAc 9:1) $R_f$=0.28.

Step 4: 4-Methoxy-2-(2-(4-nitrophenoxy)ethyl)-1,1'-biphenyl

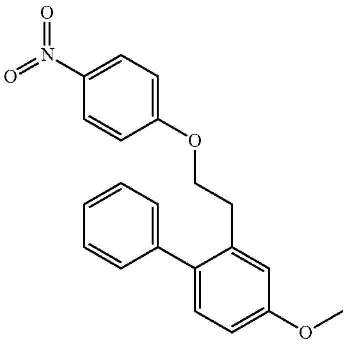 [SMILES: COc1ccc(-c2ccccc2)c(CCOc2ccc([N+](=O)[O-])cc2)c1]

To a 250-mL round-bottom flask was added phenylboronic acid (63 mg, 0.51 mmol), 1-bromo-4-methoxy-2-(2-(4-nitrophenoxy)ethyl)benzene (150 mg, 0.43 mmol), potassium carbonate (154 mg, 1.11 mmol), water (1 mL) and 2-propanol (4 mL) under $N_2$. Bis(triphenylphosphine)palladium(II) chloride (39 mg, 0.054 mmol) was then added and the yellow suspension was stirred at RT for 5 min before being heated to reflux (16 h). The mixture was filtered through a pad of celite and the filtrate was concentrated under vacuum. Water and EtOAc were added to the residue. The layers were separated and the aqueous layer was washed with EtOAc (twice). All the organic layers were combined, dried ($Na_2SO_4$), filtered and concentrated under vacuum. The crude product was purified with the Biotage Isolera Four (KP-sil 50 g column, cyclohexane/EtOAc, EtOAc 0-30%, 13 CV) yielding 4-methoxy-2-(2-(4-nitrophenoxy)ethyl)-1,1'-biphenyl as a colorless oil (120 mg, 81%). $C_{21}H_{19}NO_4$; Mw=349.39 g·mol$^{-1}$; $^1$H NMR (400 MHz, $CDCl_3$) δ 8.12-8.06 (m, 2H), 7.47-7.38 (m, 3H), 7.34-7.30 (m, 2H), 7.19 (d, J=8.4 Hz, 1H), 6.92 (d, J=2.6 Hz, 1H), 6.86 (dd, J=8.4, 2.7 Hz, 1H), 6.70-6.64 (m, 2H), 4.06 (t, J=7.4 Hz, 2H), 3.85 (s, 3H), 3.09 (t, J=7.4 Hz, 2H).

Step 5: 2-(2-(4-Nitrophenoxy)ethyl)-[1,1'-biphenyl]-4-ol

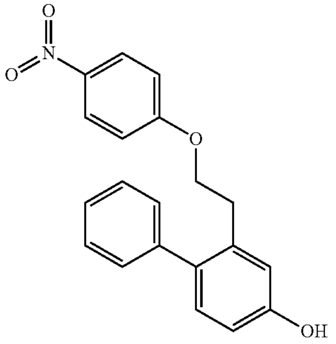 [SMILES: O=[N+]([O-])c1ccc(OCCc2cc(O)ccc2-c2ccccc2)cc1]

In a 100-mL round-bottom flask, 4-methoxy-2-(2-(4-nitrophenoxy)ethyl)-1,1'-biphenyl (115 mg, 0.329 mmol) was dissolved in $CH_2Cl_2$ (4 mL, 0.9M) under $N_2$. The brown solution was cooled down to 0° C. A $CH_2Cl_2$ solution of $BBr_3$ (0.5 M, 1.0 mL, 0.50 mmol) was added dropwise during 30 min with a syringe pump. The solution was allowed to reach RT and then stirred for 2.3 h. The mixture was quenched at 0° C. with water, then neutralized with a 6M aqueous solution of NaOH. The layers were separated and the aqueous layer was re-extracted with $CH_2Cl_2$ (twice). The combined organic layers were washed with brine, dried ($Na_2SO_4$), filtered and concentrated. The crude product was purified with the Biotage Isolera Four (KP-sil 25 g column, cyclohexane/EtOAc, EtOAc 5-40%, 13 CV), yielding 2-(2-(4-nitrophenoxy)ethyl)-[1,1'-biphenyl]-4-ol as a yellow oil (47 mg, 41%).

$C_{20}H_{17}NO_4$; Mw=349.39 g·mol$^{-1}$; $^1$H NMR (400 MHz, $CDCl_3$) δ 8.13-8.07 (m, 2H), 7.47-7.38 (m, 3H), 7.33-7.28 (m, 2H), 7.13 (d, J=8.2 Hz, 1H), 6.86 (d, J=2.7 Hz, 1H), 6.78 (dd, J=8.3, 2.7 Hz, 1H), 6.70-6.65 (m, 2H), 4.76 (s, 1H), 4.05 (t, J=7.4 Hz, 2H), 3.07 (t, J=7.4 Hz, 2H).

Step 6: 5-Nitro-24(2-(2-(4-nitrophenoxy)ethyl)-[1,1'-biphenyl]-4-yl)oxy)pyridine

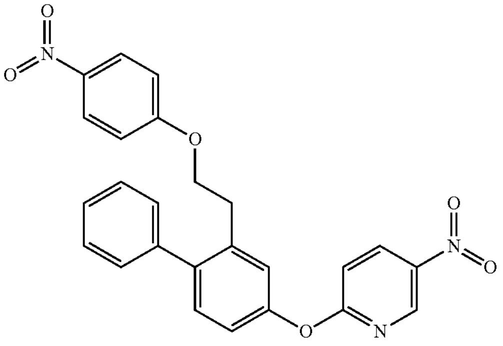 [SMILES: O=[N+]([O-])c1ccc(OCCc2cc(Oc3ccc([N+](=O)[O-])cn3)ccc2-c2ccccc2)cc1]

Following the General procedure A, 5-nitro-2-((2-(2-(4-nitrophenoxy)ethyl)-[1,1'-biphenyl]-4-yl)oxy)pyridine was obtained in 75% yield (48 mg, 0.10 mmol) from 2-(2-(4-nitrophenoxy)ethyl)-[1,1'-biphenyl]-4-ol (47 mg, 0.14 mmol) and 2-chloro-5-nitropyridine (27 mg, 0.17 mmol).

$C_{25}H_{19}N_3O_6$; Mw=457.44 g·mol$^{-1}$; $^1$H NMR (400 MHz, $CDCl_3$) δ 9.08 (dd, J=2.8, 0.6 Hz, 1H), 8.51 (dd, J=9.0, 2.8 Hz, 1H), 8.13-8.07 (m, 2H), 7.49-7.43 (m, 3H), 7.40-7.32 (m, 3H), 7.20 (d, J=2.4 Hz, 1H), 7.15-7.08 (m, 2H), 6.72-6.66 (m, 2H), 4.08 (t, J=7.2 Hz, 2H), 3.14 (t, J=7.2 Hz, 2H).

Example 23: N-Methyl-6-((6-phenylpyridin-3-yl)oxy)pyridin-3-amine

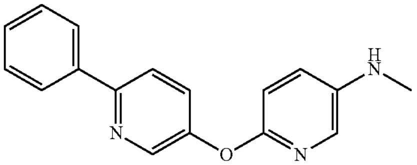 [SMILES: CNc1ccc(Oc2ccc(-c3ccccc3)nc2)nc1]

To a solution of freshly prepared MeONa (4.4 equiv, 2.609 mmol) in MeOH (0.15 M) under inert atmosphere, 6-((6-phenylpyridin-3-yl)oxy)pyridin-3-amine (1.0 equiv, 0.588 mmol, 155 mg; Example 3) was added. The so obtained suspension was stirred for 0.5 h and became a solution. A suspension of para-formaldehyde (1.4 equiv, 0.824 mmol, 27 mg) in MeOH (1 ml) was then poured into the previous solution and the mixture was stirred for 14 h. $NaBH_4$ (2.0 equiv, 1.165 mmol, 45 mg) was added to the reaction and the mixture was stirred for 3 h (completion monitored by TLC). The mixture was finally diluted with $H_2O$ at 0° C. The aqueous layer was extracted three times with EtOAc. The combined organic layers were dried over $Na_2SO_4$, filtered-off and concentrated. The crude product was purified by combi flash column chromatography using EtOAc/cyclohexane (15% to 70%) as the eluent, to afford N-methyl-6-((6-phenylpyridin-3-yl)oxy)pyridin-3-amine (0.436 mmol, 121 mg, 74% yield).

$C_{17}H_{15}N_3O$; Mw=277.33 g·mol$^{-1}$; Solid; $^1$H NMR (400 MHz, $CDCl_3$) δ 8.52 (d, J=2.7 Hz, 1H), 7.95 (d, J=7.5 Hz, 2H), 7.71 (d, J=8.6 Hz, 1H), 7.63 (d, J=3.0 Hz, 1H), 7.51-7.42 (m, 3H), 7.38 (t, J=7.3 Hz, 1H), 7.05 (dd, J=8.7, 3.0 Hz, 1H), 6.89 (d, J=8.7 Hz, 1H), 2.86 (s, 3H).

Example 24:
6-(4-(Pyridin-2-yl)phenoxy)pyridin-3-amine

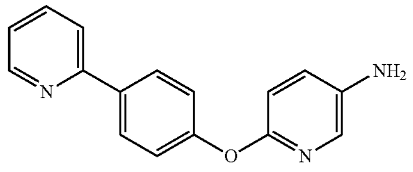 [SMILES: Nc1ccc(Oc2ccc(-c3ccccn3)cc2)nc1]

Following the General procedure B, 6-(4-(pyridin-2-yl)phenoxy)pyridin-3-amine was obtained in 67% yield (0.23 mmol, 60 mg) from 5-nitro-2-(4-(pyridin-2-yl)phenoxy)pyridine (100 mg, 0.341 mmol).

$C_{16}H_{13}N_3O$; Mw=263.30 g·mol$^{-1}$; $^1$H NMR (400 MHz, $CDCl_3$) δ 8.67 (dd, J=4.8, 0.8 Hz, 1H), 7.98 (d, J=8.7 Hz, 2H), 7.76-7.66 (m, 3H), 7.23-7.17 (m, 1H), 7.15 (d, J=8.8 Hz, 2H), 7.12-7.06 (m, 1H), 6.81 (d, J=8.6 Hz, 1H), 3.24 (s, 2H).

The starting material was prepared as follows:

Step 1: 5-Nitro-2-(4-(pyridin-2-yl)phenoxy)pyridine

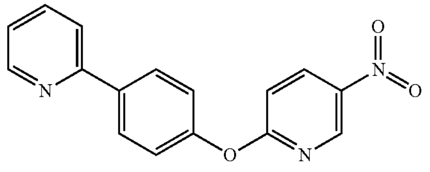 [SMILES: O=[N+]([O-])c1ccc(Oc2ccc(-c3ccccn3)cc2)nc1]

Following the General procedure A, 5-nitro-2-(4-(pyridin-2-yl)phenoxy)pyridine was obtained in 97% yield (500 mg, 1.70 mmol) from 4-(pyridin-2-yl)phenol (1.75 mmol, 0.300 g) and 2-chloro-5-nitropyridine (1.75 mmol, 0.278 g).

$C_{16}H_{11}N_3O_3$; Mw=293.28 g·mol$^{-1}$; $^1$H NMR (300 MHz, $CDCl_3$) δ 9.11-9.05 (m, 1H), 8.91-8.85 (m, 1H), 8.62 (d, J=4.8 Hz, 1H), 8.52 (dd, J=9.1, 2.8 Hz, 1H), 7.94-7.85 (m, 1H), 7.67 (d, J=8.6 Hz, 2H), 7.42-7.36 (m, 1H), 7.29 (d, J=8.6 Hz, 2H), 7.11 (d, J=9.0 Hz, 1H).

Example 25:
6-(4-(Pyridin-3-yl)phenoxy)pyridin-3-amine

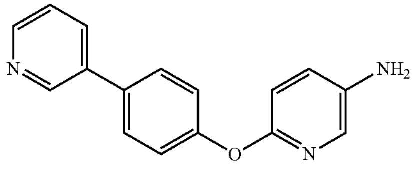 [SMILES: Nc1ccc(Oc2ccc(-c3cccnc3)cc2)nc1]

Following the General procedure B, 6-(4-(pyridin-3-yl)phenoxy)pyridin-3-amine was obtained in 52% yield (1.25 mmol, 330 mg) from the 5-nitro-2-(4-(pyridin-3-yl)phenoxy)pyridine (710 mg, 2.42 mmol).

$C_{16}H_{13}N_3O$; Mw=263.30 g·mol$^{-1}$; $^1$H NMR (400 MHz, $CDCl_3$) δ 8.85-8.81 (m, 1H), 8.56 (dd, J=4.8, 1.6 Hz, 1H), 7.84 (ddd, J=7.9, 2.4, 1.6 Hz, 1H), 7.74 (dd, J=3.0, 0.6 Hz, 1H), 7.55 (d, J=8.7 Hz, 2H), 7.34 (ddd, J=7.9, 4.8, 0.9 Hz, 1H), 7.17 (d, J=8.7 Hz, 2H), 7.11 (dd, J=8.6, 3.0 Hz, 1H), 6.83 (dd, J=8.6, 0.7 Hz, 1H), 3.48 (s, 2H).

The starting material was prepared as follows:

Step 1: 5-Nitro-2-(4-(pyridin-3-yl)phenoxy)pyridine

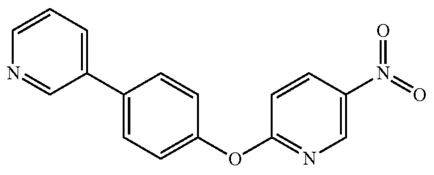 [SMILES: O=[N+]([O-])c1ccc(Oc2ccc(-c3cccnc3)cc2)nc1]

Following the General procedure A, 5-nitro-2-(4-(pyridin-3-yl)phenoxy)pyridine was obtained in 40% yield (270 mg, 0.92 mmol) from 4-(pyridin-3-yl)phenol (2.34 mmol, 0.400 g) and 2-chloro-5-nitropyridine (2.34 mmol, 0.370 g).

$C_{16}H_{11}N_3O_3$; Mw=293.28 g·mol$^{-1}$; $^1$H NMR (300 MHz, $CDCl_3$) δ 9.07 (dd, J=2.8, 0.6 Hz, 1H), 8.70 (ddd, J=4.8, 1.7, 1.1 Hz, 1H), 8.50 (dd, J=9.1, 2.8 Hz, 1H), 8.10 (d, J=8.9 Hz, 2H), 7.79-7.74 (m, 2H), 7.28 (d, J=9.0 Hz, 3H), 7.08 (dd, J=9.1, 0.6 Hz, 1H).

Example 26:
6-(4-(Pyridin-4-yl)phenoxy)pyridin-3-amine

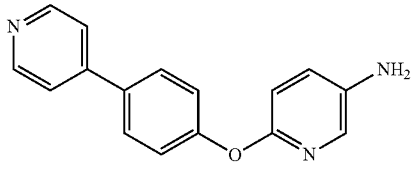 [SMILES: Nc1ccc(Oc2ccc(-c3ccncc3)cc2)nc1]

Following the General procedure B, 6-(4-(pyridin-4-yl)phenoxy)pyridin-3-amine was obtained in 57% yield (0.40 mmol, 100 mg) from the 5-nitro-2-(4-(pyridin-4-yl)phenoxy)pyridine (19 mg, 0.672 mmol).

$_{16}H_{13}N_3O$; Mw=263.30 g·mol$^{-1}$; $^1$H NMR (400 MHz, $CDCl_3$) δ 8.64 (dd, J=4.6, 1.6 Hz, 2H), 7.75 (d, J=3.0 Hz, 1H), 7.66-7.60 (m, 2H), 7.50 (dd, J=4.6, 1.6 Hz, 2H), 7.20-7.10 (m, 3H), 6.85 (d, J=8.6 Hz, 1H).

The starting material was prepared as follows:

Step 1: 5-Nitro-2-(4-(pyridin-4-yl)phenoxy)pyridine

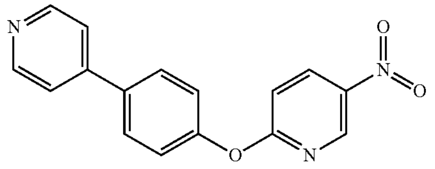 [SMILES: O=[N+]([O-])c1ccc(Oc2ccc(-c3ccncc3)cc2)nc1]

Following the General procedure E, 5-nitro-2-(4-(pyridin-4-yl)phenoxy)pyridine was obtained in 95% yield (33 mg, 0.11 mmol) from 2-(4-bromophenoxy)-5-nitropyridine (50 mg, 0.17 mmol; Example 10: Step 1) and pyridin-4-ylboronic acid (25 mg, 0.20 mmol).

$C_{16}H_{11}N_3O_3$; Mw=293.28 g·mol$^{-1}$; $^1$H NMR (300 MHz, $CDCl_3$) δ 9.06 (d, J=2.7 Hz, 1H), 8.69 (d, J=6.2 Hz, 2H), 8.62 (dd, J=9.1, 2.7 Hz, 1H), 7.70 (d, J=8.7 Hz, 2H), 7.52 (d, J=6.2 Hz, 2H), 7.30 (d, J=8.7 Hz, 2H), 7.11 (d, J=9.1 Hz, 1H).

Example 27: 6-((4'-Fluoro-[1,1'-biphenyl]-4-yl)oxy)-N-methylpyridin-3-amine

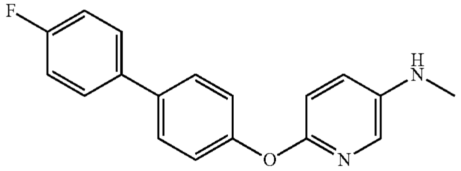 [SMILES: CNc1ccc(Oc2ccc(-c3ccc(F)cc3)cc2)nc1]

Following the General procedure C, 6-((4'-fluoro-[1,1'-biphenyl]-4-yl)oxy)-N-methylpyridin-3-amine was obtained in 73% yield (0.221 mmol, 85 mg) from 6-((4'-fluoro-[1,1'-biphenyl]-4-yl)oxy)pyridin-3-amine (0.303 mmol, 65 mg; expl. 10).

$C_{18}H_{15}FN_2O$; Mw=294.33 g·mol$^{-1}$; $^1$H NMR (400 MHz, $CDCl_3$) δ 7.68 (d, J=3.0 Hz, 1H), 7.53-7.47 (m, 4H), 7.14-7.08 (m, 4H), 7.05 (dd, J=8.7, 3.0 Hz, 1H), 6.86 (d, J=8.7 Hz, 1H), 2.86 (s, 3H).

Example 28: 6-((4'-Fluoro-[1,1'-biphenyl]-4-yl)oxy)-2-methylpyridin-3-amine

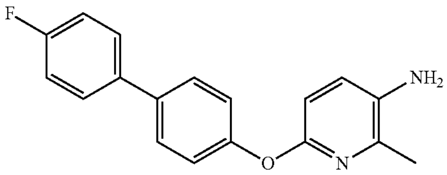

Following the General procedure B, 6-((4'-fluoro-[1,1'-biphenyl]-4-yl)oxy)-2-methylpyridin-3-amine was obtained in 72% yield (1.11 mmol, 330 mg) from 6-((4'-fluoro-[1,1'-biphenyl]-4-yl)oxy)-2-methyl-3-nitropyridine (1.54 mmol, 500 mg).

$C_{18}H_{15}FN_2O$; Mw=294.33 g·mol$^{-1}$; $^1$H NMR (400 MHz, DMSO-$d_6$) δ 7.71-7.63 (m, 2H), 7.63-7.56 (m, 2H), 7.32-7.22 (m, 2H), 7.08 (d, J=8.3 Hz, 1H), 7.02-6.96 (m, 2H), 6.67 (d, J=8.3 Hz, 1H), 4.90 (s, 2H), 2.18 (s, 3H).

The starting materials were prepared as followed:

Step 1: 6-(4-Bromophenoxy)-2-methyl-3-nitropyridine

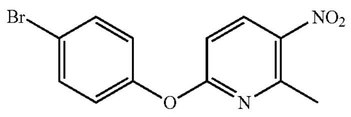 [SMILES: Cc1nc(Oc2ccc(Br)cc2)ccc1[N+](=O)[O-]]

Following the General procedure A, 6-(4-bromophenoxy)-2-methyl-3-nitropyridine was obtained in 93% yield (26.9 mmol, 8.31 g) from 6-chloro-2-methyl-3-nitropyridine (29 mmol, 5.00 g) and 4-bromophenol (32 mmol, 5.50 g).

$C_{12}H_9BrN_2O_3$; Mw=309.12 g mol$^{-1}$; $^1$H NMR (400 MHz, $CDCl_3$) δ 8.38 (d, J=8.9 Hz, 1H), 7.72-7.42 (m, 2H), 7.15-6.99 (m, 2H), 6.84 (d, J=8.9 Hz, 1H), 2.73 (s, 3H).

Step 2: 6-((4'-Fluoro-[1,1'-biphenyl]-4-yl)oxy)-2-methyl-3-nitropyridine

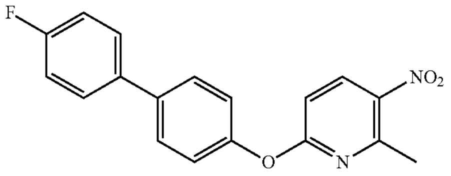 [SMILES: Cc1nc(Oc2ccc(-c3ccc(F)cc3)cc2)ccc1[N+](=O)[O-]]

Following the General procedure E, a mixture of (4-fluorophenyl)boronic acid (4.85 mmol, 679 mg), 6-(4-bromophenoxy)-2-methyl-3-nitropyridine (3.23 mmol, 1.00 g), $K_2CO_3$ (8.09 mmol, 1.12 g), and $Pd(PPh_3)_4$ (0.162 mmol, 187 mg, 5% mol) in 4:1 mixture of dioxane/$H_2O$ (0.1 M) was converted to 6-((4'-fluoro-[1,1'-biphenyl]-4-yl)oxy)-2-methyl-3-nitropyridine in 90% yield (2.94 mmol, 900 mg).

$C_{18}H_{13}FN_2O_3$; Mw=324.31 g·mol$^{-1}$; $^1$H NMR (400 MHz, $CDCl_3$) δ 8.38 (d, J=8.9 Hz, 1H), 7.62-7.58 (m, 2H), 7.58-7.53 (m, 2H), 7.25-7.21 (m, 2H), 7.19-7.11 (m, 2H), 6.84 (dd, J=8.9, 0.7 Hz, 1H), 2.77 (s, 3H).

Example 29: 6-((4'-Fluoro-[1,1'-biphenyl]-4-yl)oxy)-4-methylpyridin-3-amine

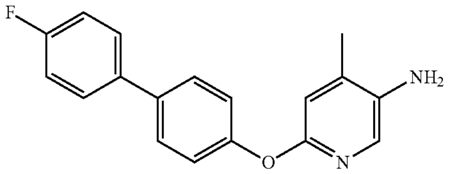 [SMILES: Cc1cc(Oc2ccc(-c3ccc(F)cc3)cc2)ncc1N]

Following the General procedure B, 6-((4'-fluoro-[1,1'-biphenyl]-4-yl)oxy)-4-methylpyridin-3-amine was obtained in 86% yield (476 mmol, 0.140 g) from 24(4'-fluoro-[1,1'-biphenyl]-4-yl)oxy)-4-methyl-5-nitropyridine (555 mmol, 0.180 g).

$C_{18}H_{15}FN_2O$; Mw=294.33 g·mol$^{-1}$; $^1$H NMR (400 MHz, $CDCl_3$) δ 7.69 (s, 1H), 7.54-7.46 (m, 4H), 7.14-7.06 (m, 4H), 6.72 (s, 1H), 2.20 (s, 3H), 2.07 (s, 2H).

The starting materials were prepared as followed:

Step 1: 2-(4-Bromophenoxy)-4-methyl-5-nitropyridine

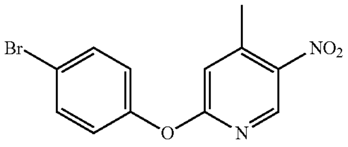 [SMILES: Cc1cc(Oc2ccc(Br)cc2)ncc1[N+](=O)[O-]]

Following the General procedure A, 2-(4-bromophenoxy)-4-methyl-5-nitropyridine was obtained in 40% yield (11 mmol, 3.50 g) from 4-bromophenol (31.9 mmol, 5.51 g) and 2-chloro-4-methyl-5-nitropyridine (29 mmol, 5.00 g).

$C_{12}H_9BrN_2O_3$; Mw=309.12 g·mol$^{-1}$; $^1$H NMR (400 MHz, $CDCl_3$) δ 8.86 (s, 1H), 7.55 (d, J=8.9 Hz, 2H), 7.04 (d, J=8.9 Hz, 2H), 6.86 (d, J=1.0 Hz, 1H), 2.68 (app d, J=1.0 Hz, 3H).

Step 2: 2-((4'-Fluoro-[1,1'-biphenyl]-4-yl)oxy)-4-methyl-5-nitropyridine

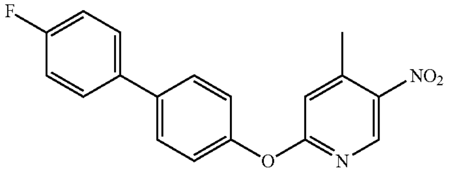

Following the General procedure E, 2-((4'-fluoro-[1,1'-biphenyl]-4-yl)oxy)-4-methyl-5-nitropyridine was obtained in 82% yield (1.13 mmol, 0.30 g) from 2-(4-bromophenoxy)-4-methyl-5-nitropyridine (1.13 mmol, 0.350 mg) and (4-fluorophenyl)boronic acid (1.70 mmol, 0.238 mg).

$C_{18}H_{13}FN_2O_3$; Mw=324.31 g·mol$^{-1}$; $^1$H NMR (400 MHz, $CDCl_3$) δ 8.91 (s, 1H), 7.63-7.58 (m, 2H), 7.57-7.52 (m, 2H), 7.23-7.19 (m, 2H), 7.17-7.11 (m, 2H), 6.89 (d, J=0.9 Hz, 1H), 2.69 (s, 3H).

Example 30: 2-Methyl-6-((6-phenylpyridin-3-yl)oxy)pyridin-3-amine

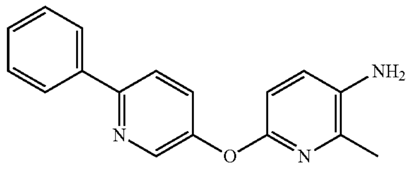

Following the General procedure B, 2-methyl-6-((6-phenylpyridin-3-yl)oxy)pyridin-3-amine was obtained in 89% yield (1.08 mmol, 300 mg) from 2-methyl-3-nitro-6-((6-phenylpyridin-3-yl)oxy)pyridine (1.22 mmol, 374 mg).

$C_{17}H_{15}N_3O$; Mw=277.33 g·mol$^{-1}$; $^1$H NMR (400 MHz, DMSO-$d_6$) δ 8.40 (d, J=2.5 Hz, 1H), 8.15-7.98 (m, 2H), 7.94 (d, J=8.7 Hz, 1H), 7.55-7.45 (m, 3H), 7.44-7.37 (m, 1H), 7.10 (d, J=8.4 Hz, 1H), 6.75 (d, J=8.4 Hz, 1H), 4.93 (s, 2H), 2.17 (s, 3H).

The starting material was prepared as follows:

Step 1: 6-Phenylpyridin-3-ol

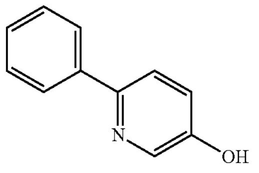 [SMILES: Oc1ccc(-c2ccccc2)nc1]

Following the General procedure D, a mixture of phenylboronic acid (11.49 mmol, 1.40 g), 6-bromopyridin-3-ol (5.75 mmol, 1.00 g), $Na_2CO_3$ (11.49 mmol, 1.22 g), and $Pd(PPh_3)_4$ (0.287 mmol, 332 mg) in a 3:1 mixture of DME/$H_2O$ (0.32 M) was converted to 6-phenylpyridin-3-ol in 61% yield (3.50 mmol, 600 mg).

$C_{11}H_9NO$; Mw=171.20 g mol$^{-1}$; $^1$H NMR (400 MHz, DMSO-$d_6$) δ 9.19 (s, 1H), 7.40-7.34 (m, 1H), 7.15-7.09 (m, 2H), 6.95 (dd, J=8.6, 0.7 Hz, 1H), 6.65-6.57 (m, 2H), 6.54-6.49 (m, 1H), 6.40 (dd, J=8.6, 2.9 Hz, 1H).

Step 2: 2-Methyl-3-nitro-6-((6-phenylpyridin-3-yl)oxy)pyridine

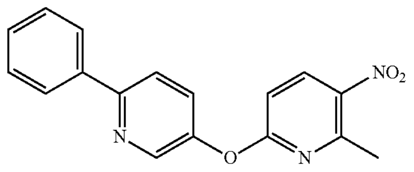 [SMILES: Cc1nc(Oc2ccc(-c3ccccc3)nc2)ccc1[N+](=O)[O-]]

Following the General procedure A, 2-methyl-3-nitro-6-((6-phenylpyridin-3-yl)oxy)pyridine was obtained in 95% yield (1.22 mmol, 374 mg) from 6-chloro-2-methyl-3-nitropyridine (1.27 mmol, 220 mg).

$C_{17}H_{13}N_3O_3$; Mw=307.31 g·mol$^{-1}$; $^1$H NMR (400 MHz, $CDCl_3$) δ 8.60 (dd, J=2.8, 0.7 Hz, 1H), 8.42 (d, J=8.9 Hz, 1H), 8.09-7.93 (m, 2H), 7.82 (dd, J=8.7, 0.7 Hz, 1H), 7.62 (dd, J=8.7, 2.8 Hz, 1H), 7.56-7.40 (m, 3H), 6.96 (d, J=8.9 Hz, 1H), 2.73 (s, 3H).

Example 31: 4-Methyl-6-((6-phenylpyridin-3-yl)oxy)pyridin-3-amine

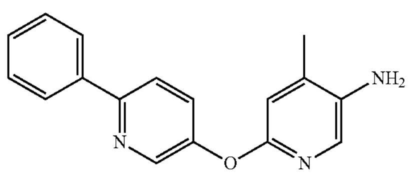 [SMILES: Cc1cc(Oc2ccc(-c3ccccc3)nc2)ncc1[N+](=O)[O-]]

Following the General procedure B, 4-methyl-6-((6-phenylpyridin-3-yl)oxy)pyridin-3-amine was obtained in 78% yield (0.30 mmol, 84 mg) from 4-methyl-5-nitro-2-((6-phenylpyridin-3-yl)oxy)pyridine (0.39 mmol, 120 mg).

$C_{17}H_{15}N_3O$; Mw=277.33 g·mol$^{-1}$; $^1$H NMR (400 MHz, $CDCl_3$) δ 8.51 (dd, J=2.8, 0.7 Hz, 1H), 7.98-7.90 (m, 2H), 7.71 (dd, J=8.6, 0.7 Hz, 1H), 7.64 (s, 1H), 7.50-7.42 (m, 3H), 7.41-7.35 (m, 1H), 6.77 (s, 1H), 3.49 (s, 2H), 2.22 (s, 3H).

The starting material was prepared as follows:

Step 1: 4-Methyl-5-nitro-2-((6-phenylpyridin-3-yl)oxy)pyridine

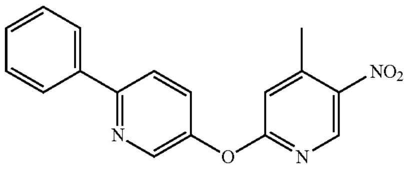

Following the General procedure A, 4-methyl-5-nitro-2-((6-phenylpyridin-3-yl)oxy)pyridine was obtained in 76% yield (0.664 mmol, 204 mg) 6-phenylpyridin-3-ol (0.956 mmol, 164 mg) and 2-chloro-4-methyl-5-nitropyridine (0.869 mmol, 150 mg).

$C_{17}H_{13}N_3O_3$; Mw=307.31 g·mol$^{-1}$; $^1$H NMR (400 MHz, $CDCl_3$) δ 8.87 (s, 1H), 8.57 (d, J=2.7 Hz, 1H), 8.02-7.97 (m, 2H), 7.82 (d, J=8.6 Hz, 1H), 7.60 (dd, J=8.6, 2.7 Hz, 1H), 7.52-7.39 (m, 3H), 6.97 (s, 1H), 2.71 (s, 3H).

Example 32: 2-Methyl-6-(4-(thiazol-5-yl)phenoxy)pyridin-3-amine

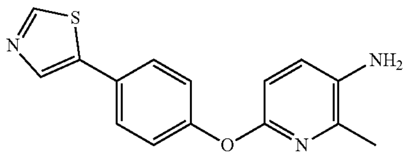

Following the General procedure B, 2-methyl-6-(4-(thiazol-5-yl)phenoxy)pyridin-3-amine was obtained in 64% yield (0.42 mmol, 120 mg) from 5-(4-((6-methyl-5-nitropyridin-2-yl)oxy)phenyl)thiazole (0.66 mmol, 206 mg).

$C_{15}H_{13}N_3OS$; Mw=283.35 g·mol$^{-1}$; $^1$H NMR (400 MHz, DMSO-$d_6$) δ 9.04 (d, J=0.7 Hz, 1H), 8.22 (d, J=0.7 Hz, 1H), 7.63 (d, J=8.8 Hz, 2H), 7.08 (d, J=8.3 Hz, 1H), 6.99 (d, J=8.7 Hz, 2H), 6.68 (d, J=8.4 Hz, 1H), 4.92 (s, 2H), 2.17 (s, 3H).

The starting material was prepared as follows:

Step 1: 5-(4-((6-Methyl-5-nitropyridin-2-yl)oxy)phenyl)thiazole

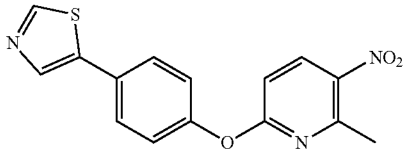 [SMILES: Cc1nc(Oc2ccc(-c3cncs3)cc2)ccc1[N+](=O)[O-]]

Following the General procedure D, a mixture of 5-(4,4,5,5-tetramethyl-1,3,2-dioxaborolan-2-yl)thiazole (4.89 mmol, 1.03 g), 6-(4-bromophenoxy)-2-methyl-3-nitropyridine (3.26 mmol, 1.01 g; expl. 28, Step 1), $Na_2CO_3$ (8.15 mmol, 864 mg), and $Pd(PPh_3)_4$ (0.163 mmol, 188 mg, 5% mol) in a 4:1 mixture of dioxane/$H_2O$ (0.06 M) was converted to 5-(4-((6-methyl-5-nitropyridin-2-yl)oxy)phenyl)thiazole in 20% yield (0.67 mmol, 209 mg).

$C_{15}H_{11}N_3O_3S$; Mw=313.33 g·mol$^{-1}$; $^1$H NMR (400 MHz, DMSO-$d_6$) δ 9.10 (app d, J=0.7 Hz, 1H), 8.52 (d, J=8.9 Hz, 1H), 8.33 (s, 1H), 7.91-7.71 (m, 2H), 7.40-7.21 (m, 2H), 7.11 (d, J=8.9 Hz, 1H), 2.60 (s, 3H).

Example 33: 4-Methyl-6-(4-(thiazol-5-yl)phenoxy)pyridin-3-amine

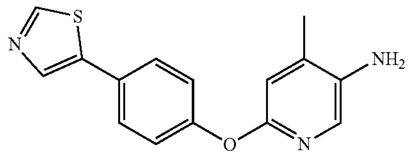

Following the General procedure B, 4-methyl-6-(4-(thiazol-5-yl)phenoxy)pyridin-3-amine was obtained in 33% yield (0.424 mmol, 0.120 g) from 5-(4-((4-methyl-5-nitropyridin-2-yl)oxy)phenyl)thiazole (1.02 mmol, 0.320 g).

$C_{15}H_{13}N_3OS$; Mw=283.35 g·mol$^{-1}$; $^1$H NMR (400 MHz, $CDCl_3$) δ 8.72 (s, 1H), 8.00 (s, 1H), 7.67 (s, 1H), 7.54 (d, J=8.7 Hz, 2H), 7.09 (d, J=8.7 Hz, 2H), 6.73 (s, 1H), 2.21 (s, 3H), 2.04 (s, 2H).

The starting material was prepared as follows:

Step 1: 5-(4-((4-Methyl-5-nitropyridin-2-yl)oxy)phenyl)thiazole

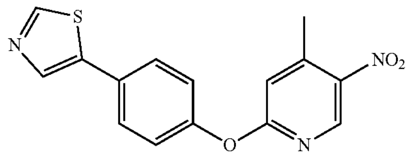 [SMILES: Cc1cc(Oc2ccc(-c3cncs3)cc2)ncc1[N+](=O)[O-]]

Following the General procedure E, 5-(4-((4-methyl-5-nitropyridin-2-yl)oxy)phenyl)thiazole was obtained in 40% yield (1.02 mmol, 0.320 g) from 5-(4,4,5,5-tetramethyl-1,3-dioxolan-2-yl)thiazole (3.78 mmol, 0.799 mg) and 2-(4-bromophenoxy)-4-methyl-5-nitropyridine (2.52 mmol, 0.780 g; expl. 29, Step 1).

$C_{15}H_{11}N_3O_3S$; Mw=313.33 g·mol$^{-1}$; $^1$H NMR (400 MHz, $CDCl_3$) δ 8.89 (s, 1H), 8.78 (s, 1H), 8.07 (s, 1H), 7.65 (d, J=8.7 Hz, 2H), 7.21 (d, J=8.7 Hz, 2H), 6.90 (s, 1H), 2.69 (s, 3H).

Example 34: N-Methyl-6-(4-(thiazol-5-yl)phenoxy)pyridin-3-amine

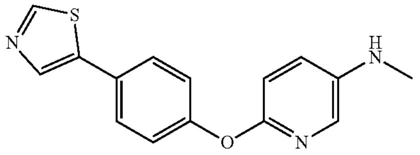 [SMILES: CNc1ccc(Oc2ccc(-c3cncs3)cc2)nc1]

Following the General procedure C, N-methyl-6-(4-(thiazol-5-yl)phenoxy)pyridin-3-amine was obtained in 59% yield (0.18 mmol, 50 mg) from 6-(4-(thiazol-5-yl)phenoxy)pyridin-3-amine (0.30 mmol, 80 mg; expl. 11).

$C_{15}H_{13}N_3OS$; Mw=283.35 g·mol$^{-1}$; $^1$H NMR (400 MHz, $CDCl_3$) δ 8.72 (s, 1H), 8.00 (s, 1H), 7.67 (d, J=3.0 Hz, 1H), 7.57-7.51 (m, 2H), 7.13-7.07 (m, 2H), 7.05 (dd, J=8.7, 3.1 Hz, 1H), 6.86 (d, J=8.7 Hz, 1H), 2.86 (s, 3H).

Example 35: 2-Methyl-6-(4-(thiazol-2-yl)phenoxy)pyridin-3-amine

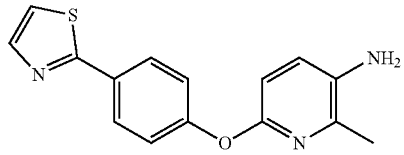 [SMILES: Cc1nc(Oc2ccc(-c3nccs3)cc2)ccc1[N+](=O)[O-]]

Following the General procedure B, 2-methyl-6-(4-(thiazol-2-yl)phenoxy)pyridin-3-amine was obtained in 68% yield (0.434 mmol, 123 mg) from 2-(4-((6-methyl-5-nitropyridin-2-yl)oxy)phenyl)thiazole (0.638 mmol, 200 mg).

$C_{15}H_{13}N_3OS$; Mw=283.35 g·mol$^{-1}$; $^1$H NMR (400 MHz, $CDCl_3$) δ 7.85 (d, J=8.8 Hz, 2H), 7.76 (d, J=3.3 Hz, 1H), 7.22 (d, J=3.3 Hz, 1H), 7.01 (d, J=8.8 Hz, 2H), 6.97 (d, J=8.4 Hz, 1H), 6.59 (d, J=8.4 Hz, 1H), 2.30 (s, 3H).

The starting material was prepared as follows:

Step 1: 2-(4-((6-Methyl-5-nitropyridin-2-yl)oxy)phenyl)thiazole

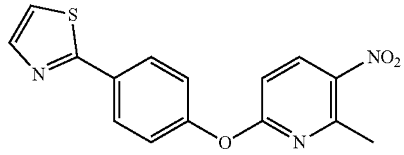

Following the General procedure A, 2-(4-((6-methyl-5-nitropyridin-2-yl)oxy)phenyl)thiazole was obtained in 51% yield (1.44 mmol, 0.450 g) from 4-(2-thiazolyl)phenol (2.82 mmol, 500 mg) and 6-chloro-2-methyl-3-nitropyridine (3.10 mmol, 536 mg).

$C_{15}H_{11}N_3O_3S$; Mw=313.33 g·mol$^{-1}$; $^1$H NMR (400 MHz, $CDCl_3$) δ 8.39 (d, J=8.9 Hz, 1H), 8.04 (d, J=8.5 Hz, 2H), 7.88 (s, 1H), 7.36 (s, 1H), 7.25 (d, J=8.2 Hz, 2H), 6.87 (d, J=8.9 Hz, 1H), 2.74 (s, 3H).

Example 36: 4-Methyl-6-(4-(thiazol-2-yl)phenoxy)pyridin-3-amine

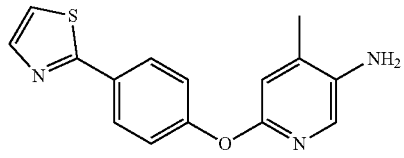 [SMILES: Cc1cc(Oc2ccc(-c3nccs3)cc2)ncc1N]

Following the General procedure F, 4-methyl-6-(4-(thiazol-2-yl)phenoxy)pyridin-3-amine was obtained in 94% yield (1.16 mmol, 330 mg) from 2-(4-((4-methyl-5-nitropyridin-2-yl)oxy)phenyl)thiazole (1.24 mmol, 390 mg).

$C_{15}H_{13}N_3OS$; Mw=283.35 g·mol$^{-1}$; $^1$H NMR (400 MHz, $CDCl_3$) δ 7.95-7.90 (m, 2H), 7.83 (d, J=3.3 Hz, 1H), 7.69 (s, 1H), 7.28 (d, J=3.3 Hz, 1H), 7.12-7.07 (m, 2H), 6.73 (s, 1H), 2.21 (s, 3H).

The starting material was prepared as follows:

Step 1: 2-(4-((4-Methyl-5-nitropyridin-2-yl)oxy)phenyl)thiazole

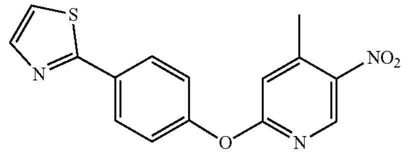 [SMILES: Cc1cc(Oc2ccc(-c3nccs3)cc2)ncc1[N+](=O)[O-]]

Following the General procedure A, 2-(4-((4-methyl-5-nitropyridin-2-yl)oxy)phenyl)thiazole was obtained in 72% yield (1.24 mmol, 390 mg) from 4-(thiazol-2-yl)phenol (1.91 mmol, 339 mg) and 2-chloro-4-methyl-5-nitropyridine (1.74 mmol, 300 mg).

$C_{15}H_{11}N_3O_3S$; Mw=313.33 g·mol$^{-1}$; $^1$H NMR (400 MHz, $CDCl_3$) δ 8.89 (s, 1H), 8.09-7.99 (m, 2H), 7.87 (d, J=3.3 Hz, 1H), 7.34 (d, J=3.3 Hz, 1H), 7.25-7.20 (m, 2H), 6.90-6.87 (m, 1H), 2.68 (s 3H).

Example 37: 6-((2,2'-Dimethyl-[1,1'-biphenyl]-4-yl)oxy)-2-methylpyridin-3-amine

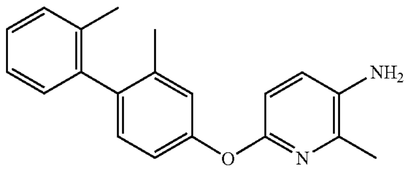 [SMILES: Cc1ccccc1-c1ccc(Oc2ccc(N)c(C)n2)cc1C]

Following the General procedure B, 6-((2,2'-dimethyl-[1,1'-biphenyl]-4-yl)oxy)-2-methylpyridin-3-amine was obtained in 80% yield (0.60 mmol, 183 mg) from 6-((2,2'-dimethyl-[1,1'-biphenyl]-4-yl)oxy)-2-methyl-3-nitropyridine (0.75 mmol, 250 mg).

$C_{20}H_{20}N_2O$; Mw=304.39 g·mol$^{-1}$; $^1$H NMR (400 MHz, methanol-$d_4$) δ 7.29-7.16 (m, 4H), 7.06-7.03 (m, 1H), 7.01 (d, J=8.3 Hz, 1H), 6.88 (d, J=2.6 Hz, 1H), 6.80 (dd, J=8.3, 2.6 Hz, 1H), 6.63 (dd, J=8.5, 0.7 Hz, 1H), 2.33 (s, 3H), 2.05 (s, 3H), 1.99 (s, 3H).

The starting material was prepared as follows:

Step 1: 6-(4-Bromo-3-methylphenoxy)-2-methyl-3-nitropyridine

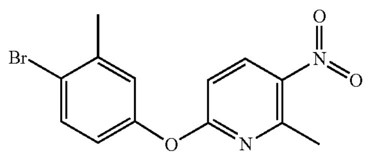 [SMILES: Cc1cc(Oc2ccc([N+](=O)[O-])c(C)n2)ccc1Br]

Following the General procedure A, 6-(4-bromo-3-methylphenoxy)-2-methyl-3-nitropyridine was obtained in 94% yield (5.46 mmol, 1.76 g) from 6-chloro-2-methyl-3-nitropyridine (5.79 mmol, 1.00 g) and 4-bromo-3-methylphenol (6.37 mmol, 1.19 g).

$C_{13}H_{11}BrN_2O_3$; Mw=323.15 g $mol^{-1}$; $^1H$ NMR (400 MHz, $CDCl_3$) δ 8.36 (d, J=8.9 Hz, 1H), 7.56 (d, J=8.6 Hz, 1H), 7.05 (d, J=2.6 Hz, 1H), 6.88 (dd, J=8.6, 2.6 Hz, 1H), 6.80 (d, J=8.9 Hz, 1H), 2.74 (s, 3H), 2.42 (s, 3H).

Step 2: 6-((2,2'-Dimethyl-[1,1'-biphenyl]-4-yl)oxy)-2-methyl-3-nitropyridine

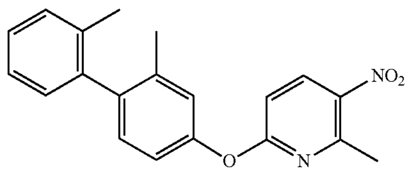 [SMILES: Cc1ccccc1-c1ccc(Oc2ccc([N+](=O)[O-])c(C)n2)cc1C]

Following the General procedure D, a mixture of o-tolylboronic acid (3.71 mmol, 505 mg), 6-(4-bromo-3-methylphenoxy)-2-methyl-3-nitropyridine (2.48 mmol, 800 mg), $Na_2CO_3$ (4.95 mmol, 525 mg), and $Pd(PPh_3)_4$ (0.124 mmol, 143 mg, 5% mol) in a 3:1 mixture of DME/$H_2O$ (0.43 M) was converted to 6-((2,2'-dimethyl-[1,1'-biphenyl]-4-yl)oxy)-2-methyl-3-nitropyridine in 90% yield (2.24 mmol, 750 mg).

$C_{20}H_{18}N_2O_3$; Mw=334.38 g·$mol^{-1}$; $^1H$ NMR (400 MHz, $CDCl_3$) δ 8.38 (d, J=8.9 Hz, 1H), 7.33-7.21 (m, 3H), 7.19-7.09 (m, 2H), 7.07 (d, J=2.5 Hz, 1H), 7.02 (dd, J=8.2, 2.5 Hz, 1H), 6.81 (d, J=8.9 Hz, 1H), 2.81 (s, 3H), 2.10 (s, 3H), 2.08 (s, 3H).

Example 38: N-Methyl-6-(4-(thiazol-2-yl)phenoxy)pyridin-3-amine

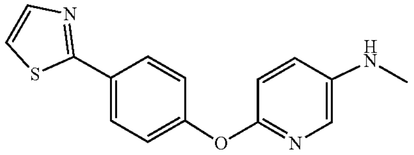 [SMILES: CNc1ccc(Oc2ccc(-c3nccs3)cc2)nc1]

Following the General procedure C, N-methyl-6-(4-(thiazol-2-yl)phenoxy)pyridin-3-amine was obtained in 86% yield (0.32 mmol, 90 mg) from 6-(4-(thiazol-2-yl)phenoxy)pyridin-3-amine (0.371 mmol, 100 mg; expl. 16).

$C_{15}H_{13}N_3OS$; Mw=283.35 g·$mol^{-1}$; $^1H$ NMR (400 MHz, $CDCl_3$) δ 7.96-7.90 (m, 2H), 7.83 (d, J=3.3 Hz, 1H), 7.68 (dd, J=3.1, 0.6 Hz, 1H), 7.28 (d, J=3.3 Hz, 1H), 7.13-7.07 (m, 2H), 7.03 (dd, J=8.7, 3.1 Hz, 1H), 6.86 (dd, J=8.7, 0.6 Hz, 1H), 2.87 (s, 3H).

Example 39: 6-((4'-Fluoro-[1,1'-biphenyl]-4-yl)oxy)-N,4-dimethylpyridin-3-amine

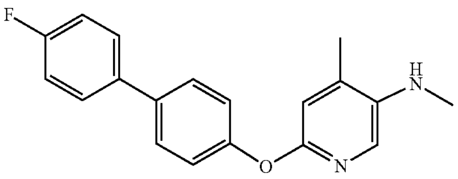 [SMILES: CNc1cnc(Oc2ccc(-c3ccc(F)cc3)cc2)cc1C]

Following the General procedure C, 6-((4'-fluoro-[1,1'-biphenyl]-4-yl)oxy)-N,4-dimethylpyridin-3-amine was obtained in 45% yield (0.15 mmol, 0.047 g) from 6-((4'-fluoro-[1,1'-biphenyl]-4-yl)oxy)-4-methylpyridin-3-amine (0.34 mmol, 100 mg; expl. 29). $C_{19}H_{17}FN_2O$; Mw=308.35 g·$mol^{-1}$; $^1H$ NMR (400 MHz, $CDCl_3$) δ 7.55 (s, 1H), 7.45-7.35 (m, 4H), 7.10 (t, J=8.3 Hz, 4H), 6.73 (s, 1H), 3.36 (s, 1H), 2.91 (s, 3H), 2.17 (s, 3H).

Example 40: 6-((4'-Fluoro-[1,1'-biphenyl]-4-yl)oxy)-N,2-dimethylpyridin-3-amine

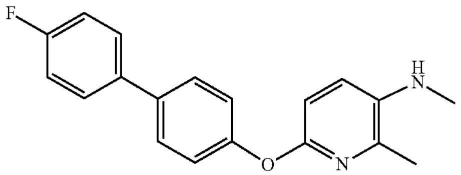 [SMILES: CNc1ccc(Oc2ccc(-c3ccc(F)cc3)cc2)nc1C]

Following the General procedure C, 6-((4'-fluoro-[1,1'-biphenyl]-4-yl)oxy)-N,2-dimethylpyridin-3-amine was obtained in 72% yield (0.19 mmol, 0.060 g) from 6-((4'-fluoro-[1,1'-biphenyl]-4-yl)oxy)-2-methylpyridin-3-amine (0.27 mmol, 80 mg; expl. 28).

$C_{19}H_{17}FN_2O$; Mw=308.35 g·$mol^{-1}$; $^1H$ NMR (400 MHz, $CDCl_3$) δ 7.55-7.45 (m, 4H), 7.19-7.00 (m, 5H), 6.74 (d, J=8.6 Hz, 1H), 2.92 (s, 3H), 2.42 (s, 3H), 1.65-1.48 (bs, 1H).

Example 41: N,4-Dimethyl-6-(4-(thiazol-5-yl)phenoxy)pyridin-3-amine

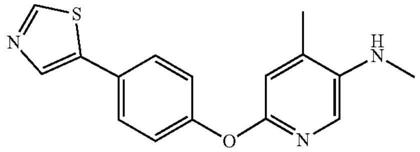 [SMILES: CNc1cnc(Oc2ccc(-c3cncs3)cc2)cc1C]

Following the General procedure C, N,4-dimethyl-6-(4-(thiazol-5-yl)phenoxy)pyridin-3-amine was obtained in 51% yield (0.091 mmol, 0.027 g) from 4-methyl-6-(4-(thiazol-5-yl)phenoxy)pyridin-3-amine (0.18 mmol, 0.050 g; expl. 33).

$C_{16}H_{15}N_3OS$; Mw=297.38 g·$mol^{-1}$; $^1H$ NMR (400 MHz, DMSO-$d_6$) δ 9.03 (d, J=0.7 Hz, 1H), 8.22 (d, J=0.7 Hz, 1H), 7.63 (d, J=8.7 Hz, 2H), 7.00-6.95 (m, 3H), 6.79 (d, J=8.5 Hz, 1H), 5.20 (q, J=5.0 Hz, 1H), 2.73 (d, J=4.9 Hz, 3H), 2.21 (s, 3H).

Example 42: N,2-Dimethyl-6-(4-(thiazol-5-yl)phenoxy)pyridin-3-amine

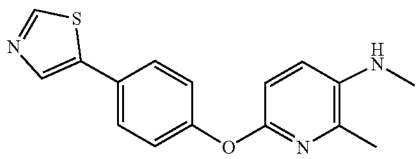 [SMILES: CNc1ccc(Oc2ccc(-c3cncs3)cc2)nc1C]

Following the General procedure C, N,2-dimethyl-6-(4-(thiazol-5-yl)phenoxy)pyridin-3-amine was obtained in 55% (0.098 mmol, 29 mg) from 2-methyl-6-(4-(thiazol-5-yl)phenoxy)pyridin-3-amine (0.18 mmol, 50 mg; expl. 32).

$C_{16}H_{15}N_3OS$; Mw=297.38 g $mol^{-1}$; $^1H$ NMR (400 MHz, DMSO-$d_6$) δ 9.03 (d, J=0.7 Hz, 1H), 8.22 (d, J=0.7 Hz, 1H), 7.78-7.50 (m, 2H), 7.05-6.90 (m, 3H), 6.79 (d, J=8.5 Hz, 1H), 5.20 (q, J=5.0 Hz, 1H), 2.73 (d, J=4.9 Hz, 3H), 2.21 (s, 3H).

Example 43: 6-((2,2'-Dimethyl-[1,1'-biphenyl]-4-yl)oxy)-N,2-dimethylpyridin-3-amine

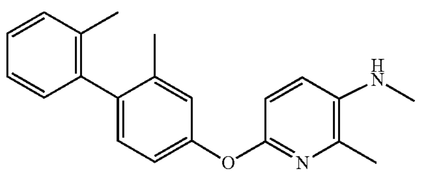 [SMILES: CNc1ccc(Oc2ccc(-c3ccccc3C)c(C)c2)nc1C]

Following the General procedure C, 6-((2,2'-dimethyl-[1,1'-biphenyl]-4-yl)oxy)-N,2-dimethylpyridin-3-amine was obtained in 82% yield (0.22 mmol, 69 mg) from 6-((2,2'-dimethyl-[1,1'-biphenyl]-4-yl)oxy)-2-methylpyridin-3-amine (0.26 mmol, 80 mg; expl. 37).

$C_{21}H_{22}N_2O$; Mw=318.42 g $mol^{-1}$; $^1H$ NMR (400 MHz, $CDCl_3$) δ 7.26-7.18 (m, 3H), 7.10 (d, J=6.8 Hz, 1H), 7.03 (dd, J=8.4, 3.3 Hz, 2H), 6.92 (d, J=2.5 Hz, 1H), 6.85 (dd, J=8.3, 2.5 Hz, 1H), 6.74 (d, J=8.5 Hz, 1H), 2.91 (s, 3H), 2.40 (s, 3H), 2.07 (s, 3H), 2.01 (s, 3H), 1.70-1.48 (bs, 1H).

Example 44: N,2-Dimethyl-6-(4-(thiazol-2-yl)phenoxy)pyridin-3-amine

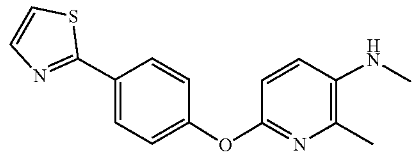 [SMILES: CNc1ccc(Oc2ccc(-c3nccs3)cc2)nc1C]

Following the General procedure C, N,2-dimethyl-6-(4-(thiazol-2-yl)phenoxy)pyridin-3-amine was obtained in 93% yield (0.404 mmol, 0.120 g) from 2-methyl-6-(4-(thiazol-2-yl)phenoxy)pyridin-3-amine (0.434 mmol, 0.123 g; expl. 35).

$C_{16}H_{15}N_3OS$; Mw=297.38 g·$mol^{-1}$; $^1H$ NMR (400 MHz, $CDCl_3$) δ 7.89 (d, J=8.9 Hz, 2H), 7.80 (d, J=8.9 Hz, 2H), 7.25 (d, J=3.3 Hz, 1H), 7.04 (d, J=8.9 Hz, 2H), 6.94 (d, J=8.5 Hz, 1H), 6.74 (d, J=8.5 Hz, 1H), 2.88 (s, 3H), 2.32 (s, 3H).

Example 45: N,2-Dimethyl-6-((6-phenylpyridin-3-yl)oxy)pyridin-3-amine

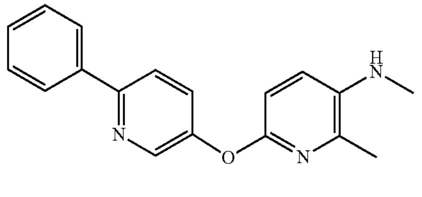 [SMILES: CNc1ccc(Oc2ccc(-c3ccccc3)nc2)nc1C]

Following the General procedure C, N,2-dimethyl-6-((6-phenylpyridin-3-yl)oxy)pyridin-3-amine was obtained in 80% yield (0.23 mmol, 67 mg) from 2-methyl-6-((6-phenylpyridin-3-yl)oxy)pyridin-3-amine (0.29 mmol, 80 mg; expl. 30).

$C_{18}H_{17}N_3O$; Mw=291.35 g $mol^{-1}$; $^1H$ NMR (400 MHz, DMSO-$d_6$) δ 8.40 (d, J=2.8 Hz, 1H), 8.03 (app d, J=8.2, 2H), 7.93 (d, J=8.7 Hz, 1H), 7.51-7.44 (m, 3H), 7.43-7.37 (m, 1H), 6.98 (d, J=8.2 Hz, 1H), 6.86 (d, J=8.4 Hz, 1H), 5.21 (q, J=5.0 Hz, 1H), 2.73 (d, J=4.9 Hz, 3H), 2.20 (s, 3H).

Example 46: 6-(4-(6-Methoxypyridin-3-yl)phenoxy)-4-methylpyridin-3-amine

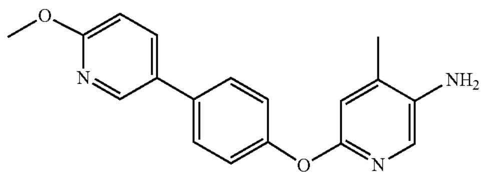 [SMILES: COc1ccc(-c2ccc(Oc3cc(C)c(N)cn3)cc2)cn1]

Following the General procedure B, 6-(4-(6-methoxypyridin-3-yl)phenoxy)-4-methylpyridin-3-amine was obtained in 55% yield (0.490 mmol, 165 mg) from 2-(4-(6-methoxypyridin-3-yl)phenoxy)-4-methyl-5-nitropyridine (0.892 mmol, 0.300 g).

$C_{18}H_{17}N_3O_2$; Mw=307.35 g·$mol^{-1}$; δ $^1H$ NMR (400 MHz, $CDCl_3$) δ 8.21 (d, J=5.4 Hz, 1H), 7.71 (s, 1H), 7.62 (d, J=8.8 Hz, 2H), 7.16 (d, J=8.8 Hz, 2H), 7.12 (dd, J=5.4, 1.5 Hz, 1H), 6.97-6.94 (m, 3H), 6.77 (s, 1H), 4.01 (s, 3H), 2.24 (s, 3H).

The starting material was prepared as follows:

Step 1: 2-(4-(6-Methoxypyridin-3-yl)phenoxy)-4-methyl-5-nitropyridine

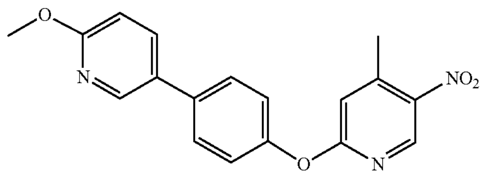 [SMILES: COc1ccc(-c2ccc(Oc3cc(C)c([N+](=O)[O-])cn3)cc2)cn1]

Following the General procedure E, 2-(4-(6-methoxypyridin-3-yl)phenoxy)-4-methyl-5-nitropyridine was obtained in 55% yield (0.892 mmol, 0.300 g) from 2-(4-bromophenoxy)-4-methyl-5-nitropyridine (1.62 mmol, 0.500 g; expl. 29, Step 1) and (6-methoxypyridin-3-yl)boronic acid (1.95 mmol, 0.298 g).

$C_{18}H_{15}N_3O_4$; Mw=337.33 g·$mol^{-1}$; $^1H$ NMR (400 MHz, $CDCl_3$) δ 8.91 (s, 1H), 8.40 (d, J=2.1 Hz, 1H), 7.79 (dd, J=8.6, 2.6 Hz, 1H), 7.59 (d, J=8.7 Hz, 2H), 7.23 (d, J=8.6 Hz, 2H), 6.90 (s, 1H), 6.86-6.81 (m, 1H), 3.99 (s, 3H), 2.69 (s, 3H).

Example 47: 6-(4-(2-Methoxypyridin-4-yl)phenoxy)-4-methylpyridin-3-amine

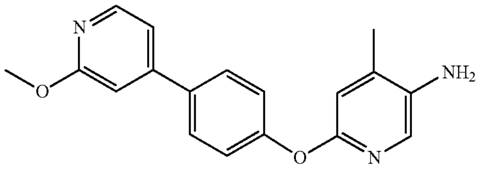 [SMILES: COc1cc(-c2ccc(Oc3cc(C)c(N)cn3)cc2)ccn1]

Following the General procedure B, 6-(4-(2-methoxypyridin-4-yl)phenoxy)-4-methylpyridin-3-amine was obtained in 20% yield (0.091 mmol, 28 mg) from 2-(4-(2-methoxypyridin-4-yl)phenoxy)-4-methyl-5-nitropyridine (0.446 mmol, 0.150 g).

$C_{18}H_{17}N_3O_2$; Mw=307.35 g·mol$^{-1}$; δ $^1$H NMR (400 MHz, $CDCl_3$) δ 8.38 (d, J=2.0 Hz, 1H), 7.78 (dd, J=8.6, 2.6 Hz, 1H), 7.70 (s, 1H), 7.53-7.48 (m, 2H), 7.17-7.12 (m, 2H), 6.85-6.80 (m, 1H), 6.75 (s, 1H), 4.00 (s, 3H), 2.23 (m, 3H), 1.61 (s, 2H).

The starting material was prepared as follows:

Step 1: 2-(4-(2-Methoxypyridin-4-yl)phenoxy)-4-methyl-5-nitropyridine

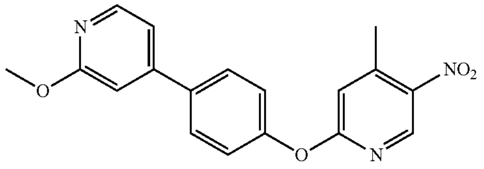 [SMILES: COc1cc(-c2ccc(Oc3cc(C)c([N+](=O)[O-])cn3)cc2)ccn1]

Following the General procedure E, 2-(4-(2-methoxypyridin-4-yl)phenoxy)-4-methyl-5-nitropyridine was obtained in 28% yield (0.446 mmol, 0.150 g) from 2-(4-bromophenoxy)-4-methyl-5-nitropyridine (1.62 mmol, 0.500 g; expl. 29, Step 1) and (2-methoxypyridin-4-yl)boronic acid (1.95 mmol, 0.298 g).

$C_{18}H_{15}N_3O_4$; Mw=337.33 g·mol$^{-1}$; $^1$H NMR (400 MHz, $CDCl_3$) δ 8.91 (s, 1H), 8.40 (dd, J=2.6, 0.7 Hz, 1H), 7.79 (dd, J=8.6, 2.6 Hz, 1H), 7.61-7.55 (m, 2H), 7.25-7.20 (m, 2H), 6.90 (d, J=1.0 Hz, 1H), 6.83 (dd, J=8.6, 0.7 Hz, 1H), 3.99 (s, 3H), 2.69 (d, J=0.8 Hz, 3H).

Example 48: 6-(4-(1H-Imidazol-4-yl)phenoxy)-4-methylpyridin-3-amine

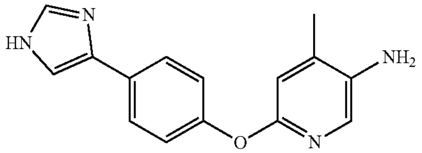 [SMILES: Cc1cc(Oc2ccc(-c3c[nH]cn3)cc2)ncc1N]

Following the General procedure B, 6-(4-(1H-imidazol-4-yl)phenoxy)-4-methylpyridin-3-amine was obtained in 61% yield (86 μmol, 23 mg) from 2-(4-(1H-imidazol-4-yl)phenoxy)-4-methyl-5-nitropyridine (0.10 mmol, 0.040 g).

$C_{15}H_{14}N_4O$; Mw 266.30; $^1$H NMR (400 MHz, methanol-$d_4$) δ 7.72 (d, J=1.2 Hz, 1H), 7.71-7.64 (m, 2H), 7.62 (s, 1H), 7.37 (d, J=1.2 Hz, 1H), 7.02-6.92 (m, 2H), 6.77-6.64 (m, 1H), 3.35 (s, 1H), 2.20 (s, 3H).

The starting material was prepared as follows:

Step 1: 4-Bromo-1-trityl-1H-imidazole

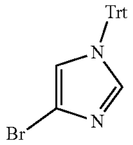

To a solution of 4-bromo-1H-imidazole (10.00 mmol, 2.00 g) in $CHCl_3$ (20 mL) was added TEA (40.00 mmol, 4.00 g, 6.0 mL) and the mixture was cooled to 0° C. To this was added a solution of trityl-Cl (10.00 mol, 4.00 g) in 20 ml of $CHCl_3$ and the mixture was stirred at RT for 2 h. The reaction mixture was diluted with 1M HCl and extracted with $CHCl_3$ (3×). The combined organic layers were washed with brine, dried with $Na_2SO_4$, filtered, and concentrated under reduced pressure to get 4-bromo-1-trityl-1H-imidazole (4.40 g). This was used without any further purification.

$C_{22}H_{17}BrN_2$; Mw=389.30 g mol$^{-1}$; $^1$H NMR (400 MHz, $CDCl_3$) δ 7.39-7.30 (m, 10H), 7.16-7.08 (m, 6H), 6.80 (d, J=1.6 Hz, 1H).

Step 2: 4-Methyl-5-nitro-2-(4-(4,4,5,5-tetramethyl-1,3,2-dioxaborolan-2-yl)phenoxy)pyridine

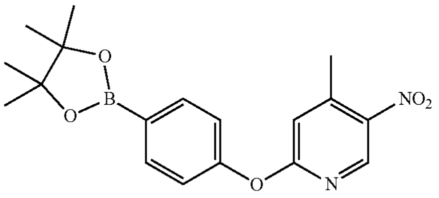 [SMILES: Cc1cc(Oc2ccc(B3OC(C)(C)C(C)(C)O3)cc2)ncc1[N+](=O)[O-]]

Following the General procedure E, 4-methyl-5-nitro-2-(4-(4,4,5,5-tetramethyl-1,3,2-dioxaborolan-2-yl)phenoxy)pyridine was obtained in 95% yield (3.09 mmol, 1.10 g) from 2-(4-bromophenoxy)-4-methyl-5-nitropyridine (3.23 mmol, 1.0 g; expl. 29, Step 1) and bis(pinacolato)diborane (4.79 mmol, 1.22 g).

$C_{18}H_{21}BN_2O_5$; Mw=356.19 g·mol$^{-1}$; $^1$H NMR (400 MHz, $CDCl_3$) δ 8.88 (s, 1H), 7.90 (d, J=8.5 Hz, 2H), 7.14 (d, J=8.5 Hz, 2H), 6.82 (s, 1H), 2.66 (s, 3H), 1.35 (s, 12H).

Step 3: 4-Methyl-5-nitro-2-(4-(1-trityl-1H-imidazol-4-yl)phenoxy)pyridine

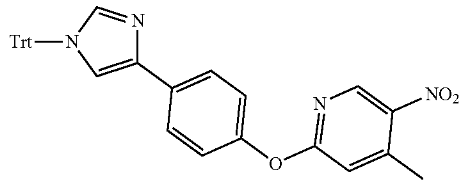

Following the General procedure E, 4-methyl-5-nitro-2-(4-(1-trityl-1H-imidazol-4-yl)phenoxy)pyridine was obtained in 51% yield (0.15 mmol, 81 mg) from 4-methyl-5-nitro-2-(4-(4,4,5,5-tetramethyl-1,3,2-dioxaborolan-2-yl)phenoxy)pyridine (0.3 mmol, 0.1 g) and 4-bromo-1-trityl-1H-imidazole (0.4 mmol, 0.2 g).

$C_{34}H_{26}N_4O_3$; Mw=538.61; $^1H$ NMR (400 MHz, $CDCl_3$) δ 8.89 (s, 1H), 7.82-7.76 (m, 2H), 7.53-7.48 (m, 1H), 7.45-7.27 (m, 9H), 7.24-7.18 (m, 6H), 7.13-7.07 (m, 3H), 6.80 (d, J=1.0 Hz, 1H), 2.65 (d, J=0.8 Hz, 3H).

Step 4: 2-(4-(1H-Imidazol-4-yl)phenoxy)-4-methyl-5-nitropyridine

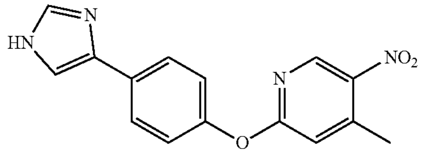 [SMILES: Cc1cc(Oc2ccc(-c3c[nH]cn3)cc2)ncc1[N+](=O)[O-]]

To a solution of 4-methyl-5-nitro-2-(4-(1-trityl-1H-imidazol-4-yl)phenoxy)pyridine (0.15 mmol, 0.081 g) in DCM (10 mL) was added HCl in dioxane (0.19 mL, 4 molar, 0.75 mmol) and stirred at RT overnight. The reaction mixture was concentrated to dryness and the residue was suspended in the saturated solution of $NaHCO_3$ and extracted with $CHCl_3$ (3×). The combined organic layers were dried over $Na_2SO_4$, filtered and concentrated under reduced pressure to get crude. This was purified using Biotage, 25 g silica column, DCM and MeOH as eluent to get 2-(4-(1H-imidazol-4-yl)phenoxy)-4-methyl-5-nitropyridine (0.1 mmol, 0.04 g)

$C_{15}H_{12}N_4O_3$; Mw=296.29; $^1H$ NMR (400 MHz, $CDCl_3$) δ 8.91 (s, 1H), 7.82 (d, J=8.4 Hz, 2H), 7.73 (s, 1H), 7.34 (d, J=1.1 Hz, 1H), 7.23-7.09 (m, 2H), 6.90-6.79 (m, 1H), 2.67 (d, J=0.8 Hz, 3H).

Example 49: 6-(4-(2H-Tetrazol-5-yl)phenoxy)-4-methylpyridin-3-amine

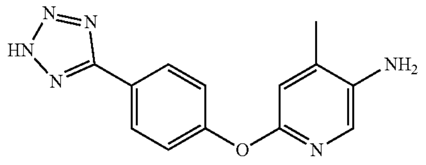 [SMILES: Cc1cc(Oc2ccc(-c3nn[nH]n3)cc2)ncc1N]

In a flask, 2-(4-(2H-tetrazol-5-yl)phenoxy)-4-methyl-5-nitropyridine (0.14 mmol, 42 mg) was dissolved in EtOH (1.4 mL, 0.10 molar) and flushed with nitrogen. Pd/C (0.014 mmol, 15 mg) was added, a hydrogen balloon was attached and the mixture evacuated/backfilled (3×).

The mixture was then left stirring for 5 h. Upon full conversion, the mixture was evacuated/backfilled (3×) with nitrogen, filtered through a syringe filter, and concentrated under reduced pressure. The crude material was purified on a Biotage C18 column (25 g, 5-95% MeOH/$H_2O$+0.1% HCOOH) to afford 6-(4-(2H-tetrazol-5-yl)phenoxy)-4-methylpyridin-3-amine (0.097 mmol, 26 mg) in 69% yield as a pale yellow solid.

$C_{13}H_{12}N_6O$; Mw=268.28 g $mol^{-1}$; $^1H$ NMR (400 MHz, DMSO-$d_6$) δ 7.99 (d, J=8.8 Hz, 2H), 7.58 (s, 1H), 7.12 (d, J=8.7 Hz, 2H), 6.79 (s, 1H), 2.12 (s, 3H).

The starting material was prepared as follows:

Step 1: 4-(2H-Tetrazol-5-yl)phenol

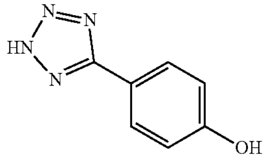 [SMILES: Oc1ccc(-c2nn[nH]n2)cc1]

A 100 mL round bottomed flask equipped with a Teflon coated magnetic stirring bar, and a Findenser™ cooler, was charged with 4-hydroxybenzonitrile (8.39 mmol, 1.00 g), sodium azide (25.2 mmol, 1.64 g), and triethylamine hydrochloride (25.2 mmol, 3.47 g) and toluene (42.0 mL, 0.20 M). The reaction mixture was heated at 100° C. overnight with vigorous stirring. Then it was cooled to ambient temperature and poured into a separatory funnel and extracted with $H_2O$ (3×). The combined aqueous phases were treated dropwise with HCl (conc.) to precipitate the product. The precipitate was collected by vacuum filtration, and dried under vacuum to afford 4-(2H-tetrazol-5-yl)phenol in 88% yield (7.40 mmol, 1.19 g) as an off-white solid.

$C_7H_6N_4O$; Mw=162.15 g $mol^{-1}$; $^1H$ NMR (400 MHz, DMSO-$d_6$) δ 10.16 (s, 1H), 7.86 (d, J=8.7 Hz, 2H), 6.95 (d, J=8.7 Hz, 2H).

Step 2: 2-(4-(2H-Tetrazol-5-yl)phenoxy)-4-methyl-5-nitropyridine

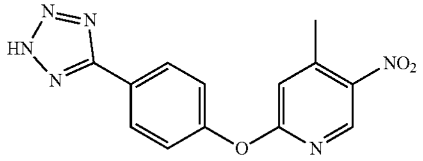 [SMILES: Cc1cc(Oc2ccc(-c3nn[nH]n3)cc2)ncc1[N+](=O)[O-]]

To a 100-mL round-bottom flask were added 4-(2H-tetrazol-5-yl)phenol (0.62 mmol, 100 mg), 2-chloro-4-methyl-5-nitropyridine (1.85 mmol, 319 mg), and anhydrous $K_2CO_3$ (1.85 mmol, 256 mg). DMF (2.1 mL, 0.30 molar) was added and the resulting brown suspension was heated to 60° C. overnight. Upon full conversion by TLC, the reaction mixture was allowed to cool to RT, concentrated to a minimal amount of solvent, and loaded directly on Biotage C18 column (30 g cartridge, 5-95% MeOH/$H_2O$+0.1% HCOOH) to afford 2-(4-(2H-tetrazol-5-yl)phenoxy)-4-methyl-5-nitropyridine (0.15 mmol, 45 mg) in 24% yield.

$C_{13}H_{10}N_6O_3$; Mw=298.26 g $mol^{-1}$; $^1H$ NMR (400 MHz, DMSO-$d_6$) δ 8.87 (s, 1H), 8.22-7.99 (m, 2H), 7.52-7.36 (m, 2H), 7.30 (s, 1H), 2.63 (s, 3H).

Example 50: 6-(4-(1H-Pyrazol-4-yl)phenoxy)-4-methylpyridin-3-amine

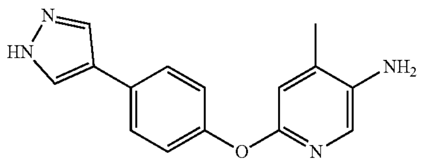 [SMILES: Cc1cc(Oc2ccc(-c3cn[nH]c3)cc2)ncc1N]

To a solution of 4-methyl-6-(4-(1-trityl-1H-pyrazol-4-yl) phenoxy)pyridin-3-amine (0.08 mmol, 0.04 g), in DCM (0.4 mL), was added a 4M solution of HCl (0.2 mL, 0.8 mmol) in dioxane. The mixture was stirred at RT overnight. The mixture was diluted in $H_2O$ and the two layers separated. The aqueous layer was washed with DCM. The aqueous layer was basified to pH=8 with saturated aqueous solution of $NaHCO_3$. The aqueous layer was extracted with EtOAc (3×). The combined organic layers were dried over $MgSO_4$, filtered and concentrated under reduce pressure. 6-(4-(1H-pyrazol-4-yl)phenoxy)-4-methylpyridin-3-amine was obtained as a light green solid in 90% yield (0.072 mmol, 19 mg).

$C_{15}H_{14}N_4O$; Mw=266.30 g $mol^{-1}$; $^1H$ NMR (400 MHz, methanol-$d_4$) δ 7.91 (s, 2H), 7.61 (s, 1H), 7.58-7.52 (m, 2H), 7.00-6.92 (m, 2H), 6.72-6.67 (m, 1H), 2.20 (app d, J=0.8 Hz, 3H).

The starting material was prepared as follows:

Step 1: 4-Bromo-1-trityl-1H-pyrazole

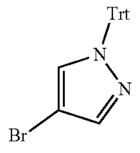

4-Bromo-1H-pyrazole (3.40 mmol, 500 mg) was dissolved in DMF (4.00 mL, 0.85 molar), set under $N_2$, and cooled to 0° C. To the solution were added tBuOK (4.08 mmol, 458 mg, 1.20 eq.) and trityl-Cl (3.74 mmol, 1.04 g, 1.10 eq.) and the mixture was left stirring at RT overnight. The reaction mixture was diluted with $H_2O$, and the aqueous layer was extracted with EtOAc (3×). The combined organic layers were washed with brine, dried with $Na_2SO_4$, filtered, and concentrated under reduced pressure. The crude material was purified by column chromatography using cyclohexane:EtOAc as eluent to afford 4-bromo-1-trityl-1H-pyrazole (2.638 mmol, 1.027 g) in 77% yield as a white solid.

$C_{22}H_{17}BrN_2$; Mw=389.30 g $mol^{-1}$; $^1H$ NMR (400 MHz, DMSO-$d_6$) δ 7.76 (d, J=0.7 Hz, 1H), 7.51 (d, J=0.7 Hz, 1H), 7.43-7.31 (m, 9H), 7.11-6.99 (m, 6H).

Step 2: 4-Methyl-5-nitro-2-(4-(1-trityl-1H-pyrazol-4-yl)phenoxy)pyridine

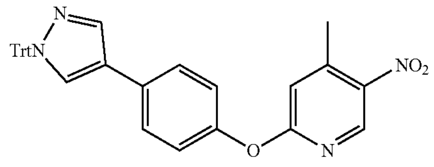

Following the General procedure D, a mixture of 4-methyl-5-nitro-2-(4-(4,4,5,5-tetramethyl-1,3,2-dioxaborolan-2-yl)phenoxy)pyridine (0.85 mmol, 302 mg; expl. 48, Step2), 4-bromo-1-trityl-1H-pyrazole (0.77 mmol, 300 mg), $K_2CO_3$ (1.54 mmol, 213 mg), and $Pd(PPh_3)_4$ (0.08 mmol, 89 mg, 10% mol) in a 3:1 mixture of DME/$H_2O$ (0.13 M) was converted to 4-methyl-5-nitro-2-(4-(1-trityl-1H-pyrazol-4-yl)phenoxy)pyridine (0.41 mmol, 223 mg) in 54% yield. $C_{34}H_{26}N_4O_3$; Mw=538.61 g $mol^{-1}$; $^1H$ NMR (400 MHz, $CDCl_3$) δ 8.87 (s, 1H), 7.93 (d, J=0.8 Hz, 1H), 7.60 (d, J=0.9 Hz, 1H), 7.52-7.46 (m, 2H), 7.40-7.27 (m, 9H), 7.22-7.16 (m, 6H), 7.13-7.07 (m, 2H), 6.82 (d, J=1.0 Hz, 1H), 2.66 (s, 3H).

Step 3: 4-Methyl-6-(4-(1-trityl-1H-pyrazol-4-yl) phenoxy)pyridin-3-amine

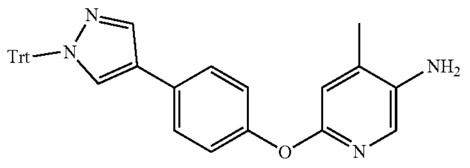

Following the General procedure B, 4-methyl-6-(4-(1-trityl-1H-pyrazol-4-yl)phenoxy)pyridin-3-amine (0.08 mmol, 0.04 g) was prepared in 42% yield from 4-methyl-5-nitro-2-(4-(1-trityl-1H-pyrazol-4-yl)phenoxy)pyridine (0.20 mmol, 0.10 g).

$C_{34}H_{28}N_4O$; Mw=508.61 g $mol^{-1}$; $^1H$ NMR (400 MHz, $CDCl_3$) δ 7.89 (d, J=0.8 Hz, 1H), 7.64 (s, 1H), 7.55 (d, J=0.8 Hz, 1H), 7.41-7.37 (m, 2H), 7.40-7.27 (m, 9H), 7.22-7.17 (m, 6H), 7.01 (d, J=8.7 Hz, 2H), 6.65 (t, J=0.7 Hz, 1H), 3.42 (s, 2H), 2.18 (app d, J=0.8 Hz, 3H).

Example 51: 6,6'-((4'-Fluoro-[1,1'-biphenyl]-2,4-diyl)bis(oxy))bis(pyridin-3-amine)

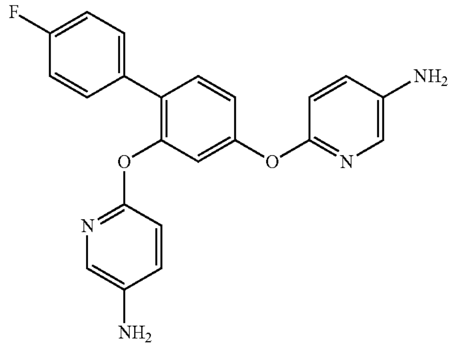 [SMILES: Nc1ccc(Oc2ccc(-c3ccc(F)cc3)c(Oc3ccc(N)cn3)c2)nc1]

Following the General procedure B, 6,6'-((4'-fluoro-[1,1'-biphenyl]-2,4-diyl)bis(oxy))bis(pyridin-3-amine) (0.05 mmol, 0.02 g), was prepared from 6,6'-((4'-fluoro-[1,1'-biphenyl]-2,4-diyl)bis(oxy))bis(3-nitropyridine) (0.156 mmol, 0.070 g) in 32% yield after purification.

$C_{22}H_{17}FN_4O_2$; Mw=388.39 g $mol^{-1}$; $^1H$ NMR (400 MHz, $CDCl_3$) δ 7.73 (dd, J=3.1, 0.7 Hz, 1H), 7.64 (dd, J=3.0, 0.7 Hz, 1H), 7.49-7.44 (m, 2H), 7.34 (d, J=8.5 Hz, 1H), 7.08 (dd, J=8.6, 3.0 Hz, 1H), 7.03-6.95 (m, 3H), 6.91 (dd, J=8.6, 2.4 Hz, 1H), 6.81-6.77 (m, 2H), 6.61 (dd, J=8.6, 0.7 Hz, 1H), 3.53 (s, 4H). $^{19}F$ NMR (377 MHz, $CDCl_3$) δ −115.99.

The starting material was prepared as follows:

Step 1: 4'-Fluoro-2-methoxy-[1,1'-biphenyl]-4-ol

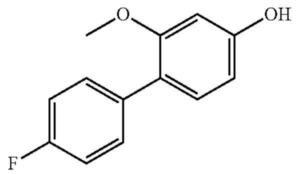 [SMILES: COc1cc(O)ccc1-c1ccc(F)cc1]

Following the General procedure D, a mixture of 4-bromo-3-methoxyphenol (9.9 mmol, 2.0 g), (4-fluorophenyl)boronic acid (11 mmol, 1.5 g), $K_2CO_3$ (20 mmol, 2.7 g), and $Pd(PPh_3)_2Cl_2$ (0.985 mmol, 0.691 g) in a 3:1 mixture of 2-propanol/$H_2O$ (0.1 M) was converted to 4'-fluoro-2-methoxy-[1,1'-biphenyl]-4-ol (5.45 mmol, 1.19 g) in 55% yield.

$C_{13}H_{11}FO_2$; Mw=218.22 g·mol$^{-1}$; 1H NMR (400 MHz, $CDCl_3$) δ 7.48-7.40 (m, 2H), 7.14 (d, J=8.2 Hz, 1H), 7.10-7.01 (m, 2H), 6.51 (d, J=2.4 Hz, 1H), 6.47 (dd, J=8.2, 2.4 Hz, 1H), 3.79 (s, 3H).

Step 2: 4'-Fluoro-[1,1'-biphenyl]-2,4-diol

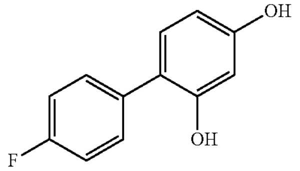 [SMILES: Oc1ccc(-c2ccc(F)cc2)c(O)c1]

4'-Fluoro-2-methoxy-[1,1'-biphenyl]-4-ol (916 mol, 200 mg) was dissolved in DCM (9.16 mL, 0.1M), set under $N_2$, and cooled to −78° C. $BBr_3$ (1.83 mmol, 1.83 mL, 1M in DCM) was added dropwise. After 30 min at that temperature, the mixture was left to reach RT slowly overnight. Still a small amount of starting material was observed, nevertheless the reaction mixture was quenched by slow addition of water. The aqueous layer was neutralized/basified with 15% NaOH and extracted with DCM (3×). The combined organic layers were dried with $Na_2SO_4$, filtered, and concentrated under reduced pressure. The crude material was purified by flash column chromatography using EtOAc:cyclohexane to afford 4'-fluoro-[1,1'-biphenyl]-2,4-diol (0.74 mmol, 152 mg) in 81% yield as a white solid.

$C_{12}H_9FO_2$; Mw=204.20 g mol$^{-1}$; $^1$H NMR (400 MHz, $CDCl_3$) δ 7.48-7.33 (m, 2H), 7.18-7.07 (m, 2H), 7.09-7.05 (m, 1H), 6.65-6.35 (m, 2H), 5.07 (s, 1H), 4.81 (s, 1H).

Step 3: 6,6'-((4'-Fluoro-[1,1'-biphenyl]-2,4-diyl)bis(oxy))bis(3-nitropyridine)

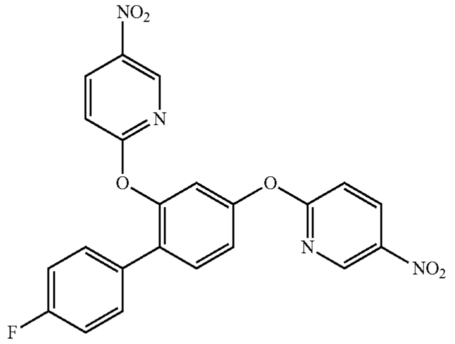 [SMILES: O=[N+]([O-])c1ccc(Oc2ccc(-c3ccc(F)cc3)c(Oc3ccc([N+](=O)[O-])cn3)c2)nc1]

Following the General procedure A, 6,6'-((4'-fluoro-[1,1'-biphenyl]-2,4-diyl)bis(oxy))bis(3-nitropyridine) was obtained in 63% yield (0.44 mmol, 195 mg) from 4'-fluoro-[1,1'-biphenyl]-2,4-diol (0.69 mmol, 140 mg) and 2-chloro-5-nitropyridine (1.51 mmol, 239 mg). $C_{22}H_{13}FN_4O_6$; Mw=448.37 g mol$^{-1}$; $^1$H NMR (400 MHz, $CDCl_3$) δ 9.09 (dd, J=2.8, 0.6 Hz, 1H), 8.93 (dd, J=2.8, 0.6 Hz, 1H), 8.52 (dd, J=9.0, 2.8 Hz, 1H), 8.37 (dd, J=9.0, 2.8 Hz, 1H), 7.53 (d, J=8.5 Hz, 1H), 7.44-7.36 (m, 2H), 7.23 (dd, J=8.4, 2.4 Hz, 1H), 7.13 (dd, J=9.1, 0.6 Hz, 1H), 7.10 (d, J=2.3 Hz, 1H), 7.04-6.98 (m, 2H), 6.91 (dd, J=9.0, 0.6 Hz, 1H).

Example 52: 6-((2,2'-Dimethyl-[1,1'-biphenyl]-4-yl)oxy)-4-methylpyridin-3-amine

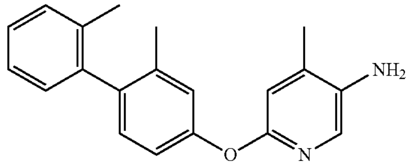 [SMILES: Cc1cc(Oc2ccc(-c3ccccc3C)c(C)c2)ncc1N]

Following the General procedure B, 6-((2,2'-dimethyl-[1,1'-biphenyl]-4-yl)oxy)-4-methylpyridin-3-amine was obtained in 61% yield (0.31 mmol, 94 mg) from 2-((2,2'-dimethyl-[1,1'-biphenyl]-4-yl)oxy)-4-methyl-5-nitropyridine (0.508 mmol, 170 mg) $C_{20}H_{20}N_2O$; Mw=304.39 g·mol$^{-1}$; $^1$H NMR (400 MHz, $CDCl_3$) δ 7.71 (s, 1H), 7.25-7.23 (m, 2H), 7.23-7.18 (m, 1H), 7.13-7.09 (m, 1H), 7.05 (d, J=8.3 Hz, 1H), 6.94 (d, J=2.6 Hz, 1H), 6.88 (dd, J=8.3, 2.5 Hz, 1H), 6.73-6.71 (m, 1H), 2.21 (s, 3H), 2.08 (s, 3H), 2.02 (s, 3H).

The starting material was prepared as follows:

Step 1: 2,2'-Dimethyl-[1,1'-biphenyl]-4-ol

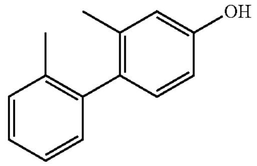

Following the General procedure D, 2,2'-dimethyl-[1,1'-biphenyl]-4-ol was obtained in 85% yield (4.54 mmol, 0.900 g) from 4-bromo-3-methylphenol (5.3 mmol, 1.0 g) and o-tolylboronic acid (6.95 mmol, 0.944 g).

$C_{14}H_{14}O$; Mw=198.26 g·mol$^{-1}$; $^{1}H$ NMR (400 MHz, $CDCl_3$) δ 7.28-7.18 (m, 3H), 7.11-7.07 (m, 1H), 6.97 (d, J=8.2 Hz, 1H), 6.77 (d, J=2.4 Hz, 1H), 6.71 (dd, J=8.2, 2.6 Hz, 1H), 5.21 (app d, 1H), 2.06 (s, 3H), 2.01 (s, 3H).

Step 2: 2-((2,2'-Dimethyl-[1,1'-biphenyl]-4-yl)oxy)-4-methyl-5-nitropyridine

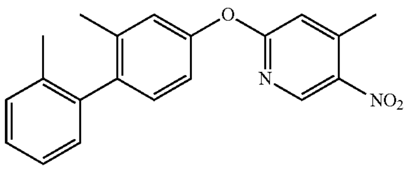 [SMILES: Cc1ccccc1-c1ccc(Oc2cc(C)c([N+](=O)[O-])cn2)cc1C]

Following the General procedure A, 2-((2,2'-dimethyl-[1,1'-biphenyl]-4-yl)oxy)-4-methyl-5-nitropyridine was obtained in 61% yield (0.526 mmol, 176 mg) from 2-chloro-4-methyl-5-nitropyridine (0.869 mmol, 150 mg) and 2,2'-dimethyl-[1,1'-biphenyl]-4-ol (0.956 mmol, 190 mg).

$C_{20}H_{18}N_2O_3$; Mw=334.37 g mol$^{-1}$; $^{1}H$ NMR (400 MHz, $CDCl_3$) δ 7.30-7.27 (m, 3H), 7.25-7.21 (m, 1H), 7.19-7.13 (m, 2H), 7.05 (d, J=2.5 Hz, 1H), 7.00 (dd, J=8.2, 2.4 Hz, 1H), 6.86 (s, 1H), 2.69 (s, 3H), 2.10 (s, 3H), 2.08 (s, 3H).

Example 53: 6-((6-(4-Fluorophenyl)pyridin-3-yl)oxy)-2-methylpyridin-3-amine

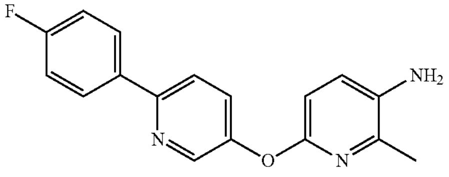

Following the General procedure B, 6-((6-(4-fluorophenyl)pyridin-3-yl)oxy)-2-methylpyridin-3-amine was obtained in 89% yield (2.80 mmol, 732 mg) from 6-((6-(4-fluorophenyl)pyridin-3-yl)oxy)-2-methyl-3-nitropyridine (2.80 mmol, 910 mg).

$C_{17}H_{14}FN_3O$; Mw=295.31 g mol$^{-1}$; $^{1}H$ NMR (400 MHz, $CDCl_3$) δ 8.49 (dd, J=2.8, 0.7 Hz, 1H), 7.98-7.88 (m, 2H), 7.64 (dd, J=8.4, 0.7 Hz, 1H), 7.45 (dd, J=8.7, 2.8 Hz, 1H), 7.19-7.08 (m, 2H), 7.04 (d, J=8.4 Hz, 1H), 6.68 (dd, J=8.4, 0.7 Hz, 1H), 3.50 (s, 2H), 2.33 (s, 3H).

The starting material was prepared as follows:

Step 1: 2-Bromo-5-(methoxymethoxy)pyridine

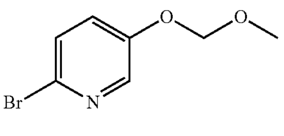

To a solution of 6-bromopyridin-3-ol (29 mmol, 5.0 g), in dry DMF (29 mL), under $N_2$, at 0° C., was added portion-wise NaH (29 mmol, 1.1 g, 60% wt). The mixture was stirred at 0° C. for 1 h. Methyl chloromethyl ether (29 mmol, 2.3 g, 2.2 mL,) was then slowly added. The mixture was stirred at 0° C. for 1 h and then allowed to warm to RT over the weekend. The reaction mixture was cooled to 0° C. and saturated $NaHCO_3$ solution was added. The mixture was warmed to RT and diluted with $H_2O$. The mixture was extracted with AcOEt (3×). The combined organic layers were washed with $H_2O$ (3×) and brine. The mixture was dried over $MgSO_4$, filtered and concentrated under reduced pressure. The product, 2-bromo-5-(methoxymethoxy)pyridine (29 mmol, 6.3 g), was isolated as a colorless oil in quantitative yield.

$C_7H_8BrNO_2$; Mw=218.05 g mol$^{-1}$; $^{1}H$ NMR (400 MHz, $CDCl_3$) δ 8.15 (dd, J=3.1, 0.6 Hz, 1H), 7.35 (dd, J=8.7, 0.6 Hz, 1H), 7.27-7.20 (m, 1H), 5.15 (s, 2H), 3.46 (s, 3H).

Step 2: 2-(4-Fluorophenyl)-5-(methoxymethoxy)pyridine

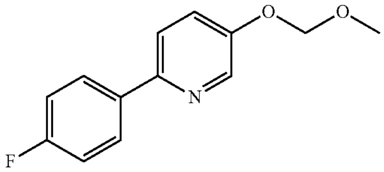 [SMILES: COCOc1ccc(-c2ccc(F)cc2)nc1]

Following the General procedure D, a mixture of (4-fluorophenyl)boronic acid (32.0 mmol, 4.4 g), 2-bromo-5-(methoxymethoxy)pyridine (29.0 mmol, 6.3 g), $K_2CO_3$ (58.0 mmol, 8.0 g), and $Pd(PPh_3)_2Cl_2$ (2.9 mmol, 2.0 g) in 4:1 mixture of 2-propanol/$H_2O$ (0.1 M) was converted to 2-(4-fluorophenyl)-5-(methoxymethoxy)pyridine in 56% yield (16.20 mmol, 3.79 g).

$C_{13}H_{12}FNO_2$; Mw=233.24 g mol$^{-1}$; $^{1}H$ NMR (400 MHz, $CDCl_3$) δ 8.46 (dd, J=2.9, 0.7 Hz, 1H), 7.97-7.83 (m, 2H), 7.60 (dd, J=8.7, 0.7 Hz, 1H), 7.43 (dd, J=8.7, 2.9 Hz, 1H), 7.13 (dd, J=8.9, 8.5 Hz, 2H), 5.23 (s, 2H), 3.51 (s, 3H).

Step 3: 6-(4-Fluorophenyl)pyridin-3-ol

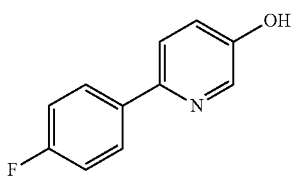 [SMILES: Oc1ccc(-c2ccc(F)cc2)nc1]

To a solution of 2-(4-fluorophenyl)-5-(methoxymethoxy)pyridine (16.20 mmol, 3.79 g), in dioxane (20 mL), at RT was added a 4M HCl (146 mmol, 36.6 mL) dioxane solution. The mixture was heated at 80° C. overnight. The reaction mixture was cooled to RT and concentrated under reduced pressure. The residue was dissolved in $H_2O$ and extracted with DCM (3×). The aqueous layer was neutralized to pH=6-7 with solid $Na_2CO_3$. The precipitated white solid was filtered off, washed with hexane and dried under vacuo for 2 h, to afford 6-(4-fluorophenyl)pyridin-3-ol (15.0 mmol, 2.83 g) in 92% yield.

$C_{11}H_8FNO$; Mw=189.19 g $mol^{-1}$; $^1H$ NMR (400 MHz, DMSO-$d_6$) δ 10.04 (s, 1H), 8.20 (dd, J=2.9, 0.7 Hz, 1H), 8.09-7.93 (m, 2H), 7.78 (dd, J=8.7, 0.7 Hz, 1H), 7.33-7.15 (m, 3H).

Step 4: 6-((6-(4-Fluorophenyl)pyridin-3-yl)oxy)-2-methyl-3-nitropyridine

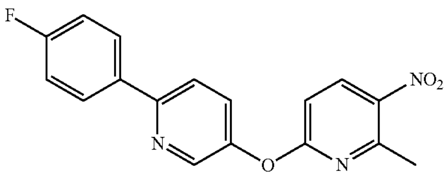 [SMILES: Cc1nc(Oc2ccc(-c3ccc(F)cc3)nc2)ccc1[N+](=O)[O-]]

Following the General procedure A, 6-((6-(4-fluorophenyl)pyridin-3-yl)oxy)-2-methyl-3-nitropyridine was obtained in 100% yield (3.00 mmol, 900 mg) from 6-(4-fluorophenyl)pyridin-3-ol (3.00 mmol, 600 mg) and 6-chloro-2-methyl-3-nitropyridine (3.00 mmol, 500 mg).

$C_{17}H_{12}FN_3O_3$; Mw=325.29 g $mol^{-1}$; $^1H$ NMR (400 MHz, $CDCl_3$) δ 8.58 (dd, J=2.7, 0.7 Hz, 1H), 8.42 (d, J=8.9 Hz, 1H), 8.03-7.96 (m, 2H), 7.76 (dd, J=8.7, 0.7 Hz, 1H), 7.60 (dd, J=8.7, 2.7 Hz, 1H), 7.20-7.14 (m, 2H), 6.96 (dd, J=8.9, 0.7 Hz, 1H), 2.72 (s, 3H).

Example 54: 6-((6-(4-Fluorophenyl)pyridin-3-yl)oxy)-N,2-dimethylpyridin-3-amine

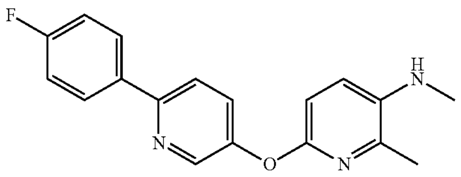 [SMILES: CNc1ccc(Oc2ccc(-c3ccc(F)cc3)nc2)nc1C]

Following the General procedure C, 6-((6-(4-fluorophenyl)pyridin-3-yl)oxy)-N,2-dimethylpyridin-3-amine was obtained in 70% yield with purification (0.810 mmol, 0.250 g) from 6-((6-(4-fluorophenyl)pyridin-3-yl)oxy)-2-methylpyridin-3-amine (1.155 mmol, 0.341 g) and paraformaldehyde (1.617 mmol, 1.40 eq.).

$C_{18}H_{16}FN_3O$; MW=309.34 g mol-1; $^1H$ NMR (400 MHz, DMSO-$d_6$) δ 8.38 (d, J=2.7 Hz, 1H), 8.08 (dd, J=8.9, 5.6 Hz, 2H), 7.93 (d, J=8.7 Hz, 1H), 7.46 (dd, J=8.7, 2.9 Hz, 1H), 7.30 (t, J=8.9 Hz, 2H), 6.98 (d, J=8.5 Hz, 1H), 6.86 (d, J=8.5 Hz, 1H), 5.21 (q, J=5.0 Hz, 1H), 2.73 (d, J=5.0 Hz, 3H), 2.20 (s, 3H).

Example 55: 6-((6-(4-Fluorophenyl)pyridin-3-yl)oxy)-4-methylpyridin-3-amine

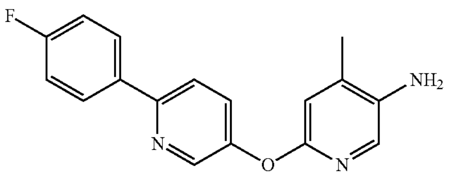 [SMILES: Cc1cc(Oc2ccc(-c3ccc(F)cc3)nc2)ncc1[N+](=O)[O-]]

Following the General procedure B, 6-((6-(4-fluorophenyl)pyridin-3-yl)oxy)-4-methylpyridin-3-amine was obtained in 96% yield (2.58 mmol, 763 mg) from 24(6-(4-fluorophenyl)pyridin-3-yl)oxy)-4-methyl-5-nitropyridine (2.70 mmol, 900 mg).

$C_{17}H_{14}FN_3O$; Mw=295.31 g $mol^{-1}$; $^1H$ NMR (400 MHz, $CDCl_3$) δ 8.48 (dd, J=2.8, 0.6 Hz, 1H), 7.95-7.89 (m, 2H), 7.66 (dd, J=8.1, 0.6 Hz, 1H), 7.64 (s, 1H), 7.47 (dd, J=8.7, 2.8 Hz, 1H), 7.19 (app t, J=8.7 Hz, 2H), 6.77 (s, 1H), 3.48 (s, 2H), 2.22 (s, 3H).

The starting material was prepared as follows:

Step 1: 2-((6-(4-Fluorophenyl)pyridin-3-yl)oxy)-4-methyl-5-nitropyridine

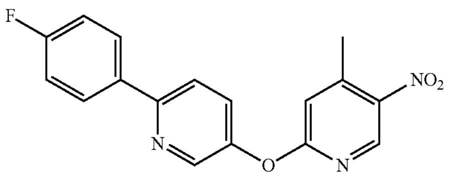

Following the General procedure A, 24(6-(4-fluorophenyl)pyridin-3-yl)oxy)-4-methyl-5-nitropyridin was obtained in 90% yield (2.70 mmol, 900 mg) from 6-(4-fluorophenyl) pyridin-3-ol (3.00 mmol, 600 mg; expl. 53, Step 3) and 2-chloro-4-methyl-5-nitropyridine (5.00 mmol, 800 mg).

$C_{17}H_{12}FN_3O_3$; Mw=325.29 g $mol^{-1}$; H NMR (400 MHz, $CDCl_3$) δ 8.86 (s, 1H), 8.55 (dd, J=2.8, 0.6 Hz, 1H), 8.01-7.95 (m, 2H), 7.76 (dd, J=8.7, 0.6 Hz, 1H), 7.60 (dd, J=8.6, 2.8 Hz, 1H), 7.17 (app t, J=8.8 Hz, 2H), 6.97 (s, 1H), 2.72 (s, 3H).

Example 56: 6-((6-(4-Fluorophenyl)pyridin-3-yl)oxy)-N,4-dimethylpyridin-3-amine

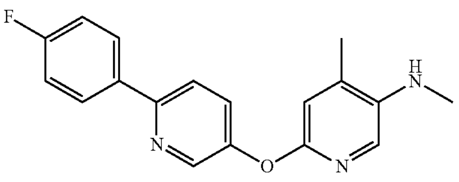 [SMILES: CNc1cnc(Oc2ccc(-c3ccc(F)cc3)nc2)cc1C]

Following the General procedure C, 6-((6-(4-fluorophenyl)pyridin-3-yl)oxy)-N,4-dimethylpyridin-3-amine was obtained in 69% yield after purification (0.786 mmol, 0.243 g) from 6-((6-(4-fluorophenyl)pyridin-3-yl)oxy)-4-methylpyridin-3-amine (1.14 mmol, 0.337 g) and paraformaldehyde (1.60 mmol, 1.40 eq.).

$C_{18}H_{16}FN_3O$; MW=309.34 g mol-1; $^1H$ NMR (400 MHz, DMSO-$d_6$) δ 8.41 (d, J=2.8 Hz, 1H), 8.11-8.03 (m, 2H), 7.94 (d, J=8.7 Hz, 1H), 7.52 (dd, J=8.7, 2.8 Hz, 1H), 7.36-7.24 (m, 3H), 6.87 (s, 1H), 5.14 (q, J=4.9 Hz, 1H), 2.74 (d, J=4.9 Hz, 3H), 2.15 (s, 3H).

Example 57: (4-Aminophenyl)(4'-fluoro-[1,1'-biphenyl]-4-yl)methanol

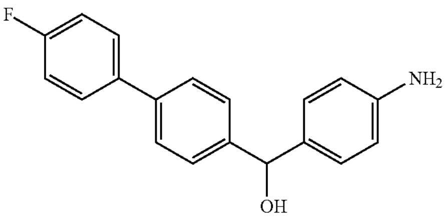 [SMILES: Nc1ccc(C(O)c2ccc(-c3ccc(F)cc3)cc2)cc1]

Following the General procedure F, (4-aminophenyl)(4'-fluoro-[1,1'-biphenyl]-4-yl)methanol was obtained in 98% yield with purification (1.55 mmol, 0.445 g) from (4'-fluoro-[1,1'-biphenyl]-4-yl)(4-nitrophenyl)methanol (1.52 mmol, 0.500 g).

$C_{19}H_{16}FNO$; Mw=293.33 g·mol$^{-1}$; $^1$H NMR (400 MHz, $CDCl_3$) δ 7.56-7.48 (m, 4H), 7.47-7.41 (m, 2H), 7.22-7.15 (m, 2H), 7.13-7.07 (m, 2H), 6.71-6.60 (m, 2H), 5.80 (s, 1H).

The starting material was prepared as follows:

Step 1: (4'-Fluoro-[1,1'-biphenyl]-4-yl)boronic acid

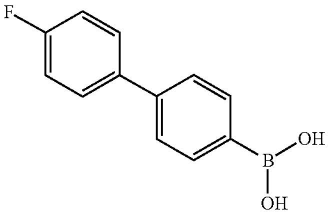 [SMILES: OB(O)c1ccc(-c2ccc(F)cc2)cc1]

To a solution of 4-bromo-4'-fluoro-1,1'-biphenyl (1.99 mmol, 0.500 g), in dry THF (19.9 ml), at −78° C., under inert atmosphere, tert-butyllithium (2.390 mmol, 1.4 ml) was added dropwise. The reaction mixture was stirred at −78° C. for 20 min before trimethyl borate (1.99 mmol, 0.222 ml) was added dropwise. After stirring for 1 h the reaction mixture was brought to RT and quenched with 1N HCl and stirred for 30 min. The reaction mixture was concentrated under vacuo and the observed precipitate was filtered off and air dried to get (4'-fluoro-[1,1'-biphenyl]-4-yl)boronic acid (1.852 mmol, 0.400 g) in 93% yield as a white powder. The NMR spectra was identical to the previously reported one (Neya, et al., WO 2003 022842).

Step 2: (4'-Fluoro-[1,1'-biphenyl]-4-yl)(4-nitrophenyl)methanol

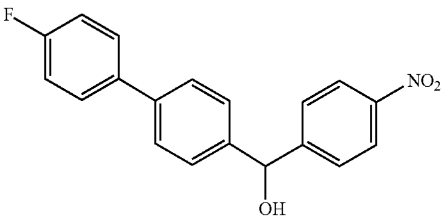 [SMILES: O=[N+]([O-])c1ccc(C(O)c2ccc(-c3ccc(F)cc3)cc2)cc1]

To a solution of chloro(1,5-cyclooctadiene)rhodium(I) dimer (0.093 mmol, 0.046 g) in dry dioxane (12.3 ml), at RT, under inert atmosphere, was added potassium hydroxide (1.852 mmol, 1.234 ml) and the mixture stirred for 3 min. To this solution (4'-fluoro-[1,1'-biphenyl]-4-yl)boronic acid (1.852 mmol, 0.400 g) was added followed by 4-nitrobenzaldehyde (3.760 mmol, 0.560 g). The mixture was stirred for 14 h at RT and then quenched by addition of brine. The mixture was extracted with EtOAc (3×). The combined organic layers were dried over $Na_2SO_4$, filtered and concentrated under reduced pressure. The residue was purified by flash chromatography (Biotage KP-Sil 50 g, hexane/EtOAc, 0-20%) to afford (4'-fluoro-[1,1'-biphenyl]-4-yl)(4-nitrophenyl)methanol (1.46 mmol, 0.473 g) in 79% yield as a white solid. $C_{19}H_{14}FNO_3$; Mw=323.32 g·mol$^{-1}$; $^1$H NMR (400 MHz, $CDCl_3$) δ 8.25-8.16 (m, 2H), 7.65-7.59 (m, 2H), 7.56-7.48 (m, 4H), 7.44-7.39 (m, 2H), 7.17-7.06 (m, 2H), 5.97 (s, 1H), 2.41 (s, 1H). $^{19}$F NMR (377 MHz, $CDCl_3$) δ −115.19.

Example 58: 4-((4'-Fluoro-[1,1'-biphenyl]-4-yl)(methoxy)methyl)aniline

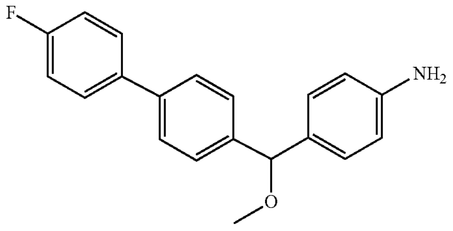 [SMILES: COC(c1ccc(N)cc1)c1ccc(-c2ccc(F)cc2)cc1]

Following the General procedure F, 44(4'-fluoro-[1,1'-biphenyl]-4-yl)(methoxy)methyl)-aniline was obtained in 78% yield with purification (1.30 mmol, 0.400 g) from 4-fluoro-4'-(methoxy(4-nitrophenyl)methyl)-1,1'-biphenyl (1.78 mmol, 0.600 g).

$C_{20}H_{18}FNO$; Mw=307.37 g·mol$^{-1}$; $^1$H NMR (300 MHz, Chloroform-d) δ 7.59-7.44 (m, 4H), 7.45-7.33 (m, 2H), 7.22-7.00 (m, 4H), 6.76-6.55 (m, 2H), 5.19 (s, 1H), 3.38 (s, 3H).

The starting material was prepared as follows:

Step 1: 4-Fluoro-4'-(methoxy(4-nitrophenyl)methyl)-1,1'-biphenyl

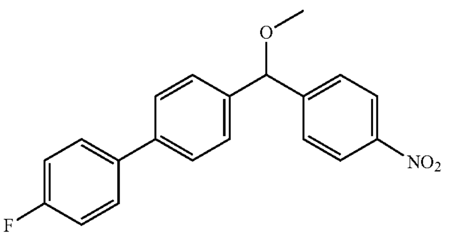 [SMILES: COC(c1ccc(-c2ccc(F)cc2)cc1)c1ccc([N+](=O)[O-])cc1]

To a solution of (4'-fluoro-[1,1'-biphenyl]-4-yl)(4-nitrophenyl)methanol (0.464 mmol, 0.15 g; expl. 57, Step 2), in acetone (4.64 ml), was added $Cs_2CO_3$ (1.392 mmol, 0.453 g) followed by iodomethane (0.696 mmol, 0.044 ml). The reaction mixture was refluxed for 4 h in a sealed tube at 60° C. The cooled reaction mixture was directly loaded on silica and the residue purified by flash chromatography (Biotage KP-Sil 25 g, hexane/EtOAc, 0-20%) to afford 4-fluoro-4'-(methoxy(4-nitrophenyl)methyl)-1,1'-biphenyl (0.406 mmol, 0.137 g) in 88% yield.

$C_{20}H_{16}FNO_3$; Mw=337.34 g·mol$^{-1}$; $^1$H NMR (400 MHz, $CDCl_3$) δ 8.22-8.17 (m, 2H), 7.61-7.48 (m, 6H), 7.41-7.36 (m, 2H), 7.15-7.07 (m, 2H), 5.36 (s, 1H), 3.43 (s, 3H).

Example 59: 4-((4'-Fluoro-[1,1'-biphenyl]-4-yl) methyl)aniline

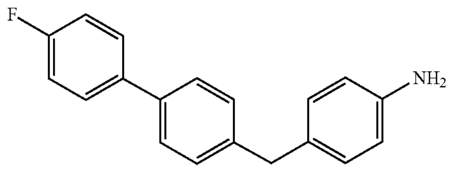 [SMILES: Nc1ccc(Cc2ccc(-c3ccc(F)cc3)cc2)cc1]

Following the General procedure F, 44(4'-fluoro-[1,1'-biphenyl]-4-yl)methyl)aniline was obtained in 60% yield with purification (1.30 mmol, 0.154 g) from 4-fluoro-4'-(fluoro(4-nitrophenyl)methyl)-1,1'-biphenyl (0.92 mmol, 0.300 g).

$C_{19}H_{16}FN$; Mw=277.34 g·mol$^{-1}$; $^1$H NMR (400 MHz, $CDCl_3$) δ 7.56-7.50 (m, 2H), 7.49-7.44 (m, 2H), 7.27-7.24 (m, 2H), 7.16-7.09 (m, 2H), 7.06-7.01 (m, 2H), 6.71-6.66 (m, 2H), 3.94 (s, 2H).

The starting material was prepared as follows:

Step 1: 4-Fluoro-4'-(fluoro(4-nitrophenyl)methyl)-1,1'-biphenyl

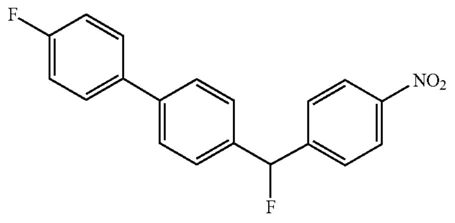 [SMILES: O=[N+]([O-])c1ccc(C(F)c2ccc(-c3ccc(F)cc3)cc2)cc1]

To a solution of (4'-fluoro-[1,1'-biphenyl]-4-yl)(4-nitrophenyl)methanol (1.54 mmol, 0.500 g; expl. 57, Step 2), in dry DCM (7.73 ml), under inert atmosphere, at −78° C., was added dropwise diethylamino-sulfur-trifluoride (1.85 mmol, 0.245 ml). The reaction mixture was stirred at the same temperature for 2 h then brought to RT. The reaction was then quenched using saturated $NaHCO_3$ solution. The two layers were separated, and the aqueous layer was extracted with DCM (3×). The combined organic layers were dried over $Na_2SO_4$, filtered and concentrated under reduced pressure to afford 4-fluoro-4'-(fluoro(4-nitrophenyl)methyl)-1,1'-biphenyl (1.38 mmol, 0.450 g) in 89% yield as yellow solid.

$C_{19}H_{13}F_2NO_2$; Mw=325.31 g·mol$^{-1}$; $^1$H NMR (400 MHz, $CDCl_3$) δ 8.29-8.22 (m, 2H), 7.59-7.49 (m, 6H), 7.42-7.36 (m, 2H), 7.17-7.09 (m, 2H), 6.58 (d, J=47.0 Hz, 1H).

Example 60: (4-Aminophenyl)(4'-fluoro-[1,1'-biphenyl]-4-yl)methanone hydrochloride

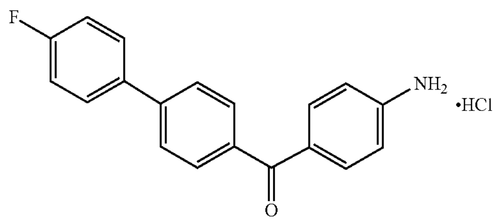 [SMILES: Nc1ccc(C(=O)c2ccc(-c3ccc(F)cc3)cc2)cc1 ; Cl]

To the solution of tert-butyl (4-(4'-fluoro-[1,1'-biphenyl]-4-carbonyl)phenyl)carbamate (0.51 mmol, 0.200 g) in DCM (10 ml) was added 3 ml of 4M HCl in dioxane. This was stirred at RT overnight. The reaction mixture was concentrated to dryness and the residue was suspended in $Et_2O$, sonicated for 10 min and filtered off. The residue was washed with $Et_2O$ and then air-dried to get (4-aminophenyl)(4'-fluoro-[1,1'-biphenyl]-4-yl)methanone hydrochloride in 58% yield (0.29 mmol, 0.098 g).

$C_{19}H_{14}FNO$ HCl; Mw=291.33 g·mol$^{-1}$; $^1$H NMR (400 MHz, DMSO-$d_6$) δ 9.33 (s), 7.90-7.74 (m, 8H), 7.72-7.65 (m, 2H), 7.41-7.30 (m, 2H).

The starting material was prepared as follows:

Step 1: tert-butyl((4'-fluoro-[1,1'-biphenyl]-4-yl)(4-nitrophenyl)methoxy)dimethylsilane

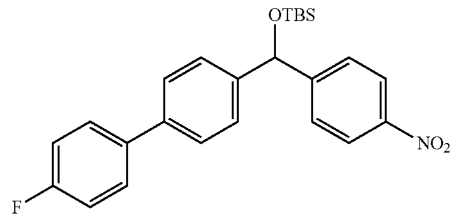

To a solution of (4'-fluoro-[1,1'-biphenyl]-4-yl)(4-nitrophenyl)methanol (3.09 mmol, 1.00 g; expl. 57, Step 2) in DMF (31 ml) at RT was added imidazole (6.09 mmol, 0.421 g) and tert-butyl dimethyl silyl chloride (4.02 mmol, 0.606 g) and the reaction mixture was stirred overnight. The reaction was quenched by the addition of brine and extracted with $Et_2O$ (3×).

The combined organic layers were washed with water (5×) and the separated organic layer were dried over $Na_2SO_4$, filtered and concentrated under reduced pressure to get crude material. This was purified by flash chromatography (Biotage KP-Sil 50 g, hexane/EtOAc, 0-20%) to afford tert-butyl((4'-fluoro-[1,1'-biphenyl]-4-yl)(4-nitrophenyl)methoxy)dimethylsilane (1.37 mmol, 0.600 g) in 44% yield as a white solid.

$C_{25}H_{28}FNO_3Si$; Mw=437.58 g·mol$^{-1}$; $^1$H NMR (400 MHz, $CDCl_3$) δ 8.20-8.17 (m, 2H), 7.61-7.46 (m, 6H), 7.41-7.36 (m, 2H), 7.15-7.06 (m, 2H), 5.86 (s, 1H), 0.94 (app d, 9H), 0.04 (bs, 3H), 0.01 (bs, 3H).

Step 2: 4-(((tert-butyldimethylsilyl)oxy)(4'-fluoro-[1,1'-biphenyl]-4-yl)methyl)aniline

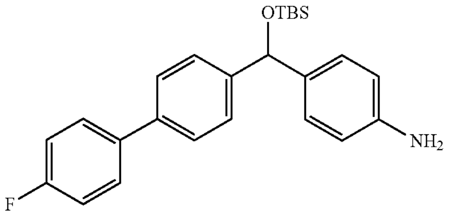 [SMILES: CC(C)(C)[Si](C)(C)OC(c1ccc(-c2ccc(F)cc2)cc1)c1ccc([N+](=O)[O-])cc1]

Following the General procedure F, 4-(((tert-butyldimethylsilyl)oxy)(4'-fluoro-[1,1'-biphenyl]-4-yl)methyl)aniline was obtained in 99% yield (12.50 mmol, 5.10 g) from tert-butyl((4'-fluoro-[1,1'-biphenyl]-4-yl)(4-nitrophenyl)methoxy)dimethylsilane (12.57 mmol, 5.50 g).

$C_{25}H_{30}FNOSi$; Mw=407.60 g·mol$^{-1}$; $^1$H NMR (400 MHz, $CDCl_3$) δ 7.56-7.35 (m, 6H), 7.17-7.03 (m, 4H), 6.66-6.59 (m, 2H), 5.70 (s, 1H), 0.92 (app d, 9H), 0.01 (s, 3H), −0.03 (s, 3H).

Step 3: tert-butyl (4-(((tert-butyldimethylsilyl)oxy)(4'-fluoro-[1,1'-biphenyl]-4-yl)methyl)phenyl)carbamate

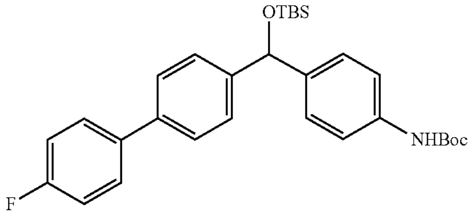 [SMILES: CC(C)(C)OC(=O)Nc1ccc(C(O[Si](C)(C)C(C)(C)C)c2ccc(-c3ccc(F)cc3)cc2)cc1]

To a solution of 4-(((tert-butyldimethylsilyl)oxy)(4'-fluoro-[1,1'-biphenyl]-4-yl)methyl)aniline (14.72 mmol, 6.00 g) in DCM (75 ml) at RT was added DMAP (1.472 mmol, 0.18 g) and triethyl amine (29.4 mmol, 4.1 ml). To this stirred solution a solution of Boc anhydride (10.83 mmol, 5.50 g) in DCM (20 ml) was added. The reaction mixture was stirred at RT overnight. Then it was washed with water and 1N HCl. The organic layer was dried over $Na_2SO_4$, filtered and concentrated to get tert-butyl (4-(((tert-butyldimethylsilyl)oxy)(4'-fluoro-[1,1'-biphenyl]-4-yl)methyl)phenyl)carbamate. (12.80 mmol, 6.5 g) in 87% yield.

$C_{30}H_{38}FNO_3Si$; Mw=507.71 g·mol$^{-1}$; $^1$H NMR (400 MHz, $CDCl_3$) δ 7.54-7.48 (m, 2H), 7.48-7.27 (m, 8H), 7.15-7.04 (m, 2H), 5.75 (d, J=2.1 Hz, 1H), 1.41 (d, J=4.9 Hz, 9H), 0.98-0.81 (m, 9H), 0.09 until −0.12 (m, 6H).

Step 4: tert-butyl (4-((4'-fluoro-[1,1'-biphenyl]-4-yl)(hydroxy)methyl)phenyl)carbamate

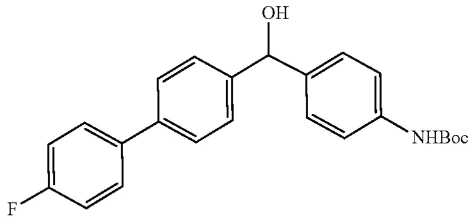

To a solution of tert-butyl (4-(((tert-butyldimethylsilyl)oxy)(4'-fluoro-[1,1'-biphenyl]-4-yl)methyl)phenyl)carbamate (10.83 mmol, 5.50 g), in THF (110 mL), at RT, under inert atmosphere, was added tetrabutylammonium fluoride (16.25 mmol, 8.12 ml). The reaction mixture was stirred at RT for 4 h. Then it was diluted with saturated $NH_4Cl$ solution and extracted with $Et_2O$ (2×). The combined organic layers were dried over $Na_2SO_4$, filtered and concentrated under reduced pressure. The residue was purified by flash chromatography (Biotage KP-Sil 100 g, hexane/EtOAc, 0-80%) to afford tert-butyl (4-((4'-fluoro-[1,1'-biphenyl]-4-yl)(hydroxy)methyl)phenyl)carbamate (6.40 mmol, 2.52 g) in 59% yield, as a foam.

$C_{24}H_{24}FNO_3$; Mw=393.45 g·mol$^{-1}$; $^1$H NMR (400 MHz, $CDCl_3$) δ 7.54-7.46 (m, 4H), 7.41-7.34 (m, 4H), 7.23-7.18 (m, 2H), 7.14-7.07 (m, 2H), 5.87 (s, 1H), 2.26 (s, 1H), 1.44 (s, 9H).

Step 5: tert-butyl (4-(4'-fluoro-[1,1'-biphenyl]-4-carbonyl)phenyl)carbamate

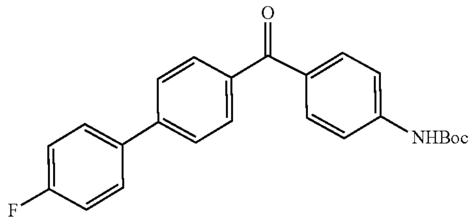 [SMILES: CC(C)(C)OC(=O)Nc1ccc(C(=O)c2ccc(-c3ccc(F)cc3)cc2)cc1]

To a solution of tert-butyl (4-((4'-fluoro-[1,1'-biphenyl]-4-yl)(hydroxy)methyl)phenyl)carbamate (0.762 mmol, 0.300 g), in DCM (80 mL), was added $MnO_2$ (4.57 mmol, 0.40 g) and the suspension was stirred at RT for 16 h. The reaction mixture was filtered through a fritted funnel and the filtrate was concentrated under reduced pressure. The residue was purified by flash chromatography (Biotage KP-Sil 25 g, hexane/EtOAc, 0-40%) to afford tert-butyl (4-(4'-fluoro-[1,1'-biphenyl]-4-carbonyl)phenyl)carbamate (0.588 mmol, 0.230 g) in 77% yield as a yellow solid.

$C_{24}H_{22}FNO_3$; Mw=391.43 g·mol$^{-1}$; $^1$H NMR (400 MHz, $CDCl_3$) δ 7.94-7.80 (m, 4H), 7.71-7.56 (m, 4H), 7.46-7.41 (m, 2H), 7.21-7.13 (m, 2H), 1.48 (s, 9H).

Biological Properties of Compounds

Identification of Compounds Exhibiting High Potency Against NOTCH Driven Human Cancers In order determine anti-cancer potency of compounds NOTCH positive/driven human T cell acute lymphoblastic leukemia cell line RPMI 8402 was treated with selected compounds and downregulation of NOTCH target genes was measured.

Materials and Methods

Cell Culture

One million human NOTCH positive T-ALL cell line RPMI8402 were treated with NOTCH targeting compounds at 1 μM concentration for 24 hours. Following treatment cells were harvested and washed with 1×PBS. Total RNA and total protein lysates were extracted as described below.

RNA Extraction

Total RNA was extracted from cells using TRIzol® extraction kit (Invitrogen). Briefly, $1\times10^6$ cells were washed with ice-cold 1×PBS and lysed in 1 ml of TRIzol® solution for 5 minutes at room temperature to dissociate nucleoprotein complexes. Lysed cells were then treated with 200 μl of chloroform and shaked vigorously for 15-30 seconds and incubated at room temperature for 2-3 minutes. The samples were centrifuged at 14000 rpm using Eppendorf table top centrifuge for 10 minutes at 4° C. Following centrifugation, upper aqueous phase was transferred to new eppendorf tubes. To precipitate total RNA 500 μl of isomyl alcohol was added to the separated aqueous phase and incubated at room temperature for 10 minutes. A RNA pellet was obtained by centrifuging the samples at 4° C. for 10 minutes. RNA pellet obtained was washed with 1 ml ice cold 75% ethanol and spun down at 14000 rpm at 4° C. RNA pellet was dried off of excess of ethanol and resuspended in 40 μl DPEC water.

cDNA Synthesis

Total RNA extracted from the cell was used to synthesize cDNA by reverse transcription reaction. Reverse transcription was performed according to one of the two following protocols.

In first protocol, SuperScript™ RT (Invitrogen) was used for reverse transcription reaction. RNA concentration was measured using NanoDrop®ND-1000 spectrophotometer (Witec AG) and 500 ng of total RNA was mixed with a 10 mM mix of dNTPs and 100 ng of random primers. The reaction mix was incubated at 65° C. for 5 minutes and quickly incubated on ice for 1 minute. Following incubation on ice, 5× first strand buffer and 0.1M DTT were added and mix was incubated for 2 minutes at 25° C. To start the reverse transcription reaction, 200 U of SuperScrip™ II RT was added to the reaction mix and incubated at 42° C. for 50 minutes. The reaction was stopped by incubating the reaction mix at 75° C. for 15 minutes.

In second protocol, reverse transcription was performed using PrimeScript RT Master Mix (Takara). RNA concentration was measured using NanoDrop®ND-1000 spectrophotometer (Witec AG) and 1 μg of total RNA was mixed with 4 μL 5× PrimeScript RT Master Mix in a total reaction volume of 20 μL. The reaction mix was incubated at 37° C. for 15 minutes followed by heat inactivation at 85° C. for 5 seconds.

Quantitative Real Time PCR Analyses

QRT-PCR were carried out using 7900 HT Fast Real-Time PCR system (Applied Biosystems) or QuantStudio 3 system (ThermoFisher). Briefly, 12.5 ng of template cDNA was used with a primer concentration of 0.5 μM each and 1×SYBR Green dye in a final volume of 10 μL in a 96 well or 384 well plate format. The melting curves and ct values were analyzed with SDS software (Applied Biosystems) or with QuantStudio Design and Analysis software (ThermoFisher).

Western Blot Analyses

Cells were lysed in RIPA buffer (50 mM Tris·Cl, pH 7.5, 150 mM NaCl, 1% nonidet P-40, 0.5% sodium deoxycholate and 0.1% SDS) for 30 minutes at 4° C. Lysed cells were centrifuged to remove the debris at 14000 rpm at 4° C. Supernatant was transferred to a new eppendorf tube. The protein concentration was determined by Bradford assay using spectrophotometer (Ultrospec 3000 pro).

Initially for western blotting, 40 μg of protein were denatured in 1×SDS gel loading buffer (100 mM Tris·Cl, pH 6.8, 200 mM DTT, 4% SDS, 0.2% bromophenol, 20% glycerol) by heating at 99° C. for 5 minutes. Denatured protein samples were stored on ice until loading on to the acrylamide gel. The samples were run on 8% or 10% acrylamide gel in Tris-glycine electrophoresis buffer (25 mM Tris, 250 mM glycine, 0.1% SDS). Following separation on the acrylamide gel, protein samples were transferred on to PVDF membrane (PEQ lab, catalog number 39-3010) using transfer buffer (39 mM glycine, 48 mM Tris base, 0.037% SDS and 20% methanol).

For immunoblotting, membranes were blocked with 5% milk and incubated overnight with primary antibodies at 4° C. Membrane were washed with 1×TBST (1×TBS+0.5 tween 20) for 5 minutes (3 times) and incubated with HRP-conjugated secondary antibodies for one hour at room temperature. Signal was detected with Super Signal West chemiluminescent substrate (Thermo Scientific, catalog number 34077).

Later on western blotting was carried out using Jess (ProteinSimple, biotechne). Samples containing 0.8 μg protein was denatured in loading buffer containing DTT by heating at 95° C. for 5 minutes. Samples were run on 12-230 kDa gel matrix, with incubation time for primary and secondary antibodies of 1 hour and 30 minutes, respectively. Data were analysed using Compass for SW (ProteinSimple, biotechne) software.

Alamarblue/PrestoBlue Proliferation Assay

Alamarblue® and PrestoBlue proliferation assays were performed to determine the growth kinetics of Notch inhibitor treated cells. Alamar Blue® and PrestoBlue consists of a cell permeable substrate resazurin. In metabolically active and proliferating cells, resazurin is converted to resorufin due to an intrinsic reducing power of live cells and produces a red fluorescence. Therefore production of resorufin serves as an indicator of the viability of the cell population.

Proliferation assays were performed by seeding 5000 cells/well in a 96 well plate. Cells were treated with DMSO or compounds for 72 hours using concentration ranges of 0.01-10 μM. Each concentration was tested in 4 replicates. To determine the growth kinetics, 10 μl of Alamar Blue® or PrestoBlue (Invitrogen) was added to each well and incubated for 4 hours. Readout was taken using Tecan F500 (Tecan) multiplate reader or Varioskan LUX (ThermoFisher) multiplate reader.

Example 27: Compounds Exhibiting High Potency Against NOTCH Driven Human Cancers In order to determine anti-cancer potency of compounds compared to 6-(4-tert-butylphenoxy)pyridin-3-amine (described in WO2013/093885), NOTCH positive/driven human T cell acute lymphoblastic leukemia cell line RPMI 8402 was treated with selected compounds. As shown in FIG. 1 and table 1, 4-([1,1'-Biphenyl]-4-yloxy)aniline, 6-([1,1'-Biphenyl]-4-yloxy)-N-methylpyridin-3-amine, 4-([1,1'-Biphenyl]-4-yloxy)-3-fluoro-N-methylaniline, 6-((4'-Fluoro-[1,1'-biphenyl]-4-yl)oxy)pyridin-3-amine, 6-([1,1'-Biphenyl]-4-yloxy)-4-methylpyridin-3-amine), 6-([1,1'-

Biphenyl]-4-yloxy)-2-methylpyridin-3-amine, N-Methyl-6-((6-phenylpyridin-3-yl)oxy)pyridin-3-amine and 6-((2-(2-(4-Aminophenoxy)ethyl)-[1,1'-biphenyl]-4-yl)oxy)pyridin-3-amine exhibit 1.05×-9× higher anti-proliferative potency than 6-(4-tert-butylphenoxy)pyridin-3-amine.

TABLE 1

Anti-proliferative effect of compounds on NOTCH positive human leukemic cells. Cells were treated with compounds (concentration range 0.01-10 μM) for 72 hours. Anti-proliferative effect was measured using Alamar blue assay (See Material and methods for details). $IC_{50}$ values were calculated using Graph prism software.

| Compound | Anti-proliferative $IC_{50}$ values (μM) (fold change compared to 6-(4-tert-butylphenoxy)pyridin-3-amine) |
|---|---|
| 6-(4-tert-butylphenoxy)pyridin-3-amine* | 0.74 (1X) |
| 4-([1,1'-Biphenyl]-4-yloxy)aniline | 0.17 (4.35x) |
| 6-([1,1'-Biphenyl]-4-yloxy)-N-methylpyridin-3-amine | 0.11 (6.72x) |
| 4-([1,1'-Biphenyl]-4-yloxy)-3-fluoro-N-methylaniline | 0.70 (1.05x) |
| 6-((4'-Fluoro-[1,1'-biphenyl]-4-yl)oxy)pyridin-3-amine | 0.083 (8.91x) |
| 6-([1,1'-Biphenyl]-4-yloxy)-4-methylpyridin-3-amine | 0.11 (4.35x) |
| 6-([1,1'-Biphenyl]-4-yloxy)-2-methylpyridin-3-amine | 0.11 (4.35x) |
| N-Methyl-6-((6-phenylpyridin-3-yl)oxy)pyridin-3-amine | 0.50 (1.5x) |
| 6-((2-(2-(4-Aminophenoxy)ethyl)-[1,1'-biphenyl]-4-yl)oxy)pyridin-3-amine | 0.92 (8.0x) |

*Comparative compound described in WO2013/093885

Example 28: Downregulation of mRNA Transcripts of NOTCH Target Genes

To further determine anti-NOTCH activity and potency of compounds (compared to 6-(4-tert-butylphenoxy)pyridin-3-amine), NOTCH positive human leukemic cell lines were treated with compounds for 24 hours at a concentration of 1 μM. The effect on NOTCH signalling was investigated by quantifying the levels of mRNA transcripts of NOTCH target genes by quantitative PCR. An increase in potency of newly synthesized compounds was calculated as percentage improvement over 6-(4-tert-butylphenoxy)pyridin-3-amine activity. As show in table 2, compounds exhibit enhanced potency in downregulating NOTCH target genes such as HES1, cMYC and DTX1.

TABLE 2

Human leukemic cells RPMI8402 were treated with compounds at mM concentration for 24 hours at 37 C. Total RNA was extracted, cDNA synthesized and RNA expression of respective genes was quantified using quantitative PCR (qPCR). The activity of 6-(4-tert-butylphenoxy)pyridin-3-amine to downregulate NOTCH target genes was set to 100% and corresponding increase in activity of various compounds was calculated using 6-(4-tert-butylphenoxy)pyridin-3-amine activity as a reference point. ND: not determined.

Figure 2:
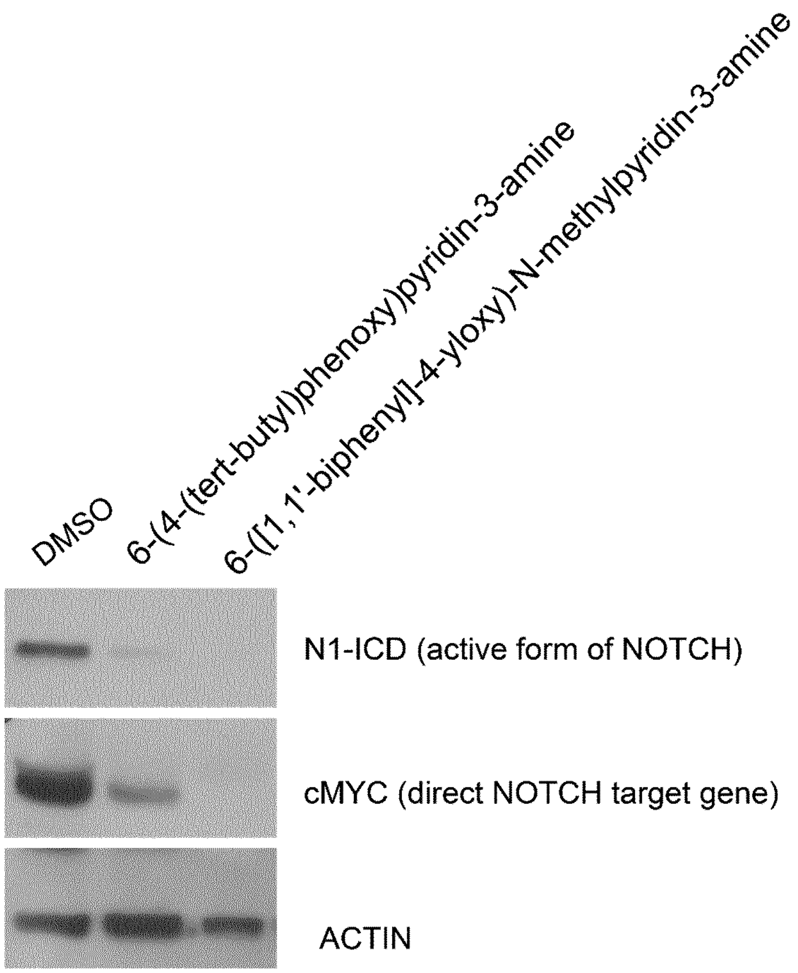
FIG. 2 shows effect of 6-([1,1-Biphenyl]-4-yloxy)-N-methylpyridin-3-amine on N1-ICD and cMYC (NOTCH target gene) in human leukemic cells. NOTCH positive human leukemic RPMI8402 cells were treated with 1 μM of 6-(4-tert-butylphenoxy)pyridin-3-amine and 6-([1,1'-Biphenyl]-4-yloxy)-N-methylpyridin-3-amine for 24 hours. Following treatment, total protein lysates were extracted and protein expression analysed by western blot. Data shows that 6-([1,1'-Biphenyl]-4-yloxy)-N-methylpyridin-3-amine has enhanced potency in downregulating NOTCH pathway in human cancer cells compared with 6-(4-tert-butylphenoxy)pyridin-3-amine.
Figure 3:
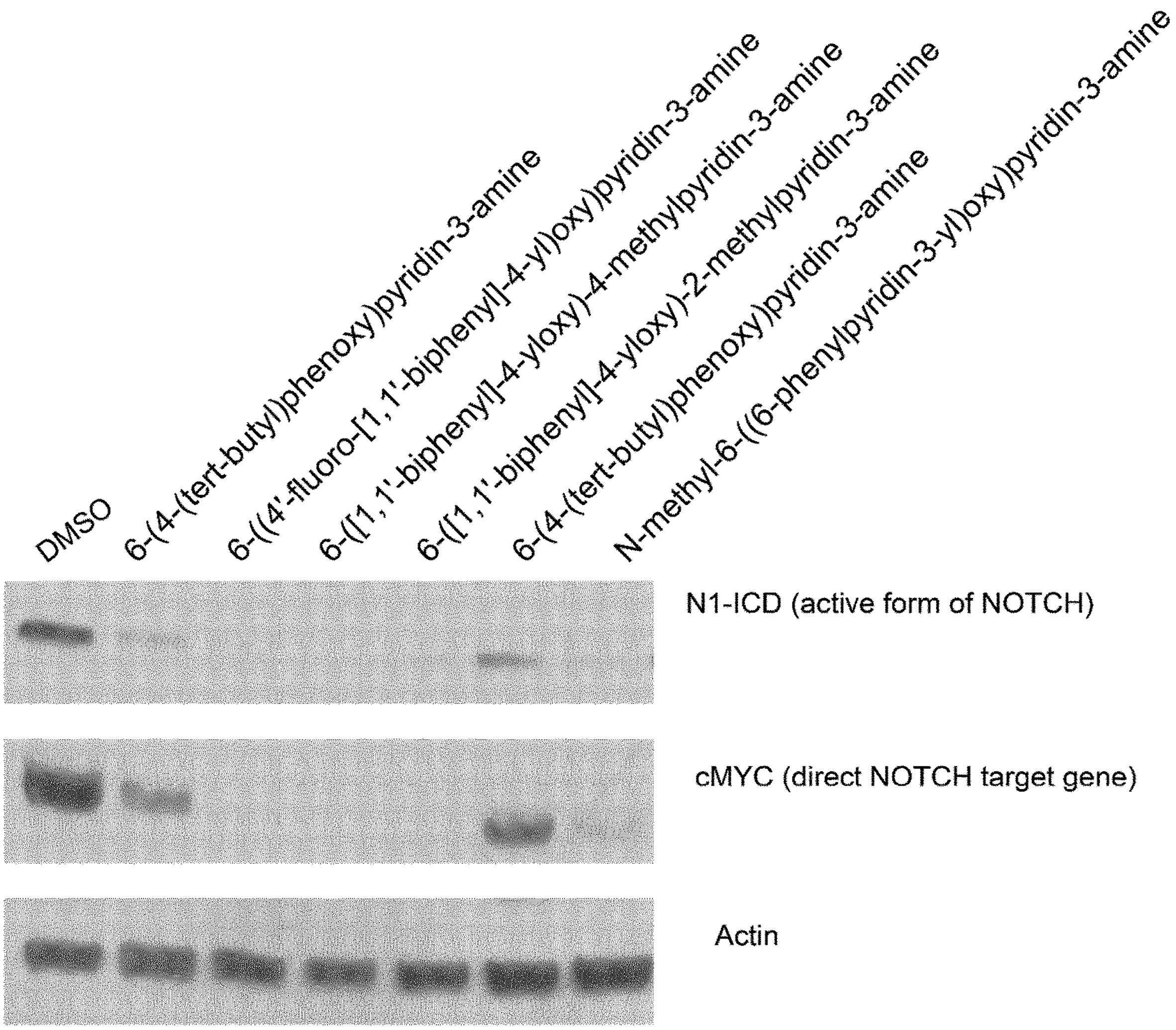
FIG. 3 shows effect of 6-((4'-Fluoro-[1,1'-biphenyl]-4-yl)oxy)pyridin-3-amine, 6-([1,1'-Biphenyl]-4-yloxy)-4-methylpyridin-3-amine, 6-([1,1'-Biphenyl]-4-yloxy)-2-methylpyridin-3-amine and N-Methyl-6-((6-phenylpyridin-3-yl)oxy)pyridin-3-amine on N1-ICD and cMYC (NOTCH target gene) in human leukemic cells. NOTCH positive human leukemic RPMI8402 cells were treated with 1 μM of 6-(4-tert-butylphenoxy)pyridin-3-amine and 6-((4'-Fluoro-

| | Percentage improvement of compounds over 6-(4-tert-Butylphenoxy)pyridin-3-amine to downregulate NOTCH target genes in human cancer cells (mRNA expression) | | |
|---|---|---|---|
| Compound name | HES1 | cMYC | DTX1 |
| 6-(4-tert-butylphenoxy)pyridin-3-amine* | 100 | 100 | 100 |
| 4-([1,1'-Biphenyl]-4-yloxy)aniline | 109 | 153 | 109 |
| 6-([1,1'-Biphenyl]-4-yloxy)-N-methylpyridin-3-amine | ND | See FIG. 2 (protein) | ND |
| 3-Fluoro-4-(4-(pyridin-4-yl)phenoxy)aniline | 135 | 188 | 122 |
| 4-([1,1'-Biphenyl]-4-yloxy)-3-fluoro-N-methylaniline | 130 | 118 | 109 |
| 6-((2,2'-Dimethyl-[1,1'-biphenyl]-4-yl)oxy)-N-methylpyridin-3-amine | ND | 134 | ND |
| 6-((4'-Fluoro-[1,1'-biphenyl]-4-yl)oxy)pyridin-3-amine | 158 | 144 | 106 |
| 6-(4-(Thiazol-2-yl)phenoxy)pyridin-3-amine | 118 | ND | 116 |
| 6-([1,1'-Biphenyl]-4-yl oxy)-4-methylpyridin-3-amine | 141 | 144 | 106 |
| 6-([1,1'-Biphenyl]-4-yloxy)-2-methylpyridin-3-amine | 145 | 139 | 107 |
| N-Methyl-6-((6-phenylpyridin-3-yl)oxy)pyridin-3-amine | ND | See FIG. 3 (protein) | ND |
| (4'-((5-Aminopyridin-2-yl)oxy)-[1,1-biphenyl]-3-yl)methanol | 109 | ND | 112 |
| 6-((3'-(Aminomethyl)-[1,1'-biphenyl]-4-yl)oxy)pyridin-3-amine | 132 | 185 | 111 |
| 2-(4'-((5-Aminopyridin-2-yl)oxy)-[1,1'-biphenyl]-3-yl)acetamide | 106 | ND | 112 |
| 6-((2-(4-Aminophenoxy)-[1,1'-biphenyl]-4-yl)oxy)pyridin-3-amine | 125 | ND | 125 |
| 6,6'-([1,1'-Biphenyl]-2,4-diylbi s(oxy))bi s(pyri din-3-amine) | 131 | 157 | 124 |
| 6-((2-(2-(4-Aminophenoxy)ethyl)-[1,1'-biphenyl]-4-yl)oxy)pyridin-3-amine | 139 | 190 | 128 |

*Comparative compound described in WO2013/093885

Example 29: Downregulation of NOTCH Target Genes at Protein Level

To further confirm an anti-NOTCH activity and potency of compounds, NOTCH positive leukemic cell lines were treated with selected-compounds for 24 hours at a concentration of 1 μM. Total protein lysates were analysed by western blot analysis using N1-ICD (cleaved and active NOTCH1 Intracellular Domain), cMYC and ACTIN specific antibodies. As shown in FIGS. 2 and 3, compared to 6-(4-tert-butylphenoxy)pyridin-3-amine (described in WO2013/093885), 6-([1,1'-Biphenyl]-4-yloxy)-N-methylpyridin-3-amine, 6-((4'-Fluoro-[1,1'-biphenyl]-4-yl)oxy) pyridin-3-amine, 6-([1,1'-Biphenyl]-4-yloxy)-4-methylpyridin-3-amine, 6-([1,1'-Biphenyl]-4-yloxy)-2-methylpyridin-3-amine and N-Methyl-6-((6-phenylpyridin-3-yl)oxy) pyridin-3-amine show a stronger downregulation of cMYC and N1-ICD (both direct target genes of NOTCH signalling in human leukemic cells).

Example 30: Compounds Exhibiting High Potency Against NOTCH Driven Human Cancers In order to determine anti-cancer potency of compounds compared to 6-(4-tert-butylphenoxy)pyridin-3-amine (described in WO2013/093885), NOTCH positive/driven human T cell acute lymphoblastic leukemia cell line RPMI 8402 was treated with selected compounds. The compounds shown in FIG. 1 and table 3, exhibit 1.5× to 24× higher anti-proliferative potency than 6-(4-tert-butylphenoxy)pyridin-3-amine.

TABLE 3

Anti-proliferative effect of compounds on NOTCH positive human leukemic cells. Cells were treated with compounds (concentration range 0.03-100 μM) for 72 hours. Anti-proliferative effect was measured using PrestoBlue assay (See Material and methods for details). $IC_{50}$ values were calculated using Graph prism software.

| Compound | Anti-proliferative $IC_{50}$ values (μM) (fold change compared to 6-(4-tert-butylphenoxy)pyridin-3-amine) |
|---|---|
| 6-(4-tert-butylphenoxy)pyridin-3-amine* | 0.74 (1X) |
| 6-((4'-fluoro-[1,1'-biphenyl]-4-yl)oxy)-2-methylpyridin-3-amine | <0.03 (>24x) |
| 6-((4'-fluoro-[1,1'-biphenyl]-4-yl)oxy)-N-methylpyridin-3-amine | 0.2 (3.7x) |
| 2-methyl-6-(4-(thiazol-2-yl)phenoxy)pyridin-3-amine | <0.03 (>24x) |
| 4-methyl-6-(4-(thiazol-2-yl)phenoxy)pyridin-3-amine | 0.05 (14.8x) |
| 2-methyl-6-(4-(thiazol-5-yl)phenoxy)pyridin-3-amine | 0.5 (1.5x) |
| 4-methyl-6-(4-(thiazol-5-yl)phenoxy)pyridin-3-amine | <0.03 (>24x) |
| N-methyl-6-(4-(thiazol-5-yl)phenoxy)pyridin-3-amine | 0.15 (4.9x) |
| 2-methyl-6-((6-phenylpyridin-3-yl)oxy)pyridin-3-amine | 0.45 (1.6x) |

*Comparative compound described in WO2013/093885

Example 31: Downregulation of NOTCH Target Genes at Protein Level

To further confirm an anti-NOTCH activity and potency of compounds, NOTCH positive leukemic cell lines were treated with selected compounds for 24 hours at a concentration of 1 μM. Total protein lysates were analysed by Jess western blot analysis using N1-ICD (cleaved and active NOTCH1 Intracellular Domain), cMYC and GAPDH specific antibodies. The compounds shown in table 4 demonstrate a stronger downregulation of cMYC and N1-ICD (both direct target genes of NOTCH signalling in human leukemic cells) when compared with 6-(4-tert-butylphenoxy)pyridin-3-amine (described in WO2013/093885).

TABLE 4

Human leukemic cells RPMI8402 were treated with compounds at 1 μM concentration for 24 hours at 37° C. Total protein lysate were analysed by Jess western blot.

| | Percentage improvement of compounds over 6-(4-tert-Butylphenoxy)pyridin-3-amine to downregulate NOTCH target genes in human cancer cells (protein expression) | |
|---|---|---|
| Compound name | cMYC | N1-ICD |
| 6-(4-tert-butylphenoxy)pyridin-3-amine* | 100 | 100 |
| 6-((4'-fluoro-[1,1'-biphenyl]-4-yl)oxy)-2-methylpyridin-3-amine | 170 | 173 |
| 6-((4'-fluoro-[1,1'-biphenyl]-4-yl)oxy)-4-methylpyridin-3-amine | 183 | 192 |
| 6-((4'-fluoro-[1,1'-biphenyl]-4-yl)oxy)-N-methylpyridin-3-amine | 183 | 197 |
| 2-methyl-6-(4-(thiazol-2-yl)phenoxy)pyridin-3-amine | 130 | 132 |
| 2-methyl-6-(4-(thiazol-5-yl)phenoxy)pyridin-3-amine | 133 | 136 |
| 4-methyl-6-(4-(thiazol-5-yl)phenoxy)pyridin-3-amine | 130 | 132 |
| N-methyl-6-(4-(thiazol-5-yl)phenoxy)pyridin-3-amine | 115 | 114 |
| 2-methyl-6-((6-phenylpyridin-3-yl)oxy)pyridin-3-amine | 159 | 159 |
| 4-methyl-6-((6-phenylpyridin-3-yl)oxy)pyridin-3-amine | 108 | 110 |
| 4-((4'-fluoro-[1,1'-biphenyl]-4-yl)methyl)aniline | 154 | 149 |
| 6-((2,2'-dimethyl-[1,1'-biphenyl]-4-yl)oxy)-2-methylpyridin-3-amine | 138 | 151 |

*Comparative compound described in WO2013/093885

Example 32: Downregulation of mRNA Transcripts of NOTCH Target Genes

To further determine anti-NOTCH activity and potency of compounds (compared to 6-(4-tert-butylphenoxy)pyridin-3-amine), NOTCH positive human leukemic cell lines were treated with compounds for 24 hours at a concentration of 1 μM. The effect on NOTCH signalling was investigated by quantifying the levels of mRNA transcripts of NOTCH target genes by quantitative PCR. As show in table 5, in comparison to 6-(4-tert-butylphenoxy)pyridin-3-amine, the listed compounds exhibit enhanced potency in downregulating NOTCH target genes such as cMYC, DTX1 and HES1.

TABLE 5

Human leukemic cells RPMI8402 were treated with compounds at 1 mM concentration for 24 hours at 37° C. Total RNA was extracted, cDNA synthesized and RNA expression of respective genes was quantified using quantitative PCR (qPCR).

| | Percentage improvement of compounds over 6-(4-tert-Butylphenoxy)pyridin-3-amine to downregulate NOTCH target genes in human cancer cells (mRNA expression) | | |
|---|---|---|---|
| Compound name | cMYC | DTX1 | HES1 |
| 6-(4-tert-butylphenoxy)pyridin-3-amine* | 100 | 100 | 100 |
| 6-((4'-fluoro-[1,1'-biphenyl]-4-yl)oxy)-2-methylpyridin-3-amine | 176 | 130 | 165 |
| 6-((4'-fluoro-[1,1'-biphenyl]-4-yl)oxy)-4-methylpyridin-3-amine | 186 | 134 | 175 |
| 6-((4'-fluoro-[1,1'-biphenyl]-4-yl)oxy)-N-methylpyridin-3-amine | 184 | 134 | 175 |
| 2-methyl-6-(4-(thiazol-2-yl)phenoxy)pyridin-3-amine | 129 | 114 | 124 |
| 4-methyl-6-(4-(thiazol-2-yl)phenoxy)pyridin-3-amine | 135 | 104 | 96 |
| 2-methyl-6-(4-(thiazol-5-yl)phenoxy)pyridin-3-amine | 141 | 118 | 129 |
| 4-methyl-6-(4-(thiazol-5-yl)phenoxy)pyridin-3-amine | 139 | 113 | 120 |
| N-methyl-6-(4-(thiazol-5-yl)phenoxy)pyridin-3-amine | 131 | 107 | 105 |
| 2-methyl-6-((6-phenylpyridin-3-yl)oxy)pyridin-3-amine | 155 | 121 | 144 |
| 4-((4'-fluoro-[1,1'-biphenyl]-4-yl)methyl)aniline | 169 | 124 | 158 |
| 6-((2,2'-dimethyl-[1,1'-biphenyl]-4-yl)oxy)-2-methylpyridin-3-amine | 122 | 111 | 116 |

*Comparative compound described in WO2013/093885

The invention claimed is:

1. A compound of formula (I)

Formula (I)

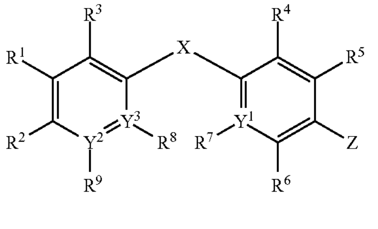

or a pharmaceutically acceptable salt thereof, wherein

X is O;

$Y^1$ is N and $R^7$ is absent;

$Y^2$ is N or C and $Y^3$ is C;

Z is $NR^{10}R^{11}$, wherein $R^{10}$ and $R^{11}$ are each independently H or $C_1$-$C_6$ alkyl;

$R^1$ is H, halogen, and $C_1$-$C_4$ alkyl;

$R^2$ is aryl or heteroaryl, wherein the aryl or the heteroaryl are optionally substituted with $C_1$-$C_6$ alkyl or halogen;

$R^3$ is H, halogen, and $C_1$-$C_4$ alkyl;

$R^4$, $R^5$, and $R^6$ are each independently H, halogen, and $C_1$-$C_4$ alkyl;

$R^8$ is selected from H, halogen, and $C_1$-$C_4$ alkyl;

$R^9$ is absent when $Y^2$ is N or is selected from H, halogen, and $C_1$-$C_4$ alkyl when $Y^2$ is C; and with the proviso that the compound of formula (I) is not 6-([1,1'-biphenyl]-4-yloxy)-pyridine-3-amine, 6-([1,1'-biphenyl]-4-yloxy)-2-methylpyridin-3-amine, 6-([1,1'-biphenyl]-4-yloxy)-4-methylpyridin-3-amine; with the proviso that the compound of formula (I) is not a (i) $Y^2$ and $Y^3$ are both C, Z is $NH_2$, $R^1$ is H, $R^2$ is phenyl, $R^3$ is H, $R^4$ is Cl, Br, or Me, $R^5$ is H, $R^6$ is H, $R^8$ is H, and $R^9$ is H; or (ii) $Y^2$ and $Y^3$ are both C, Z is $NH_2$, $R^1$ is H, $R^2$ is phenyl, $R^3$ is H, $R^4$ is H, $R^5$ is H, $R^6$ is H, $R^8$ is Cl, and $R^9$ is H; or (iii) $Y^2$ and $Y^3$ are both C, Z is $NH_2$, $R^1$ is H, $R^2$ is pyridyl substituted at the para position with methoxy, $R^3$ is H, $R^4$ is H, $R^5$ is H, $R^6$ is H, $R^8$ is H, and $R^9$ is H; or (iv) $Y^2$ and $Y^3$ are both C, Z is $NH_2$, $R^1$ is H, $R^2$ is phenyl substituted at the ortho position with methoxy and meta position with F, $R^3$ is H, $R^4$ is H, $R^5$ is H, $R^6$ is H, $R^8$ is H, and $R^9$ is H; or (v) $Y^2$ and $Y^3$ are both C, Z is $NH_2$, $R^1$ is H, $R^2$ is 1H-pyrazol-4-yl or 5-menthyl-1H-indol-3-yl, $R^3$ is H, $R^4$ is H, $R^5$ is H, $R^6$ is H, $R^8$ is H, and $R^9$ is H.

2. The compound of claim 1, or pharmaceutically acceptable salt thereof, wherein $Y^1$ is N and $R^7$ is absent, $Y^2$ is C, and $Y^3$ is C.

3. The compound of claim 1, or pharmaceutically acceptable salt thereof, wherein $Y^1$ is N and $R^7$ is absent, $Y^2$ is N, and $Y^3$ is C.

4. The compound of claim 1, or pharmaceutically acceptable salt thereof, wherein Z is $NR^{10}R^{11}$ and $R^{10}$ and $R^{11}$ are each independently H or methyl.

5. The compound of claim 4, or pharmaceutically acceptable salt thereof, wherein Z is $NR^{10}R^{11}$, $R^{10}$ is H, and $R^{11}$ is H or methyl.

6. The compound of claim 5, or pharmaceutically acceptable salt thereof, wherein Z is $NR^{10}R^{11}$, $R^{10}$ is H, and $R^{11}$ is H.

7. The compound of claim 5, or pharmaceutically acceptable salt thereof, wherein Z is $NR^{10}R^{11}$, $R^{10}$ is H and $R^{11}$ is methyl.

8. The compound of claim 1, or pharmaceutically acceptable salt thereof, wherein the compound of formula (I) is selected from:

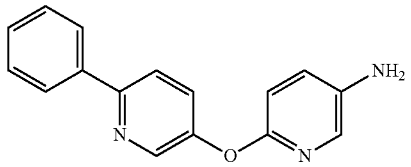

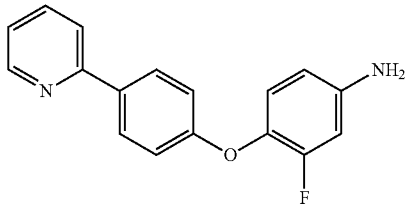

-continued
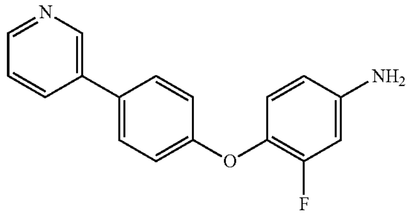
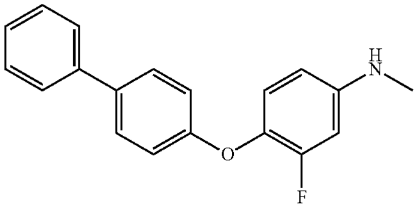
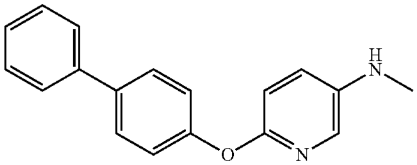
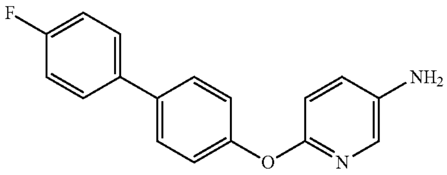
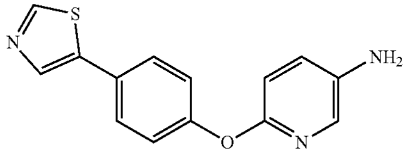
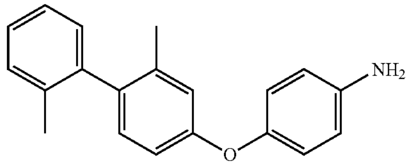
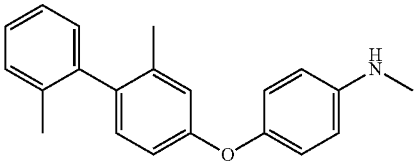
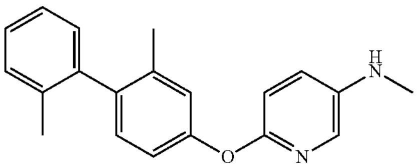
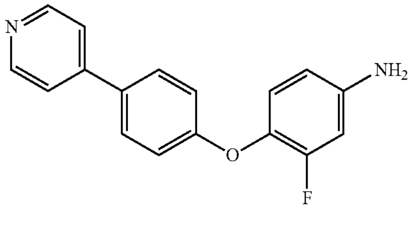
-continued
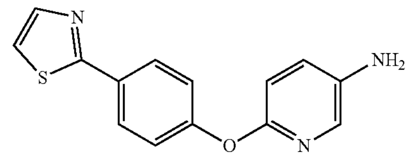
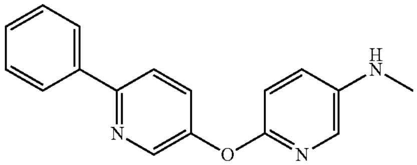
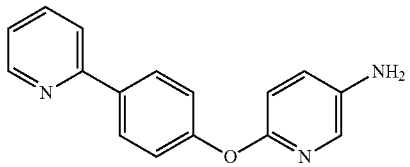
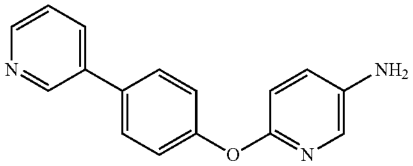
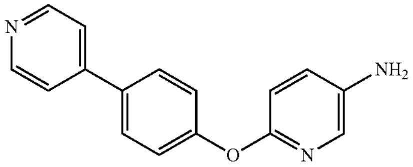
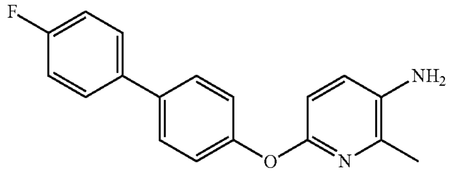
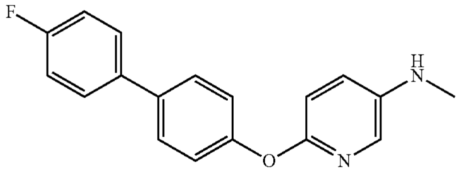
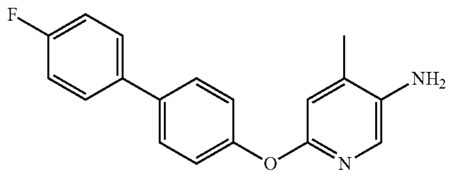
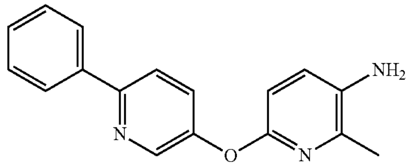
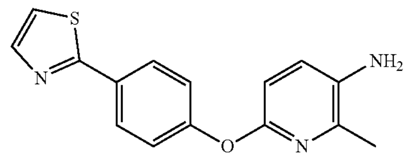

-continued
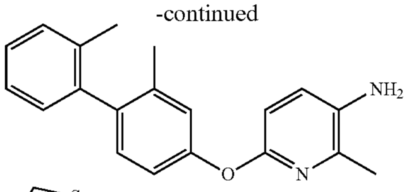
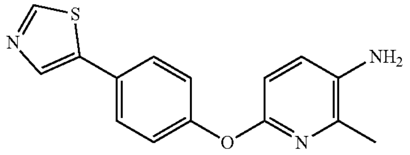
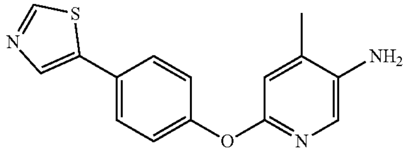
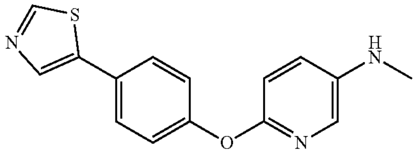
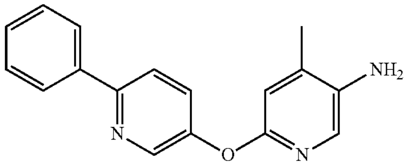
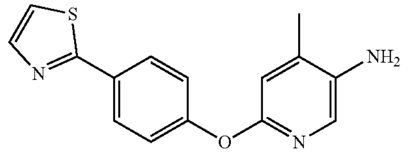
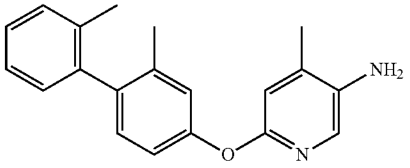
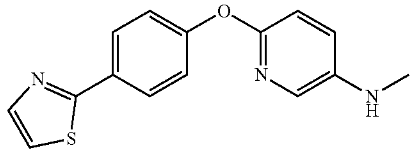
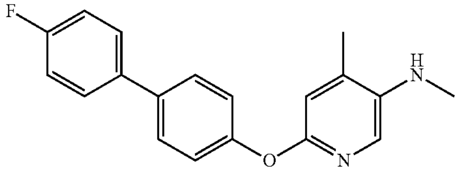
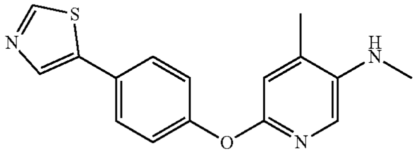
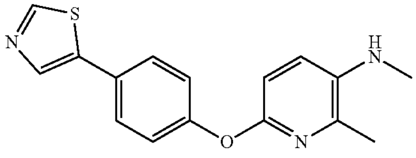
-continued
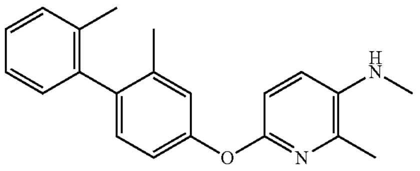
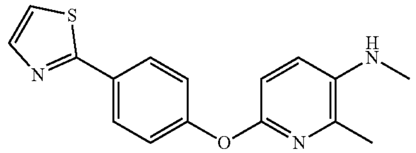
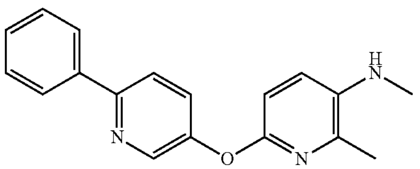
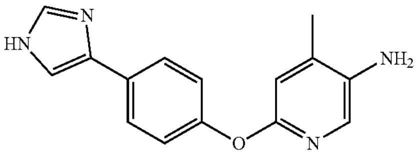
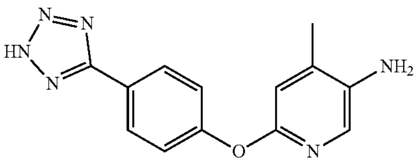
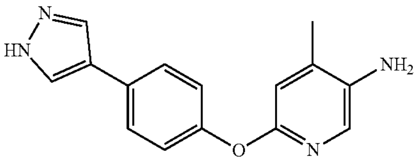
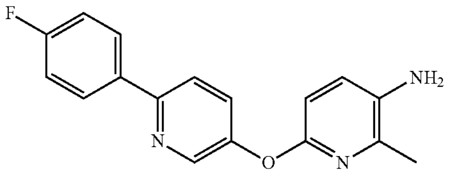
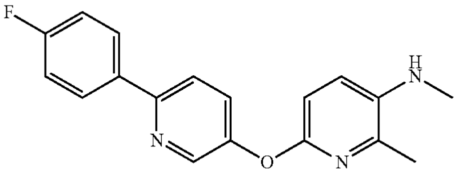
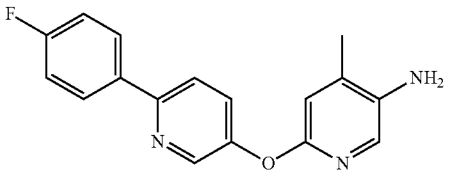
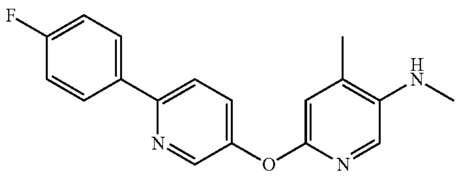 and -continued
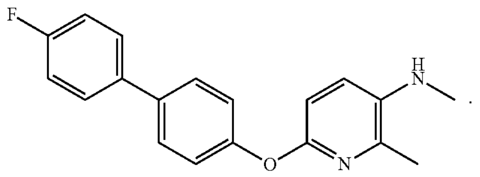
9. The compound of claim 1, or pharmaceutically acceptable salt thereof, wherein the compound of formula (I) is selected from:
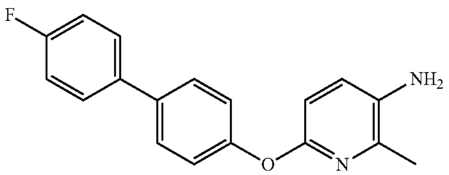
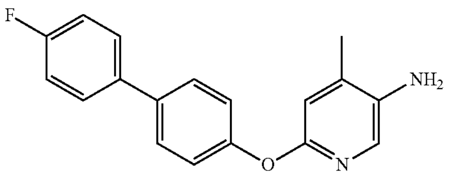
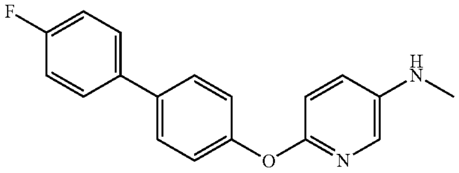
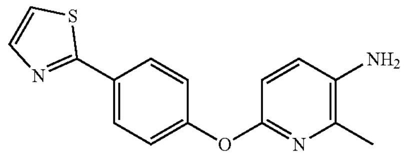
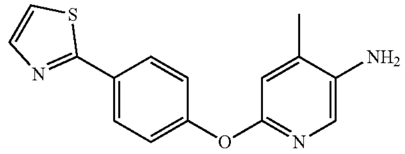
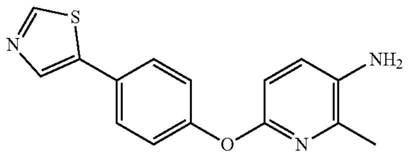
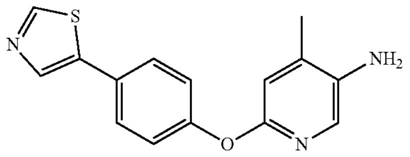
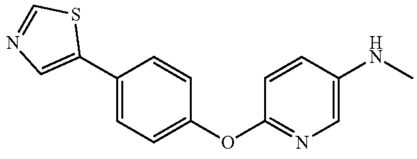
-continued
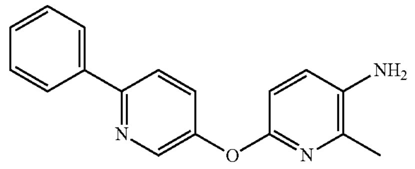
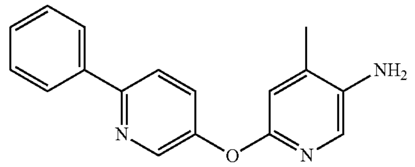
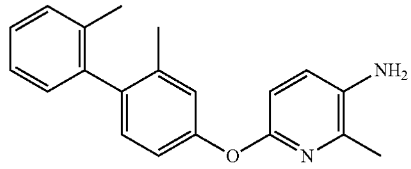
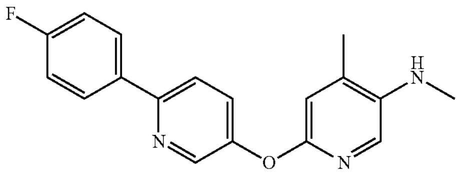
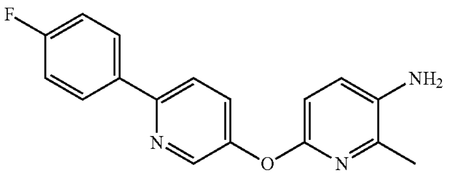
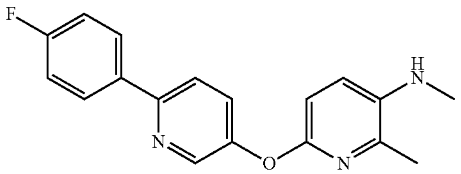
, and
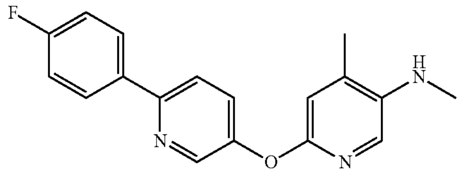
10. The compound of claim 1, wherein the compound of formula (I) is
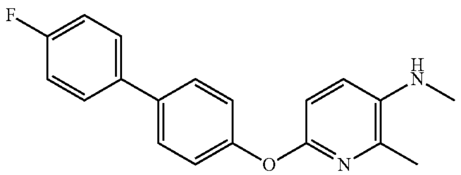 [SMILES: CNc1ccc(Oc2ccc(-c3ccc(F)cc3)cc2)nc1C]
or a pharmaceutically acceptable salt thereof.

11. The compound of claim 1, wherein the compound of formula (I) is

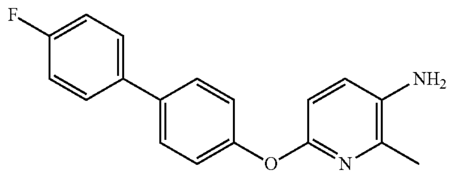

or a pharmaceutically acceptable salt thereof.

12. The compound of claim 1, wherein the compound of formula (I) is

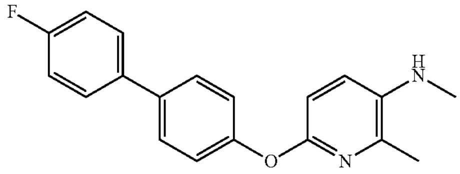 [SMILES: CNc1ccc(Oc2ccc(-c3ccc(F)cc3)cc2)nc1C]

or a pharmaceutically acceptable salt thereof.

13. The compound of claim 1, wherein the compound is

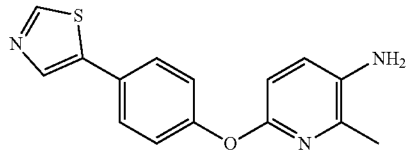 [SMILES: Cc1nc(Oc2ccc(-c3cncs3)cc2)ccc1N]

or a pharmaceutically acceptable salt thereof.

14. The compound of claim 1, wherein the compound is

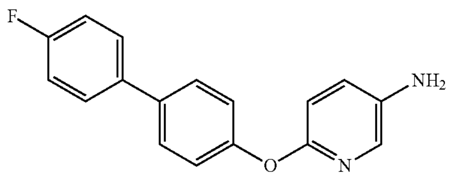 [SMILES: Nc1ccc(Oc2ccc(-c3ccc(F)cc3)cc2)nc1]

or a pharmaceutically acceptable salt thereof.

15. A pharmaceutical composition comprising a compound of claim 1 or a pharmaceutically acceptable salt thereof and a pharmaceutically acceptable excipient.

16. A method of treating a NOTCH dependent cancer in a patient, the method comprising administering to said patient an effective amount of a compound of claim 1, or a pharmaceutically acceptable salt thereof, wherein said NOTCH dependent cancer is a cancer selected from the group comprising adenoid cystic carcinoma (ACC), T cell-Acute lymphoblastic leukemia (T-ALL), chronic myeloid leukemia (CML), chronic lymphocytic leukemia (CLL), Mantle cell lymphoma, breast cancer, pancreatic cancer, prostate cancer, melanoma, brain tumors, tumor angiogenesis, liver cancer and colorectal cancer.

17. A method of treating a NOTCH dependent cancer in a patient, the method comprising administering to said patient an effective amount of a compound of claim 1, or of a pharmaceutically acceptable salt thereof, wherein said NOTCH dependent cancer is a cancer resistant to γ-secretase inhibitor treatment.

* * * * *